US012773204B2

(12) United States Patent
Smith et al.

(10) Patent No.: US 12,773,204 B2
(45) **Date of Patent: *Oct. 27, 2026**

(54) MULTIPLE-FIRING SUTURE FIXATION DEVICE AND METHODS FOR USING AND MANUFACTURING SAME

(71) Applicant: Edwards Lifesciences AG, Nyon (CH)

(72) Inventors: Kevin W. Smith, Coral Gables, FL (US); Max Pierre Mendez, Miami, FL (US); Matthew A. Palmer, Miami, FL (US); M. Sean McBrayer, Miami, FL (US); Thomas O. Bales, Jr., Miami, FL (US); Derek Dee Deville, Coral Gables, FL (US); Richard George Cartledge, Boca Raton, FL (US); Korey Kline, Miami, FL (US); Carlos Rivera, Cooper City, FL (US); George Nunez, Miami, FL (US)

(73) Assignee: Edwards Lifesciences AG, Nyon (CH)

( * ) Notice: Subject to any disclaimer, the term of this patent is extended or adjusted under 35 U.S.C. 154(b) by 735 days.

This patent is subject to a terminal disclaimer.

(21) Appl. No.: 18/046,725

(22) Filed: Oct. 14, 2022

(65) Prior Publication Data

US 2023/0064549 A1 Mar. 2, 2023

Related U.S. Application Data

(63) Continuation of application No. 16/450,907, filed on Jun. 24, 2019, now Pat. No. 11,471,150, which is a (Continued)

(51) Int. Cl.

| | |
|---|---|
| ***A61B 17/04*** | (2006.01) |
| *A61B 17/00* | (2006.01) |
| *A61B 90/30* | (2016.01) |

(52) U.S. Cl.

CPC ...... *A61B 17/0469* (2013.01); *A61B 17/0401* (2013.01); *A61B 17/0467* (2013.01); (Continued)

(58) Field of Classification Search

CPC ........... A61B 17/0485; A61B 17/0467; A61B 17/0487; A61B 17/0469; A61B 17/128; (Continued)

(56) References Cited

U.S. PATENT DOCUMENTS 1,358,477 A 11/1920 Stout
2,264,679 A 12/1941 Ravel
(Continued)

FOREIGN PATENT DOCUMENTS

CA 2141911 4/2002
CA 2141913 4/2002
(Continued)

OTHER PUBLICATIONS

LSI Solutions T-Knot Device 2, LSI Solutions, Inc., 2009-2011, http://www.lsisolutions.com/tkoutsideofcannula.
(Continued)

*Primary Examiner* — Katherine H Schwiker
(74) *Attorney, Agent, or Firm* — Klarquist Sparkman LLP

(57) ABSTRACT

A multiple-firing clip device comprises a shaft comprising an exterior surface, an interior receiving therein suture fixation clips, and a distal end opening shaped to eject a suture fixation clip therefrom. The shaft defines a lateral opening and a distal shaft portion between the lateral opening and the distal end opening. A shuttle moves on the shaft and comprises a shuttle body, a snare having a distal snare portion, and a snare extension slide movable from the shuttle body along a given extent defining a slide distance and a distal end. The shuttle extends at least the distal snare portion distally through the lateral opening from the envi-
(Continued)

ronment into the interior, through the distal shaft portion, and through the distal end opening along a length that is at least equal to the slide distance when the snare extension slide moves to the distal end of the given extent.

19 Claims, 79 Drawing Sheets

Related U.S. Application Data continuation of application No. 14/868,741, filed on Sep. 29, 2015, now Pat. No. 10,327,758, which is a continuation of application No. 14/543,240, filed on Nov. 17, 2014, now Pat. No. 10,016,193.

(60) Provisional application No. 62/069,183, filed on Oct. 27, 2014, provisional application No. 61/951,162, filed on Mar. 11, 2014, provisional application No. 61/905,578, filed on Nov. 18, 2013.

(52) U.S. Cl.
CPC ...... *A61B 17/0483* (2013.01); *A61B 17/0485* (2013.01); *A61B 17/0487* (2013.01); *A61B 2017/00398* (2013.01); *A61B 2017/0053* (2013.01); *A61B 2017/00907* (2013.01); *A61B 2017/0409* (2013.01); *A61B 2017/0414* (2013.01); *A61B 2017/0438* (2013.01); *A61B 2017/0453* (2013.01); *A61B 2017/0454* (2013.01); *A61B 2017/0474* (2013.01); *A61B 2017/0475* (2013.01); *A61B 2017/0488* (2013.01); *A61B 2017/0496* (2013.01); *A61B 2090/309* (2016.02)

(58) Field of Classification Search
CPC ........ A61B 17/1285; A61B 2017/0488; A61B 2017/0496
See application file for complete search history.

(56) References Cited

U.S. PATENT DOCUMENTS

| | | | |
|---|---|---|---|
| 2,516,710 | A | 7/1950 | Mascolo |
| 2,715,486 | A | 8/1955 | Marcoff-Moghadam et al. |
| 2,890,519 | A | 6/1959 | Storz, Jr. |
| 2,981,990 | A | 5/1961 | Balderree, Jr. |
| 3,143,742 | A | 8/1964 | Cromie |
| 3,249,104 | A | 5/1966 | Hohnstein |
| 3,274,658 | A | 9/1966 | Pile |
| 3,452,742 | A | 7/1969 | Muller |
| 3,506,012 | A | 4/1970 | Brown |
| 3,509,882 | A | 5/1970 | Blake |
| 3,526,945 | A | 9/1970 | Ray et al. |
| 3,541,591 | A | 11/1970 | Hoegerman |
| 3,547,103 | A | 12/1970 | Cook |
| 3,570,497 | A | 3/1971 | Lemole |
| 3,608,095 | A | 9/1971 | Barry |
| 3,638,654 | A | 2/1972 | Akuba |
| RE27,391 | E | 6/1972 | Merser |
| 3,753,438 | A | 8/1973 | Wood et al. |
| 3,859,668 | A | 1/1975 | Anderson |
| 3,875,648 | A | 4/1975 | Bone |
| 3,898,999 | A | 8/1975 | Haller |
| 3,910,281 | A | 10/1975 | Kletschka et al. |
| 3,954,108 | A | 5/1976 | Davis |
| 3,954,109 | A | 5/1976 | Patel |
| 3,958,576 | A | 5/1976 | Komiya |
| 3,976,079 | A | 8/1976 | Samuels et al. |
| 3,988,810 | A | 11/1976 | Emery |
| 3,996,623 | A | 12/1976 | Kaster |
| 4,038,725 | A | 8/1977 | Keefe |
| 4,039,078 | A | 8/1977 | Bone |
| 4,103,690 | A | 8/1978 | Harris |
| 4,140,125 | A | 2/1979 | Smith |
| 4,170,990 | A | 10/1979 | Baumgart et al. |
| 4,192,315 | A | 3/1980 | Hilzinger et al. |
| 4,217,902 | A | 8/1980 | March |
| 4,226,239 | A | 10/1980 | Polk et al. |
| 4,324,248 | A | 4/1982 | Perlin |
| 4,345,601 | A | 8/1982 | Fukuda |
| 4,416,266 | A | 11/1983 | Baucom |
| 4,456,017 | A | 6/1984 | Miles |
| 4,485,816 | A | 12/1984 | Krumme |
| 4,522,207 | A | 6/1985 | Klieman et al. |
| 4,535,764 | A | 8/1985 | Ebert |
| 4,548,202 | A | 10/1985 | Duncan |
| 4,549,545 | A | 10/1985 | Levy |
| 4,570,304 | A | 2/1986 | Montreuil et al. |
| 4,586,502 | A | 5/1986 | Bedi et al. |
| 4,586,503 | A | 5/1986 | Kirsch et al. |
| 4,595,007 | A | 6/1986 | Mericle |
| 4,612,932 | A | 9/1986 | Caspar et al. |
| 4,637,380 | A | 1/1987 | Orejola |
| 4,665,906 | A | 5/1987 | Jervis |
| 4,683,895 | A | 8/1987 | Pohndorf |
| 4,705,040 | A | 11/1987 | Mueller et al. |
| 4,719,924 | A | 1/1988 | Crittenden et al. |
| 4,730,615 | A | 3/1988 | Sutherland et al. |
| 4,741,330 | A | 5/1988 | Hayhurst |
| 4,743,253 | A | 5/1988 | Magladry |
| 4,750,492 | A | 6/1988 | Jacobs |
| 4,809,695 | A | 3/1989 | Gwathmey et al. |
| 4,823,794 | A | 4/1989 | Pierce |
| 4,863,460 | A | 9/1989 | Magladry |
| 4,873,975 | A | 10/1989 | Walsh et al. |
| 4,896,668 | A | 1/1990 | Popoff et al. |
| 4,899,744 | A | 2/1990 | Fujitsuka et al. |
| 4,901,721 | A | 2/1990 | Hakki |
| 4,914,789 | A | 4/1990 | Pedersen |
| 4,924,866 | A | 5/1990 | Yoon |
| 4,926,860 | A | 5/1990 | Stice et al. |
| 4,929,240 | A | 5/1990 | Kirsch et al. |
| 4,932,955 | A | 6/1990 | Merz et al. |
| 4,950,283 | A | 8/1990 | Dzubow et al. |
| 4,950,285 | A | 8/1990 | Wilk |
| 4,955,913 | A | 9/1990 | Robinson |
| 4,976,715 | A | 12/1990 | Bays et al. |
| 4,983,176 | A | 1/1991 | Cushman et al. |
| 4,990,152 | A | 2/1991 | Yoon |
| 4,997,439 | A | 3/1991 | Chen |
| 5,002,550 | A | 3/1991 | Li |
| 5,002,562 | A | 3/1991 | Oberlander |
| 5,002,563 | A | 3/1991 | Pyka et al. |
| 5,026,379 | A | 6/1991 | Yoon |
| 5,047,047 | A | 9/1991 | Yoon |
| 5,053,047 | A | 10/1991 | Yoon |
| 5,070,805 | A | 12/1991 | Plante |
| 5,071,431 | A | 12/1991 | Sauter et al. |
| 5,074,874 | A | 12/1991 | Yoon et al. |
| 5,078,731 | A | 1/1992 | Hayhurst |
| 5,100,418 | A | 3/1992 | Yoon et al. |
| 5,116,840 | A | 5/1992 | Ganguly et al. |
| 5,123,913 | A | 6/1992 | Wilk et al. |
| RE34,021 | E | 8/1992 | Mueller et al. |
| 5,152,769 | A | 10/1992 | Baber |
| 5,154,189 | A | 10/1992 | Oberlander |
| 5,158,566 | A | 10/1992 | Pianetti |
| 5,163,954 | A | 11/1992 | Curcio et al. |
| 5,171,233 | A | 12/1992 | Amplatz et al. |
| 5,171,250 | A | 12/1992 | Yoon |
| 5,171,251 | A | 12/1992 | Bregen et al. |
| 5,171,252 | A | 12/1992 | Friedland |
| 5,174,087 | A | 12/1992 | Bruno |
| 5,196,022 | A | 3/1993 | Bilweis |
| 5,219,358 | A | 6/1993 | Bendel et al. |
| 5,222,976 | A | 6/1993 | Yoon |
| 5,231,735 | A | 8/1993 | Paxton |
| 5,234,449 | A | 8/1993 | Bruker et al. |
| 5,236,440 | A | 8/1993 | Hlavacek |
| 5,242,456 | A | 9/1993 | Nash et al. |
| 5,246,443 | A | 9/1993 | Mai |

(56) References Cited

U.S. PATENT DOCUMENTS 5,258,011 A 11/1993 Drews
5,258,015 A 11/1993 Li et al.
5,269,783 A 12/1993 Sander
5,269,809 A 12/1993 Hayhurst et al.
5,279,416 A 1/1994 Malec et al.
5,282,832 A 2/1994 Toso et al.
5,290,289 A 3/1994 Sanders et al.
5,304,204 A 4/1994 Bregen
5,306,290 A 4/1994 Martins et al.
5,306,296 A 4/1994 Wright et al.
5,312,423 A 5/1994 Rosenbluth et al.
5,312,436 A 5/1994 Coffey et al.
5,330,442 A 7/1994 Green et al.
5,330,503 A 7/1994 Yoon
5,336,239 A 8/1994 Gimpelson
5,356,424 A 10/1994 Buzerak et al.
5,374,268 A 12/1994 Sander
5,381,588 A 1/1995 Nelson
5,383,904 A 1/1995 Totakura et al.
5,383,905 A 1/1995 Golds et al.
5,391,173 A 2/1995 Wilk
5,403,346 A 4/1995 Loeser
5,409,499 A 4/1995 Yi
5,437,680 A 8/1995 Yoon
5,437,685 A 8/1995 Blasnik
5,439,479 A 8/1995 Shichman et al.
5,445,167 A 8/1995 Yoon et al.
5,450,860 A 9/1995 O'Connor
5,452,733 A 9/1995 Sterman et al.
5,456,246 A 10/1995 Schmieding et al.
5,462,558 A 10/1995 Kolesa et al.
5,462,561 A 10/1995 Voda
5,474,557 A 12/1995 Mai
5,474,572 A 12/1995 Hayhurst
5,480,405 A 1/1996 Yoon
5,486,197 A 1/1996 Le et al.
5,496,336 A 3/1996 Cosgrove et al.
5,499,990 A 3/1996 Schulken et al.
5,499,991 A 3/1996 Garman et al.
5,500,000 A 3/1996 Feagin et al.
5,520,691 A 5/1996 Branch
5,520,702 A 5/1996 Sauer et al.
5,527,342 A 6/1996 Pietrzak et al.
5,531,763 A 7/1996 Mastri et al.
5,545,178 A 8/1996 Kensey et al.
5,549,619 A 8/1996 Peters et al.
5,562,685 A 10/1996 Mollenauer et al.
5,569,274 A 10/1996 Rapacki et al.
5,569,301 A 10/1996 Granger et al.
5,573,543 A 11/1996 Akopov et al.
5,582,616 A 12/1996 Bolduc et al.
5,582,619 A 12/1996 Ken
5,586,983 A 12/1996 Sanders et al.
5,591,179 A 1/1997 Edelstein
5,593,414 A 1/1997 Shipp et al.
5,593,424 A 1/1997 Northrup, III
5,609,608 A 3/1997 Benett et al.
5,626,590 A 5/1997 Wilk
5,630,824 A 5/1997 Hart
5,632,752 A 5/1997 Buelna
5,632,753 A 5/1997 Loeser
5,634,584 A 6/1997 Okorocha et al.
5,643,289 A 7/1997 Sauer et al.
5,643,295 A 7/1997 Yoon
5,645,553 A 7/1997 Kolesa et al.
5,645,568 A 7/1997 Chervitz et al.
5,665,109 A 9/1997 Yoon
5,669,917 A 9/1997 Sauer et al.
5,669,935 A 9/1997 Rosenman et al.
5,681,351 A 10/1997 Jamiolkowski et al.
5,683,417 A 11/1997 Cooper
5,695,505 A 12/1997 Yoon
5,697,943 A 12/1997 Sauer et al.
5,700,270 A 12/1997 Peyser et al.
5,700,271 A 12/1997 Whitfield et al.
5,707,380 A 1/1998 Hinchliffe et al.
5,709,693 A 1/1998 Taylor
5,709,695 A 1/1998 Northrup, III
5,716,369 A 2/1998 Riza
5,725,539 A 3/1998 Matern
5,725,542 A 3/1998 Yoon
5,725,556 A 3/1998 Moser et al.
5,728,135 A 3/1998 Bregen et al.
5,735,290 A 4/1998 Sterman et al.
5,735,877 A 4/1998 Pagedas
5,741,281 A 4/1998 Martin
5,766,183 A 6/1998 Sauer
5,776,188 A 7/1998 Shepherd et al.
5,799,661 A 9/1998 Boyd et al.
5,810,851 A 9/1998 Yoon
5,810,882 A 9/1998 Bolduc et al.
5,820,631 A 10/1998 Nobles
5,824,008 A 10/1998 Bolduc et al.
5,830,221 A 11/1998 Stein et al.
5,833,696 A 11/1998 Whitfield et al.
5,845,645 A 12/1998 Bonutti
5,849,019 A 12/1998 Yoon
5,852,851 A 12/1998 Cooper
5,861,004 A 1/1999 Kensey et al.
5,879,371 A 3/1999 Gardiner et al.
5,891,130 A 4/1999 Palermo et al.
5,891,160 A 4/1999 Williamson, IV et al.
5,895,393 A 4/1999 Pagedas
5,895,394 A 4/1999 Kienzle et al.
5,919,207 A 7/1999 Taheri
5,948,001 A 9/1999 Larsen
5,961,481 A 10/1999 Sterman et al.
5,961,539 A 10/1999 Northrup, III et al.
5,964,772 A 10/1999 Bolduc et al.
5,972,024 A 10/1999 Northrup, III et al.
5,976,159 A 11/1999 Bolduc et al.
5,984,917 A 11/1999 Fleischman et al.
5,989,242 A 11/1999 Saadat et al.
5,989,268 A 11/1999 Pugsley, Jr. et al.
5,997,556 A 12/1999 Tanner
6,001,110 A 12/1999 Adams
6,013,084 A 1/2000 Ken et al.
6,015,428 A 1/2000 Pagedas
6,039,176 A 3/2000 Wright
6,066,160 A 5/2000 Colvin et al.
6,074,409 A 6/2000 Goldfarb
6,120,524 A 9/2000 Taheri
6,132,438 A 10/2000 Fleischman et al.
6,139,540 A 10/2000 Rost et al.
6,143,004 A 11/2000 Davis et al.
6,176,413 B1 1/2001 Heck et al.
6,190,373 B1 2/2001 Palermo et al.
6,193,733 B1 2/2001 Adams
6,193,734 B1 2/2001 Bolduc et al.
6,231,592 B1 5/2001 Bonutti et al.
6,241,765 B1 6/2001 Griffin et al.
6,254,615 B1 7/2001 Bolduc et al.
6,306,141 B1 10/2001 Jervis
6,346,112 B2 2/2002 Adams
6,368,334 B1 4/2002 Sauer
6,432,123 B2 8/2002 Schwartz et al.
6,475,230 B1 11/2002 Bonutti et al.
6,514,265 B2 2/2003 Ho et al.
6,533,796 B1 3/2003 Sauer et al.
6,537,290 B2 3/2003 Adams et al.
6,551,332 B1 4/2003 Nguyen et al.
6,589,279 B1 7/2003 Anderson et al.
6,607,541 B1 8/2003 Gardiner et al.
6,613,059 B2 9/2003 Schaller et al.
6,626,930 B1 9/2003 Allen et al.
6,641,592 B1 11/2003 Sauer et al.
6,641,593 B1 11/2003 Schaller et al.
6,682,540 B1 1/2004 Sancoff et al.
6,719,767 B1 4/2004 Kimblad
6,746,457 B2 6/2004 Dana et al.
6,749,622 B2 6/2004 McGuckin, Jr. et al.
6,776,784 B2 8/2004 Ginn
6,780,198 B1 8/2004 Gregoire et al.
6,860,890 B2 3/2005 Bachman et al.

(56) References Cited

U.S. PATENT DOCUMENTS

| | | | |
|---|---|---|---|
| 6,896,686 | B2 | 5/2005 | Weber |
| 6,913,607 | B2 | 7/2005 | Ainsworth et al. |
| 6,918,917 | B1 | 7/2005 | Nguyen et al. |
| 6,921,407 | B2 | 7/2005 | Nguyen et al. |
| 6,926,730 | B1 | 8/2005 | Nguyen et al. |
| 6,945,980 | B2 | 9/2005 | Nguyen et al. |
| 6,960,221 | B2 | 11/2005 | Ho et al. |
| 7,011,669 | B2 | 3/2006 | Kimblad |
| 7,049,244 | B2 | 5/2006 | Becker et al. |
| 7,083,628 | B2 | 8/2006 | Bachman |
| 7,094,244 | B2 | 8/2006 | Schreck |
| 7,112,207 | B2 | 9/2006 | Allen et al. |
| 7,220,266 | B2 | 5/2007 | Gambale |
| 7,235,086 | B2 | 6/2007 | Sauer et al. |
| 7,264,625 | B1 | 9/2007 | Buncke |
| 7,381,210 | B2 | 6/2008 | Zarbatany et al. |
| 7,628,797 | B2 | 12/2009 | Tieu et al. |
| 7,677,525 | B2 | 3/2010 | Sanchez et al. |
| 7,713,276 | B2 | 5/2010 | Dennis |
| 7,731,727 | B2 | 6/2010 | Sauer |
| 7,833,237 | B2 | 11/2010 | Sauer |
| 7,842,051 | B2 | 11/2010 | Dana et al. |
| 7,862,548 | B2 | 1/2011 | Javer et al. |
| 7,862,584 | B2 | 1/2011 | Lyons et al. |
| 7,875,056 | B2 | 1/2011 | Jervis et al. |
| 7,959,674 | B2 | 6/2011 | Shu et al. |
| 7,981,139 | B2 | 7/2011 | Martin et al. |
| 8,021,421 | B2 | 9/2011 | Fogarty et al. |
| 8,100,923 | B2 | 1/2012 | Paraschac et al. |
| 8,105,355 | B2 | 1/2012 | Page et al. |
| 8,252,005 | B2 | 8/2012 | Findlay, III et al. |
| 8,398,657 | B2 | 3/2013 | Sauer |
| 8,398,680 | B2 | 3/2013 | Sauer et al. |
| 8,425,555 | B2 | 4/2013 | Page et al. |
| 8,465,505 | B2 | 6/2013 | Murillo et al. |
| 8,480,686 | B2 | 7/2013 | Bakos et al. |
| 8,753,373 | B2 | 6/2014 | Chau et al. |
| 9,017,347 | B2 | 4/2015 | Oba et al. |
| 10,016,193 | B2 | 7/2018 | Smith et al. |
| 11,172,924 | B2 | 11/2021 | Deville et al. |
| 2001/0025181 | A1 | 9/2001 | Freedlan |
| 2002/0029060 | A1 | 3/2002 | Hogendijk |
| 2002/0087178 | A1 | 7/2002 | Nobles et al. |
| 2003/0009196 | A1 | 1/2003 | Peterson |
| 2003/0109891 | A1 | 6/2003 | Dana et al. |
| 2003/0109922 | A1 | 6/2003 | Peterson et al. |
| 2003/0195563 | A1 | 10/2003 | Foerster |
| 2003/0233105 | A1 | 12/2003 | Gayton |
| 2004/0181238 | A1 | 9/2004 | Zarbatany et al. |
| 2004/0204724 | A1 | 10/2004 | Kissel et al. |
| 2004/0249414 | A1 | 12/2004 | Kissel et al. |
| 2005/0251206 | A1 | 11/2005 | Maahs et al. |
| 2005/0251209 | A1 | 11/2005 | Saadat et al. |
| 2006/0047314 | A1 | 3/2006 | Green |
| 2006/0079913 | A1 | 4/2006 | Whitfield et al. |
| 2006/0089571 | A1 | 4/2006 | Gertner |
| 2006/0161183 | A1 | 7/2006 | Sauer |
| 2006/0184203 | A1 | 8/2006 | Martin et al. |
| 2006/0229566 | A1 | 10/2006 | Hanagasaki |
| 2006/0265010 | A1 | 11/2006 | Paraschac et al. |
| 2006/0265042 | A1 | 11/2006 | Catanese et al. |
| 2006/0276871 | A1 | 12/2006 | Lamson et al. |
| 2006/0282119 | A1 | 12/2006 | Perchik |
| 2007/0005079 | A1 | 1/2007 | Zarbatany et al. |
| 2007/0005081 | A1 | 1/2007 | Findlay et al. |
| 2007/0010829 | A1 | 1/2007 | Nobles et al. |
| 2007/0043384 | A1 | 2/2007 | Ortiz et al. |
| 2007/0049952 | A1 | 3/2007 | Weiss |
| 2007/0049970 | A1 | 3/2007 | Belef et al. |
| 2007/0073342 | A1 | 3/2007 | Stone et al. |
| 2007/0078430 | A1 | 4/2007 | Adams |
| 2007/0088391 | A1 | 4/2007 | McAlexander et al. |
| 2007/0179530 | A1 | 8/2007 | Tieu et al. |
| 2007/0255296 | A1 | 11/2007 | Sauer |
| 2007/0270907 | A1 | 11/2007 | Stokes et al. |
| 2008/0086152 | A1 | 4/2008 | McKay et al. |
| 2008/0154286 | A1 | 6/2008 | Abbott et al. |
| 2008/0255591 | A1 | 10/2008 | Harada et al. |
| 2008/0281356 | A1 | 11/2008 | Chau et al. |
| 2009/0018554 | A1 | 1/2009 | Thorne et al. |
| 2009/0143821 | A1 | 6/2009 | Stupak |
| 2009/0234295 | A1 | 9/2009 | Lampropoulos et al. |
| 2009/0272783 | A1 | 11/2009 | Crainich et al. |
| 2009/0281377 | A1 | 11/2009 | Newell et al. |
| 2009/0281568 | A1 | 11/2009 | Cendan et al. |
| 2010/0001038 | A1 | 1/2010 | Levin et al. |
| 2010/0076462 | A1 | 3/2010 | Bakos et al. |
| 2010/0174296 | A1 | 7/2010 | Vakharia et al. |
| 2010/0198235 | A1 | 8/2010 | Pierce et al. |
| 2010/0324597 | A1 | 12/2010 | Shikhman |
| 2010/0324598 | A1 | 12/2010 | Anderson |
| 2011/0087241 | A1 | 4/2011 | Nguyen |
| 2011/0087242 | A1 | 4/2011 | Pribanic et al. |
| 2011/0224485 | A1 | 9/2011 | Boulnois et al. |
| 2011/0224714 | A1 | 9/2011 | Gertner |
| 2011/0245850 | A1 | 10/2011 | Van et al. |
| 2011/0251641 | A1 | 10/2011 | Sauer et al. |
| 2011/0283514 | A1 | 11/2011 | Fogarty et al. |
| 2012/0053599 | A1 | 3/2012 | Shikhman et al. |
| 2012/0080495 | A1 | 4/2012 | Holcomb et al. |
| 2012/0089182 | A1 | 4/2012 | Page et al. |
| 2012/0101526 | A1 | 4/2012 | Bennett |
| 2012/0102526 | A1 | 4/2012 | Lejeune |
| 2012/0165865 | A1 | 6/2012 | Fujisaki et al. |
| 2013/0035702 | A1 | 2/2013 | Heneveld |
| 2013/0053884 | A1 | 2/2013 | Roorda |
| 2013/0110164 | A1 | 5/2013 | Milazzo et al. |
| 2013/0158600 | A1 | 6/2013 | Conklin et al. |
| 2013/0165953 | A1 | 6/2013 | Oba et al. |
| 2013/0204298 | A1 | 8/2013 | Graul et al. |
| 2013/0231701 | A1 | 9/2013 | Voss et al. |
| 2013/0267998 | A1 | 10/2013 | Vijay et al. |
| 2013/0282028 | A1 | 10/2013 | Conklin et al. |
| 2014/0031864 | A1 | 1/2014 | Jafari et al. |
| 2014/0236188 | A1 | 8/2014 | Mehl et al. |
| 2015/0018879 | A1 | 1/2015 | Moehle et al. |
| 2015/0142021 | A1 | 5/2015 | Smith et al. |
| 2016/0183937 | A1 | 6/2016 | Miraki et al. |

FOREIGN PATENT DOCUMENTS

| | | | |
|---|---|---|---|
| CN | 2194162 | Y | 4/1995 |
| CN | 2558335 | Y | 7/2003 |
| DE | 1959201 | U | 4/1967 |
| DE | 2349794 | A1 | 10/1974 |
| DE | 2550559 | B2 | 2/1978 |
| DE | 2747618 | A1 | 5/1978 |
| DE | 69512446 | T2 | 5/2000 |
| DE | 69612447 | T2 | 7/2001 |
| EP | 0669101 | A1 | 8/1995 |
| EP | 0669103 | A1 | 8/1995 |
| EP | 0755655 | A2 | 1/1997 |
| EP | 0755656 | A2 | 1/1997 |
| EP | 1484023 | A1 | 12/2004 |
| EP | 2455001 | A2 | 5/2012 |
| EP | 2462876 | A2 | 6/2012 |
| JP | 2004174002 | A | 6/2004 |
| JP | 2007252923 | A | 10/2007 |
| WO | WO-2001028455 | A1 | 4/2001 |
| WO | 01049207 | A2 | 7/2001 |
| WO | 0166001 | A2 | 9/2001 |
| WO | WO-2001087165 | A1 | 11/2001 |
| WO | WO-2004024006 | A1 | 3/2004 |
| WO | WO-2004112841 | A2 | 12/2004 |
| WO | WO-2007002071 | A1 | 1/2007 |
| WO | WO-2012005671 | A1 | 1/2012 |
| WO | WO-2014011794 | A1 | 1/2014 |

(56) References Cited

FOREIGN PATENT DOCUMENTS

| | | | |
|---|---|---|---|
| WO | WO-2014055767 | A1 | 4/2014 |
| WO | WO-2014100545 | A1 | 6/2014 |

OTHER PUBLICATIONS

LSI Solutions T-Knot Device, LSI Solutions, Inc., 2009-2011, http://www.lsisolutions.com/tkatscrubtable.

TK Quick Load, LSI Solutions, http://www.lsisolutions.com/tkquickload.

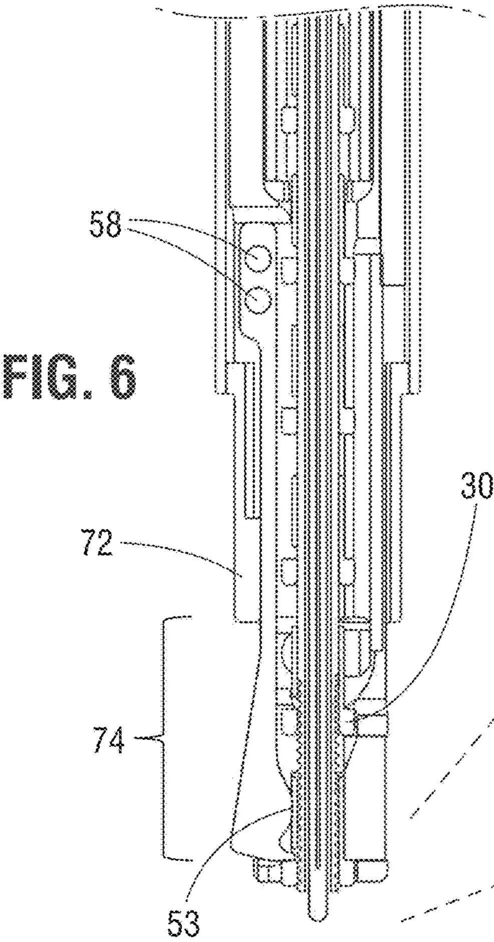
FIG. 6
FIG. 6A
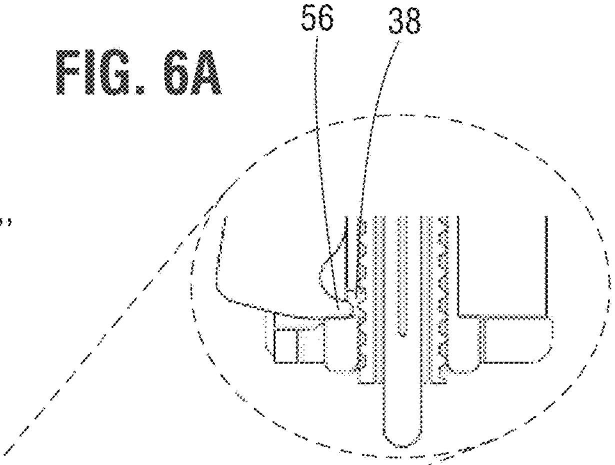
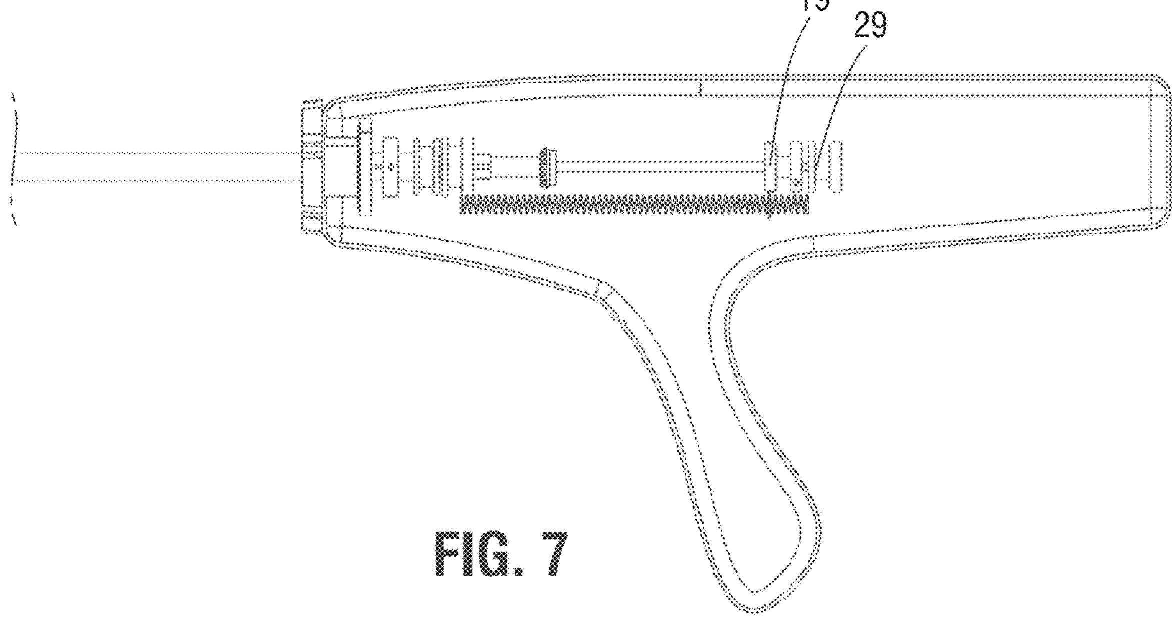
FIG. 7

FIG. 17
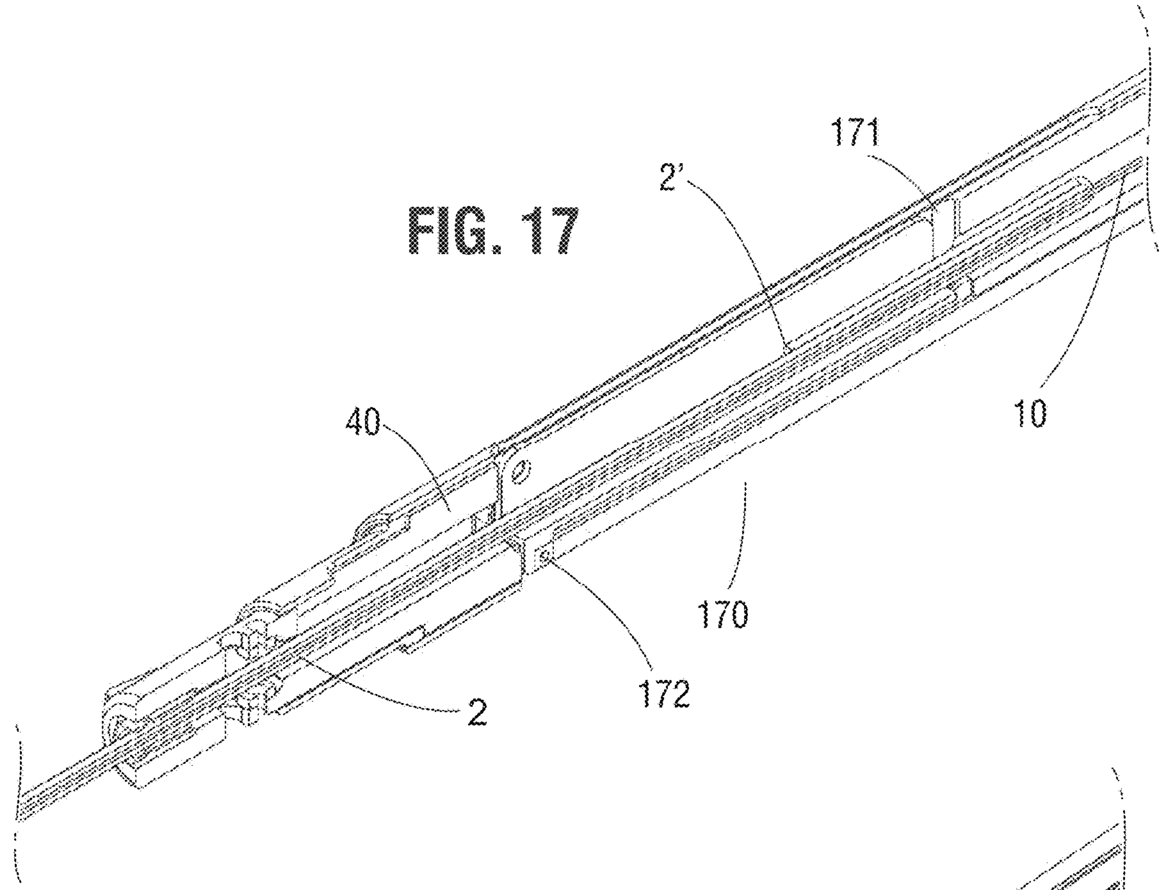
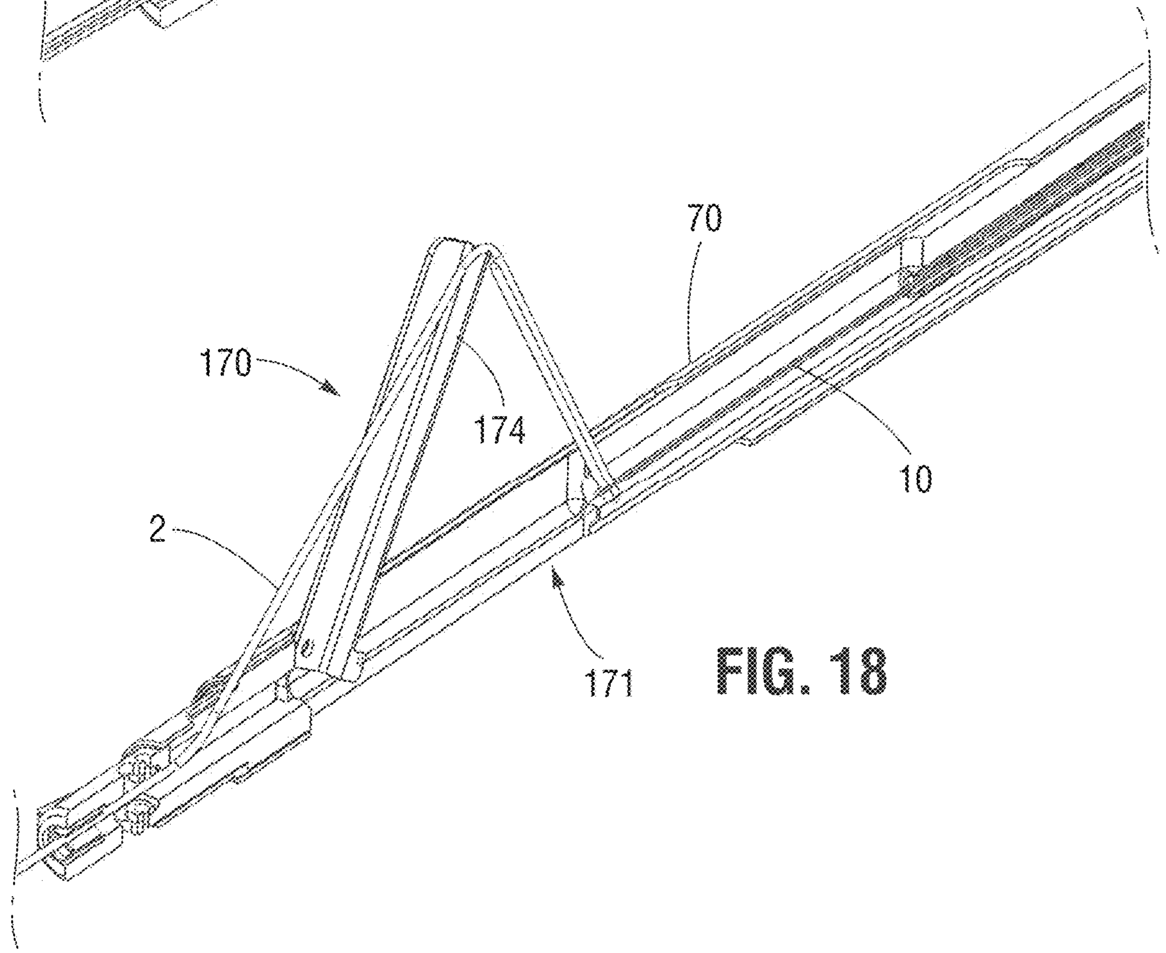
FIG. 18

FIG. 25
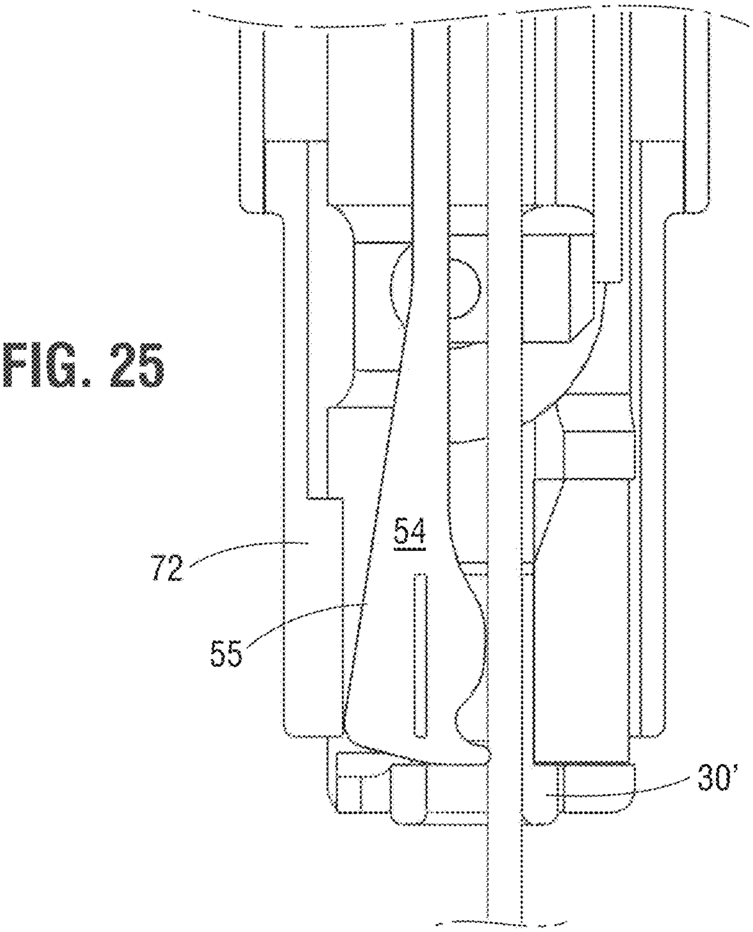
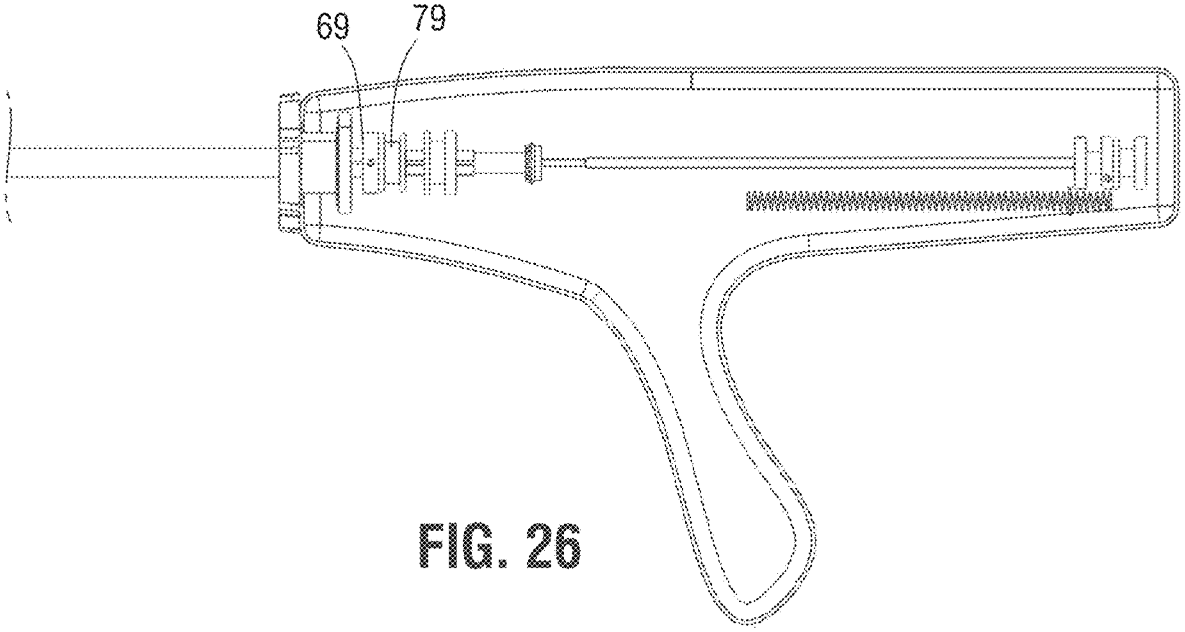
FIG. 26

FIG. 32
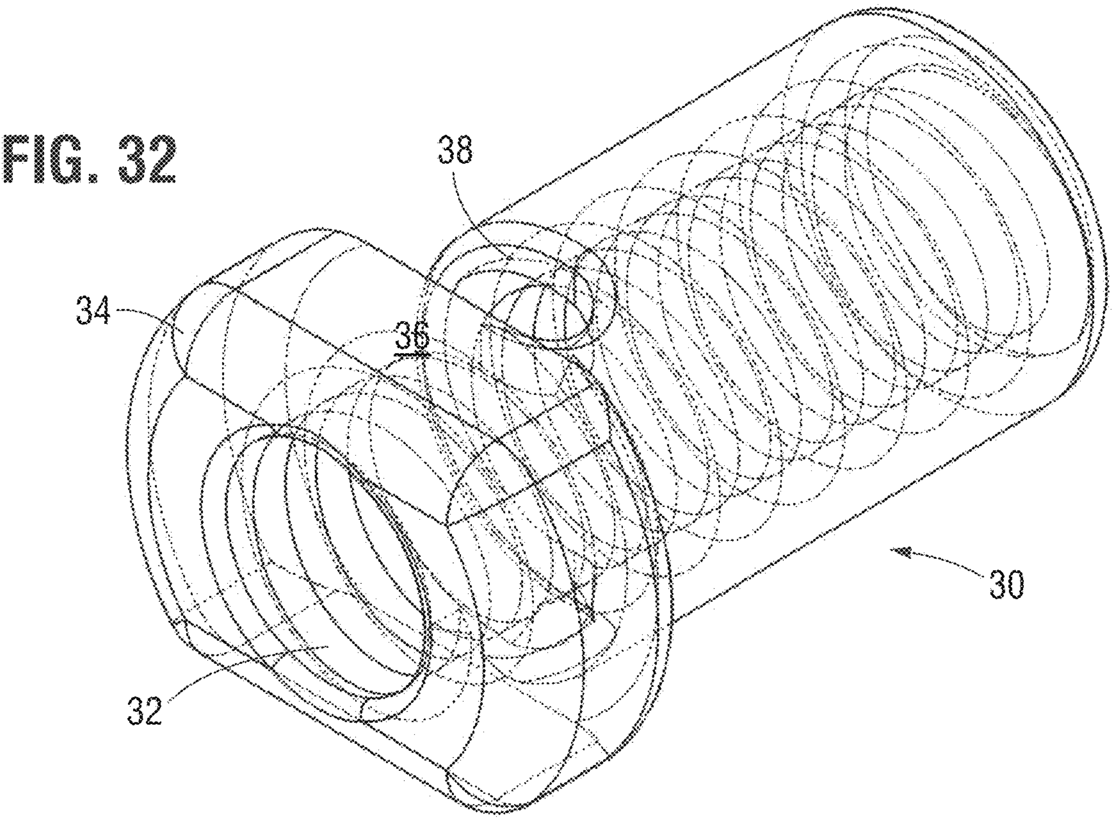
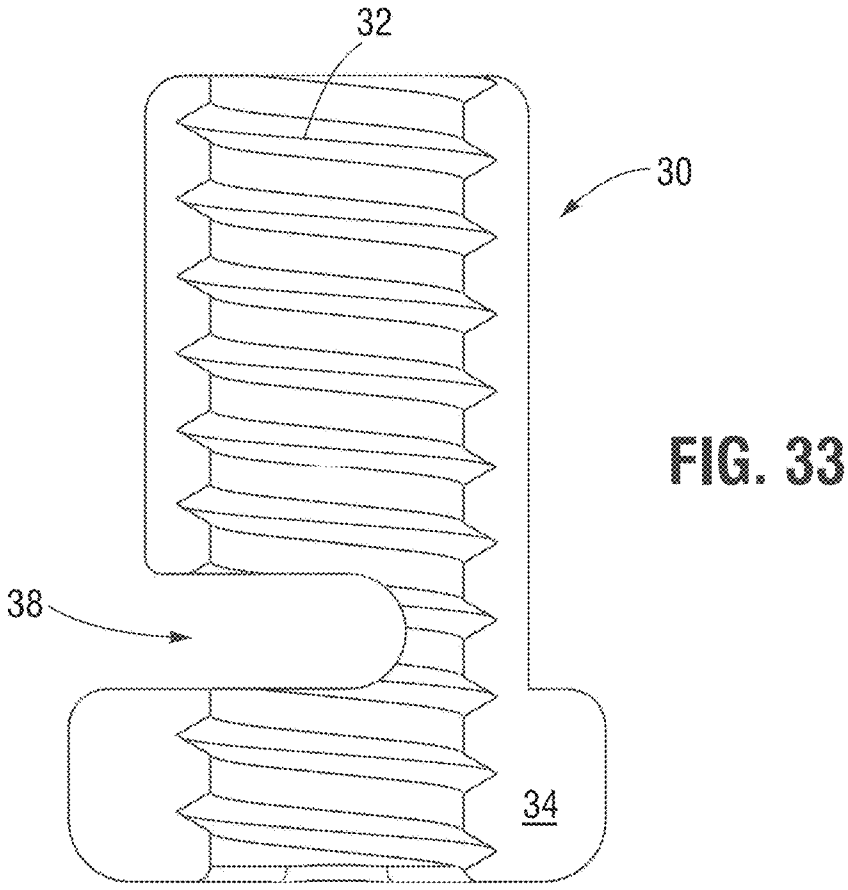
FIG. 33

MULTIPLE-FIRING SUTURE FIXATION DEVICE AND METHODS FOR USING AND MANUFACTURING SAME

CROSS-REFERENCE TO RELATED APPLICATIONS

This application is a continuation of U.S. patent application Ser. No. 16/450,907 filed Jun. 24, 2019, now U.S. Pat. No. 11,471,150, which is a continuation of U.S. patent application Ser. No. 14/868,741, filed on Sep. 29, 2015, now U.S. Pat. No. 10,327,758, which is a continuation of U.S. patent application Ser. No. 14/543,240, filed on Nov. 17, 2014, now U.S. Pat. No. 10,016,193, which claims the benefit of U.S. Patent Application Nos. 61/905,578, filed Nov. 18, 2013; 61/951,162, filed Mar. 11, 2014; and 62/069,183, filed Oct. 27, 2014, the entire disclosures all of which are incorporated by reference for all purposes.

FIELD OF THE INVENTION

The present invention lies in the field of securing cords, such as surgical sutures. The present disclosure relates to a multiple-firing suture fixation device and methods for using and manufacturing same.

BACKGROUND OF THE INVENTION

Surgical instruments, such as the Cor-Knot manufactured by LSI Solutions and as described in U.S. Pat. No. 7,833,237 to Sauer, are used to replace hand tied knots at remotes sites within the body. Such instruments, however, are limited to use with a single suture and a single crimp and generate significant waste during the suture tying process, which waste must be accounted for and could be lost within the patient during surgery if safeguards are not taken. In this system, a single suture crimp is loaded into the end effector and is secured for a single crimp use. To load the crimp and the snare that passes the suture through the crimp, a loading hook is passed through an end effector. The loading hook has the crimp at its distal end and is attached to a snare loop, which is threaded through the crimp. To secure the crimp between the handle and the snare loop, the snare loop is secured and held outwards as a loop by a teardrop shaped plastic handle. After the hook is threaded into the end effector and the crimp is pressed into the distal end of the end effector, the user must remove the large, plastic handle and dispose of it properly. As such, the action of loading a reload crimp into the device generates a teardrop shaped piece of plastic waste for every single crimp. Care must be taken because there is no positive method of securing the crimp into the ready position within the crimping device. If the crimp becomes dislodged, it may not form a proper securing crimp. This may require the suture to be replaced, which may be extremely difficult. Once the snare loop is used to pull the sutures through the crimp, the snare loop must also be discarded. If during the process of passing the sutures through the crimp the sutures do not fully pass through the crimp, it is possible that the very small crimp could be dislodged from the crimping device and potentially lost within the patient.

It would be beneficial to provide a cord-loading device that has minimal or no waste generated during a procedure and that provides multiple crimps that do not need to be individually loaded during the procedure.

SUMMARY OF THE INVENTION

A multiple-firing suture fixation device and methods for using and manufacturing same that overcome the hereinafore-mentioned disadvantages of the heretofore-known devices and methods of this general type are described and shown herein.

The multiple-firing crimp device does not generate waste during a procedure and allows enough crimps for a complete procedure to be loaded before the procedure and, therefore, do not need to be individually loaded during the procedure. The multiple-firing crimp device holds a number of crimps within the device prior to performing a procedure. During the procedure, the multiple-firing crimp device automatically loads a single crimp in a crimp-delivery position that is ready to be crimped and is in a position allowing cords to pass therethrough for crimping after the cords are tightened. The multiple-firing crimp device provides a mechanism that passes the cords through one crimp, placing the crimp in a read-to-fire position. The multiple-firing crimp device provides a reliable, reusable way of passing the cords through one crimp at a time for each of the multiple loaded crimps. There is no waste or separate parts to account for during or after a surgical procedure.

As used herein, the multiple-firing crimp device is able to be used on cords. As defined herein, the term cords is not limited to a plurality of cords, cords can be a single cord as well. For example, four lengths of cord can be threaded through a crimp for securing one or more of the cords therein after crimping occurs. Cords also are not limited to a particular type of material. The material can be made of natural fibers, man-made or synthetic fibers, plastics, and/or metals, to name a few. Cords also are not limited to a particular structure. The material can be made of twisted strands, twisted strands with a central core, or a single strand or wire, to name a few. One exemplary embodiment described herein relates to securing a surgical suture with a crimp of the multiple-firing crimp device. The embodiments described herein, however, are not limited to surgical sutures, even though the example of surgical sutures is referred to or is used herein.

Traditionally, surgical sutures are cut by advancing a movable knife. One exemplary embodiment of the multiple-firing crimp device uses a movable knife. Another exemplary embodiment of the multiple-firing crimp device, instead, uses a fixed knife and a blunt pusher that contacts the suture and moves it to and against the fixed knife for cutting. This configuration prevents cutting from happening prematurely and allows precise control of the distance that the suture is cut from the crimp.

If a snare is damaged during a procedure, the entirety of shuttle containing the snare can be removed from the handle and the shaft and an entirely new shuttle from a separate, sterilized package can be used in place of the damaged shuttle.

In general, the systems and methods herein provide ways to pull cords such as surgical sutures through a set of cord clips. In any multi-fire clip/crimp applier device for fixing cords, a user must be able to pull the cords through a single clip where multiple clips are loaded in the device. In other words, the device must be a reusable clip-threading device. The mechanism that pulls through the clip must be easy to use, have a low profile, and, significantly, should not be able to leave behind any separate parts and should not produce waste during use. The challenges associated with such a device arise because the device must have a low profile in general and also must be able to thread cords through a very small diameter clip (e.g., crimp).

Many steps are undertaken in order to crimp a clip onto cords with a multi-fire crimp applier. First, the clip must be loaded from a magazine of multiple clips. Then, the cords must be threaded through that one clip that is to secure the cords but not be threaded within or interfere with the other clips in the magazine. Then, the clip must be secured (e.g., crimped) onto the cords at a location that is, typically, very close to a cord-tying location (e.g., a surgical site). Finally, the device must be able to cut the cords after the clip, dispose of the cut ends, and present a new clip for use next with as little user manipulation as possible.

It is beneficial to provide an automated device. In such a device, there are different moving assemblies, such as a clip carriage, a snare-extender, a cord lifter, a crimper, and a cutter. A handle contains automated motors, servos, and/or transmissions to carry out the functions of each of these movement assemblies. The handle is provided with a single mechanical control device for each of these assemblies or combination control devices that effect two or more functions. Alternatively some or all of the automated actions can be replaced with mechanical systems. In any embodiment, simplicity in the entire process of installing a new clip, securing the clip at the cords, and loading another clip for repetitive cycles is important. One exemplary embodiment provides a shuttle that translates on the shaft of the device and, when positioned distally, presents a loop into which the cords to be secured are passed. The loop is, then, pulled back into the shuttle before the shuttle begins to move proximally. The proximal motion of the shuttle utilizes the loop to draw the cords through the crimp and expose them to the outside of the shaft. The shuttle has a formed wire guide or channel that resides outside of the outer diameter of the device's shaft and through a window in a side of the shaft (e.g., at an upper side) and that wire guide is able to move from outside the shaft to inside the shaft and, then, into or through a proximal end of the crimp. When the tails of cords are pulled through the crimp with the shuttle, the tails are dropped off external to the shaft so that they can be grabbed by the user's hands for tensioning and subsequent crimping.

The shuttle contains various interlocks. One interlock prevents the formed wire snare from being presented until the shuttle is in a distal-most position. Another interlock prevents the shuttle from moving proximally if the snare is extended in any way. Another interlock holds the shuttle at a distal-most position for (1) extending the snare and (2) retracting the cords with movement of a shuttle saddle to position the cords in a radiused tip of the snare. Another interlock prevents the snare from moving when the cords reside in the tip and the shuttle is moving proximally to pass the cords through the crimp and thereafter present the cords outside the shaft for handling by the user.

An exemplary embodiment of the snare is formed and created from Nitinol and has a tight-radiused tip section that prevents the snare from pinching on the cords it snares while it pulls the cords through the crimp and then moves the cords to the outside of the shaft. This tight-radiused tip also ensures entry into a snare guide tube. The reservoir tip of the snare is stopped short of coming into the shuttle to form an open loop that allows the free tails of the cords to be exposed after passing through the crimp and falling free outside the shaft. The snare may be formed of any number of materials such as stainless steel, titanium, or a polymer.

Ideally, when the handle is in the middle of any of the crimping, cutting, or loading processes, the handle prevents the shuttle from moving away from the nose of the handle. In contrast, when the shuttle is advanced away from the handle, handle functions may be enabled or disabled as appropriate when the shuttle is either moving or is away from the nose.

Additional interlocks are present to enable/lock out functions in the handle based on a position of the shuttle when in its most proximal position, e.g., resting against the handle. After the shuttle is at the nose of the handle, the user can pull on the cords that run through the crimp and hang loose through a window of the shaft. When in the snaring position, the shuttle can be held by friction and/or with one or more detents.

With the foregoing and other objects in view, there is provided, a multiple-firing crimp device comprises crimps, a hollow shaft, a crimp movement assembly, and a snare. Each crimp has an internal hollow. The shaft has a distal crimping location, an exterior surface, and an interior in which is stacked the plurality of crimps to define a first crimp, the crimps moving therein along a longitudinal axis. The shaft defines a lateral opening proximal to the crimping location and communicates between the interior and the environment outside the exterior surface. The crimp movement assembly within the interior of the shaft delivers the first crimp to the distal crimping location by moving the first crimp longitudinally from a first proximal position into the distal crimping location and returning to a second proximal position without the first crimp. The snare pulls at least one cord from distal of the first crimp through the first crimp and through a portion of the shaft and out the side of the shaft through the lateral opening.

With the objects in view, there is also provided a multiple-firing crimp device comprises crimps, a hollow shaft, a crimp movement assembly, a snare, and a snare movement assembly. Each crimp has an internal hollow. The shaft has a distal crimping location, an exterior surface, and an interior in which is stacked the plurality of crimps to define a first crimp, the crimps moving therein along a longitudinal axis. The shaft defines a lateral opening proximal to the crimping location and communicating between the interior and the environment outside the exterior surface. The crimp movement assembly within the interior of the shaft delivers the first crimp to the distal crimping location by moving the first crimp longitudinally from a first proximal position into the distal crimping location and returning to a second proximal position without the first crimp. The snare pulls at least one cord from distal of the first crimp through the first crimp and through a portion of the shaft and out the side of the shaft through the lateral opening. The snare movement assembly includes the snare. The snare is shaped to pass through the internal hollow of the first crimp, to pass out of the interior of the shaft distally past the distal crimping location, and to secure the at least one cord temporarily. The snare movement assembly moves the snare to pull a portion of the at least one cord secured in the snare proximally through the first crimp and to present at least some of the portion of the at least one cord out through the opening for access by a user.

In accordance with another feature, there is provided a snare movement assembly having the snare. The snare is shaped to pass through the internal hollow of the first crimp, to pass out of the interior of the shaft distally past the distal crimping location, and to secure the at least one cord temporarily. The snare movement assembly moves the snare to pull a portion of the at least one cord secured in the snare proximally through the first crimp and to present at least some of the portion of the at least one cord out through the opening for access by a user.

In accordance with a further feature, there is provided a crimping assembly having a crimp control device that, when actuated, crimps the first crimp within the distal crimping location and a cutting assembly having a cutting control device that, when actuated, cuts the portion of the at least one cord adjacent the first crimp.

In accordance with an added feature, the at least one cord is a surgical suture.

In accordance with an additional feature, the portion of the at least one cord secured in the snare is two free ends of a surgical suture, the end opposing the two free ends being a loop of the surgical suture secured in a surgical site, the portion of the at least one cord secured in the snare and being pulled proximally through the first crimp is the two free ends such that, at a given time, four lengths of the surgical suture are being pulled through the first crimp, and the at least some of the portion of the at least one cord pulled out through the opening for access by a user is the two free ends of the surgical suture.

In accordance with yet another feature, the first crimp is a distal-most one of the crimps.

In accordance with yet a further feature, the internal hollow is one of a lumen and a slot.

In accordance with yet an added feature, the crimps are crimp sleeves having a hollow through bore, at least a portion of the bore being internally threaded.

In accordance with yet an additional feature, the first proximal position is different from the second proximal position.

In accordance with again another feature, the first proximal position is the same as the second proximal position.

In accordance with again a further feature, when the crimp movement assembly returns to the second proximal position, the lateral opening is exposed to the environment outside the exterior surface.

In accordance with again an added feature, while or after the crimp movement assembly is in the process of returning to the second proximal position without the first crimp, the crimp movement assembly moves a previously second of the crimps into a crimp loading position to become a new first crimp.

In accordance with again an additional feature, the shaft has a distal cam driver and the crimp movement assembly comprises an exterior-threaded carriage movably disposed inside the shaft along the longitudinal axis towards and away from the distal cam driver and having a carriage distal end at which is disposed the first crimp.

In accordance with still another feature, each of the crimps has an interior thread and is threaded on the exterior threads of the carriage at a spacing from one another such that rotation of the carriage in a direction selectively carries a distal-most one of the crimps off the carriage distal end.

In accordance with still a further feature, there is provided a hammer movably disposed inside the shaft adjacent the distal cam driver and having a cam follower operatively connected to the distal cam driver to move the hammer towards and away from the longitudinal axis of the shaft when the shaft is moved along the longitudinal axis, an anvil at least partially disposed inside the shaft adjacent the distal cam driver and opposite the hammer, and the distal crimping location is between the hammer and the anvil.

In accordance with still an added feature, the snare is shaped to extend through the interior of the carriage and pass through the internal hollow of the first crimp.

In accordance with still an additional feature, the first crimp has a proximal end and which further comprises a user-movable snare movement assembly having the snare, a hollow snare guide in which is disposed the snare, the snare guide being disposed external to the shaft and, when moved distally, moving through the lateral opening and up to the proximal end of the first crimp, and a snare extension device moving the snare distally through the snare guide, through the first crimp, and past the distal crimping location of the shaft to secure the at least one cord temporarily and pull at least a portion of the at least one cord through the first crimp and out the lateral opening.

In accordance with another feature, the first crimp has a proximal end and which further comprises movable snare movement assembly having a cord lifter within the shaft, adjacent the snare, and shaped to lift at least one of the snare and the at least one cord and a snare extension device moving the snare distally along the cord lifter, through the first crimp, and past the distal crimping location of the shaft to secure the at least one cord temporarily and pull at least a portion of the at least one cord through the first crimp and past the cord lifter, the cord lifter, when actuated, presenting at least some of the portion of the at least one cord out the lateral opening for access by a user.

In accordance with another feature, there is provided a cutting assembly having a cutter within the shaft extending parallel to the longitudinal axis and shaped to cut the at least one cord adjacent the first crimp and a cutter control device connecting the cutter to the shaft to have the cutter move and cut the at least one cord adjacent the first crimp when the shaft is at a distal position with respect to one of the hammer and the anvil.

Although the devices and methods are illustrated and described herein as embodied in a multiple-firing suture fixation device and methods for using and manufacturing same, it is, nevertheless, not intended to be limited to the details shown because various modifications and structural changes may be made therein without departing from the spirit thereof and within the scope and range of equivalents of the claims. Additionally, well-known elements of exemplary embodiments will not be described in detail or will be omitted so as not to obscure the relevant details.

Additional advantages and other features characteristic of the present devices and methods will be set forth in the detailed description that follows and may be apparent from the detailed description or may be learned by practice of exemplary embodiments. Still other advantages may be realized by any of the instrumentalities, methods, or combinations particularly pointed out in the claims.

Other features that are considered as characteristic for the devices and methods are set forth in the appended claims. As required, detailed embodiments are disclosed herein; however, it is to be understood that the disclosed embodiments are merely exemplary, which can be embodied in various forms. Therefore, specific structural and functional details disclosed herein are not to be interpreted as limiting, but merely as a basis for the claims and as a representative basis for teaching one of ordinary skill in the art to variously employ the present devices and methods in virtually any appropriately detailed structure. Further, the terms and phrases used herein are not intended to be limiting; but rather, to provide an understandable description thereof. While the specification concludes with claims defining the features that are regarded as novel, it is believed that the devices and methods will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the present devices and methods. Advantages of embodiments will be apparent from the following detailed description of the exemplary embodiments thereof, which description should be considered in conjunction with the accompanying drawings in which:

FIG. 6 is a fragmentary, longitudinally cross-sectional view of the end effector of FIG. 1 with the crimp sub-assembly in a crimp-seated position ready for use;

FIG. 6A is a fragmentary, longitudinally cross-sectional view of an enlarged distal portion of the end effector of FIG. 6;

FIG. 7 is a fragmentary, side elevational and partially longitudinal cross-sectional view of the handle portion of FIG. 3 with the crimp sub-assembly actuators in a suture-use position corresponding to FIG. 6;

FIG. 17 is a fragmentary, longitudinally cross-sectional view of the end effector of FIGS. 14 and 15 with a cord-lifting device in a lowered position;

FIG. 18 is a fragmentary, longitudinally cross-sectional view of the end effector of FIG. 17 with the cord-lifting device in a lifted position positioning the cords for grasping by a user;

FIG. 25 is a fragmentary, longitudinally cross-sectional view of the end effector of FIG. 23 enlarged with respect to FIG. 23 and with the outer tube partially extended to move the hammer radially inwards and thereby crimp the crimp to the cords therewithin;

FIG. 26 is a fragmentary, side elevational and partially longitudinal cross-sectional view of the handle of FIG. 24 with the outer tube extended distally into the position corresponding to FIG. 25;

FIG. 32 is an enlarged perspective view of the crimp of FIG. 1;

FIG. 33 is a longitudinal cross-sectional view of the crimp of FIG. 1;

FIG. 118 is a perspective view of the securing clip of FIG. 117;

FIG. 119 is a perspective view of the securing clip of FIG. 117 in a partially fitted state;

FIG. 120 is a perspective view of the securing clip of FIG. 117 in a further partially fitted state;

FIG. 121 is a perspective view of an exemplary embodiment of still a further securing clip not to scale with a press-fit locking assembly in a disassembled state;

FIG. 122 is a perspective view of the securing clip of FIG. 121 with the clip in an assembled state and the press-fit locking ring disassembled;

FIG. 123 is a perspective view of the securing clip of FIG. 121 with the clip clamping a cord and with the press-fit locking ring not shown;

FIG. 124 is a perspective view of the securing clip of FIG. 123 with the press-fit locking ring partially installed; and FIG. 125 is a perspective view of the securing clip of FIG. 123 with the press-fit locking ring installed.

DETAILED DESCRIPTION OF THE INVENTION

Figure 1:
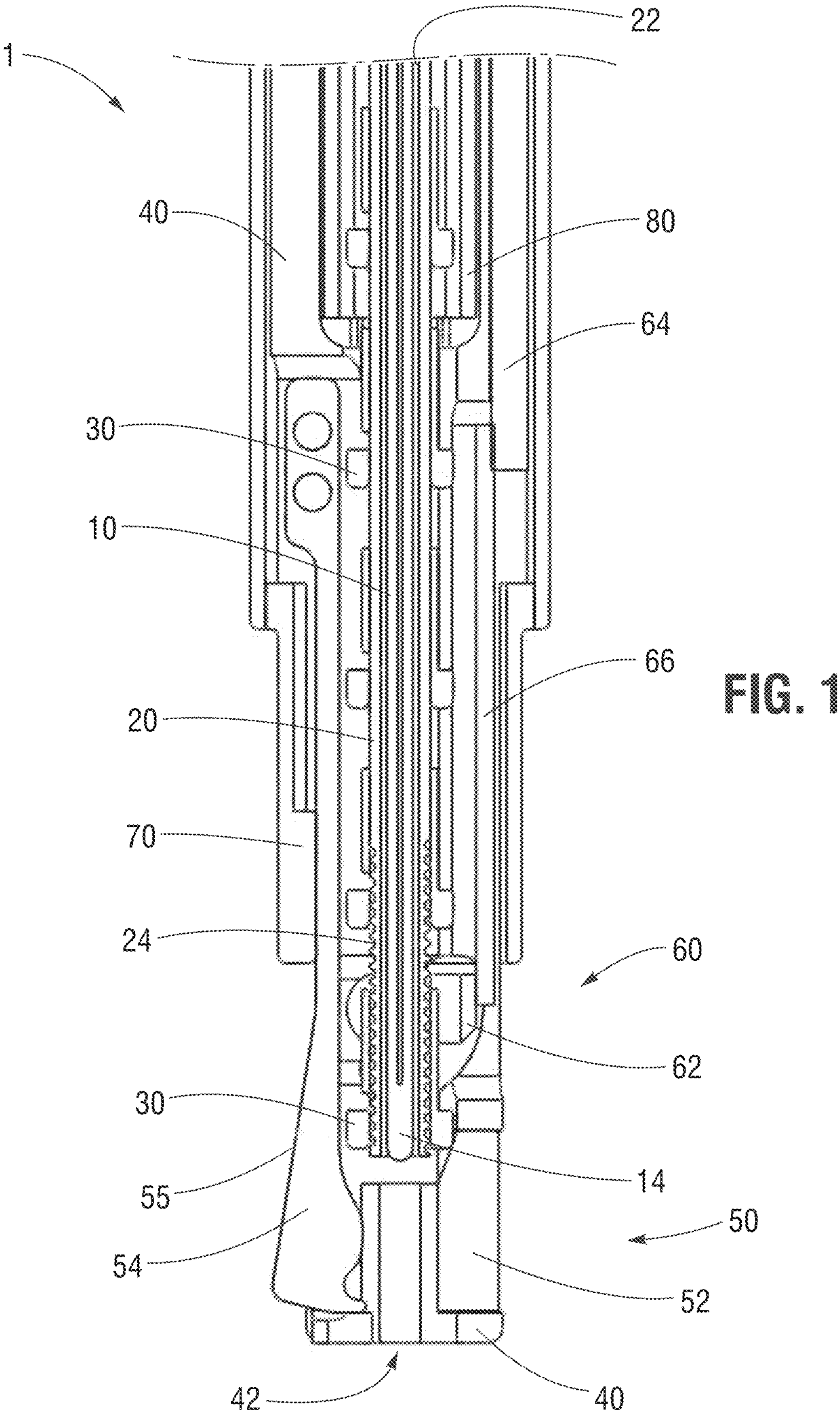
FIG. 1 is a fragmentary, longitudinal, cross-sectional view of an exemplary embodiment of an end effector for a multiple-firing crimp device with a crimp sub-assembly in a position ready to load a first crimp.

As required, detailed embodiments of the present devices and methods are disclosed herein; however, it is to be understood that the disclosed embodiments are merely exemplary of, which can be embodied in various forms. Therefore, specific structural and functional details disclosed herein are not to be interpreted as limiting, but merely as a basis for the claims and as a representative basis for teaching one skilled in the art to variously employ the present devices and methods in virtually any appropriately detailed structure. Further, the terms and phrases used herein are not intended to be limiting; but rather, to provide an understandable description of the devices and methods. While the specification concludes with claims defining the features that are regarded as novel, it is believed that the devices and methods will be better understood from a consideration of the following description in conjunction with the drawing figures, in which like reference numerals are carried forward.

Alternate embodiments may be devised without departing from the spirit or the scope of the devices and methods. Additionally, well-known elements of exemplary embodiments of the devices and methods will not be described in detail or will be omitted so as not to obscure the relevant details thereof.

Before the present devices and methods are disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

The terms "program," "software," "software application," and the like as used herein, are defined as a sequence of instructions designed for execution on a computer system. A "program," "software," "application," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

Herein various embodiments of the present devices and methods are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Figure 35:
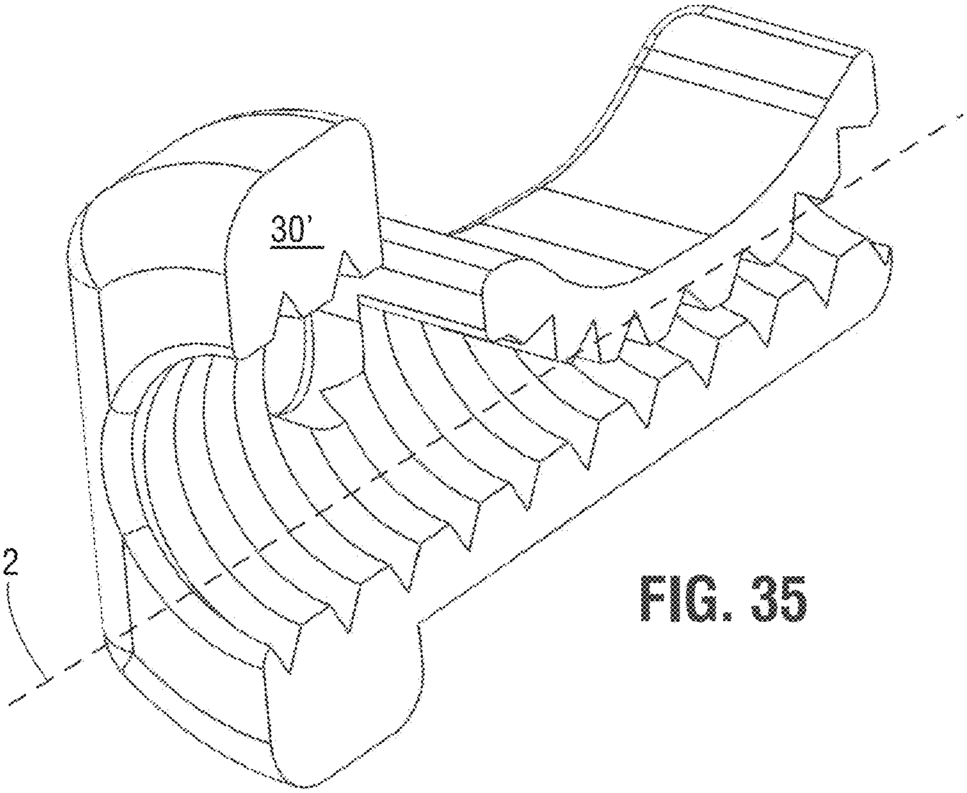
FIG. 35 is an enlarged perspective and longitudinal cross-sectional view of the crimp of FIGS. 32 and 33 after being crimped.
Figure 36:
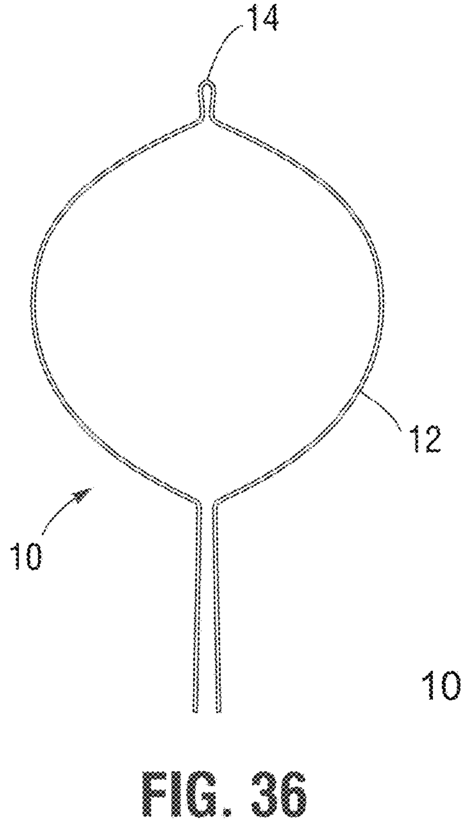
FIG. 36 is an exemplary embodiment of a distal end of a snare with a loop and its tip expanded.
Figure 37:
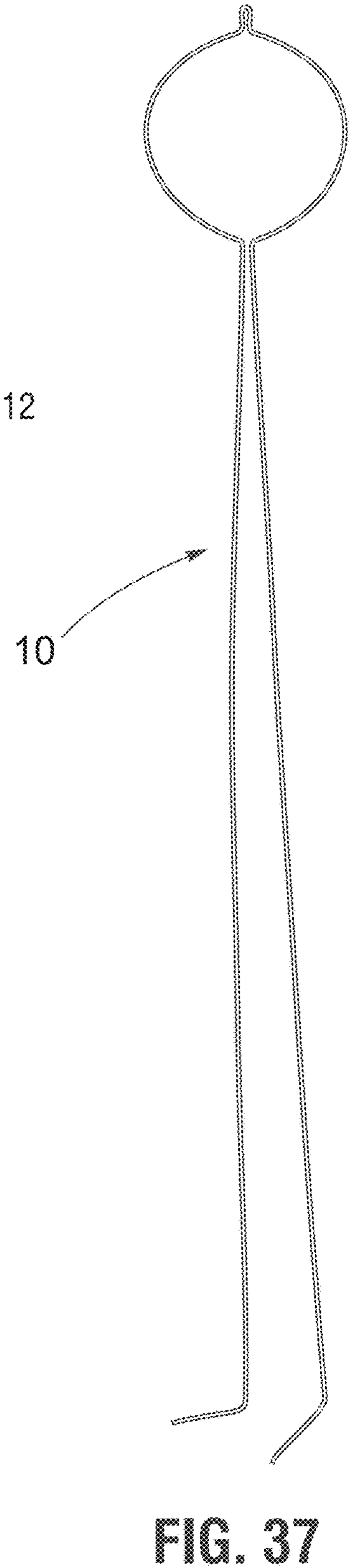
FIG. 37 is an exemplary embodiment of a snare with a loop and its tip expanded.
Figure 38:
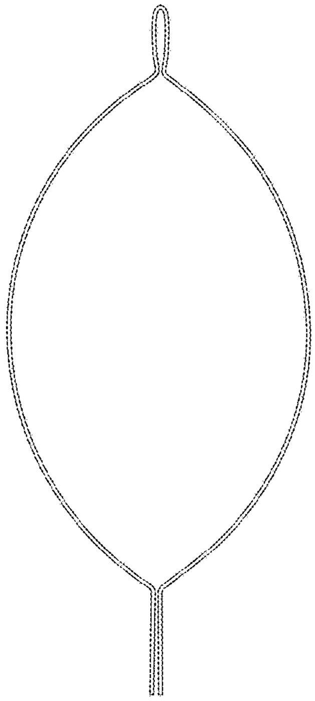
FIG. 38 is another exemplary embodiment of a distal end of a snare with a loop and its tip expanded.

Described now are exemplary embodiments. Referring now to the figures of the drawings in detail and first, particularly to FIGS. 1 to 35, there is shown a first exemplary embodiment of a multiple-firing crimp device 1. FIG. 1 shows an end effector of the multiple-firing crimp device 1 with a crimp assembly in a position ready to load a first crimp. From the center to the exterior of the crimp assembly, the innermost structure is a snare 10. In an exemplary embodiment, the snare 10 is laser cut out of a sheet of Nitinol or is a Nitinol wire and is heat set in a snare shape. Exemplary heat-set embodiments are shown in FIGS. 36 to 38. The snare 10 has a very low profile sufficient to fit, as shown in FIG. 1, within a hollow tube having an inner diameter of approximately 0.025". A loop 12 is formed in the snare 10 to provide a large area in which the user has to thread the cords to be connected together (e.g., ends of a surgical suture). For example, the loop 12 is approximately ovular with a major axis approximately 1.25" long and a minor axis approximately 1" long. The snare 10 is formed with a distal tip 14 that is described in further detail below. Herein, various snares are described and are equally applicable to temporarily secure a cord or cords. Shapes of the snares described herein are not exclusive and are not to be taken as the only shapes and/or configurations possible for snaring a cord/cords. Shapes can include closed or open loops, hooks, curves, or other shapes.

Surrounding the snare 10 is a crimp carriage 20. The crimp carriage 20 has a central lumen 22 with an inner diameter of approximately 0.025" to house therein the snare 10. One or more of the inner surface of the central lumen 22 and the snare 10 is lubricious so that the snare 10 can move out from and back into the central lumen 22 with little friction and without catching. As the snare 10 exits the central lumen 22, the loop 12 expands and forms its heat-set shape after the entirety of the loop 12 exits the distal end of the central lumen 22 (see, e.g., FIGS. 36 to 38). The outer surface of the crimp carriage 20 has an exterior thread 24. This exterior thread 24 is described in further detail below with regard to the crimps 30 and has a shape corresponding to an interior thread 32 of each crimp 30. As such, the length of the exterior thread 24 can be as long as the crimp carriage 20 but it can also be only as long as is needed to thread the desired number of crimps 30 thereon in series. Five of the crimps 30 are illustrated as threaded onto the crimp carriage 20 in FIG. 1 but the threads are only shown diagrammatically in FIG. 1 within one crimp 30 and half of a second crimp 30 (this is done for illustration purposes only). These threads are present on the crimp carriage 20 at least for the length of all of the crimps 30 that are to be loaded on the carriage 20. Alternatively the carriage can be smooth and have the crimps stacked up on it with a retention feature disposed on the end of the carriage that prevents the crimps from falling off the end of the carriage. In such an embodiment, the crimps are biased toward the retention feature by a slide that is, itself, biased distally by a compression spring. The slide has a mechanism that only allows it to slide distally along the carriage. In this way, the crimps are advanced into position and, once the distal-most crimp is moved into the ready position, the stack of remaining crimps index forward moving the next crimp into position.

Surrounding the crimp carriage 20 at the distal end of the device is the end effector body 40, which is best seen in FIGS. 17 to 22. The end effector body 40 defines a crimp loading orifice 42 in which a crimp 30 is loaded and, when loaded, is ready for firing. FIG. 1 does not show a crimp 30 in a loaded crimping position. A crimping device 50 is disposed at the orifice 42 and, in the exemplary embodiment shown, is positioned on opposing sides of the orifice 42. More particularly, an anvil 52 is present on one side of the orifice 42 and a hammer 54 is present on the other side of the orifice 42 opposite the anvil 52. The anvil 52 can be of a different material than the end effector body 40 or it can be integral with the end effector body 40. A cutting assembly 60 is also present at the end effector body 40. The cutting assembly 60, in the exemplary embodiment shown, includes a cutter 62 that is biased in a non-cutting position (shown) by a non-illustrated spring, for example. The cutter 62 is moved (e.g., rotated) by a cutter push-rod 64, 66 that extends back to the handle 100 of the multiple-firing crimp device 1; the handle 100 is diagrammatically shown in FIG. 3, for example, and is actuated by any number of actuation mechanisms, such as a motor, a relay, a lever, and/or a rack-and-pinion. To bias at least one of the movement assemblies in a proximal direction, a bias device 3 is provided and is diagrammatically shown in the handle 100 adjacent the movement assemblies. In this example, the bias device 3 is a spring.

An outer tube 70 surrounds the end effector body 40 and surrounds at least part of the cutting assembly 60 as it moves distal and proximal with respect to the end effector body 40. Also disposed within the outer tube 70 is a suture lifter 80, which is explained in further detail below.

To explain how the multiple-firing crimp device 1 operates, reference is made to the progression of FIGS. 2 through 31. The multiple-firing crimp device 1 comes pre-loaded to the user with a number of crimps 30 on the crimp carriage 20. This number is sufficient to accomplish a particular procedure. For example, if a heart valve replacement is the procedure and there are nine, twelve, or fifteen sutures needed to fix the replacement heart valve within the native valve orifice (this assumes an even spacing on a tri-leaflet valve), then the crimp carriage 20 will be fitted with nine, twelve, or fifteen crimps 30 (e.g., six crimps 30 are shown on the crimp carriage 20 in FIG. 4).

When the multiple-firing crimp device 1 is loaded with crimps 30 and is ready to use, the movement devices of the various loading/retracting, crimping, and cutting sub-assemblies within the handle 100 will be at a first rest or start position. These assemblies are shown diagrammatically within FIGS. 3, 5, 7, 9, 11, 12, 16, 20, 24, 26, 29, and 31. Ways that each of the movement sub-assemblies can actuate the various tasks of the multiple-firing crimp device 1 include any combination of levers, motors, relays, and other mechanical structures, such as a rack-and-pinion. Thus, they are not described in further detail. Here, each of the movement sub-assemblies includes a movement spool as an exemplary structure for actuating the assembly, each of which will be identified when the particular movement assembly is referenced herein. Spools are used to allow for longitudinal translation with free rotation.

Figure 2:
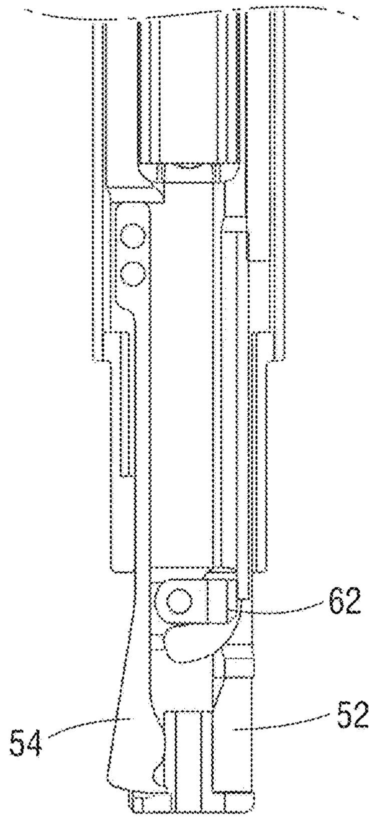
FIG. 2 is a fragmentary, longitudinal, cross-sectional view of the end effector of the multiple-firing crimp device of FIG. 1 with the crimp sub-assembly removed.
Figure 3:
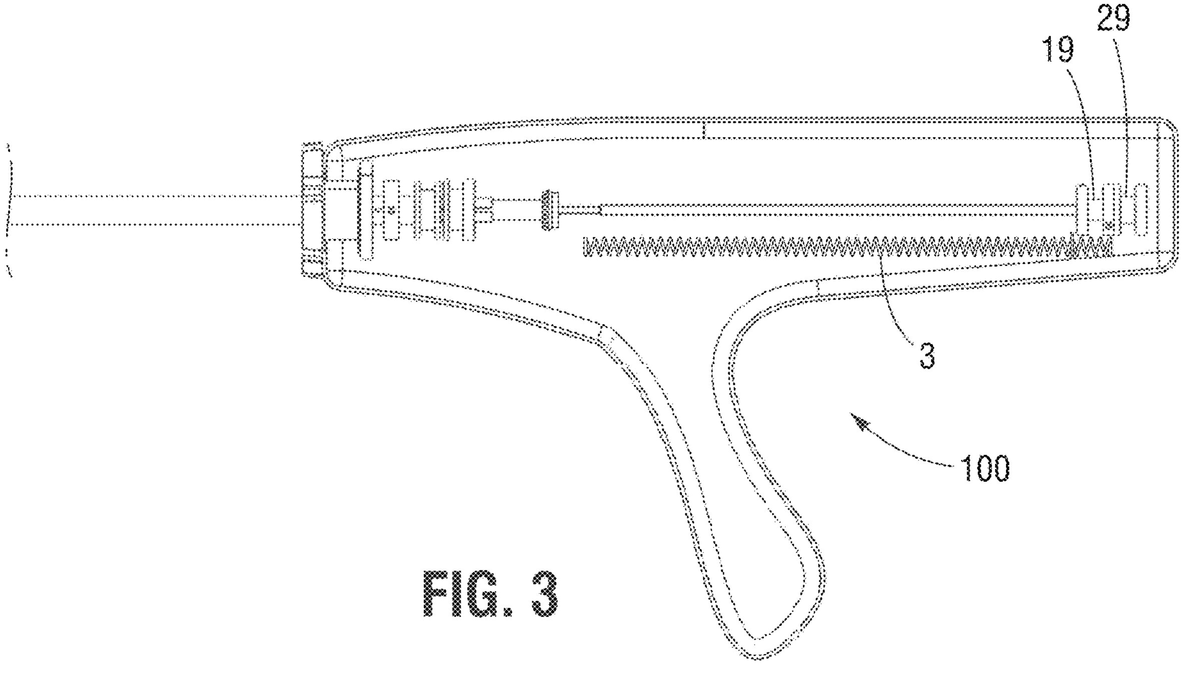
FIG. 3 is a fragmentary, side elevational and partially longitudinal cross-sectional view of an exemplary embodiment of a portion of a handle for operating the end effector of FIG. 2 with the crimp sub-assembly fully retracted.

When the multiple-firing crimp device 1 is loaded with crimps 30 prior to use, as shown in FIGS. 2 and 3, the crimp carriage 20 is retracted proximally out of the end effector body 40. Thus, the carriage spool 29 is in the furthest retracted position (i.e., proximal or closest to the user). In this state, the cutter 62 is retracted and the hammer 54 is in its steady or resting state away from the anvil 52. Significantly, no crimp 30 is loaded within the crimp orifice 42. In this state, the snare 10 is also retracted with the crimp carriage 20 and, therefore, the snare spool 19 is in the furthest retracted position as well.

Figure 4:
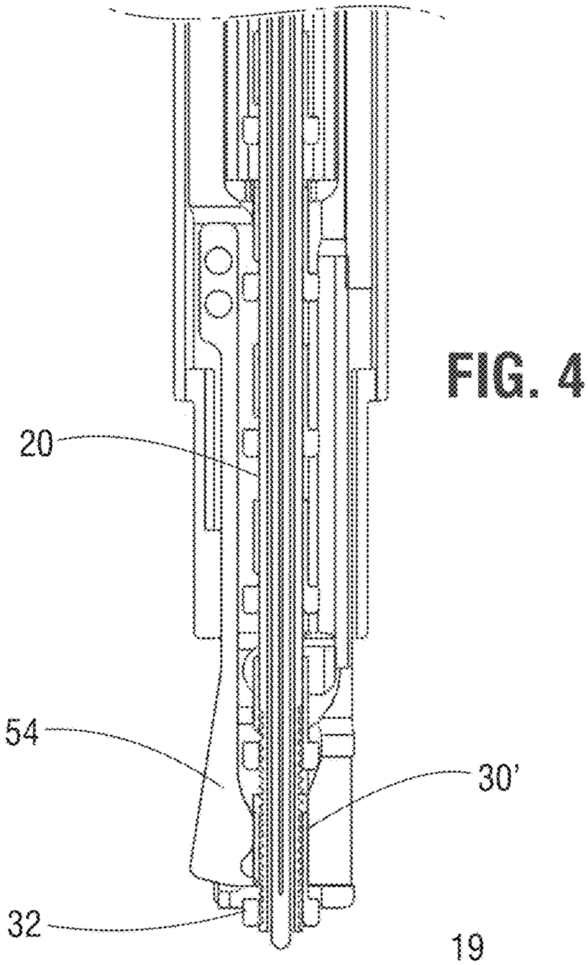
FIG. 4 is a fragmentary, longitudinal, cross-sectional view of the end effector of FIG. 1 with the crimp sub-assembly in an extended position prior to seating of a crimp.
Figure 5:
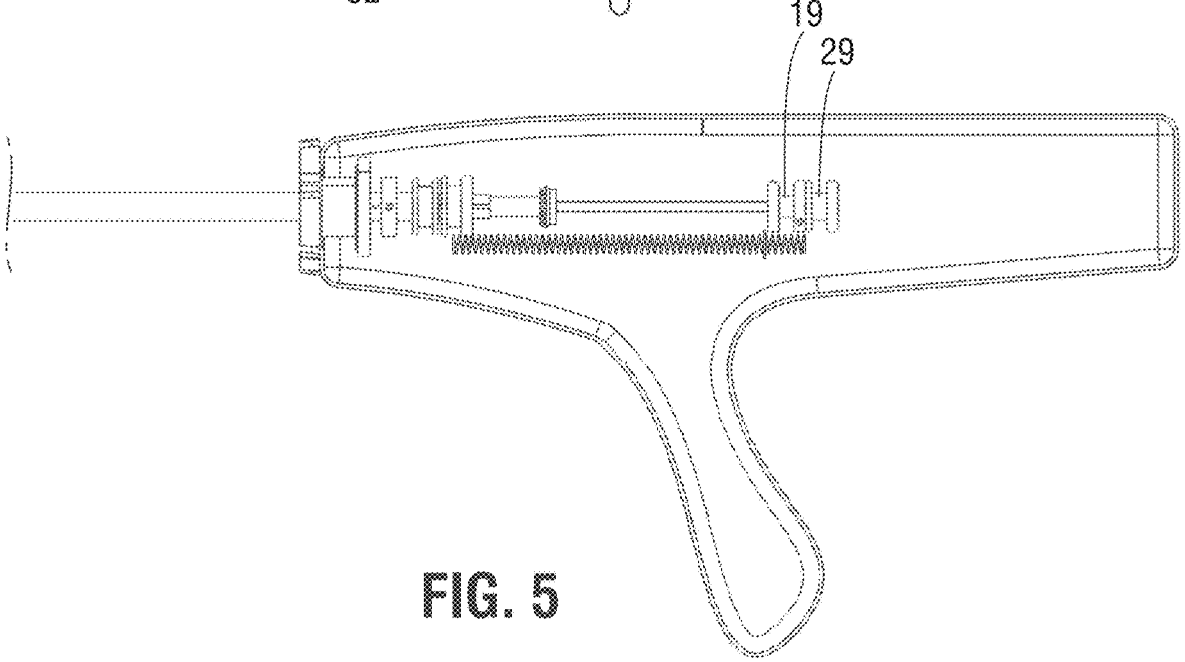
FIG. 5 is a fragmentary, side elevational and partially longitudinal cross-sectional view of the handle portion of FIG. 3 with the crimp sub-assembly actuators in a carriage-extended position corresponding to FIG. 4.

To load the multiple-firing crimp device 1 with a crimp 30 and make it ready for use, the crimp carriage 20 is extended distally. This is done by placing the carriage spool 29, along with the snare spool 19, in the position shown in FIG. 5. In this step, the snare spool 19 can be free-floating because the carriage spool 29 (having a shaft within a shaft attached to the snare spool 19) forces the snare spool 19 distally as far as the carriage spool 29 is moved. To secure the distal-most crimp 30' within the crimp orifice 42, the head 34 of the soon-to-be-loaded crimp 30' must pass the distal ends of the hammer 54 and the anvil 52, a state that is shown in FIG. 4. To describe how the crimp 30' is loaded into the crimp orifice 42 and held there, it is beneficial to first describe an exemplary embodiment of a crimp 30, which is shown in FIGS. 32 and 33. To thread the crimp 30 onto the externally threaded crimp carriage 20, the crimp 30 defines a bore having internal threads 32 corresponding to the external threads 24 of the crimp carriage 20. In this way, each crimp 30 can simply be placed in loading position at the distal end of the crimp carriage 20 and rotation of the crimp carriage 20 in a particular direction serially loads each crimp 30 thereon one after the other, as shown, for example, in FIG. 1. To prevent the crimps 30 from rotating while the crimp carriage 20 is rotating, each crimp 30 has a head 34 formed with at least one polygonal surface 36. The end effector body 40 has a corresponding shape to the polygonal surface that acts as a structure to keep each crimp 30 aligned therewithin and prevent rotation of the crimp 30. The crimp 30 has various advantageous characteristics. First, its shape delivers the highest clamp force density. Next, it presents a closed profile that houses the cord(s) therein. Finally, it is easily deformed to restrain the cord(s) therein in a reliable and secure manner.

Once the crimp carriage 20 is retracted from the crimp 30', it would, without more, rest within the crimp orifice 42 and, potentially, could fall out with movement of the multiple-firing crimp device 1. Accordingly, to positively lock the crimp 30' within the crimp orifice 42, each crimp 30 is provided with a catch 38, which can take any shape and, in the exemplary embodiment shown, is a transverse groove or cut adjacent a proximal side of the head 34 (the top side of the head 34 in the view of FIG. 33). The catch 38 can be any shape or structure and need not be the shape depicted in the figures. The catch 38 can be a hole or other depression but it can even be an extension such as a protruding boss. To effect a catch-and-securement of the crimp 30' within the crimp orifice 42, the hammer 54 is provided with a distal feature 56 having a shape that, when aligned with the catch 38, mates therewith. See, e.g., FIG. 6A. In the exemplary embodiment, the distal feature 56 is a protruding nose having a longitudinal length shorter than the longitudinal length of the catch 38. In this way, when the head 34 of the crimp 30' passes the distal feature 56 and is then retracted just slightly proximal, the distal surface of the distal feature 56 abuts the proximal surface of the head 34 and extension of the distal feature 56 into the catch prevents both proximal and distal movement. Thus, along with the polygonal surface 36, the crimp 30' is held in place in all dimensions as shown in FIGS. 6 and 6A. The distal end in FIG. 6A shows the interaction of the catch 38 and the distal feature 56 and the contact with both the distal faces of the hammer 54 and the anvil 52 to provide a proximal stop for the crimp 30'.

It is desirable to provide additional holding force on the crimp 30' to retain the crimp 30' therein. Accordingly, the hammer 54, which is shaped as a flex beam secured distally to the end effector body 40 at one or more contact points 58, has an interiorly extending section 53 that acts as a cam along the edge of the crimp 30'. As shown, for example, in FIGS. 13 and 25, when the outer tube 70 is moved distally, the distal end 72 acts as a cam driver by riding along the outer surface 55 (a cam surface) of the hammer 54, thereby radially forcing the hammer 54 inwardly. As such, with the distal end 72 of the outer tube 70 preventing the intermediate portion of the hammer 54 from flexing outward, the remaining exposed portion 74 of the distal end of the hammer 54 flexes radially outward and, thereby, imparts a strong radially inward bias against the crimp 30'. The position of the crimp carriage 20 and the snare 10 in this state defines the corresponding positions of the carriage spool 20 and the snare spool 19 that are shown in FIG. 7.

Figure 8:
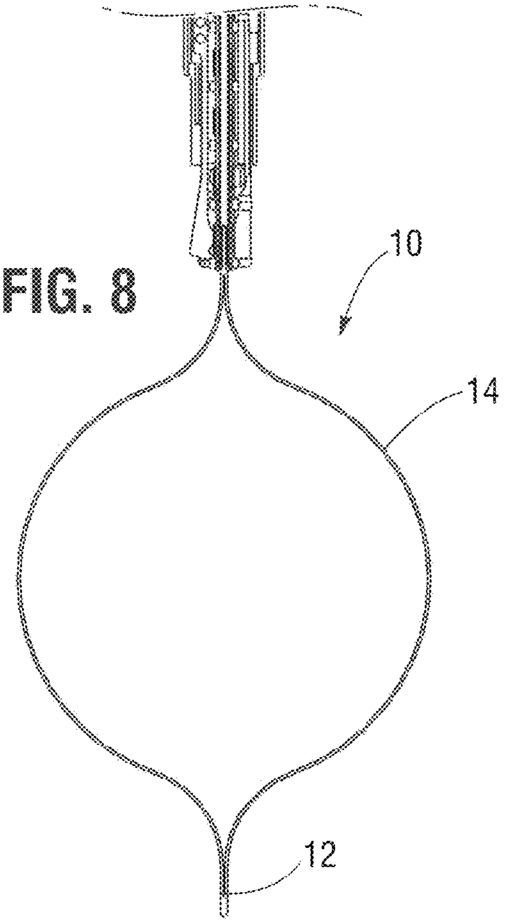
FIG. 8 is a fragmentary, longitudinally cross-sectional view of the end effector of FIG. 6 with a snare in an extended snare position ready for capturing one or more cords.
Figure 9:
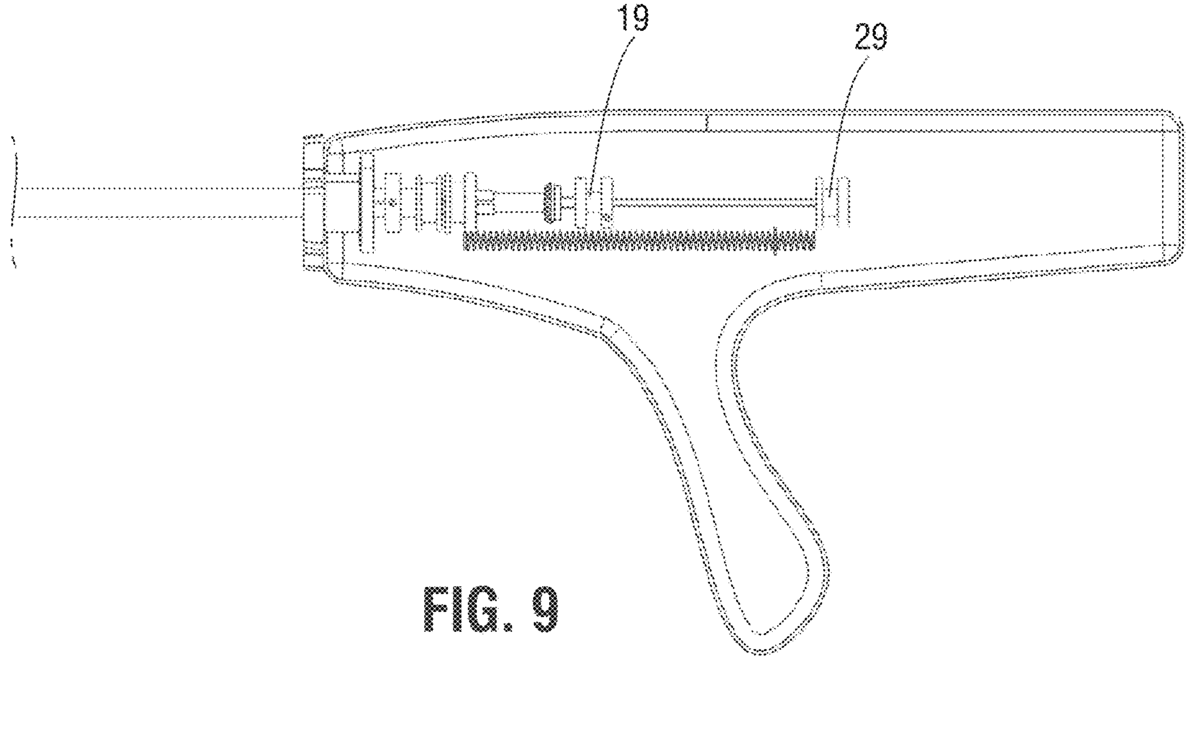
FIG. 9 is a fragmentary, side elevational and partially longitudinal cross-sectional view of the handle portion of FIG. 3 with the snare sub-assembly actuator in a snare-use position corresponding to FIG. 8.
Figure 10:
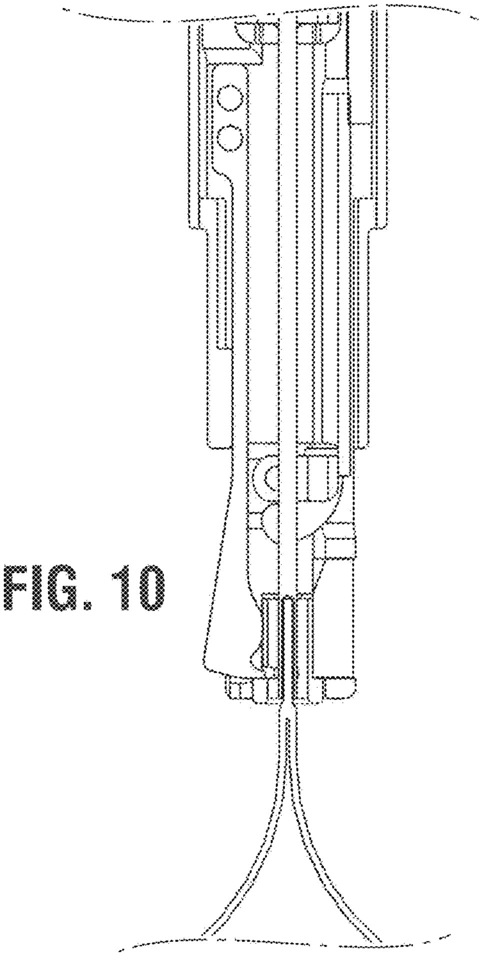
FIG. 10 is a fragmentary, longitudinally cross-sectional view of the end effector of FIG. 8 with a snare in an extended snare position ready for or capturing a suture and with the suture screw carriage disengaged from the distal-most clip and fully retracted.
Figure 11:
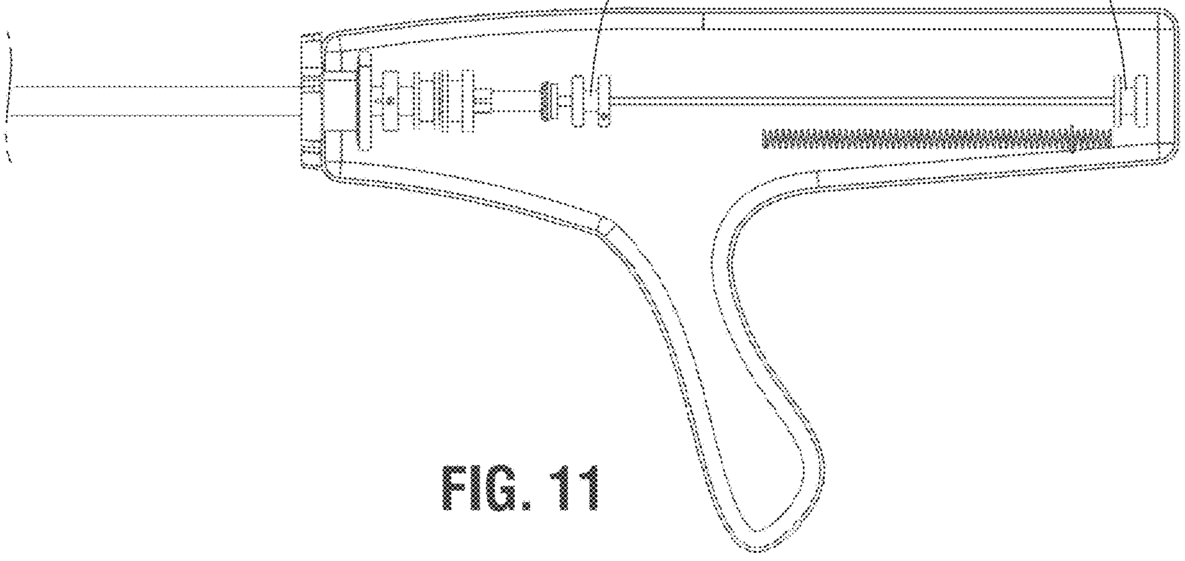
FIG. 11 is a fragmentary, side elevational and partially longitudinal cross-sectional view of the handle portion of FIG. 3 with the snare sub-assembly actuator in a snare-use position corresponding to FIG. 10 and with the suture screw carriage disengaged from the distal-most crimp and fully retracted.

Now that the crimp 30' is in position for use, in order to thread the cords into and through the hollow center of the crimp 30', the snare 10 is extended distally through the crimp 30' with the tip 14 of the snare 10 moving distally away from the distal end of the end effector body 40. As the tip 14 moves further distally, the loop 12 is permitted to open to its pre-set shape (e.g., heat-set), an example of which is shown in FIG. 8. Extension of the snare 10 occurs by moving the snare spool 19 distally away from the carriage spool 29, as shown in FIG. 9. At this point, the cords can be inserted through the loop 12 for entry into and through the crimp 30'. However, the crimp 30' is still attached to the crimp carriage 20. Accordingly, the crimp carriage 20 is rotated (by a non-illustrated device that spins the carriage spool 29, for example) to disengage the crimp 30' from the distal end of the crimp carriage 20. At the same time or either before or after, the crimp carriage 20 is moved distally out of the end effector body and is rotated further to cause the distal end thereof to move and place the previously second crimp 30" in line into the distal-most crimp position, thereby converting the second crimp 30" into the next crimp 30' to be used for the next crimping procedure. The depiction in FIG. 10 illustrates the end effector with the crimp carriage 20 entirely disengaged from the distal-most crimp 30' and retracted out of at least a portion of the end effector body 40 to not interfere with subsequent steps (even though it is shown completely out of the view of FIG. 10, this does not mean that such a distant retraction is required. It is sufficient if the carriage 20 is retracted sufficiently far enough to not interfere with subsequent steps prior to loading the next crimp 30'. The orientation of the snare and carriage movement sub-assemblies for this state is depicted with the positions of the snare spool 19 and the carriage spool 29 in FIG. 11.

Figure 12:
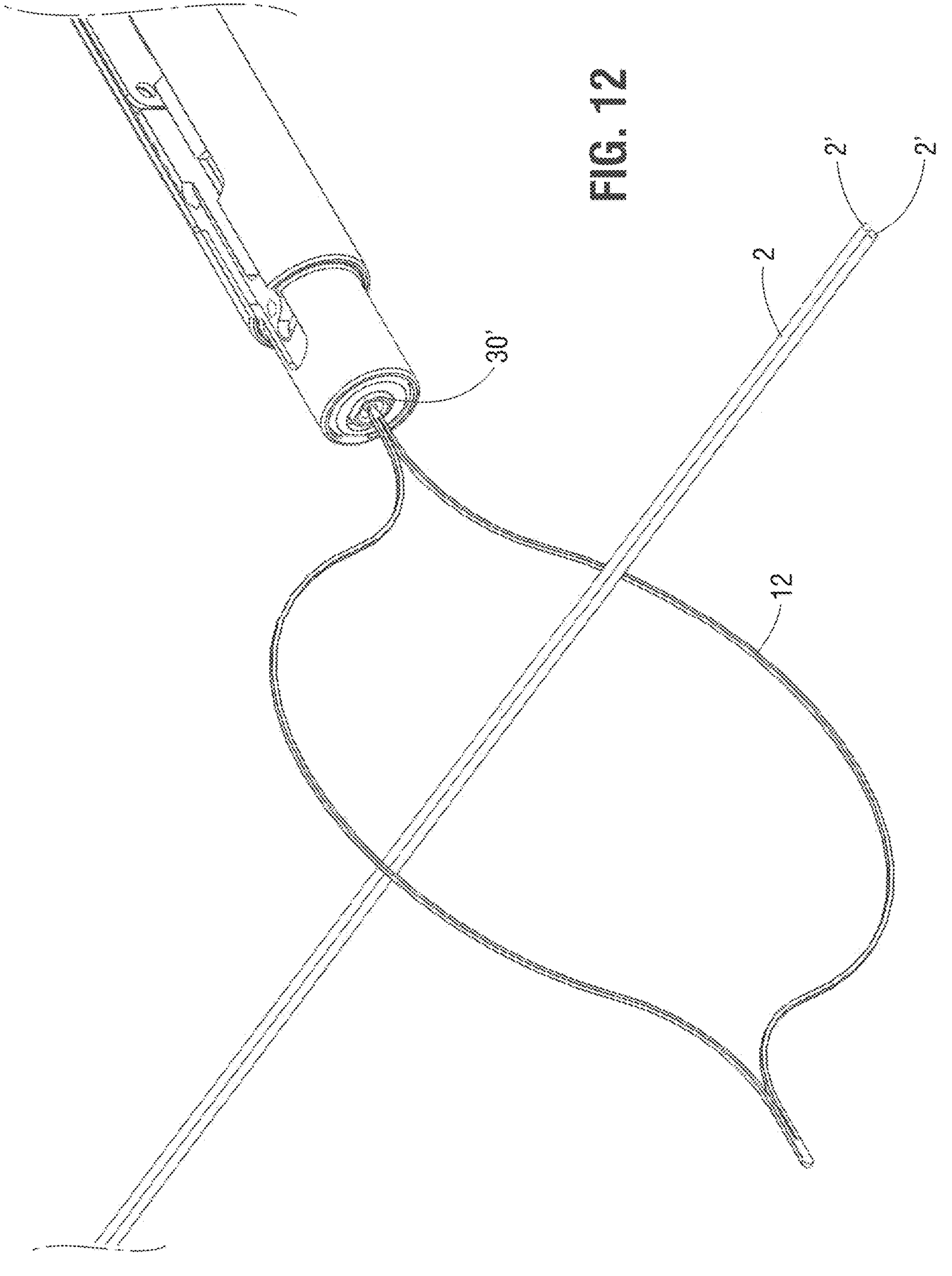
FIG. 12 is a fragmentary, perspective view of the end effector of FIGS. 8 and/or 10 with cords to be captured extended within the loop of the snare.
Figure 13:
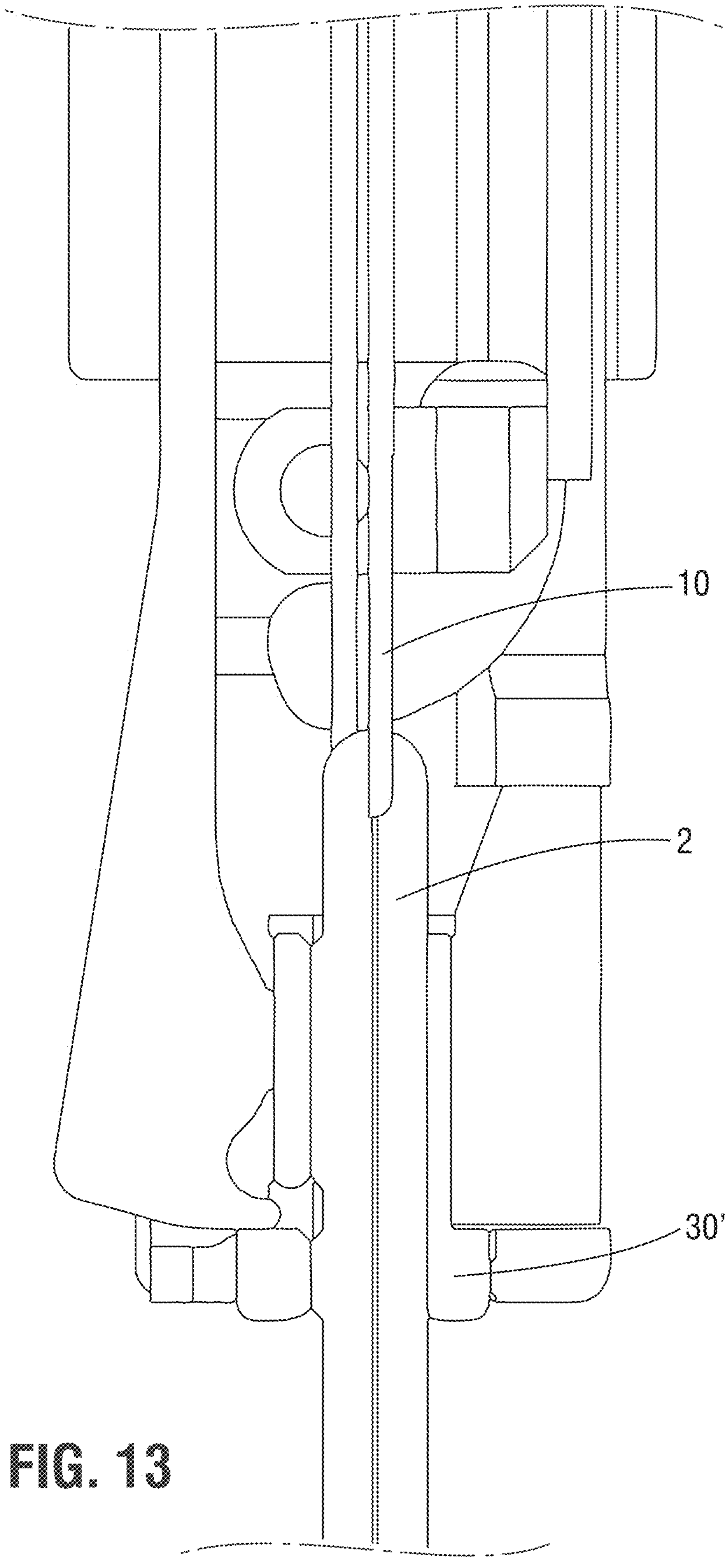
FIG. 13 is a fragmentary, longitudinally cross-sectional view of the end effector of FIG. 10 enlarged with respect to FIG. 10, with the snare in a partially retracted snare position after capturing cords and with the cords having passed partially through the crimp.
Figure 14:
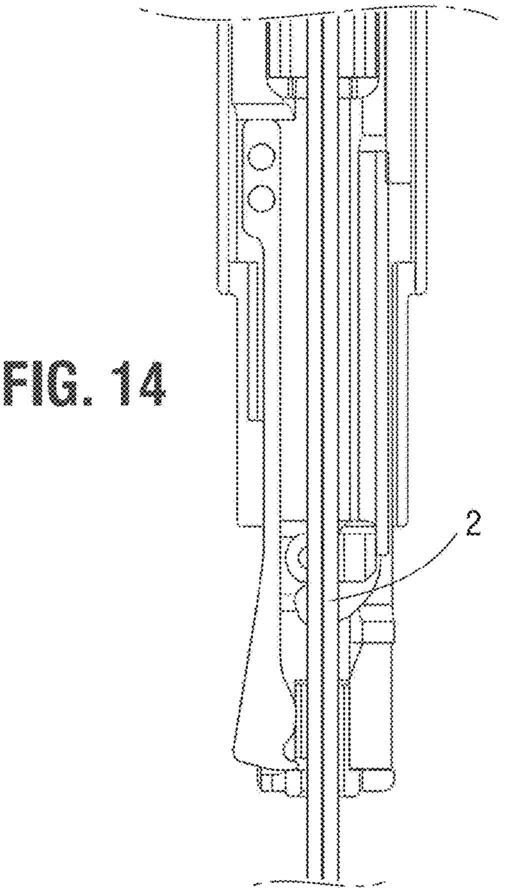
FIG. 14 is a fragmentary, longitudinally cross-sectional view of the end effector of FIG. 13 reduced with respect to FIG. 13 and with the snare in a further partially retracted snare position after capturing the cords.
Figure 15:
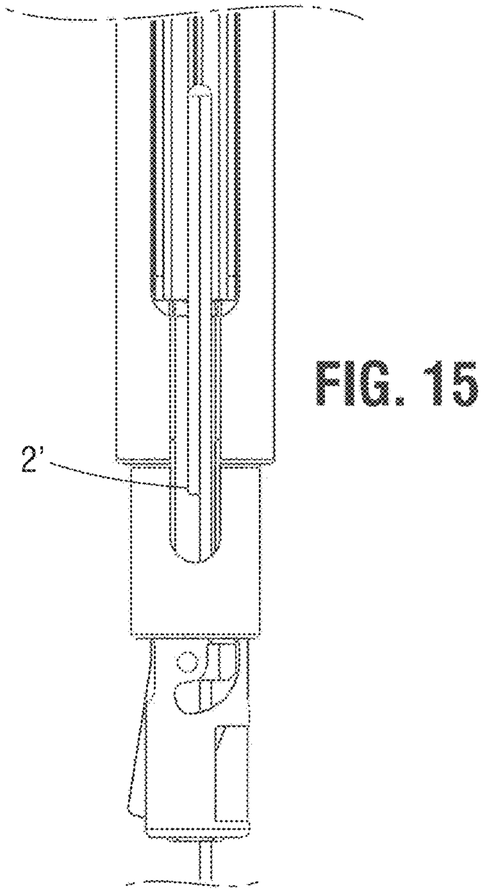
FIG. 15 is a fragmentary, side elevational view of the end effector of FIG. 14.
Figure 16:
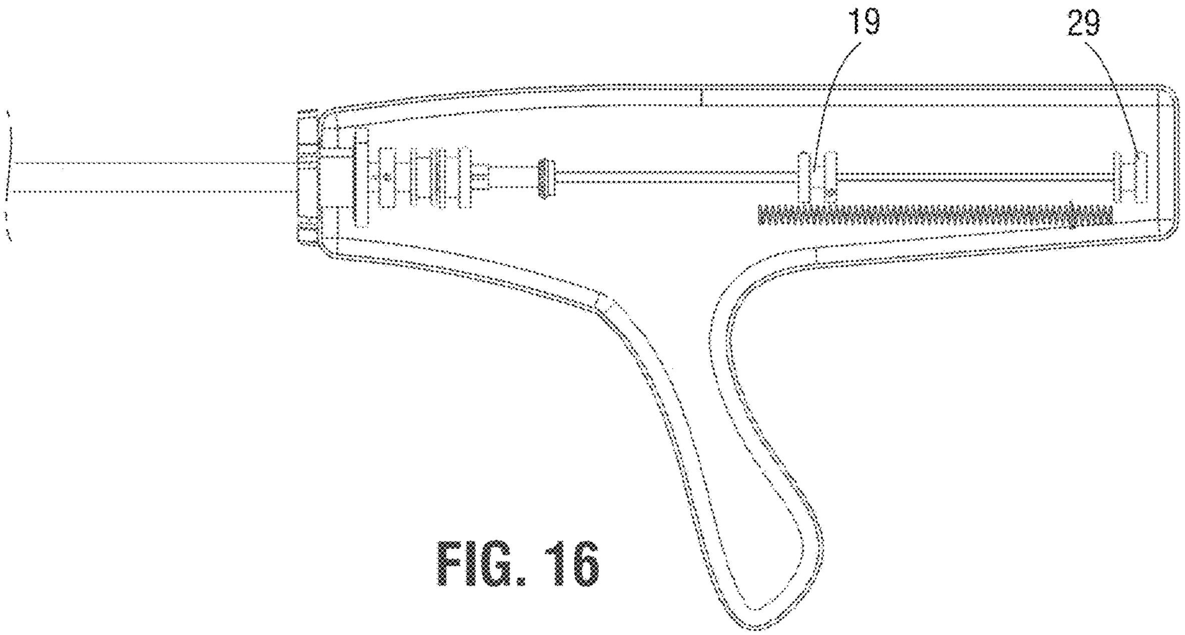
FIG. 16 is a fragmentary, side elevational and partially longitudinal cross-sectional view of the handle of FIG. 11 with the snare sub-assembly actuator further retracted than the position of the snare corresponding to FIG. 12.

In the example of FIG. 12, the free ends 2' of a looped cord 2 are passed through the loop 12 (from the left to the right in the drawing). At this point, the cords 2 are ready to be threaded through the crimp 30'. The snare 10 is drawn proximally to catch the cords 2 within the loop 12 and then in the tip 14, which, in an exemplary embodiment, forms a small extension area of the interior of the loop 12 in which the cords 2 are moved as the loop closes and moves proximally. As the proximal end of the loop 12 is drawn proximally into the crimp 30', the loop 12 compresses flat, as in the orientation of FIG. 6, and the cords 2 are, then, folded in half and reside within the interior of the tip 14. Further proximal movement draws the cords 2 through the crimp 30' as depicted in FIG. 13. The looped ends of the cords 2 in the tip 14 are drawn in further proximally into the device as shown in FIG. 14 until the free ends 2' of the cords 2 enter the end effector body 40, as shown in FIGS. 15 and 17. The orientation of the snare and carriage movement sub-assemblies for this state is depicted with the positions of the snare spool 19 and the carriage spool 29 in FIG. 16.

Now that the cords 2 are through the crimp 30' and the ends 2' are pulled sufficiently far enough into the shaft of the device, the process for presenting these ends 2' to the user begins.

Figure 19:
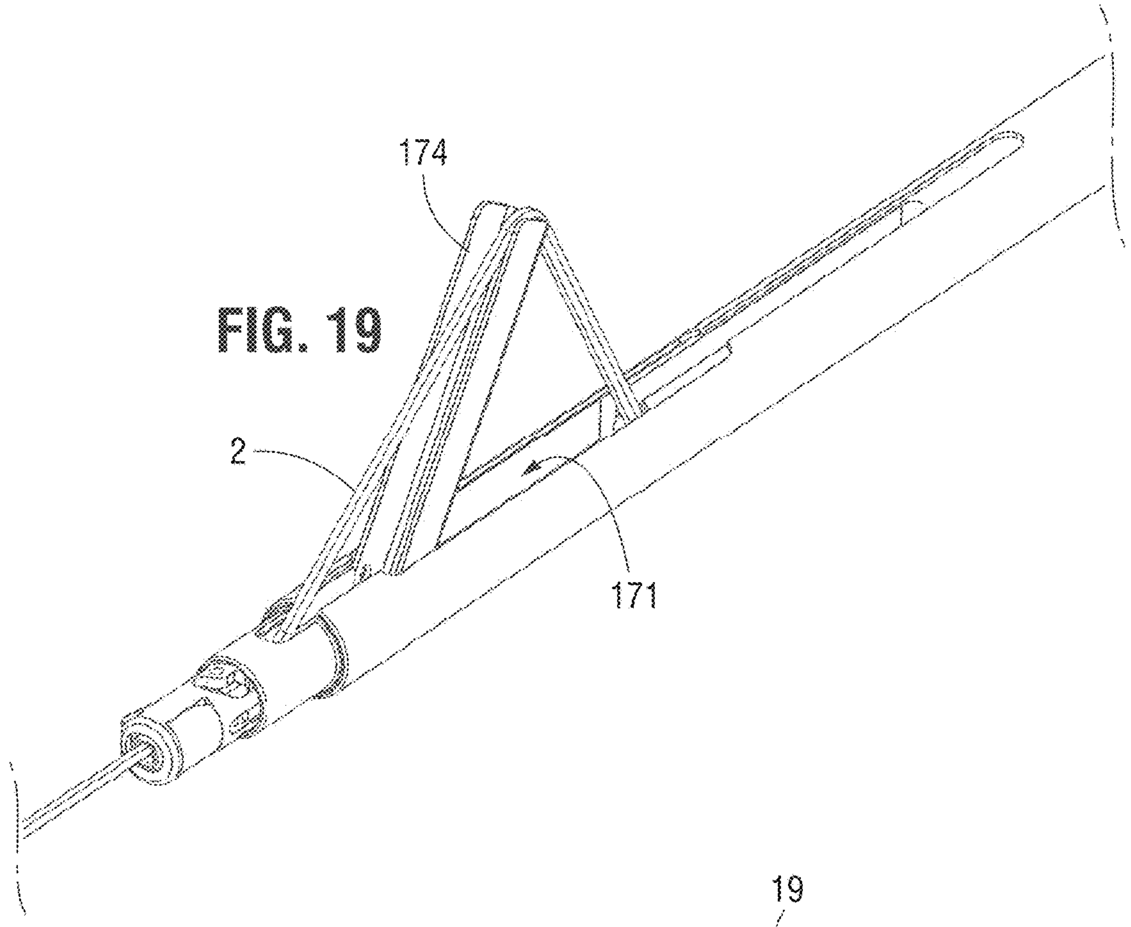
FIG. 19 is a fragmentary, perspective view of the end effector of FIG. 18.
Figure 20:
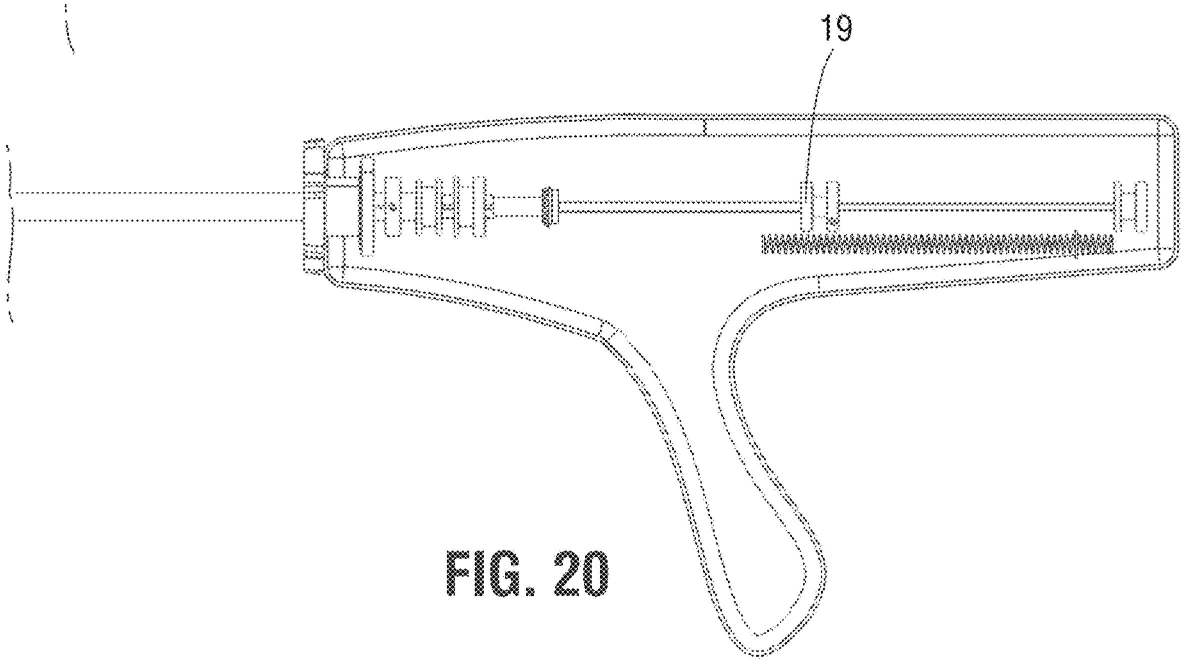
FIG. 20 is a fragmentary, side elevational and partially longitudinal cross-sectional view of the handle of FIG. 16 with the cord-lifting device actuated to position the cord lifter to the position corresponding to FIGS. 18 and 19.
Figure 21:
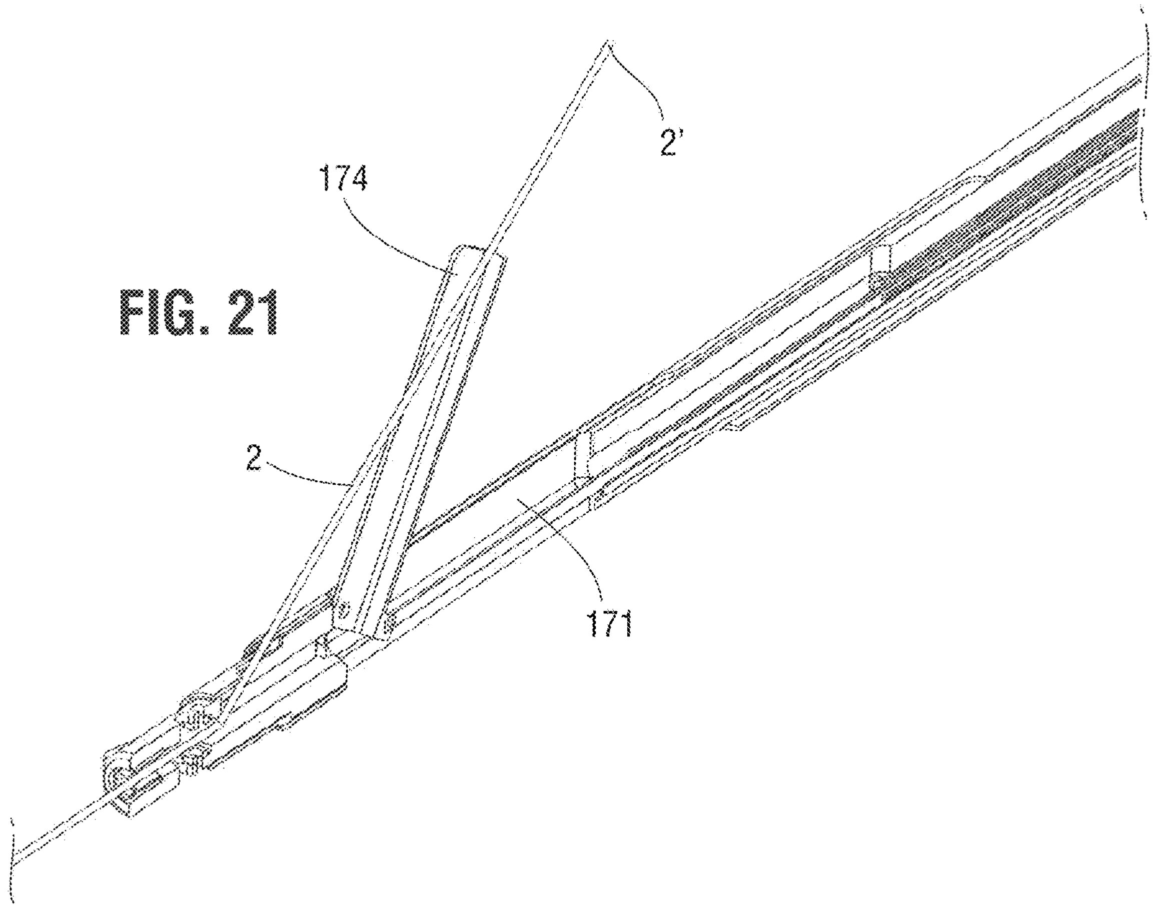
FIG. 21 is a fragmentary, longitudinally cross-sectional view of the end effector of FIG. 19 with the cord-lifting device in a lifted position, with the suture grasped by a user, and with the snare in the partially retracted position.

FIGS. 17 to 24 illustrate this process with an exemplary embodiment of a cord-lifting device 170, which is one possible way to present the ends 2' to a user. The cord-lifting device 170 is fastened to the end effector body 40 at a pivot 172 so that the cord-lifting device 170 is able to pivot away from the central axis of the outer tube 70. With this pivot 172, when the cord-lifting device 170 is actuated, the cord-lifting plate 174 pivots to lift the cords 2 out of the outer tube 70 through a window or lateral opening 171, as shown in FIG. 18. The lifting can be effected with any mechanism, for example, a push rod extending from the handle 100 and attached in an intermediate position of the cord-lifting plate 174 or extending adjacent the pivot 172 to connect to a lever that lifts the cord-lifting plate 174 when either pushed or pulled. This actuation device is not depicted for drawing clarity. At this point, the snare 10 still grasps the cords 2. Accordingly, either the snare 10 can move distally to keep retention of the cords 2, as shown in FIG. 18, or the snare 10 can remain in place and, as the cord-lifting device 170 lifts the cords 2 outwards, either the length of the cords 2 distal of the crimp 30' are pulled into the crimp 30' or the ends 2' of the cords 2 are caused to shorten their distance from the tip 14 of the snare 10. FIG. 19 illustrates the lifted cords 2 still attached to the snare 10 and the cord-lifting device 170 lifted. FIG. 20 illustrates the positions of the various movement sub-assemblies for this state.

Figure 22:
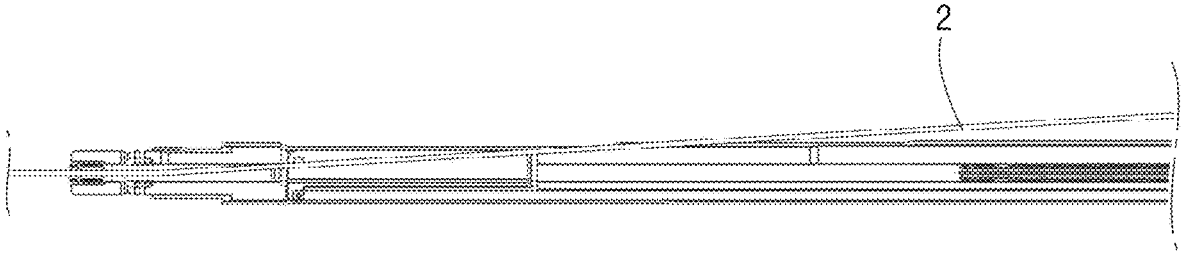
FIG. 22 is a fragmentary, longitudinally cross-sectional view of the end effector of FIG. 21 with the cord-lifting device in a lowered position, with the cords grasped by a user at an acute angle with the longitudinal axis of the end effector, and with the snare in a retracted position.
Figure 23:
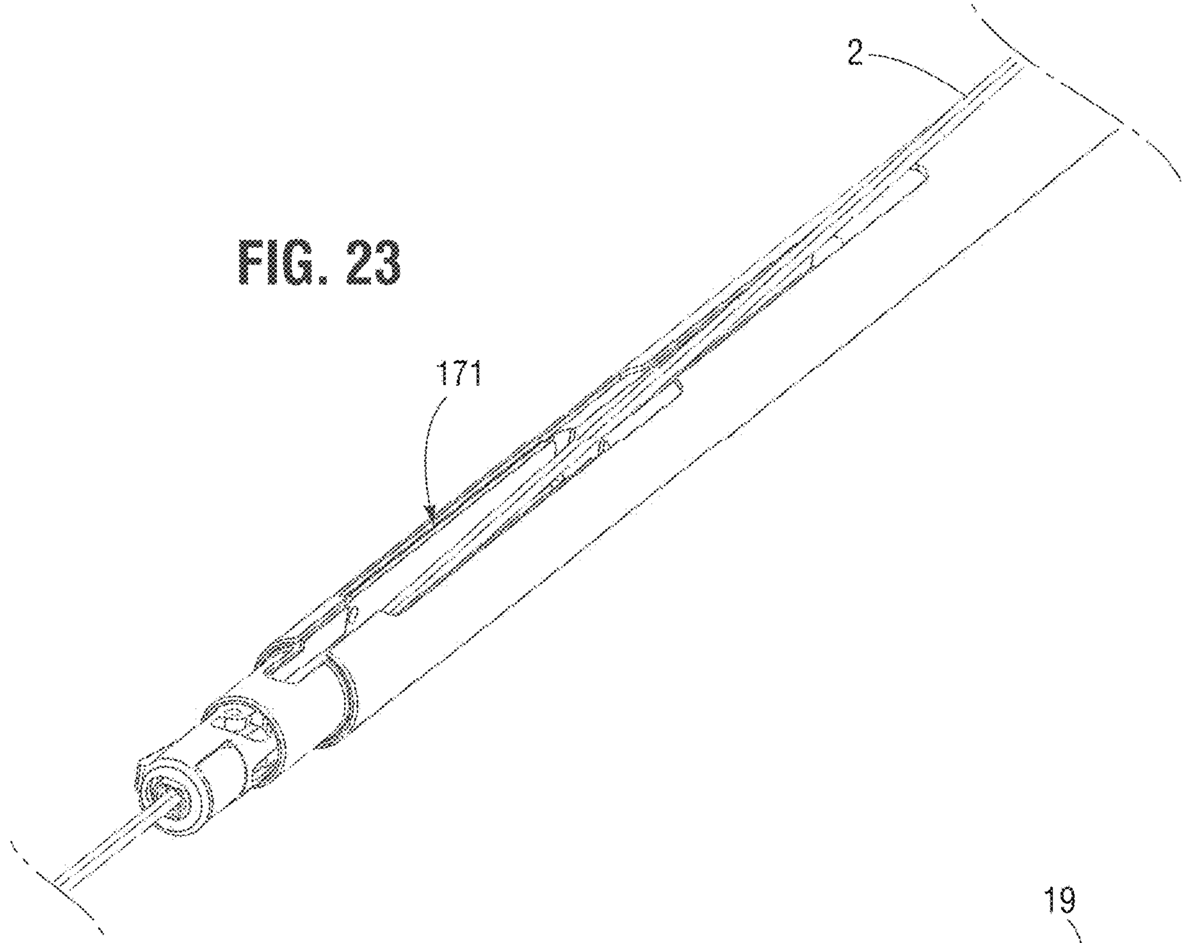
FIG. 23 is a fragmentary, perspective view of the end effector of FIG. 22.
Figure 24:
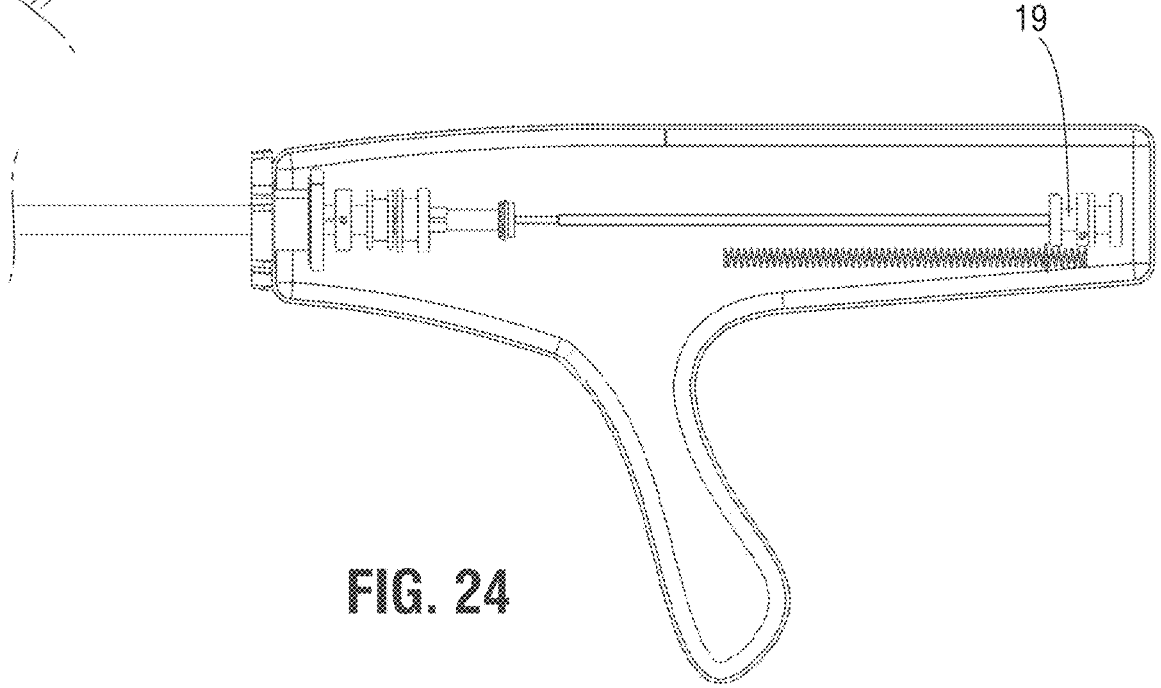
FIG. 24 is a fragmentary, side elevational and partially longitudinal cross-sectional view of the handle of FIG. 20 with the cord-lifting device returned to the unactuated position that places the cord-lifting device in the lowered position corresponding to FIGS. 22 and 23 and with the snare actuator in the retracted position.

As the snare 10 is pulled further distally, the ends 2' of the cords 2 become freed therefrom and now rest outside the outer tube 70 of the device. The user can, therefore, grasp these ends 2' and, after the cord-lifting device 170 is lowered, can pull them taut as shown in FIGS. 22 and 23. At this point, the snare 10 can be retracted in the device as shown in FIG. 24 by the position of the snare spool 19. Now, the crimp 30' can be installed/crimped/deformed on the cords 2.

Movement of the distal end of the device with respect to the opposite ends of the cords 2 held by the user (not illustrated but to the lower left of FIG. 23) will depend on the location that the user desires to fix the crimp 30'. If the current location is sufficient, then crimping will occur with the length of the cords shown to the lower left of FIG. 23 remaining as is. However, if the distance from the opposite ends of the cords 2 is desired to be short, then the user will move the device distally along the cords 2 while holding onto the free ends 2' and keeping them taut. If, for example, the cords 2 are surgical sutures and the opposite ends of the cords 2 are fixed at a surgical location, and if the surgeon wishes to have the crimp 30' be applied as close to the surgical location as possible, then the top of the head 34 of the crimp 30' will be moved along the sutures distally and up against the surgical site. When there, with tension on the sutures, the surgeon can fix the crimp 30' at a location closest to the surgical site.

Figure 27:
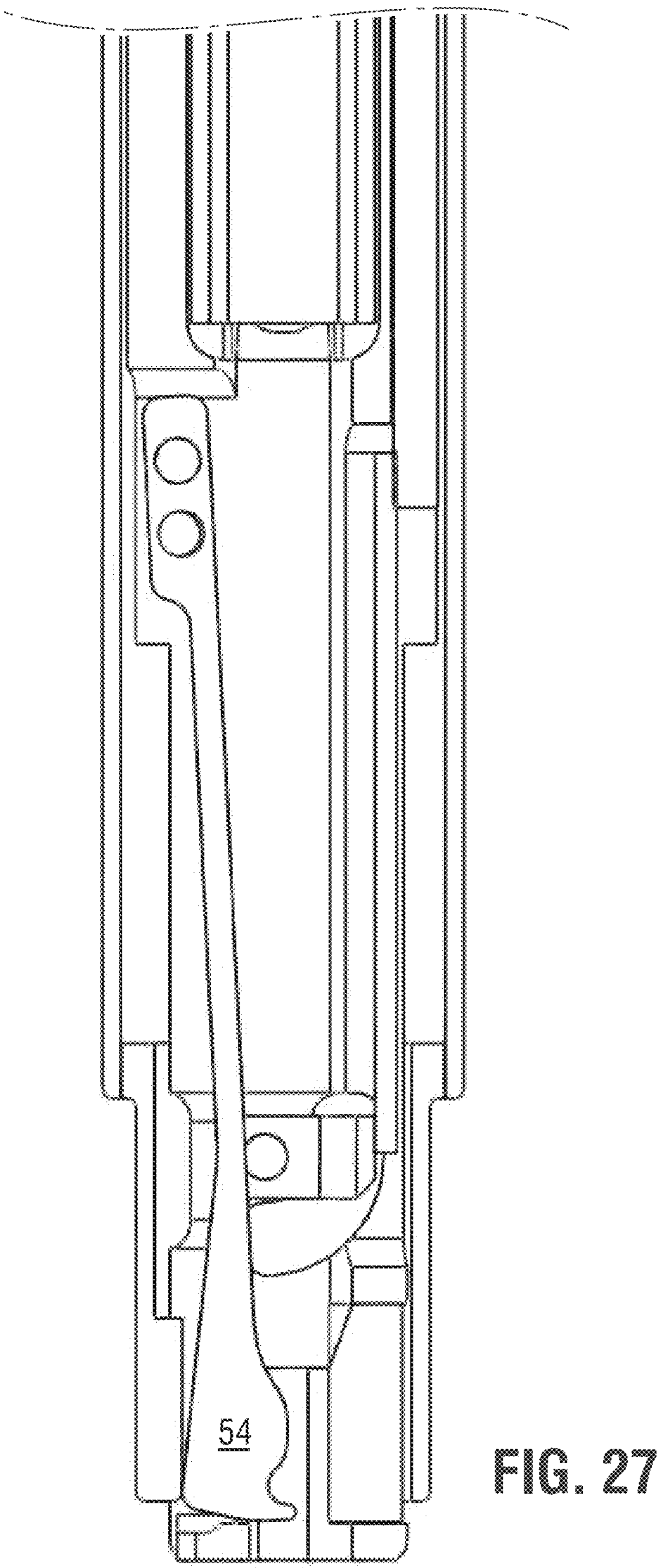
FIG. 27 is fragmentary, longitudinally cross-sectional view of the end effector of FIG. 25 with the crimp and cords removed.
Figure 28:
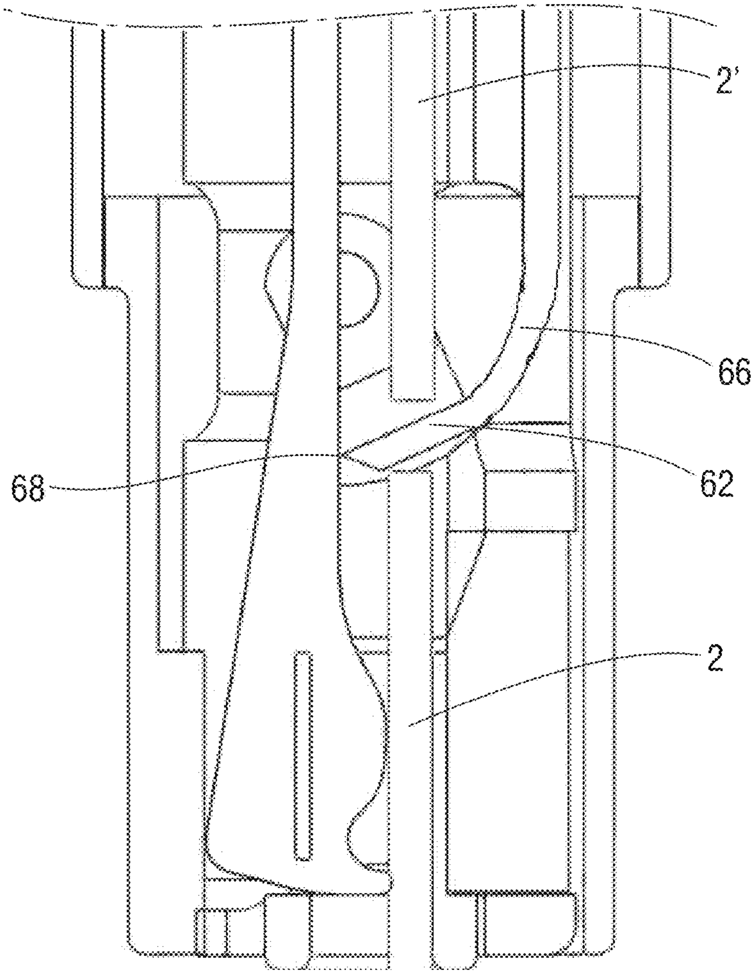
FIG. 28 is fragmentary, longitudinally cross-sectional view of the end effector of FIG. 25 with the cutter actuator fully extended to move the cutting blade and thereby cut the cords.
Figure 29:
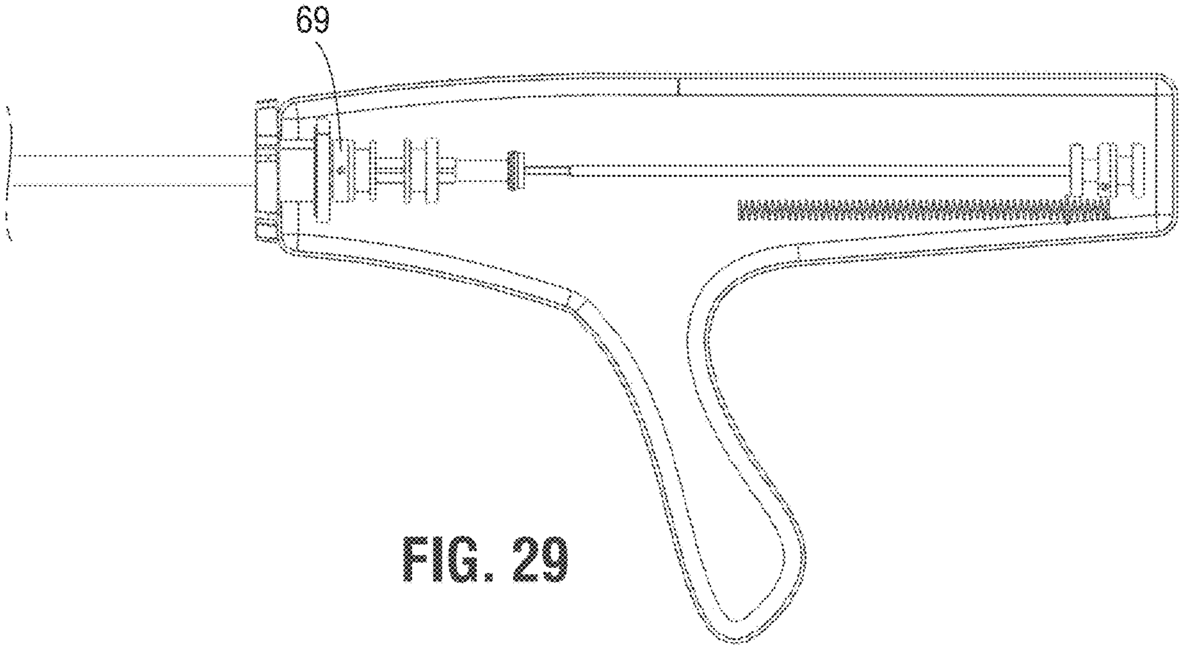
FIG. 29 is a fragmentary, side elevational and partially longitudinal cross-sectional view of the handle of FIG. 26 with the cutter actuator fully extended distally into the position corresponding to FIG. 28 to thereby cut the captured cords.
Figure 30:
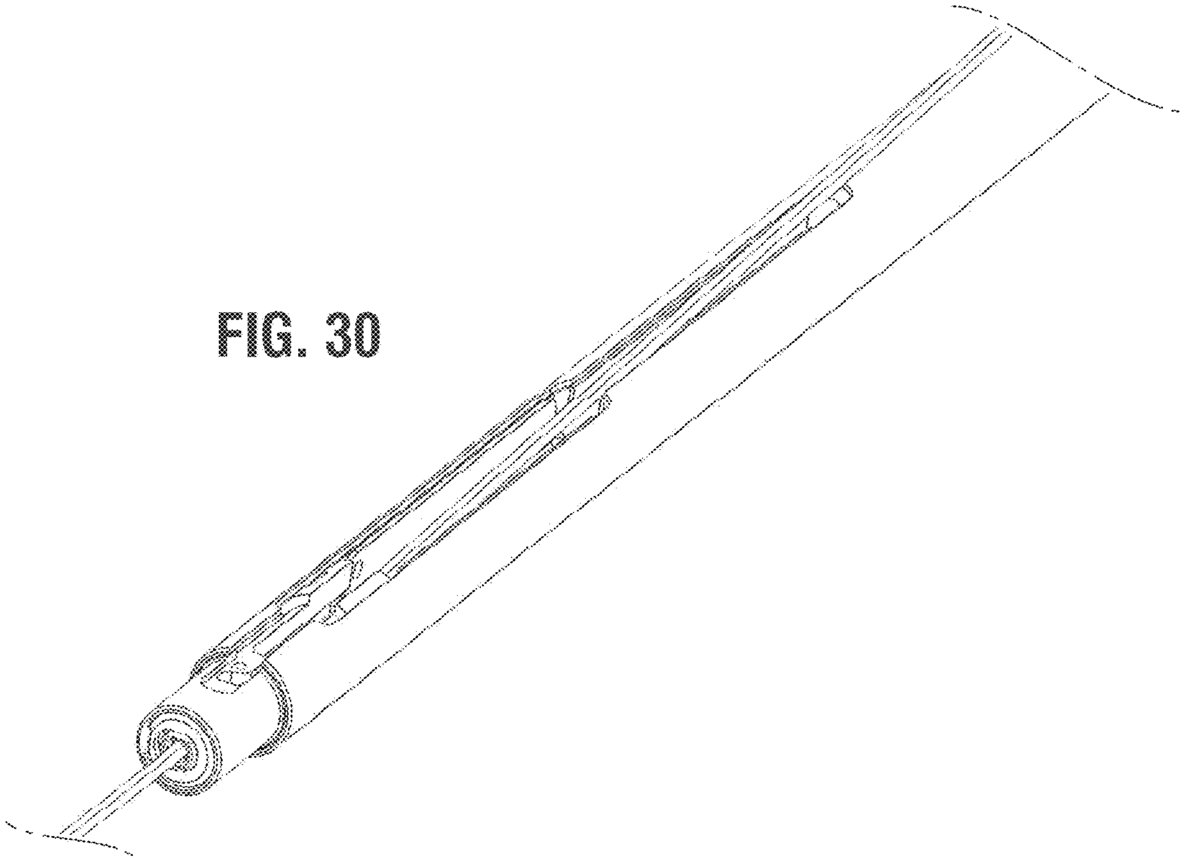
FIG. 30 is a fragmentary, perspective view of the end effector of FIG. 25.
Figure 31:
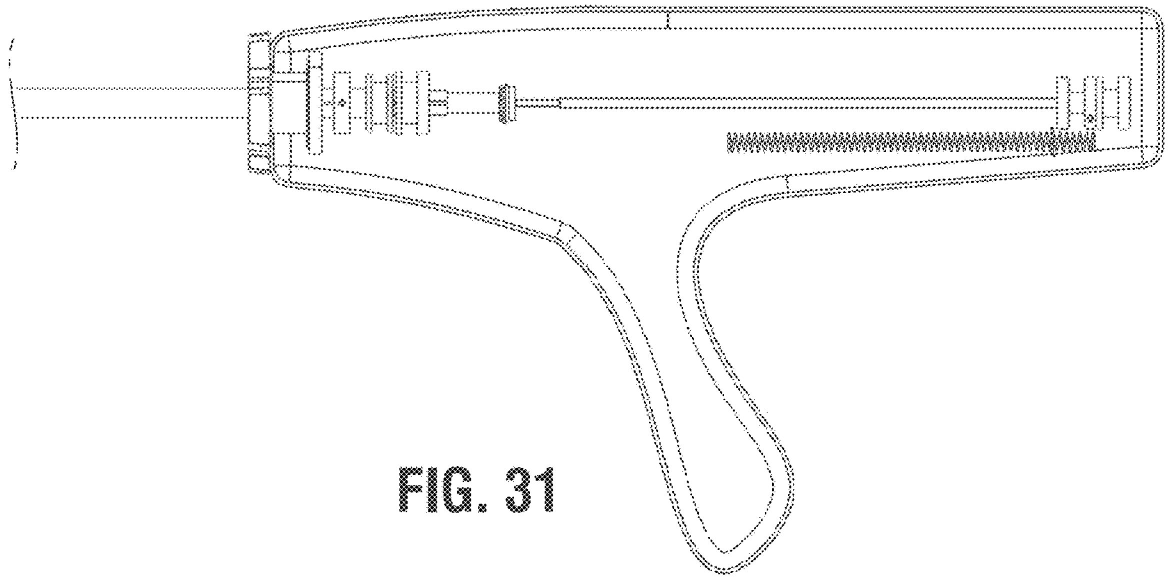
FIG. 31 is a fragmentary, side elevational and partially longitudinal cross-sectional view of the handle of FIG. 29 with the cutter and crimping actuators retracted proximally to release the crimped crimp and with the crimp sub-assembly ready to reload a new crimp into the end effector.
Figure 34:
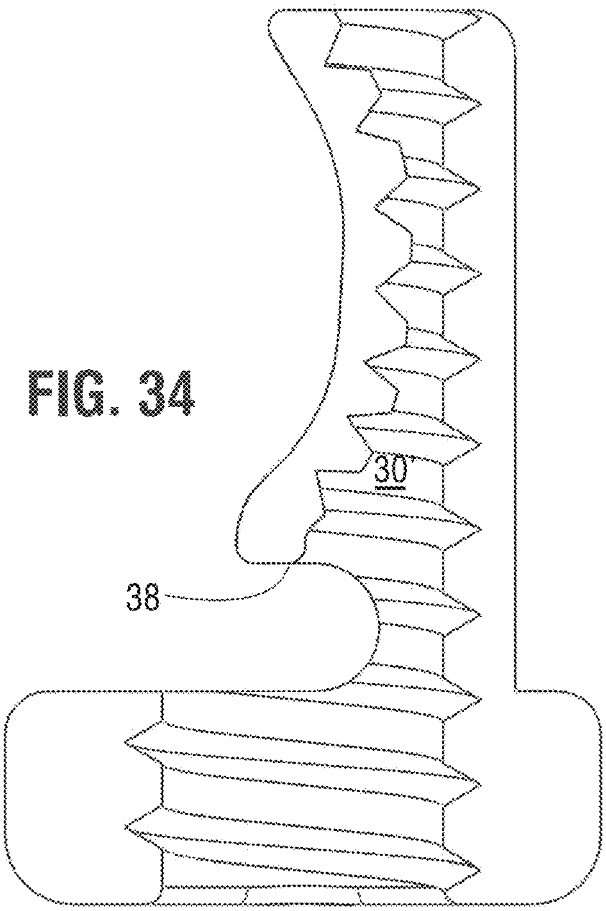
FIG. 34 is an enlarged perspective view of the crimp of FIGS. 33 and 34 after being crimped.

Crimping occurs by moving the outer tube 70 distally, which is indicated in FIG. 26 by the distal movement of the crimp spool 79. As the distance for crimping the crimp 30' is very short, the crimp spool 79 needs to only move a short distance distally. This movement can be caused manually by a lever, a toggle, or a button, for example, or by an electrical motor, such as a stepper motor. Crimping occurs by the outer surface 55 of the hammer 54 acting as a cam profile with the distal end of the outer tube 70. As the outer tube 70 moves distally parallel to the longitudinal axis of the device, the rising cam surface with respect to the outer tube 70 causes the hammer 54 to press inwards against the crimp 30' with a force sufficient to deform the crimp 30' and fix it to the cords 2, as shown in FIGS. 25, 34, and 35. In this state, the crimp 30' is crimped and, thereby, fixed to the cords 2 therewithin (shown diagrammatically with the dashed line in FIG. 35). For ease of visualization, FIG. 27 illustrates the hammer 54 in the crimping position without the crimp 30' present.

It is noted that the internal threads 32 of the crimp 30' provide additional friction and holding power when crimped onto the cords 2. The internal threads of the crimp can be adjusted to not be full depth threads. The threads also can be adjusted to optimize the ID of the crimp for clearance to pass the cords and snare as well as to present a less damaging but still gripping surface to the cords upon crimping. The catch 38 also provides crimp relief and length reduction for when the crimp 30' is squeezed. The distal-most section of the crimp 30' remains undistorted to provide a smooth transitional surface that the cords 2 can follow to prevent high stress that might damage the cords 2.

After crimping occurs, the lengths of the cords 2 on the proximal side of the fixed crimp 30' are to be trimmed off. The cutting assembly 60 described above is able to cut the cords 2 with a cutter pushrod having a relatively stiff proximal portion 64 and a relatively flexible distal portion 66 that is able to bend as the pivoting blade 62 moves (see, for example, FIG. 28). As such, cutting of the cords 2 occurs when an actuator at the handle 100 causes the proximal portion 64 to move distally. This, in turn, causes the distal portion 66 to move distally and, because it is fixed to the proximal side of the blade 62, causes the blade 62 to move about its pivot point and allow the cutting edge 68 to sever the cords 2. As the blade 62 is only required to move a very short distance, the distance that the cutting rod 64, 66 needs to move is also very short and is illustrated by the relative positions of the cutting spool 69 in FIGS. 26 and 29. It is noted that the outer tube 70 and tube spool 79 also move along with the cutting spool 69, but this movement is optional. In order to assure cutting is complete and the device is unobstructed for use of the next crimp 30, the cutting movement assembly is biased proximally (e.g., with a spring) to automatically retract the knife 62 after a cut is complete.

This cutting configuration of the cutter assembly 60 is merely one exemplary embodiment. Another embodiment can include a pusher that cuts the cords 2 by pressing the cords 2 against a fixed blade as described in further detail below. A further embodiment can have the knife cut against a cut block or stop. Yet another embodiment can apply electric current to the knife and allow it to cut as a hot wire. In any case, it is desirable to have the knife cut close to location of the crimped crimp 30' to reduce the remaining length of the cords 2 extending from the end of the crimp 30 opposite the head 34.

Like the cutting movement assembly, the movement assembly for the outer tube 70 is biased proximally (e.g., with a spring, even the same spring as the cutting movement assembly) to automatically retract the outer tube 70 after a crimp 30' fixation is complete. In this way, the hammer 54 is allowed to spring back to its ready-to-crimp position when the outer tube 70 is disengaged.

Figure 39:
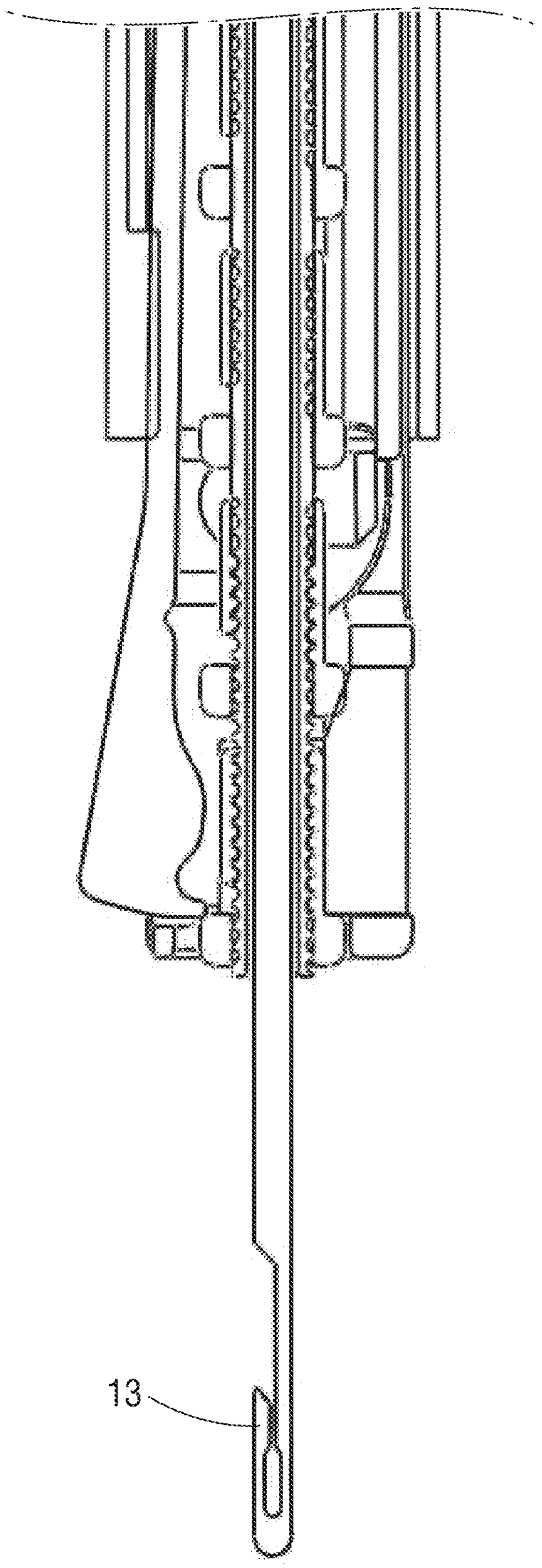
FIG. 39 is a fragmentary, longitudinally cross-sectional view of an exemplary embodiment of an alternative end effector to the device shown in FIGS. 1 to 31 and similar to FIG. 8, wherein the snare is replaced with a distal hook that hooks the cords and draws them into the assembly for securing with a loaded crimp, this embodiment allowing the user to thread the crimp with a single hand that is holding the device's handle.
Figure 40:
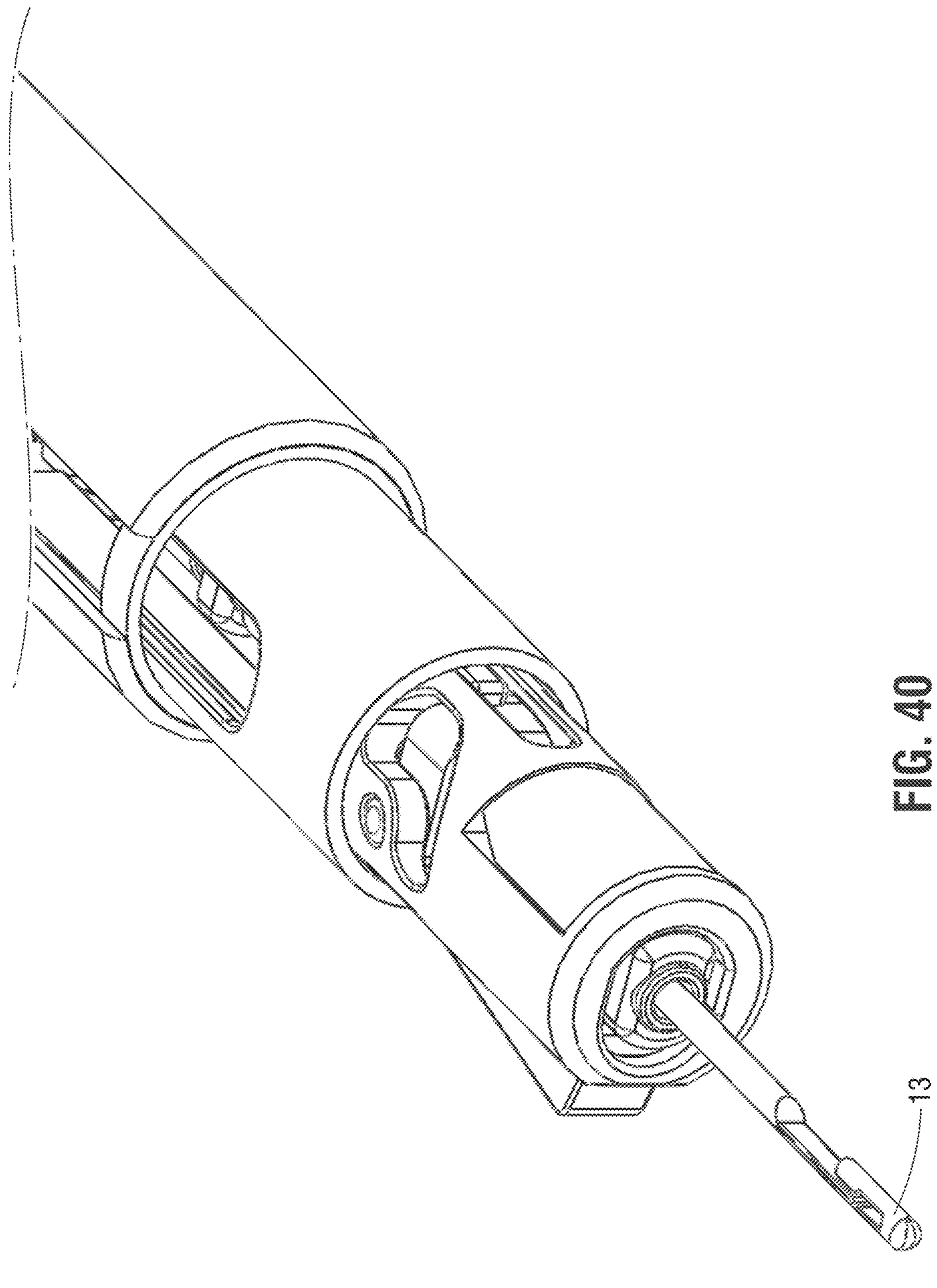
FIG. 40 is a fragmentary, enlarged perspective view of the end effector of FIG. 39.
Figure 41:
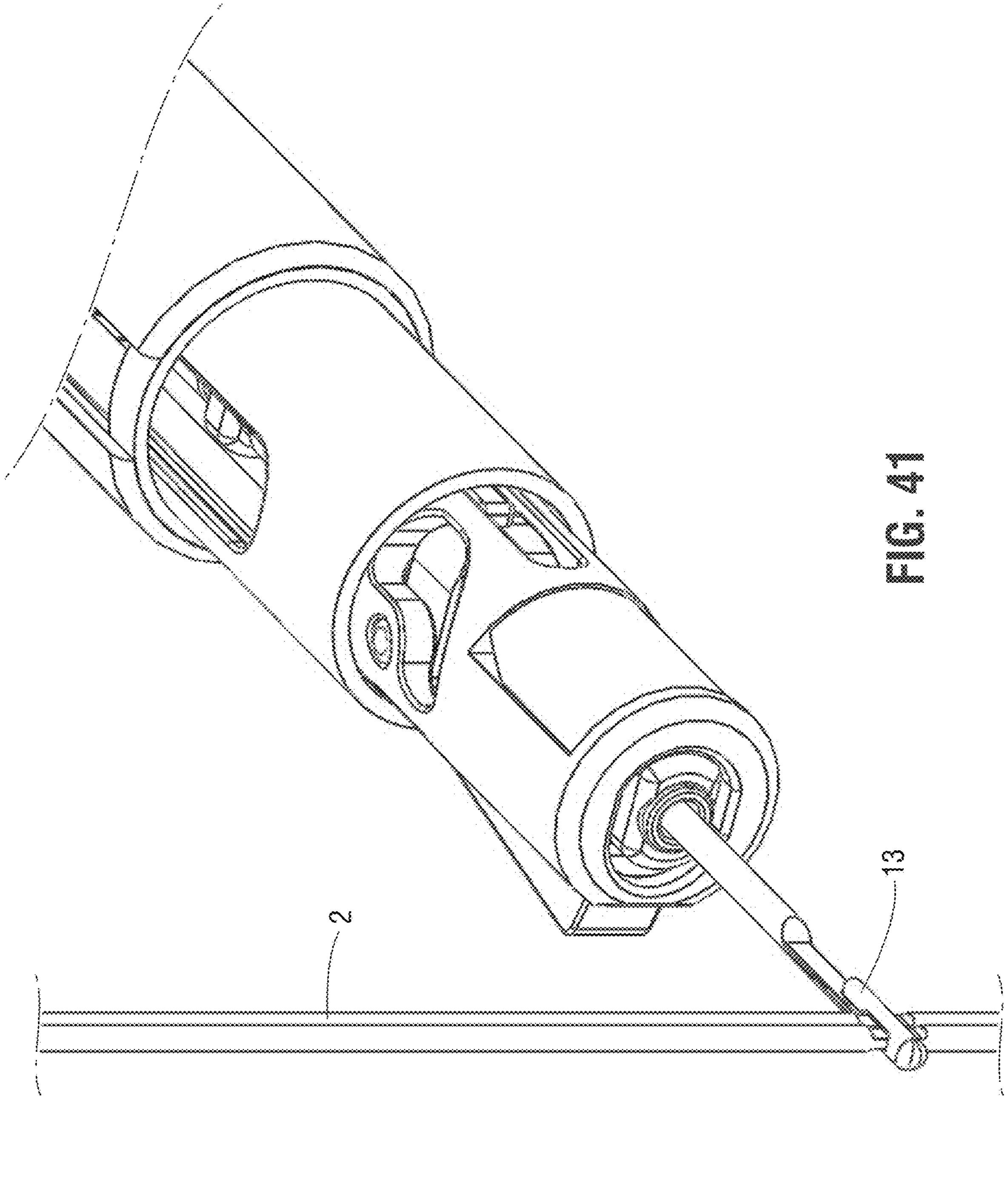
FIG. 41 is a fragmentary, enlarged perspective view of the end effector of FIG. 40 with the hook holding two leads of a suture.

An alternative to the loop 12 of the snare 10 is a hook needle configuration shown in FIGS. 39 to 41. Instead of the loop 12, the snare 10 has a hook 13 that is able to catch and hold the cords 2 as shown in FIG. 41. Like the loop 12, the hook 13 is pulled proximally until the ends 2' of the cords 2 release from the hook 13 and become loose for presentation to a user. The presentation can include the cord-lifting device 170, for example.

Figure 57:
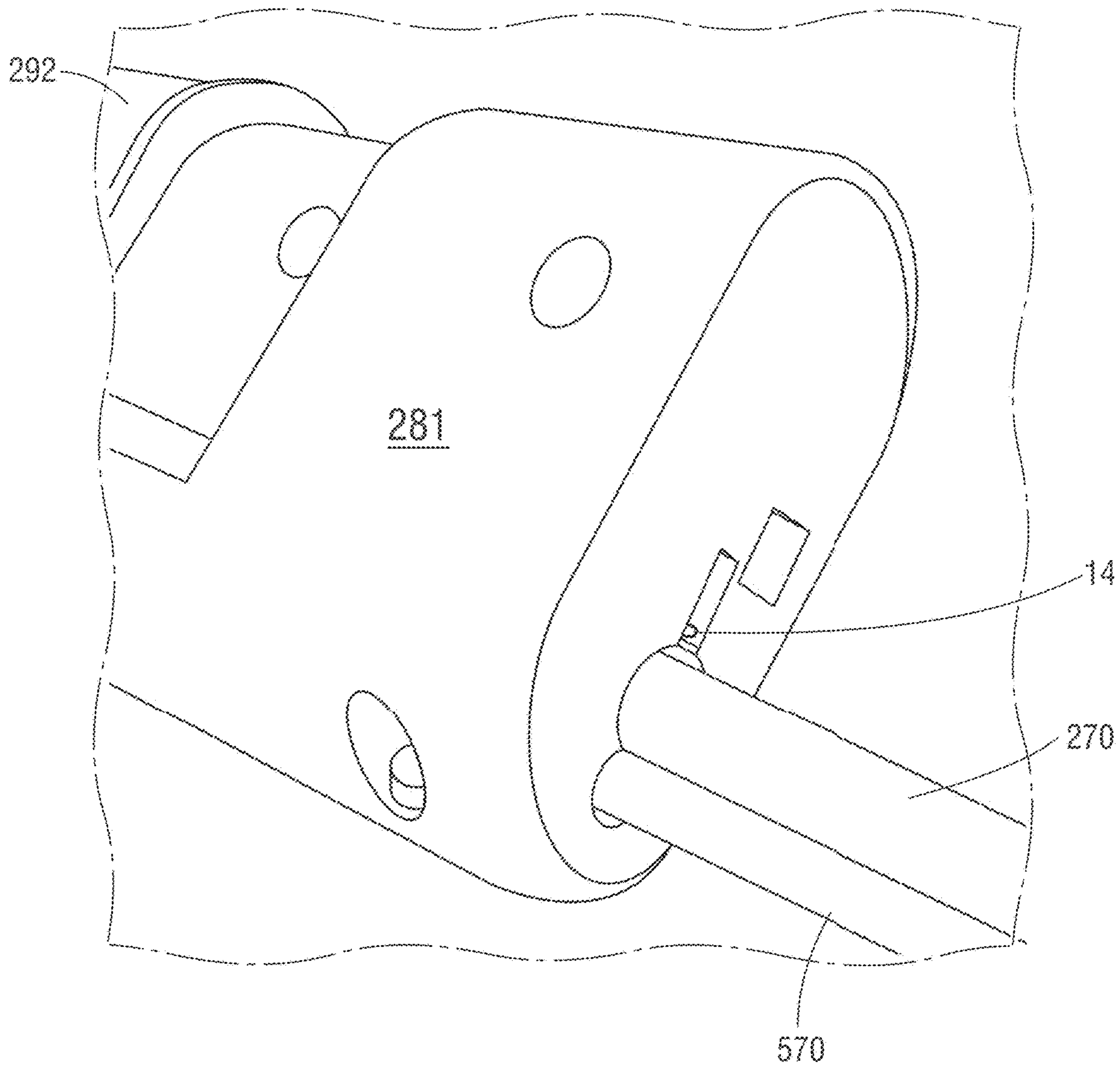
FIG. 57 is a fragmentary, perspective view of an exemplary embodiment of a shuttle for the multiple-firing crimp device of FIG. 42

Another exemplary embodiment of a multiple-firing crimp device 200 is illustrated in FIGS. 42 to 56. In this multiple-firing crimp device 200, the crimp carriage 20 and the crimps 30 along with their respective movement sub-assemblies can be similar or identical to the previous embodiments described and shown. Thus, where identical structures are present, the same reference numerals may be used herein. Different structures, in contrast, have numbers with a prefix of two hundred. In the embodiment of FIGS. 42 to 56, the movement devices for placing and operating the snare 10 are included within a shuttle 280 that is movably displaced along the outer tube 270. In order to keep the shuttle 280 rotationally aligned in one orientation about the outer tube 270, the shuttle 280 and the outer tube 270 contain an alignment structure that can take many forms. One possible form is a tongue-and-groove in which one of the shuttle 280 and the outer tube 270 has the groove and the other has the tongue. A further alignment device can attach a secondary tube or rod 570 to the bottom of the outer tube 270 and form a rail upon which a corresponding longitudinal orifice in the shuttle 280 slidably resides. In such a configuration, the cross-section of the outer tube 270 and rail can take the shape of an "8" (as shown in FIG. 57). The rail can have a different diameter than the diameter of the outer tube 270, for example, it can be smaller. Alternatively the outer tube can have a non-round profile such as an oval or a hexagon. It is noted that all of the features of the handle 100 need not be illustrated and, therefore, only a diagrammatic portion of the handle 100 is shown.

The process for completing a crimp installation is described in the transition from FIGS. 42 through 56, in which the various parts are introduced. The steps of loading the crimp 30' into the end effector body 240 and then withdrawing the crimp carriage 20 proximally for crimping is not repeated or shown here for the sake of brevity. In these figures, the crimp 30' has already been set into the end effector body 240 and is ready to be used and crimped on cords 2.

Figure 42:
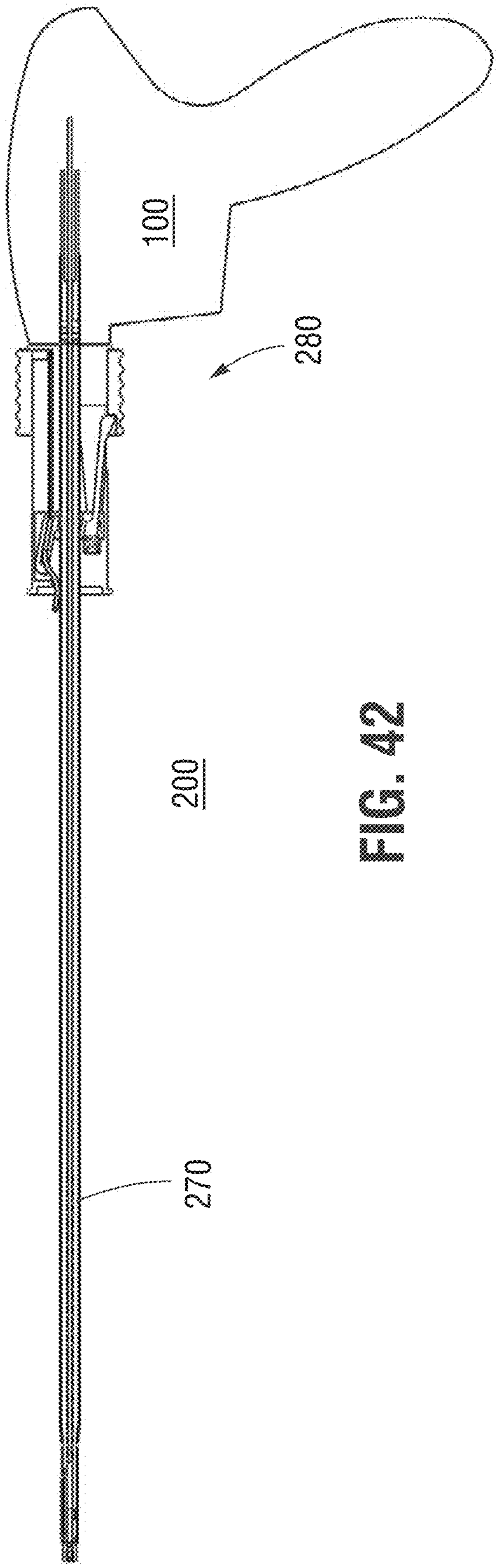
FIG. 42 is a fragmentary, longitudinally cross-sectional view of an exemplary embodiment of a multiple-firing crimp device having an end effector with a manually actuated crimp sub-assembly in a position with a first crimp loaded for use.
Figure 43:
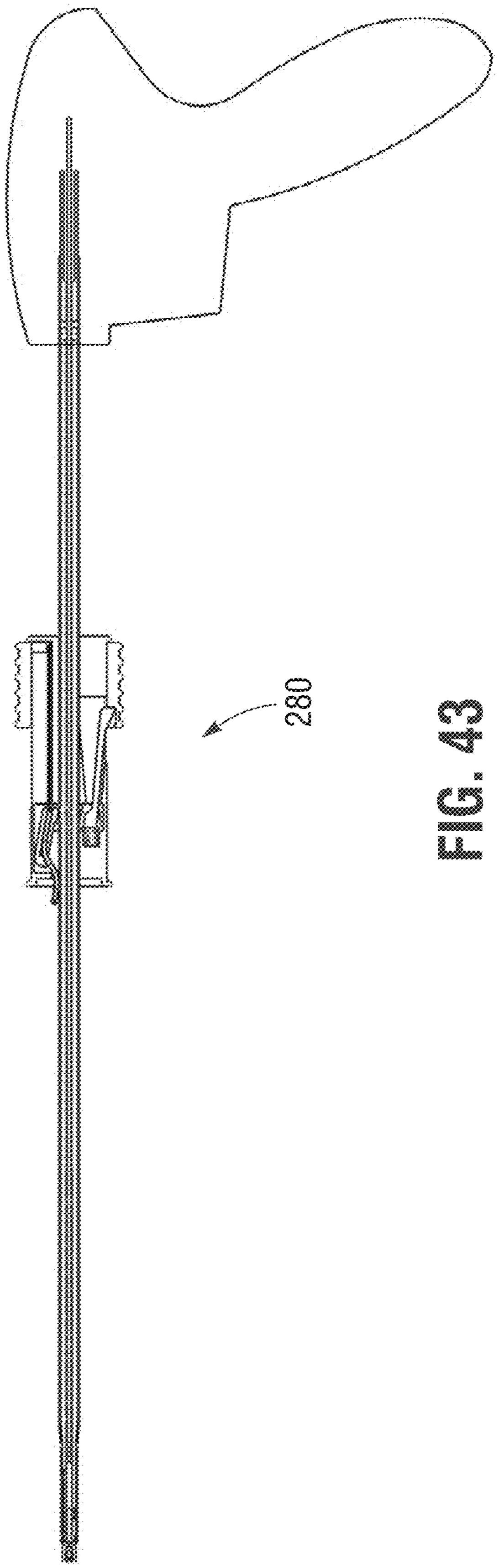
FIG. 43 is a fragmentary, longitudinally cross-sectional view of the multiple-firing crimp device of FIG. 42 with the manually actuated crimp sub-assembly in a partial snare-movement position toward the first crimp.

In FIG. 42, the manually actuated shuttle 280 is in a fully retracted position, in which position the steps of loading the crimp 30' into the end effector body 240 and then withdrawing the crimp carriage 20 proximally occurs. Accordingly, the first crimp 30' is in a position for use. FIG. 43 illustrates the shuttle 280 moving distally towards the end effector body 240. In both the fully retracted and intermediate positions almost to the distal end of the outer tube 270 (see FIGS. 44 to 48), a snare-extension tube 212 resides outside the outer tube 270.

Figure 44:
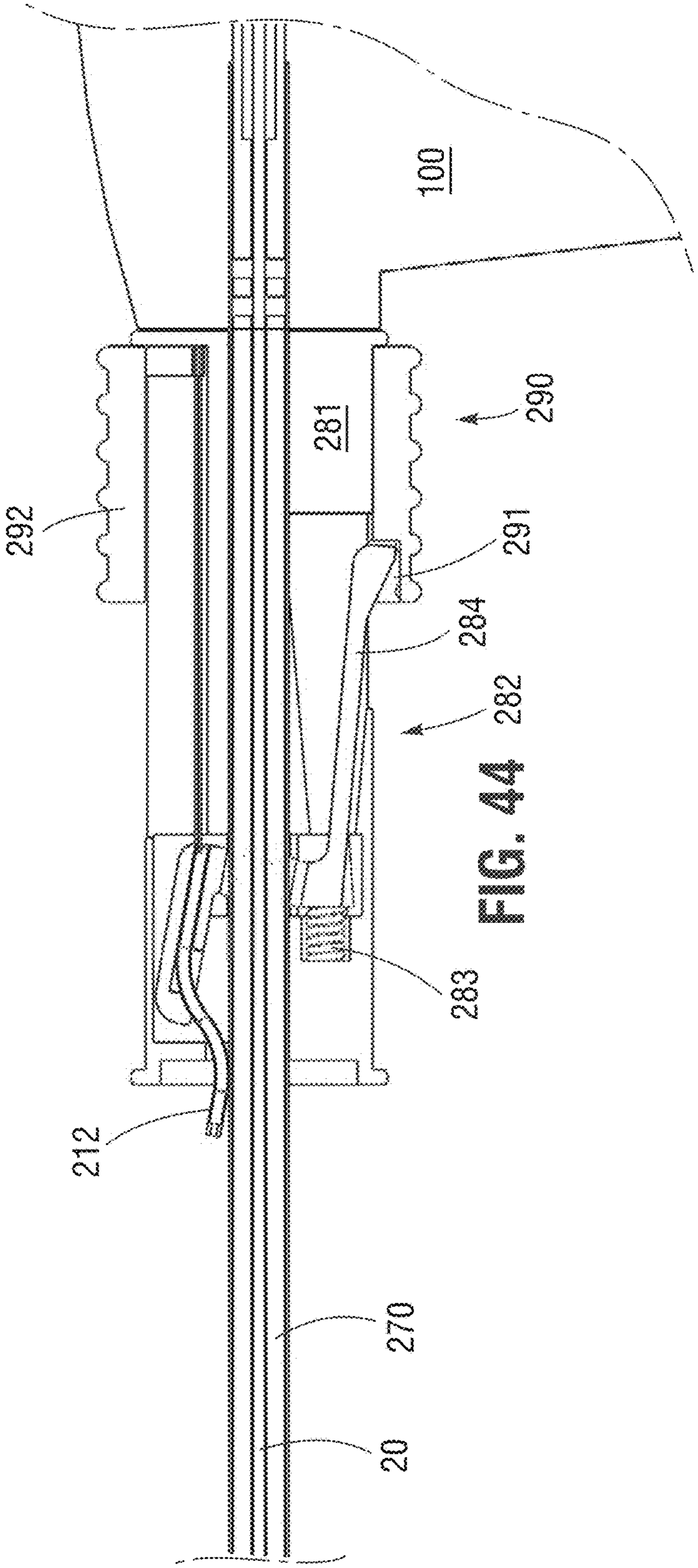
FIG. 44 is a fragmentary, enlarged, longitudinally cross-sectional view of the multiple-firing crimp device of FIG. 42.
Figure 45:
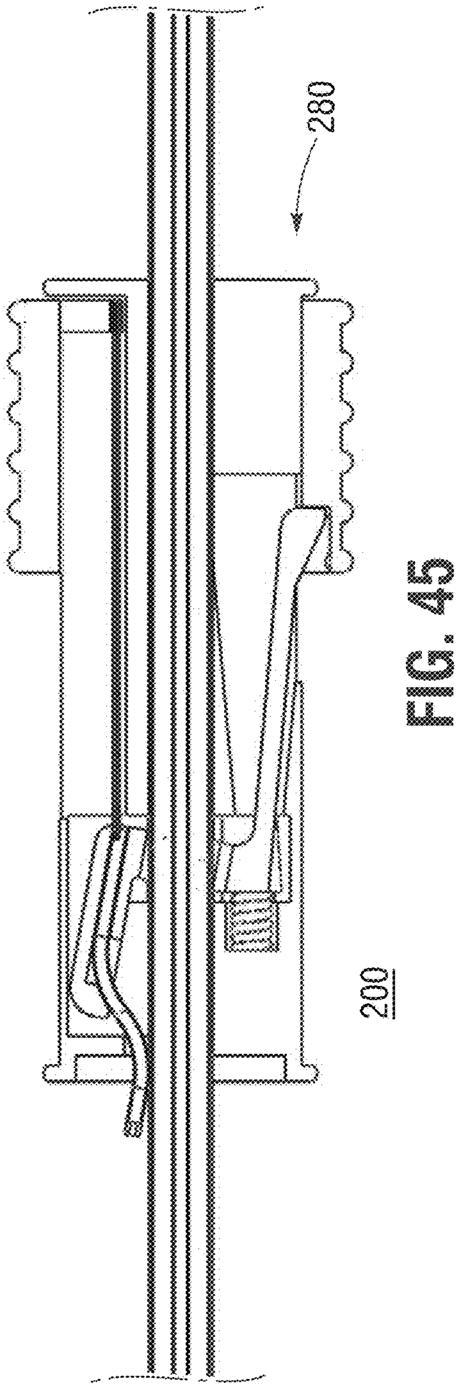
FIG. 45 is a fragmentary, enlarged, longitudinally cross-sectional view of the multiple-firing crimp device of FIG. 43.

The shuttle 280 includes a snare-aligning assembly 282 and a snare-movement assembly 290, both of which are illustrated, for example, in FIG. 44. The snare-aligning assembly 282 pivots the snare-extension tube 212 into and out of alignment with the central axis of the outer tube 270 so that the distal end of the snare-extension tube 212 can be placed adjacent or even enter the longitudinal cavity of the crimp 30' from the proximal side and, thereby, allow extension of the snare 210 directly through the crimp 30'. The pivot of the snare-aligning assembly 282 is disposed approximately at the midpoint of a vertical height of the shuttle body 281 and, because the outer tube 270 is present in these figures, the pivot is obscured from view. The pivoting action can be seen in the transition from FIG. 48 to 49. The snare-aligning assembly 282 is biased with a force from a bias device 283 that presses the snare-extension tube 212 downwards against the outer surface of the outer tube 270. In this manner, the outer surface of the outer tube 270 acts as a cam surface to the snare-extension tube 212.

Additionally, the snare-aligning assembly 282 also has a lock-out arm 284 extending proximally from the bias device 283 and residing in a pocket 291 of the snare-movement assembly 290. The lock-out arm 284 has a proximal surface that opposes the distal-facing interior surface of the pocket 291 and, when the proximal end of the lock-out arm 284 is disposed in the pocket 291, the proximal surface prevents distal longitudinal movement of a snare-extender slide 292 until the lock-out arm 284 exits the pocket 291. In this manner, until the snare-aligning assembly 282 is able to pivot the snare-extension tube 212 into alignment with the crimp 30', the snare-extender slide 292 is longitudinally fixed from moving distally.

Figure 46:
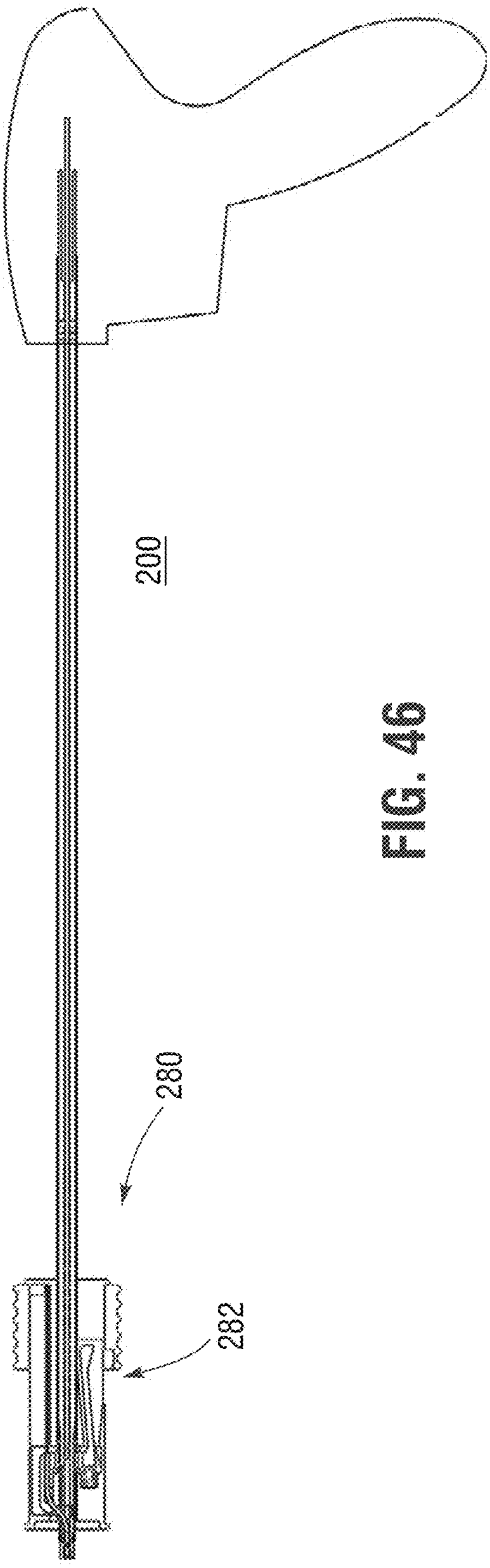
FIG. 46 is a fragmentary, longitudinally cross-sectional view of the multiple-firing crimp device of FIG. 42 with the manually actuated crimp sub-assembly lowering the snare guide tube into the snare guide tube loading track and axially aligning with the center of the first crimp.
Figure 47:
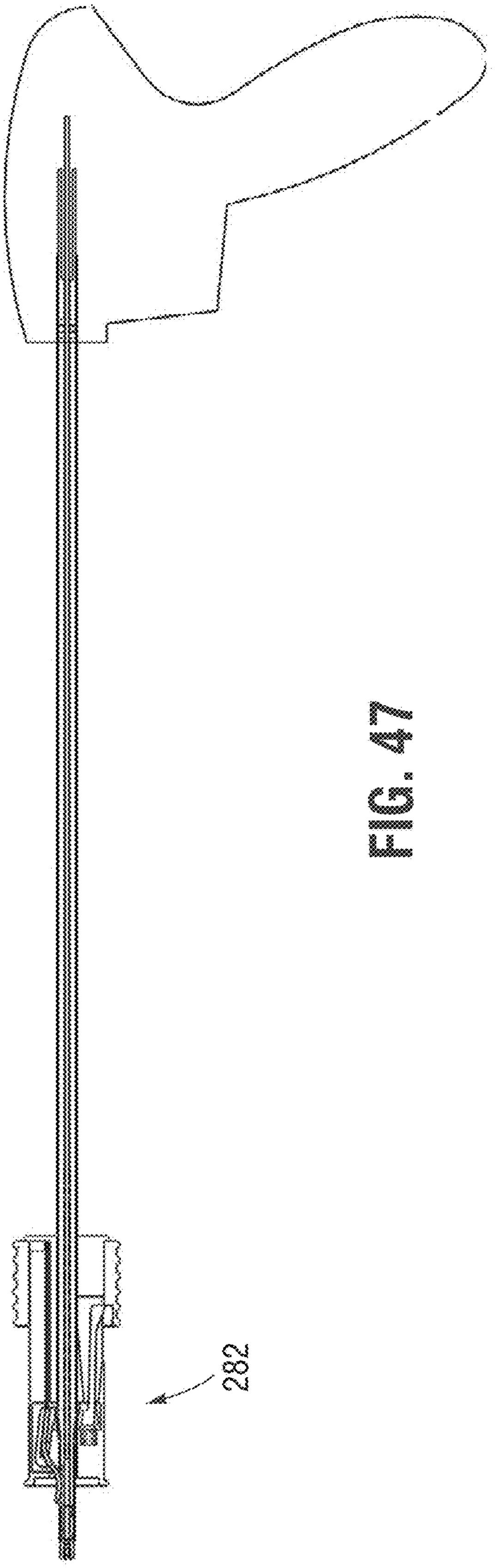
FIG. 47 is a fragmentary, longitudinally cross-sectional view of the multiple-firing crimp device of FIG. 42 with the manually actuated crimp sub-assembly inserting the snare guide tube up to the center of the first crimp for receiving therein the snare, the lowering of the snare guide tube unlocking the snare shuttle for distal movement.
Figure 48:
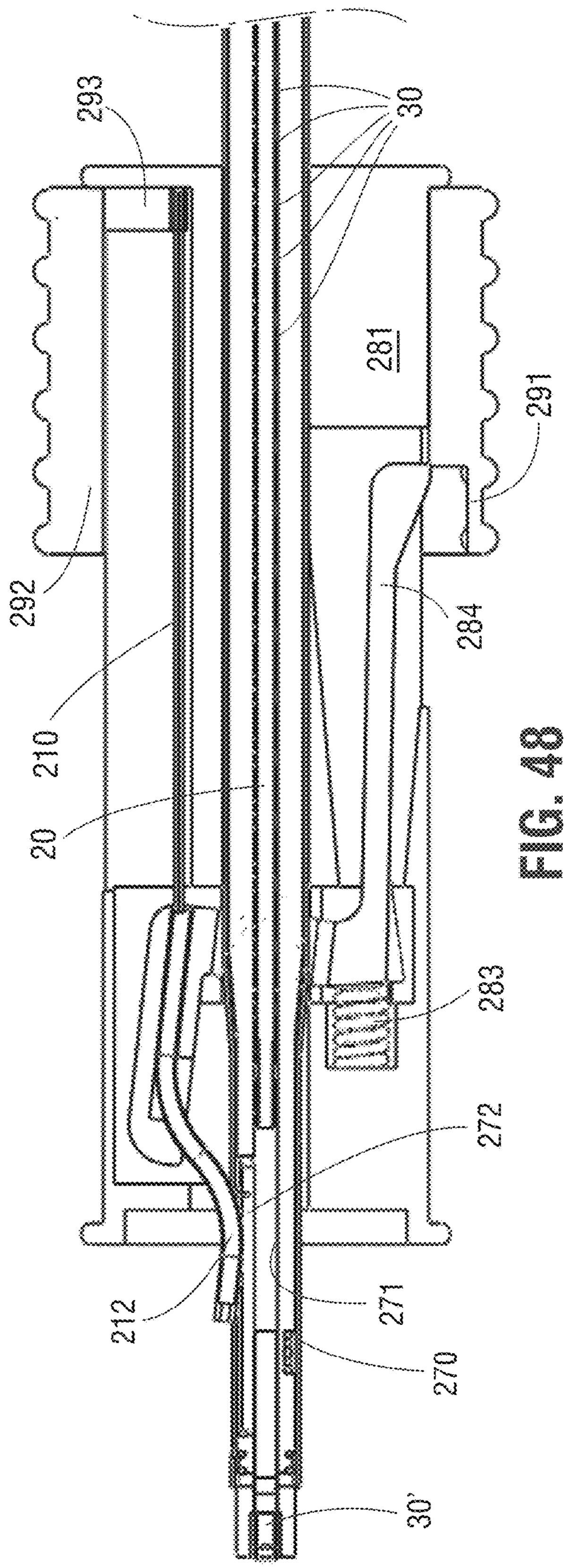
FIG. 48 is a fragmentary, enlarged, longitudinally cross-sectional view of the multiple-firing crimp device of FIG. 46.
Figure 49:
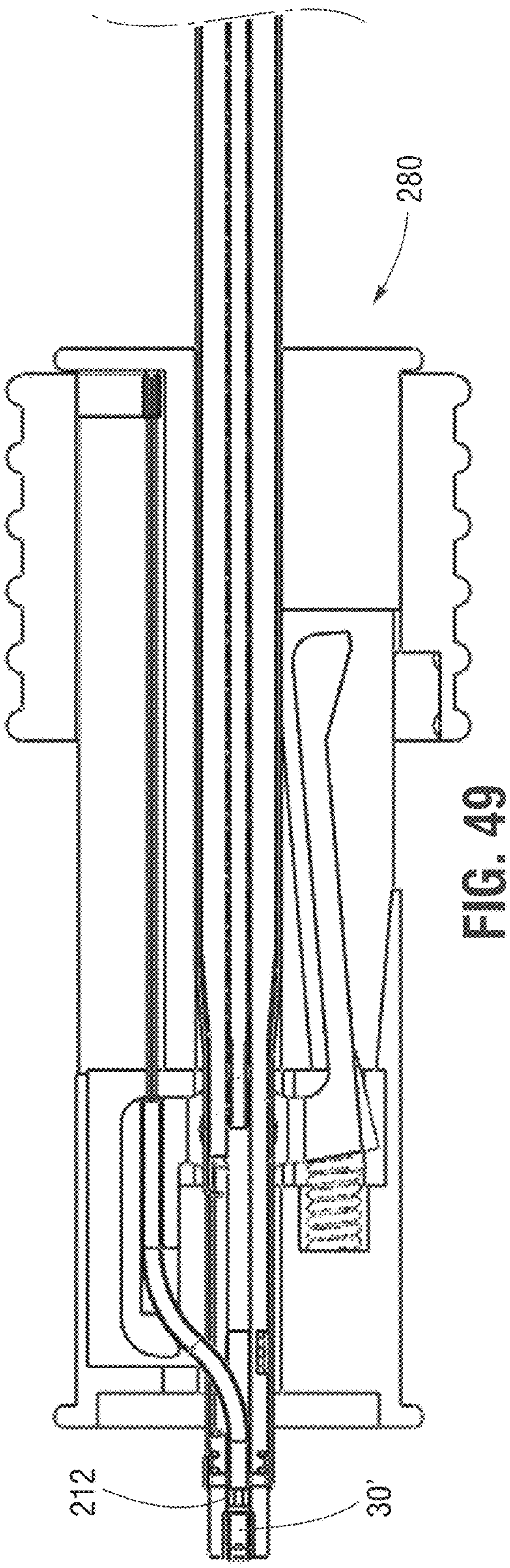
FIG. 49 is a fragmentary, enlarged, longitudinally cross-sectional view of the multiple-firing crimp device of FIG. 47.
Figure 50:
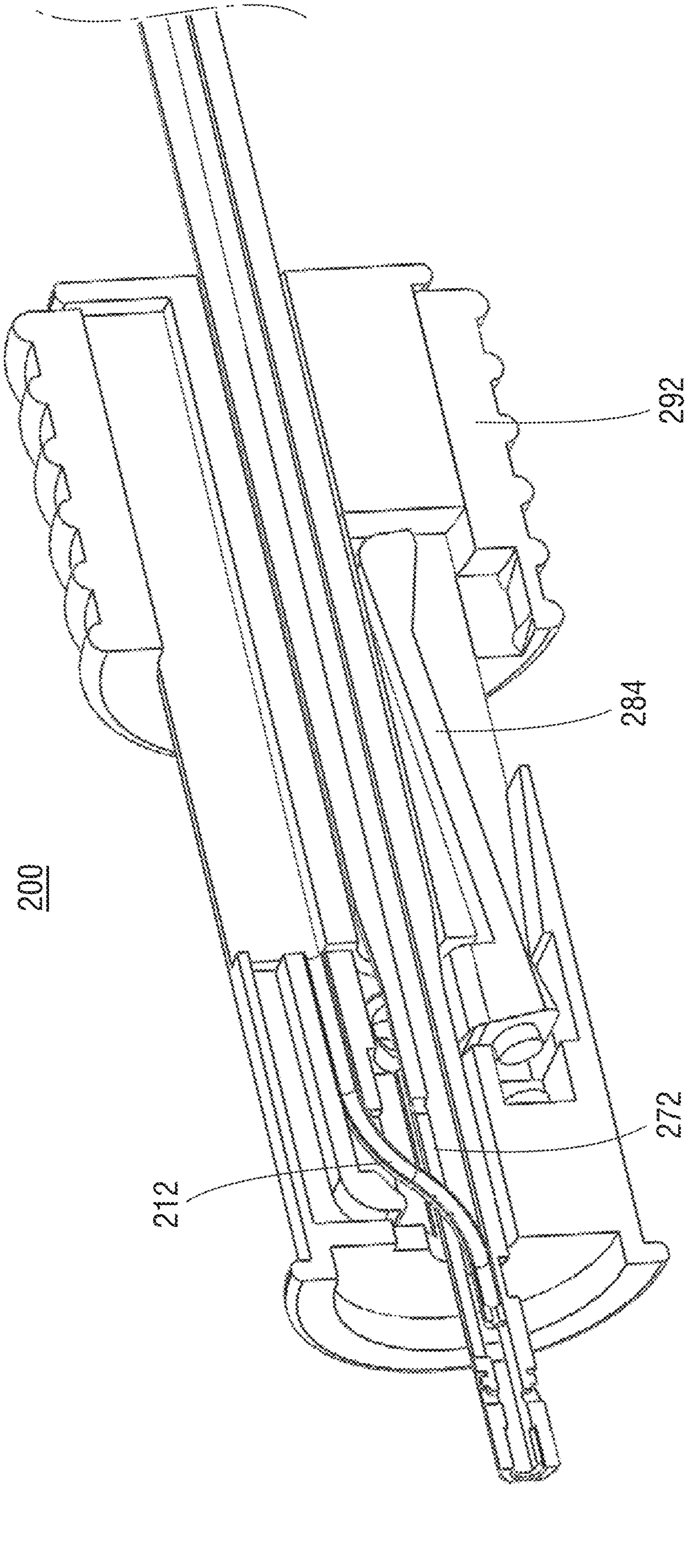
FIG. 50 is a fragmentary, enlarged, partially longitudinally cross-sectional view of the multiple-firing crimp device of FIG. 47.

FIGS. 46 and 47 illustrate the longitudinal positions of the shuttle 280 on the outer tube 270 at which the pivoting movement of the snare-aligning assembly 282 is made possible, which movement unlocks the snare-extender slide 292. FIGS. 48 and 49 are close-up views of the shuttle 280 in its respective positions in FIGS. 46 and 47. Movement of the snare-extension tube 212 is dependent upon the exterior surface of the outer tube 270. Accordingly, to allow the distal end of the snare-extension tube 212 to align with the lumen in which the crimp carriage 20 travels, the outer tube 270 has a longitudinal slot 272. The shape of the slot 272 acts as a track to guide and insert the distal end of the snare-extension tube 212 up to or into the proximal end of the crimp 30'. As such, when the shuttle 280 passes the position on the outer tube 270 shown in FIG. 48, the snare-extension tube 212 enters the slot 272 and drops against and into the inner carriage lumen 271 of the outer tube 270, as shown in FIGS. 49 and 50. When this dropping movement occurs, the pivot of the snare-aligning assembly 282 is complete and the lock-out arm 284 no longer impedes distal movement of the snare-extender slide 292. In this state, the distal opening of the snare-extension tube 212 is axially aligned with the center of the crimp 30'.

Also revealed in detail in FIGS. 48 and 49 is the crimp carriage 20 carrying a set of crimps 30. In these views, eighteen crimps 30 are illustrated. This number, however, is only exemplary and the number can be as little or as great as desired dependent upon the procedure being carried out. In these figures, the carriage lumen 271 has the polygonal shape to keep the crimps 30 aligned but this keying feature is not illustrated.

With the snare-extender slide 292 unlocked for distal movement, extension of the snare is now made possible. The snare 210 is different from the above embodiments in that the distal end is no longer connected to the handle 100. Here, in contrast, the snare 210 is connected, at its proximal end, to a tab 293 that is fixed to or integral with the snare-extender slide 292. As such, the longitudinal length of the snare 210 (or its movement shaft) is significantly shorter than those in the previous embodiments. In this manner, when the snare-extender slide 292 moves distally, the snare 210 also moves distally. In these figures, the distal portion of the snare with the loop 12 and the tip 14 are within the snare-extension tube 212 but are hidden for clarity. As the snare 210 is relatively flexible and could possibly buckle when pushed distally out of the snare-extension tube 212, a non-illustrated support tube (typically polymer based) surrounds the proximal portion of the snare 210 within the shuttle body 281. This support tube can be attached to or be integral with the extender slide 292. The length of the support tube should be such that the distal end of the support tube is not able to be freed from the proximal end of the snare-extension tube 212, thus keeping the two always aligned and preventing exit of the snare 210 from either.

Figure 51:
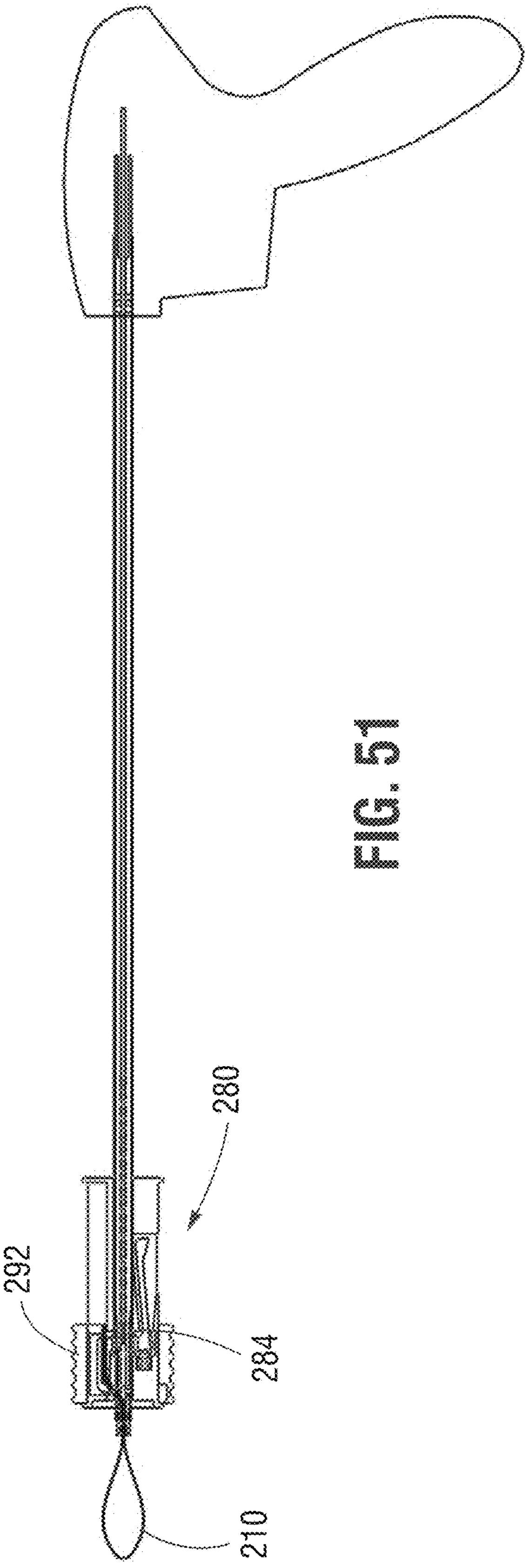
FIG. 51 is a fragmentary, longitudinally cross-sectional view of the multiple-firing crimp device of FIG. 42 with the manually actuated crimp sub-assembly extending the snare through the snare guide tube and through and out from the first crimp for receiving therein the cords to be snared, movement of the outer body being locked and only permitting movement of the snare shuttle for snare movement.
Figure 52:
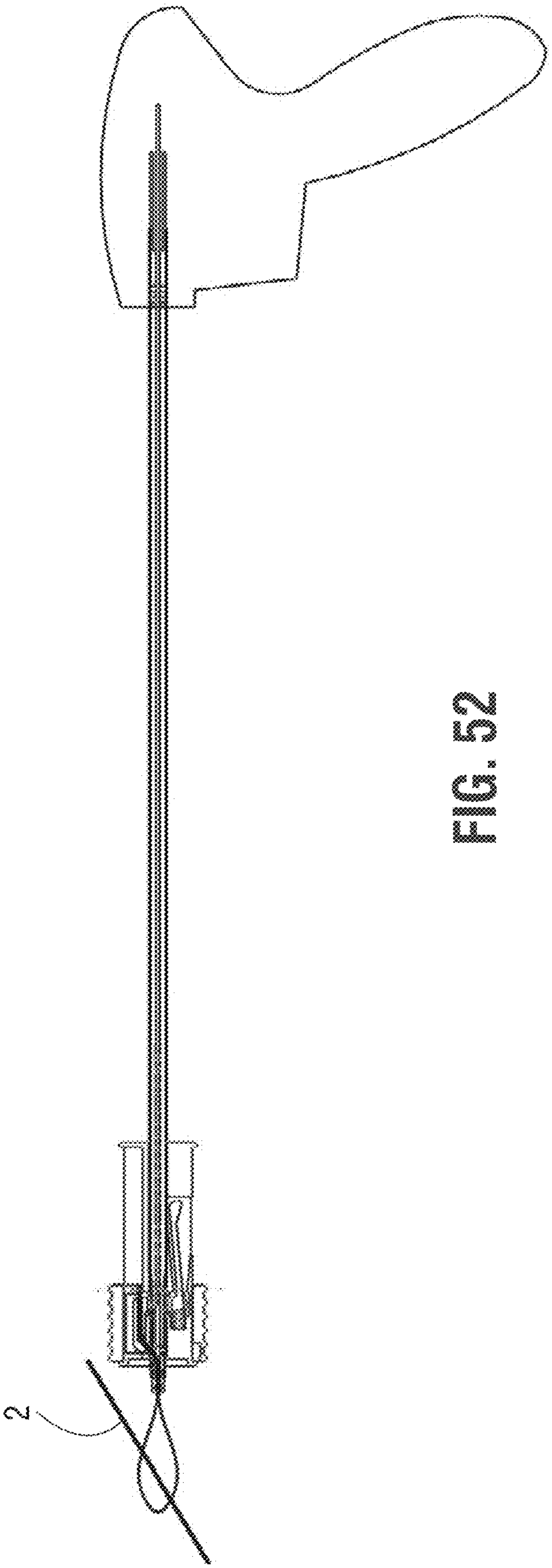
FIG. 52 is a fragmentary, longitudinally cross-sectional view of the multiple-firing crimp device of FIG. 51 with cords in the snare.
Figure 53:
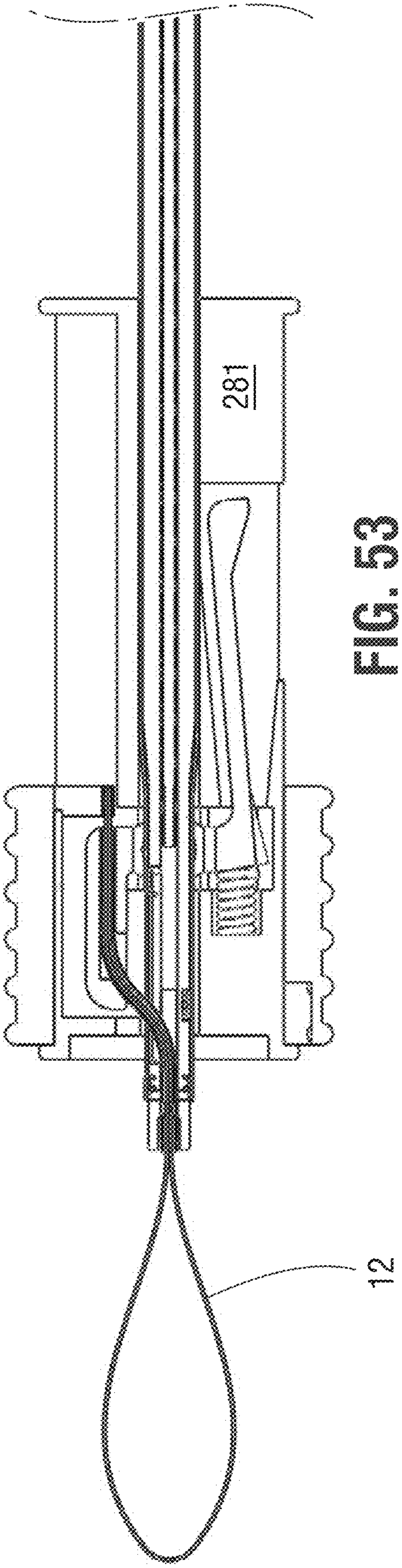
FIG. 53 is a fragmentary, enlarged, longitudinally cross-sectional view of the multiple-firing crimp device of FIG. 51.
Figure 54:
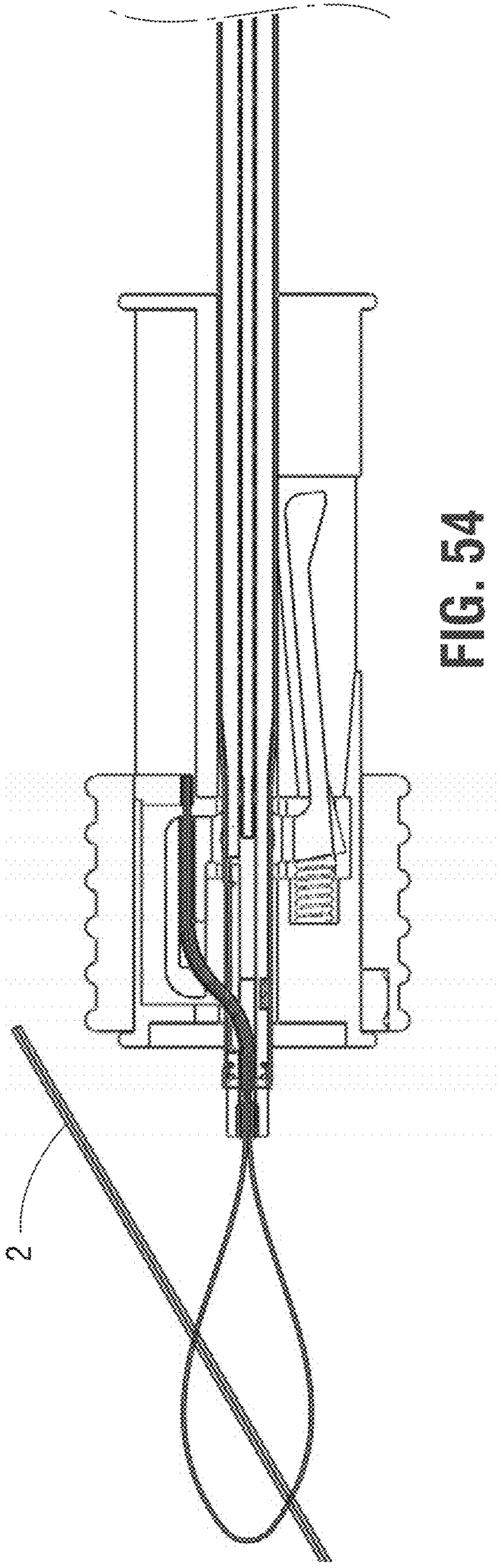
FIG. 54 is a fragmentary, enlarged, longitudinally cross-sectional view of the multiple-firing crimp device of FIG. 52.
Figure 55:
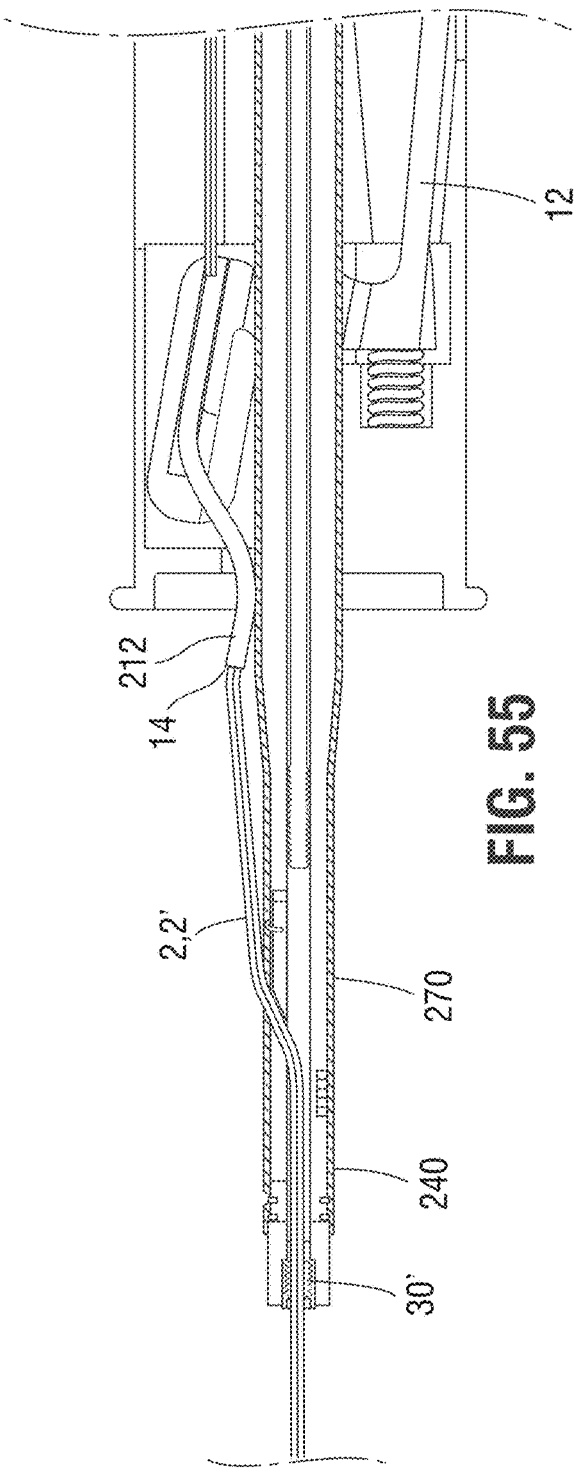
FIG. 55 is a fragmentary, enlarged, longitudinally cross-sectional view of the multiple-firing crimp device of FIG. 42 with the manually actuated crimp sub-assembly having retracted the snare and the cords along with the snare guide tube out from the distal end of the shaft assembly and having pulled the cords through the first crimp, movement of the outer body being free in the proximal direction and movement of the snare shuttle being free to retract the snared cords.
Figure 56:
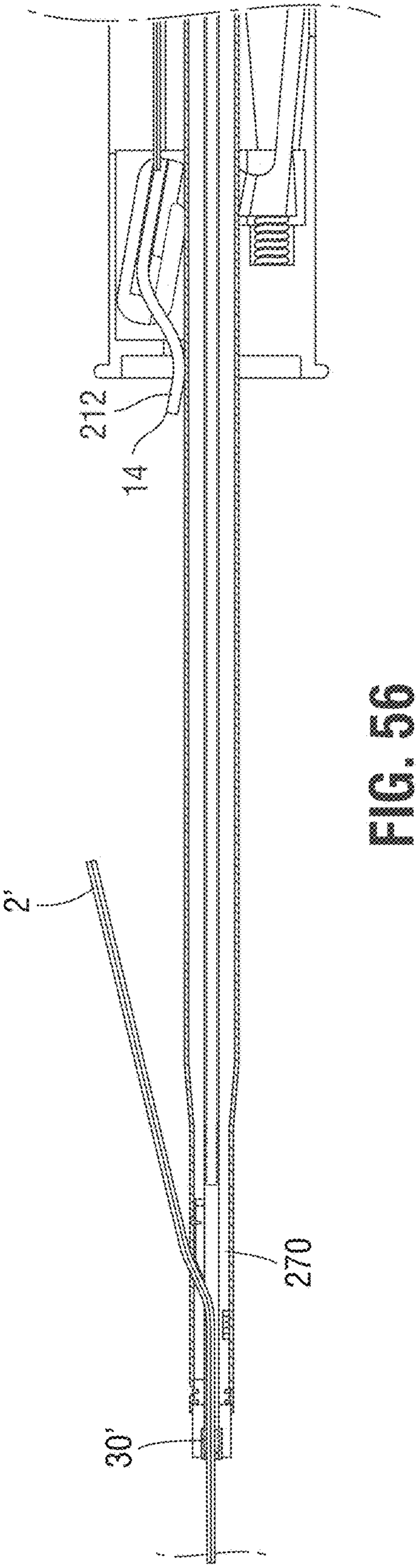
FIG. 56 is a fragmentary, enlarged, longitudinally cross-sectional view of the multiple-firing crimp device of FIG. 42 with the manually actuated crimp sub-assembly having completely retracted the snare from the cords to allow a user to manually pull the free ends of the previously snared suture tight and to place the crimp adjacent to the loop of the cords where crimping is to take place after the user pulls tightly on the cords to place the distal end of the device at the cord-tying location.

The snare 210 can now be extended, as shown in FIGS. 51 and 53. As the snare-extender slide 292 moves distally, the distal end of the snare 210 emerges from inside the crimp 30' and finally exits to the environment distal of the shuttle 280 so that the loop 12 opens to define an area into which the cords 2 are inserted, as shown in FIGS. 52 and 54. In FIGS. 51 to 54, the tip 14 of the snare 210 is not illustrated for clarity.

It is undesirable for the shuttle 280 to move longitudinally in any way while the snare 210 is moving distally from the position shown in FIGS. 49 and 50. Accordingly, movement of the shuttle body 281 is locked when the snare-extender slide 292 moves. Such a movement prevention device is not illustrated in FIGS. 42 to 56, but there is one shown in FIG. 60, in which a spring clip 590 engages an opening in the shaft 270 (or 570) when the shuttle is in its distal-most snare-extending position. The motion of the spring clip 590 into the opening frees the snare-extender slide 292, allowing it to now move distally while simultaneously locking the shuttle 280 in the snare-extending position.

Once the cords 2 are inserted into the exposed and expanded loop 12 of the snare 10, retraction of the cords 2 through the center of the crimp 30' is now possible. To effect this retraction, the user moves the snare-extender slide 292 proximally, in which position all but the tip 14 is retracted back into the shuttle body 281, as shown in FIG. 57. The orientation of the tip 14 while the snare-extender slide 292 is in it proximal-most position is illustrated in FIG. 57. At this point, a portion or all of the free ends of the cords 2 are still within the end effector body 240 or are distal of the crimp 30' while the cords 2 are threaded through the tip 14. Now that the snare-extender slide 292 is proximal, proximal movement of the shuttle body 281 becomes possible given the fact that the spring clip 590 is free to flex back to its home position outside the opening in the shaft 270, 570 (because the interlock holding the shuttle body 281 has disengaged). The user continues retraction of the shuttle 280 with the snare and the coupled cords 2 proximally until the free ends 2' pass entirely through the crimp 30', exit the shaft through slot 272, completely shorten, and finally exit the tip 14, as is shown in the transition from FIG. 55 to FIG. 56.

At this point, the user is presented with the free ends 2' outside the outer tube 270 and is now able to manually pull the free ends 2' of the previously snared cords 2 tight and place the crimp 30' adjacent to the distal loop of the cords 2 (not illustrated but to the left of FIG. 56) where crimping is to take place. While pulling tightly on the free ends 2' of the cords 2, the user can place the distal end of the device where the crimp 30' is being held at a cord-fixing location. Actuation devices of the handle 100 (as described above) cause the crimp 30' to compress on and fix the cords 2 together and, thereafter, also cut the cords 2 just proximal of the crimped crimp 30'. The shuttle 280 is moved to its start position shown in FIGS. 42 and 44, thereby placing the device in a position to load the next crimp 30" into the crimp orifice 42.

The snare 10 is secured at its proximal end to the snare-extender slide 292 (e.g., at tab 293) positioned adjacent the proximal end of the shuttle 280. Because the travel distance of the snare-extender slide 292 is greater than or equal to the length of the snare that is to extend outward from the shuttle 280 in the distal direction, the shuttle 280 must have a longitudinal length that is dependent upon and is at least as long as the length of that snare. In other words, the extension of the snare 10 by the snare-extender slide 292 is 1:1. If the length of the shuttle 280 requires it to have significant weight or to have a length that is greater than is needed, it would be desirable to provide an assembly that permits a greater than 1:1 ratio and reduces the longitudinal length and/or weight.

Figure 58:
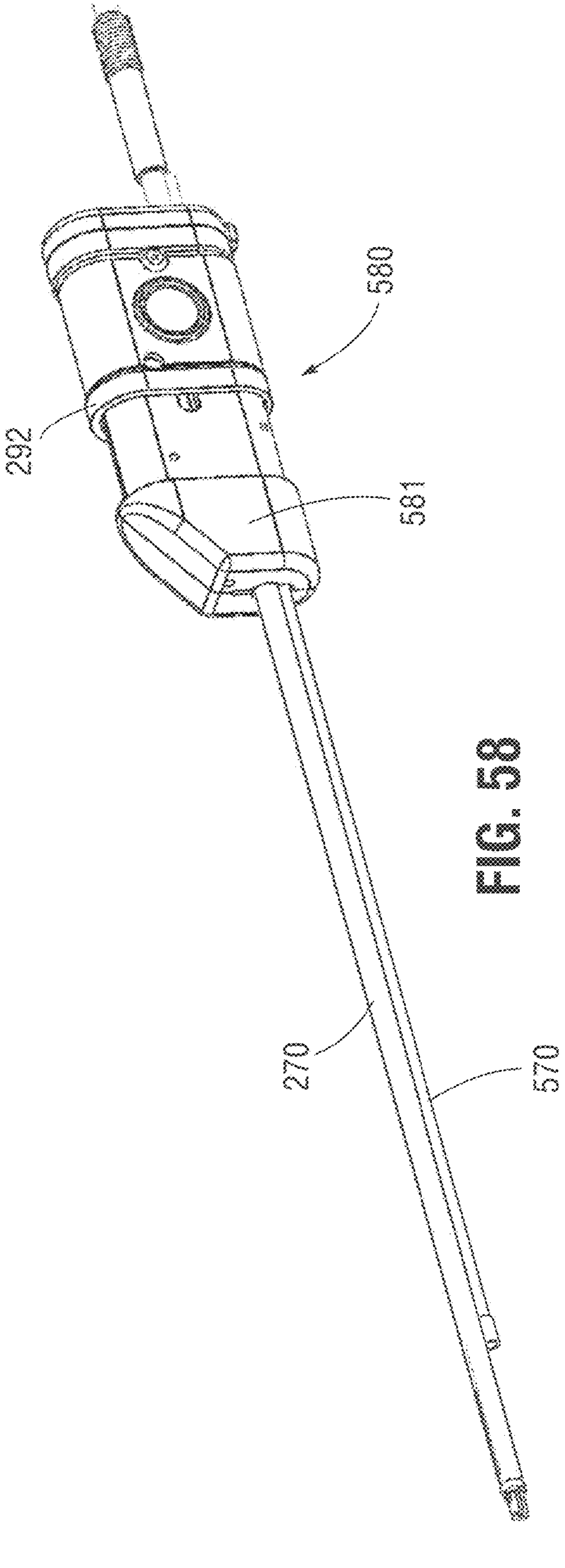
FIG. 58 is a fragmentary, perspective view of an exemplary embodiment of a multiple-firing crimp device having an end effector with a manually actuated crimp sub-assembly in a position with a first crimp loaded for use, with a shuttle in a ready to use state, and with a handle removed.

In the embodiments of FIGS. 58 to 74, the movement devices for placing and operating the snare 10 are included within a shuttle 580 that is movably displaced along the outer tube 270. This shuttle 580 is able to be shorter and lighter than the shuttle 280. To keep the shuttle 580 rotationally aligned in one orientation about the outer tube 270, the shuttle 580 and the outer tube 270 contain an alignment structure that can take many forms. One possible form is a tongue-and-groove in which one of the shuttle 580 and the outer tube 270 has the groove and the other has a tongue. A further alignment device can attach a secondary tube or rod 570 to the bottom of the outer tube 270 and form a rail upon which a corresponding longitudinal orifice in the shuttle 580 slidably resides. In such a configuration, as shown in FIG. 58, the cross-section of the outer tube 270 and the rail 570 takes the shape of an "8". As above, the rail 570 can have a different diameter than the diameter of the outer tube 270, for example, it can be smaller. It is noted here that all of the features of the handle 100 need not be illustrated here and, therefore, the handle 100 is omitted.

The shuttle 580 depicted in FIGS. 58 to 74 provides a snare extension to slide movement length in a ratio that is greater than 1:1 and, at the same time, reduces the longitudinal length and weight of the shuttle 580. These features are provided by removing the longitudinal tube fixed to the snare-movement slide and replacing it with a rack-and-pinion snare-movement assembly having the snare wrapped around a snare discharge spool. In this shuttle 580 for the multiple-firing crimp devices herein, the crimp carriage 20 and the crimps 30 along with their respective movement sub-assemblies can be similar or identical to the previous embodiments described and shown. Thus, where identical structures are present, the same reference numerals will be used herein. Different structures, in contrast, will have numbers with a prefix of five hundred.

Figure 59:
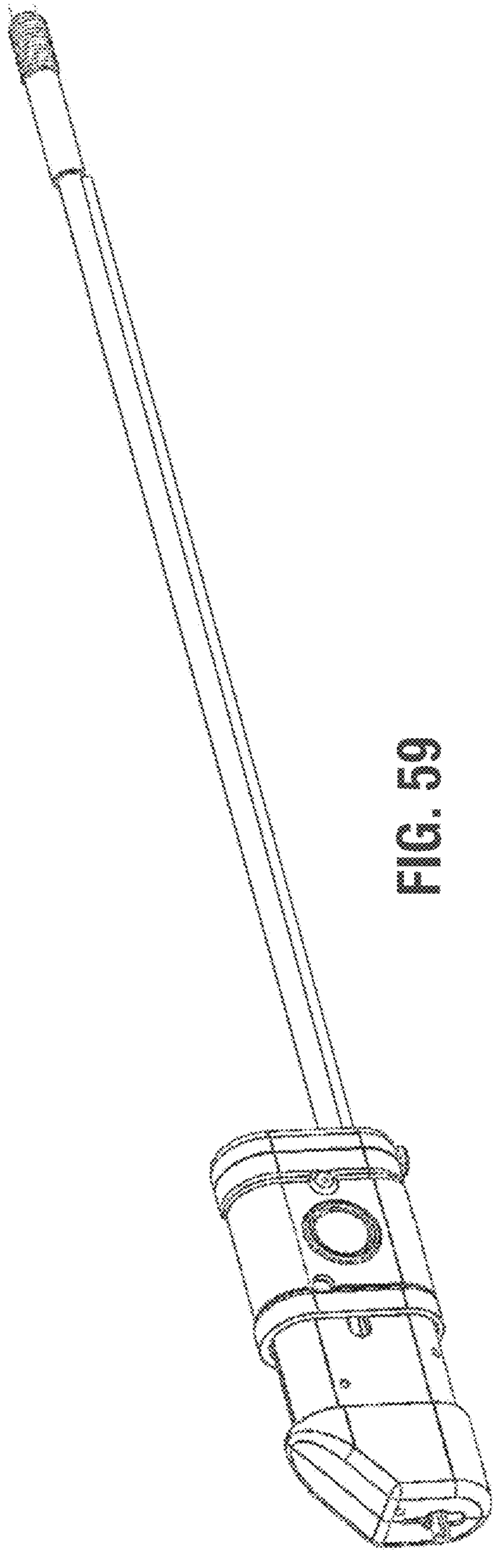
FIG. 59 is a fragmentary, perspective view of the multiple-firing crimp device of FIG. 58 with the manually actuated crimp sub-assembly with the shuttle in a snare-movement position.
Figure 60:
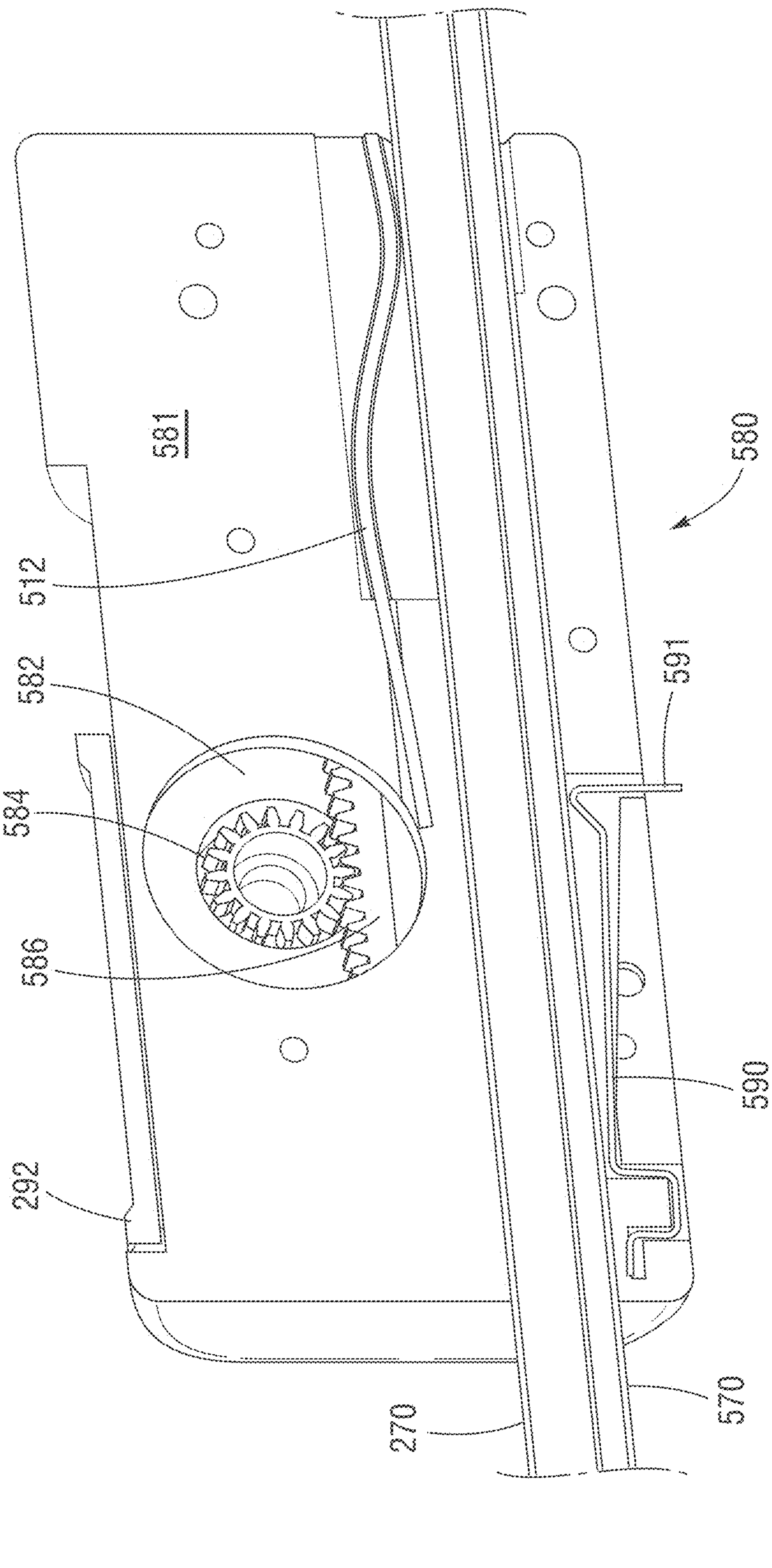
FIG. 60 is a fragmentary, enlarged, longitudinally cross-sectional view of the multiple-firing crimp device of FIG. 58 with the shuttle in an intermediate position between the handle and the crimp and with a snare scroll removed.
Figure 61:
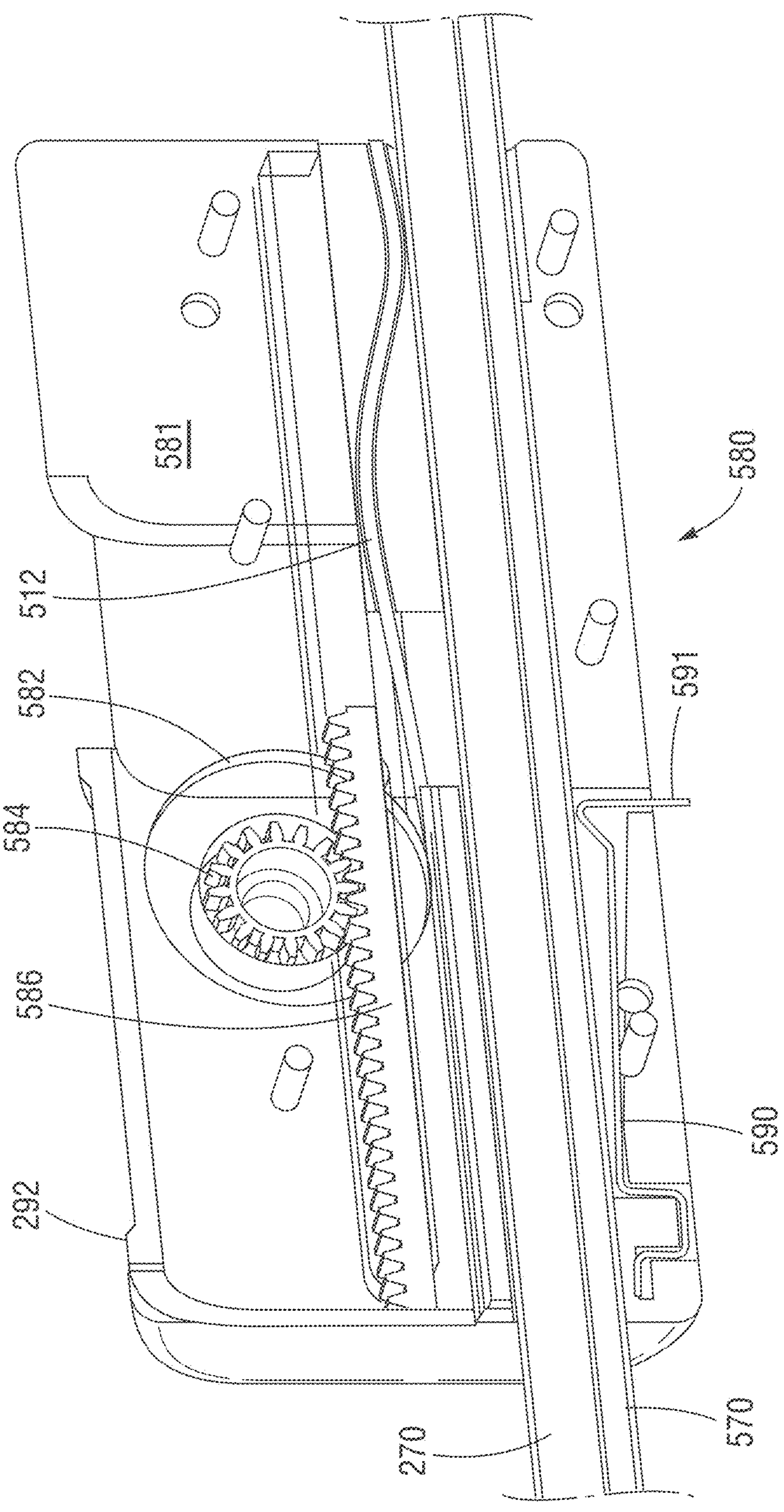
FIG. 61 is a fragmentary, enlarged, partially transparent, longitudinally cross-sectional view of the multiple-firing crimp device of FIG. 58 with the shuttle in an intermediate position between the handle and the crimp and with the snare scroll removed.
Figure 62:
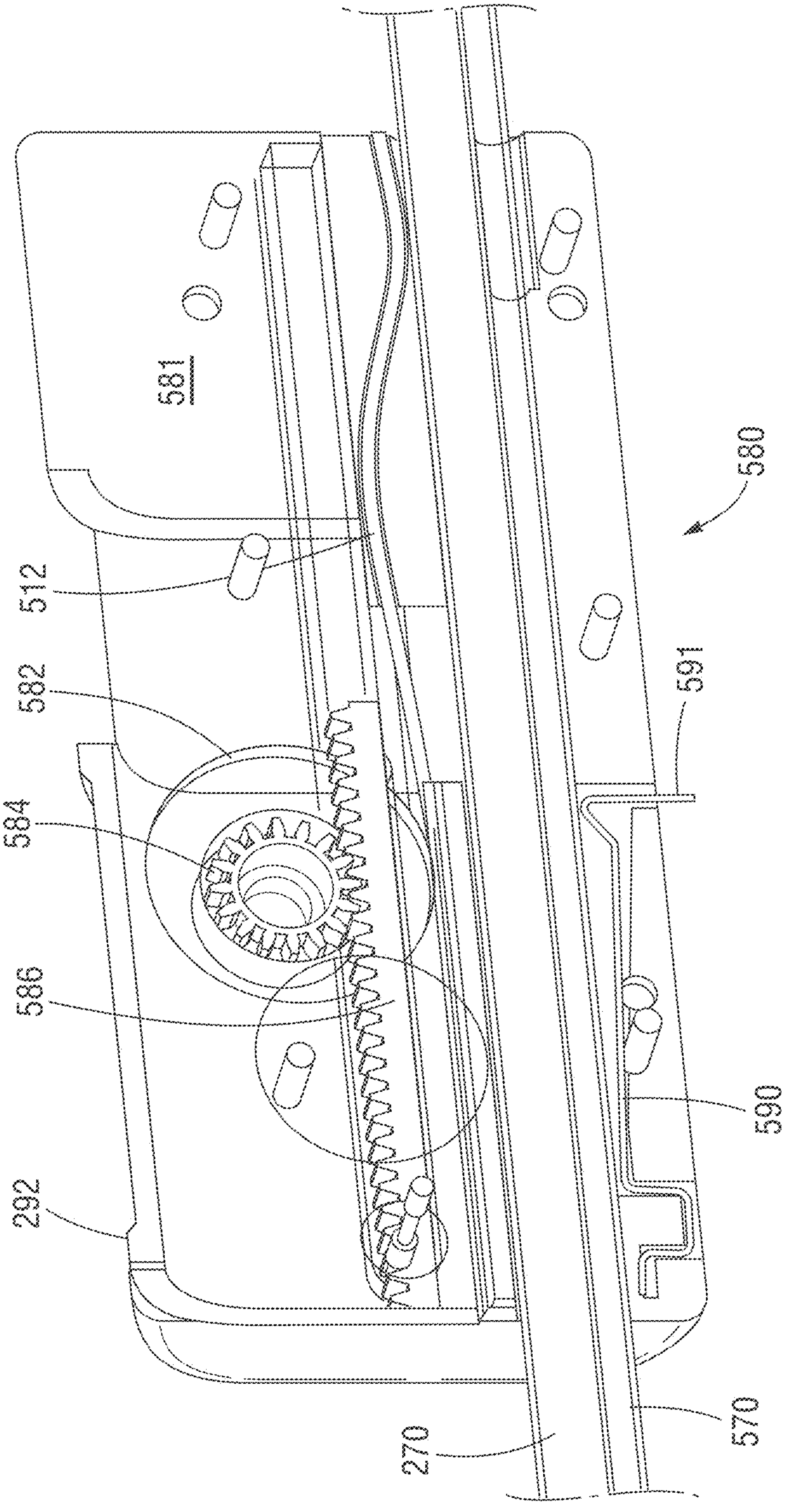
FIG. 62 is a fragmentary, enlarged, transparent, longitudinally cross-sectional view of the multiple-firing crimp device of FIG. 58 with the shuttle in an intermediate position between the handle and the crimp and with the snare scroll removed.
Figure 63:
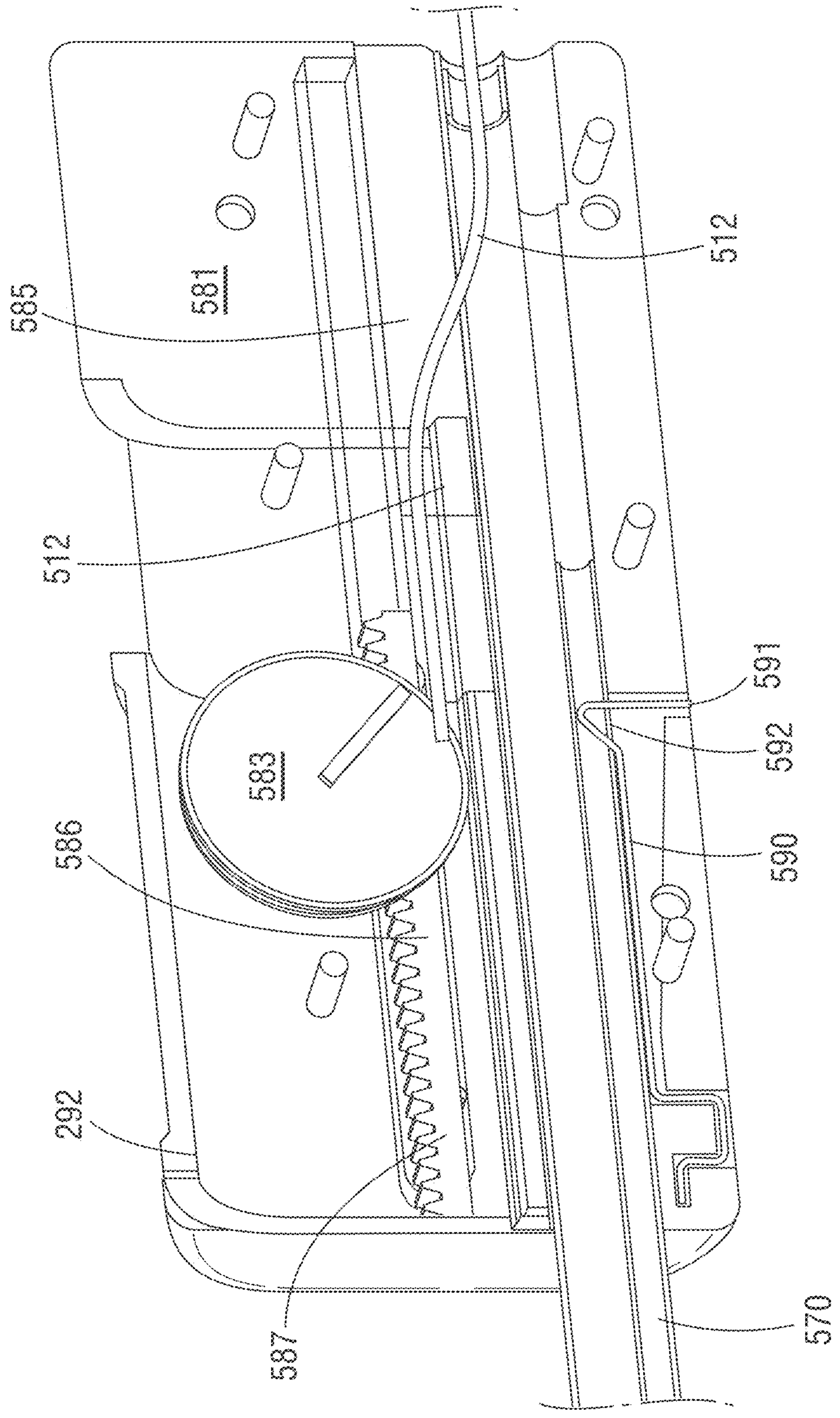
FIG. 63 is a fragmentary, enlarged, partially transparent, longitudinally cross-sectional view of the multiple-firing crimp device of FIG. 59 with the shuttle in a snare-movement position.
Figure 64:
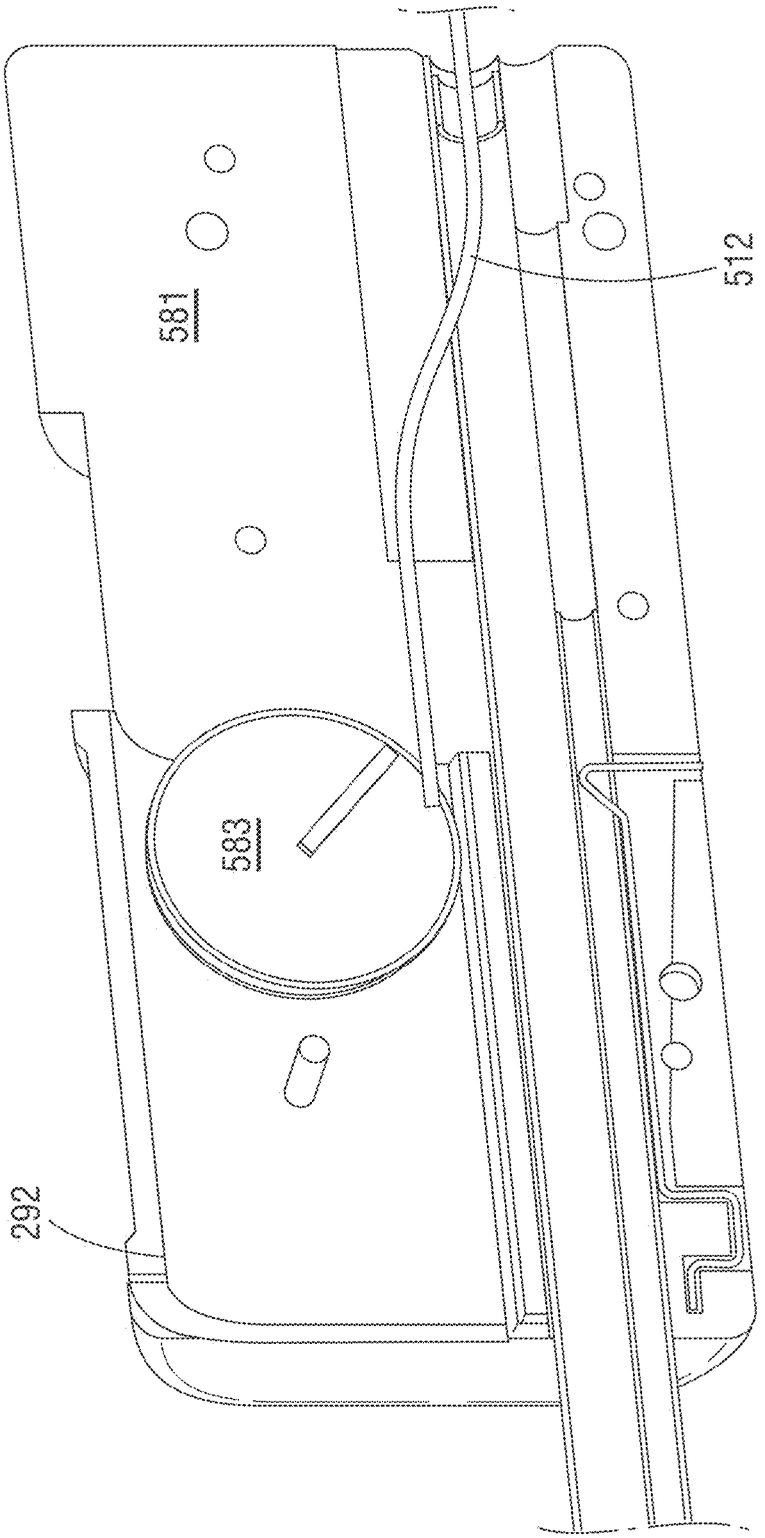
FIG. 64 is a fragmentary, enlarged, longitudinally cross-sectional view of the multiple-firing crimp device of FIG. 59 with the shuttle in the snare-movement position.
Figure 65:
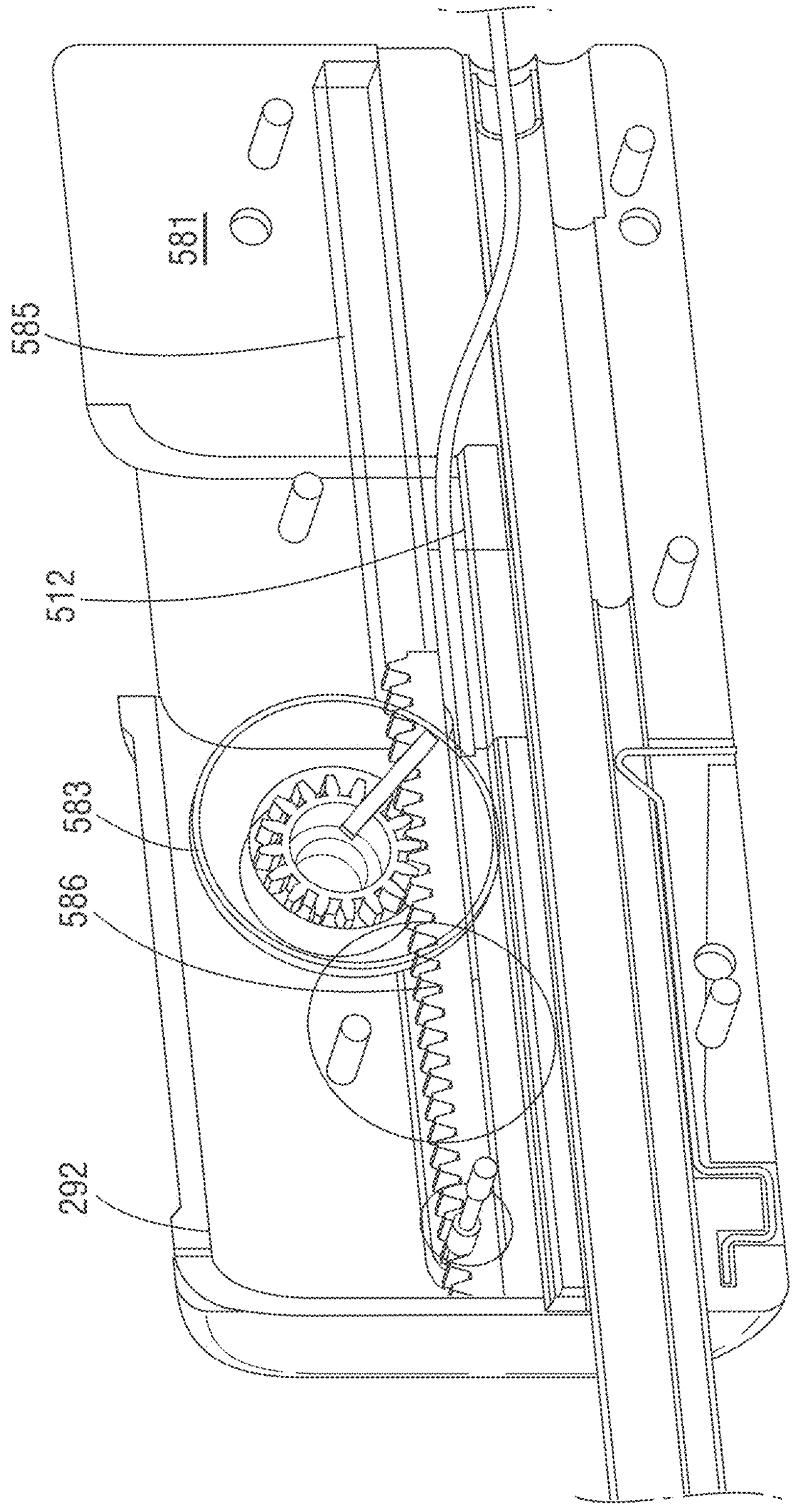
FIG. 65 is a fragmentary, enlarged, transparent, longitudinally cross-sectional view of the multiple-firing crimp device of FIG. 59 with the shuttle in the snare-movement position.
Figure 66:
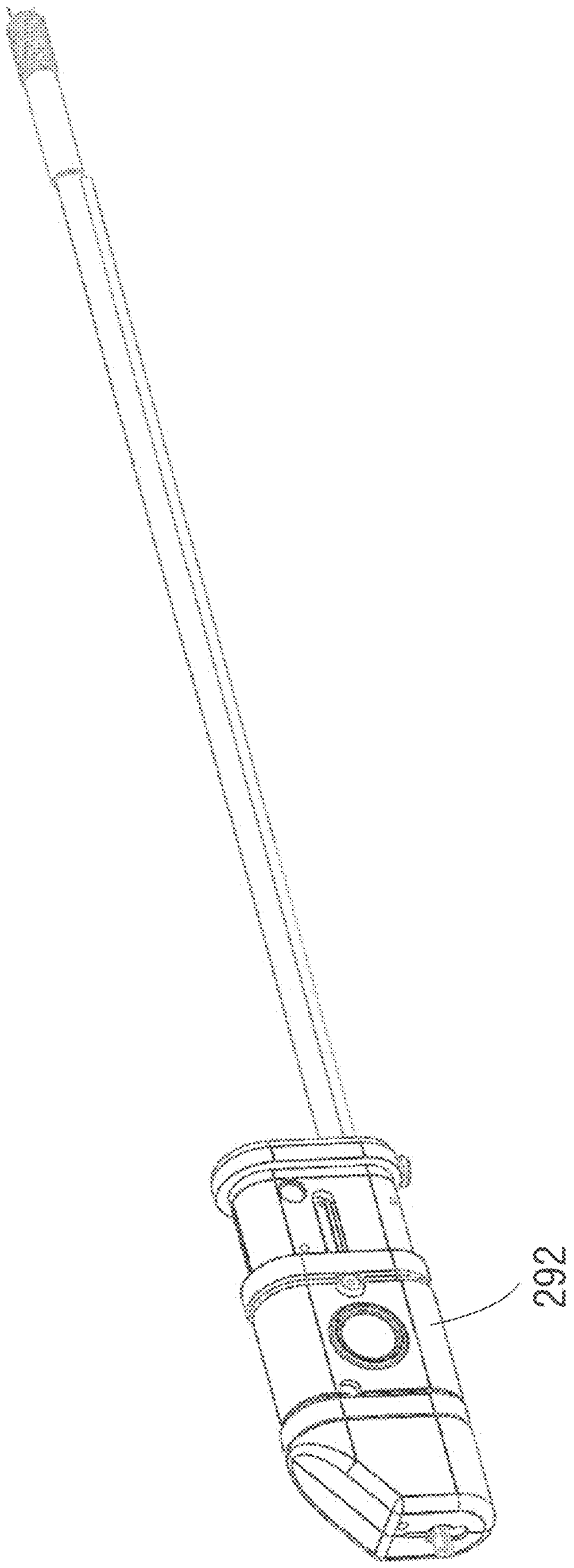
FIG. 66 is a fragmentary, perspective view of the multiple-firing crimp device of FIG. 58 with the manually actuated crimp sub-assembly with the shuttle in a snare-extended position.
Figure 67:
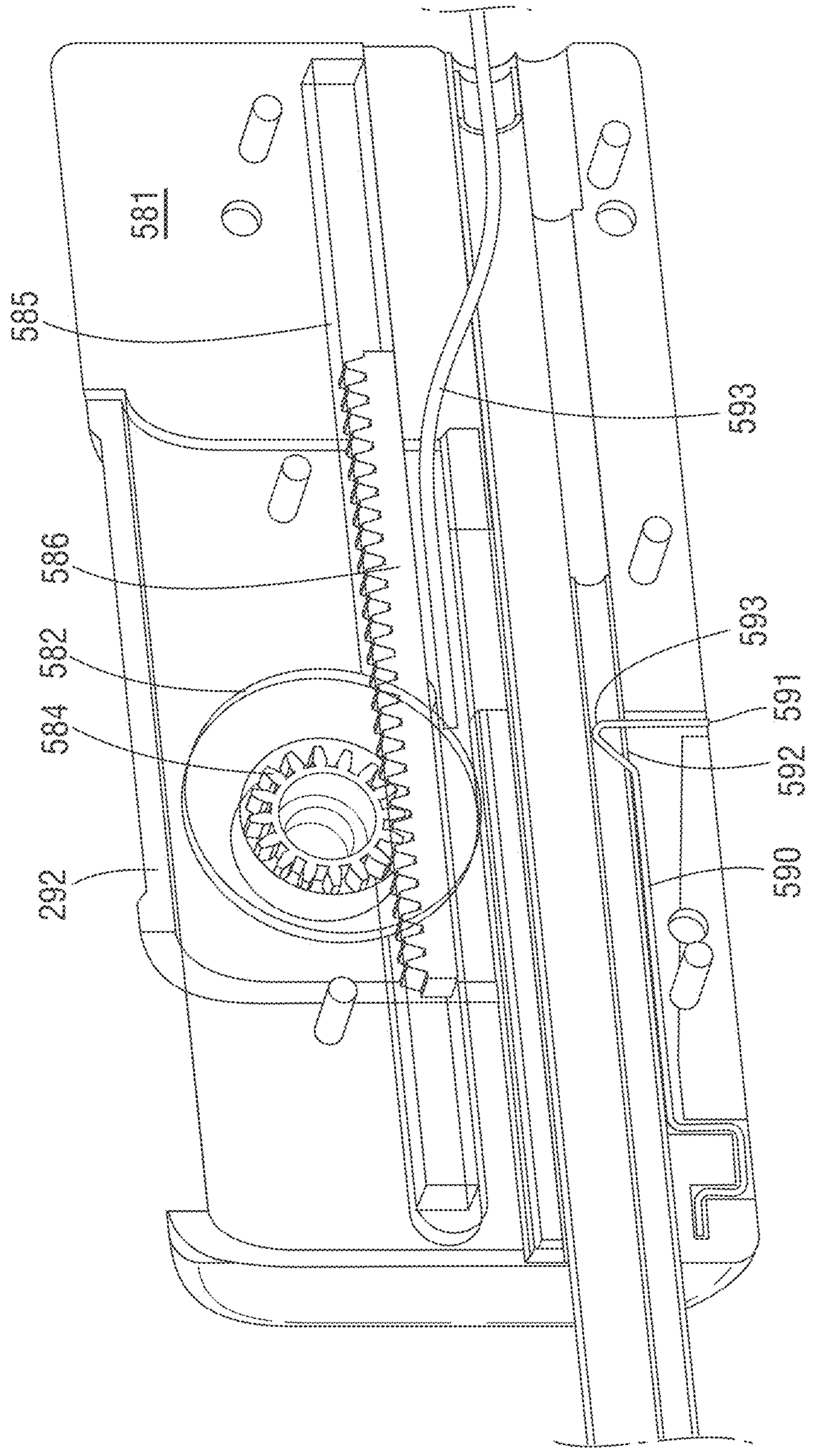
FIG. 67 is a fragmentary, enlarged, partially transparent, longitudinally cross-sectional view of the multiple-firing crimp device of FIG. 66 with the shuttle in the snare-extended position.
Figure 68:
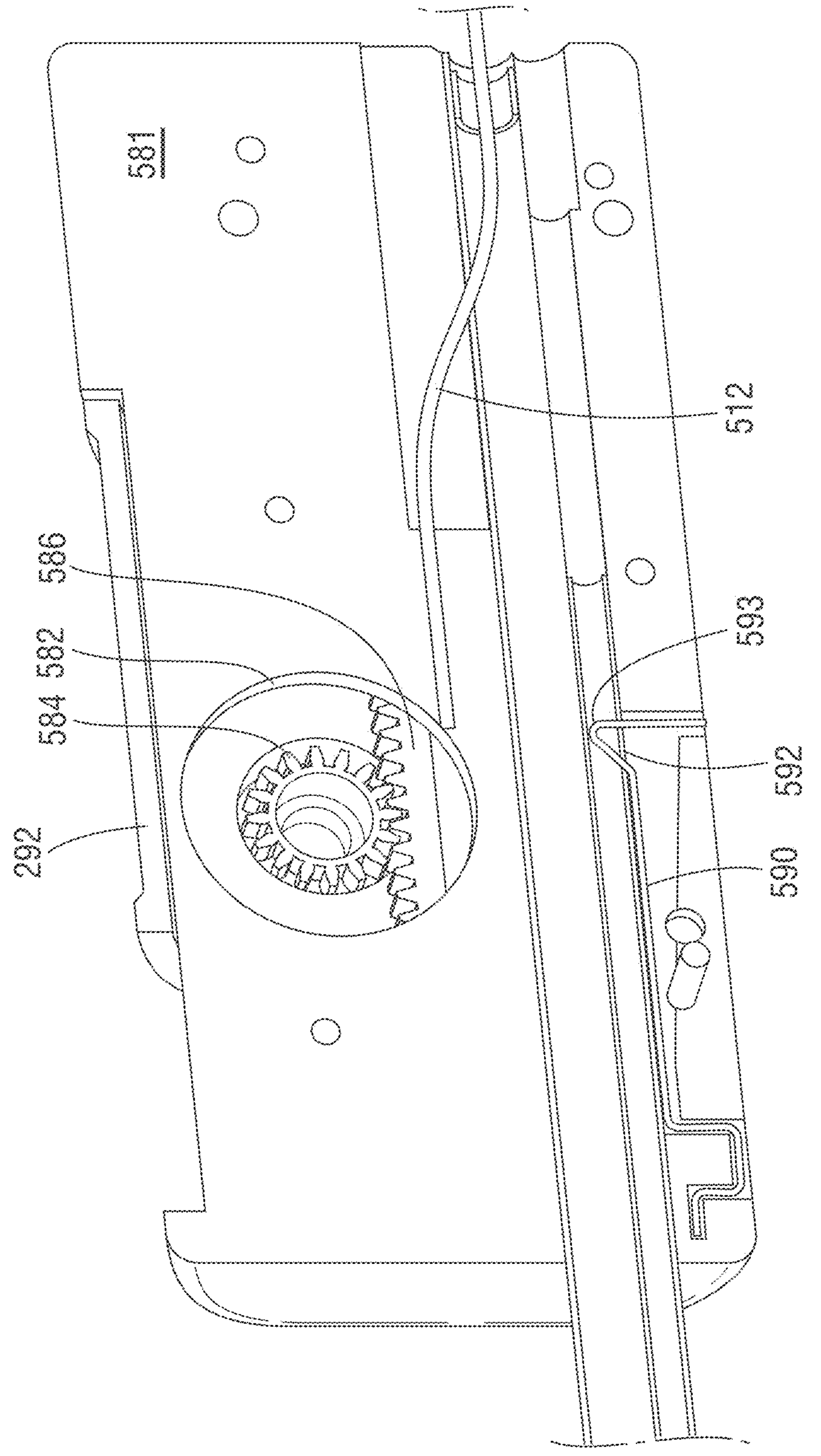
FIG. 68 is a fragmentary, enlarged, longitudinally cross-sectional view of the multiple-firing crimp device of FIG. 66 with the shuttle in the snare-extended position.
Figure 69:
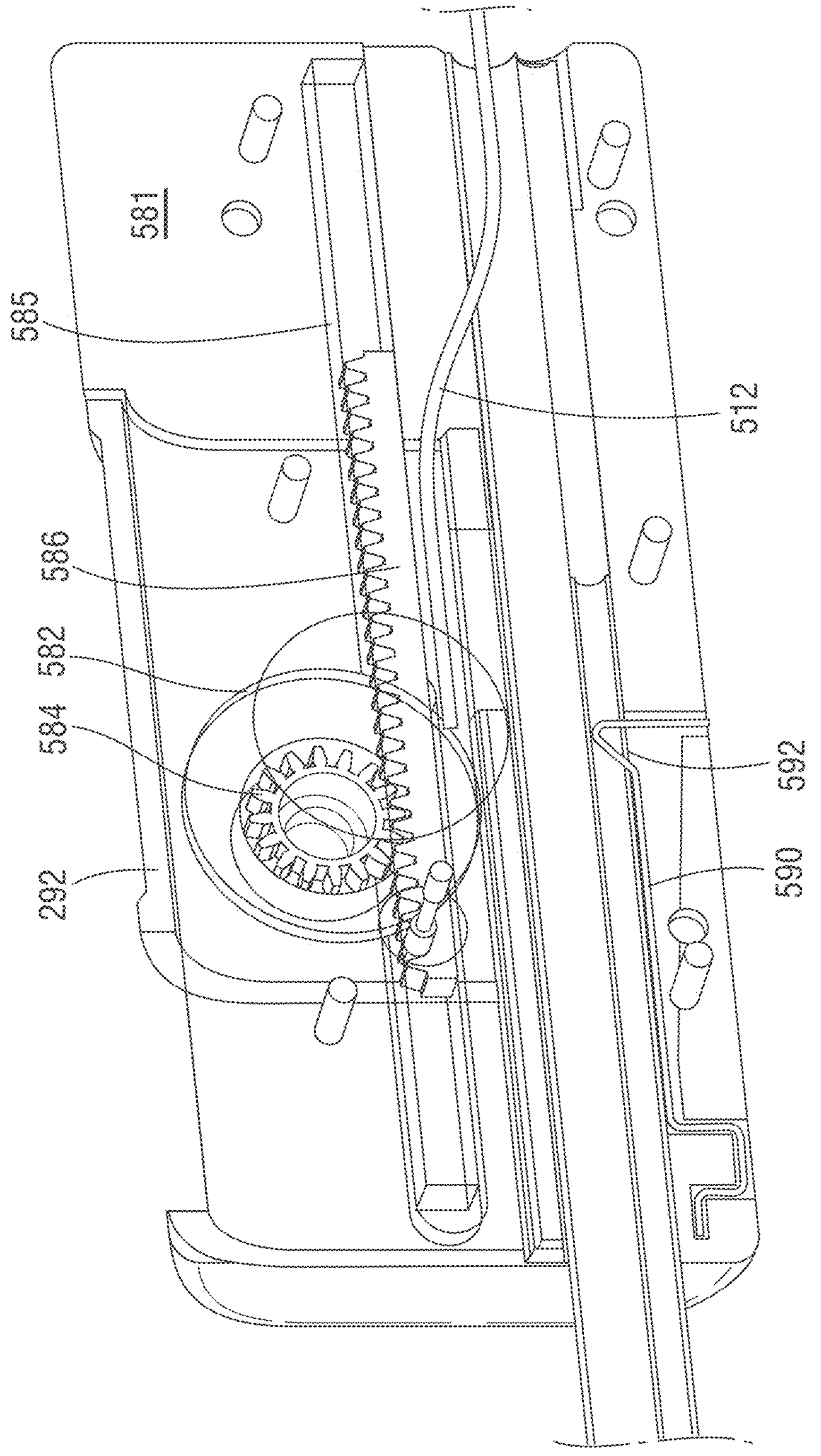
FIG. 69 is a fragmentary, enlarged, transparent, longitudinally cross-sectional view of the multiple-firing crimp device of FIG. 66 with the shuttle in the snare-extended position.
Figure 70:
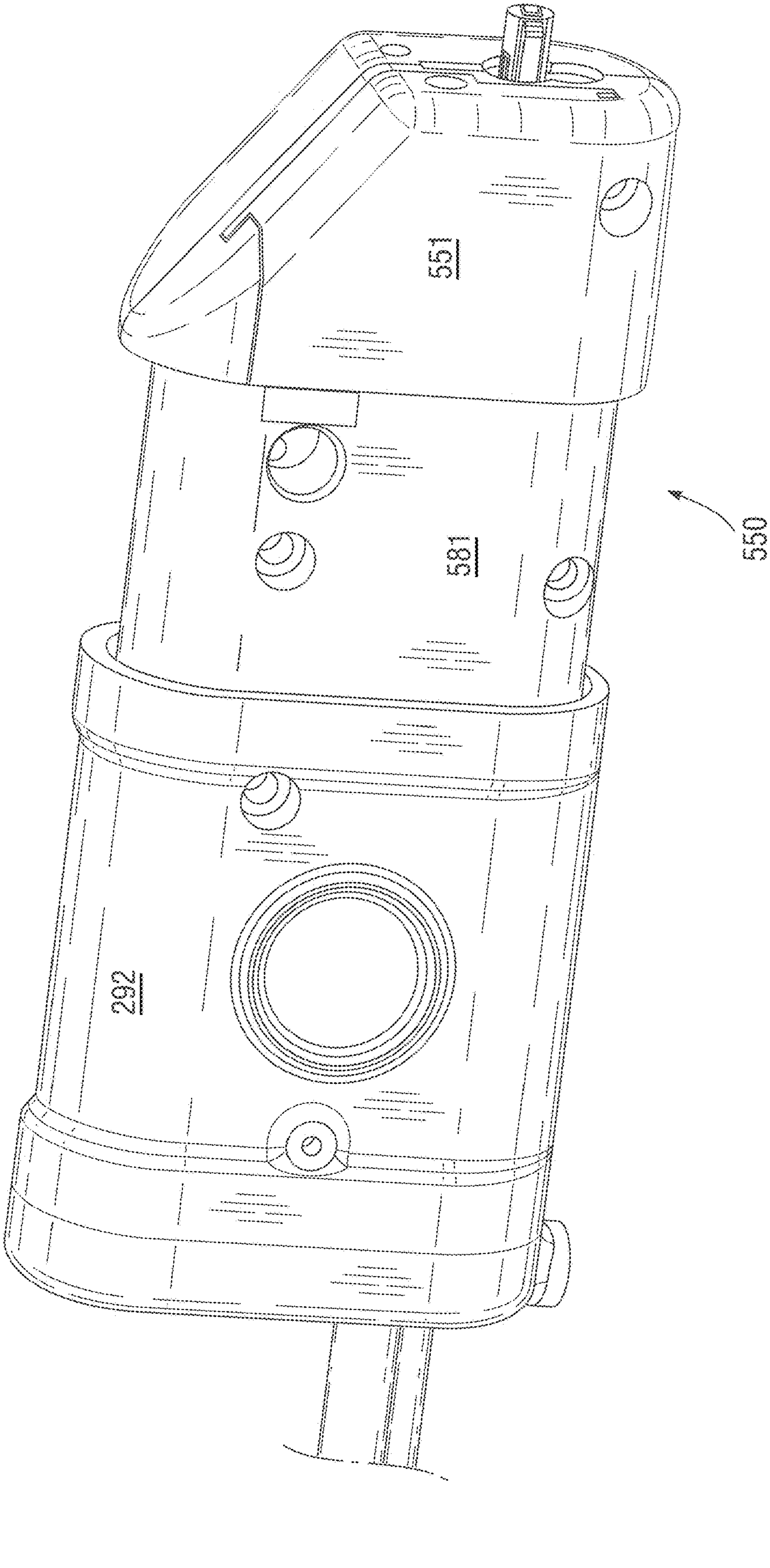
FIG. 70 is a fragmentary, perspective view of an exemplary embodiment of a distal end of a multiple-firing crimp device having a distal headlight assembly in an off state and an end effector with a manually actuated crimp sub-assembly in a position with a first crimp loaded for use and with a shuttle in a ready to use state.
Figure 71:
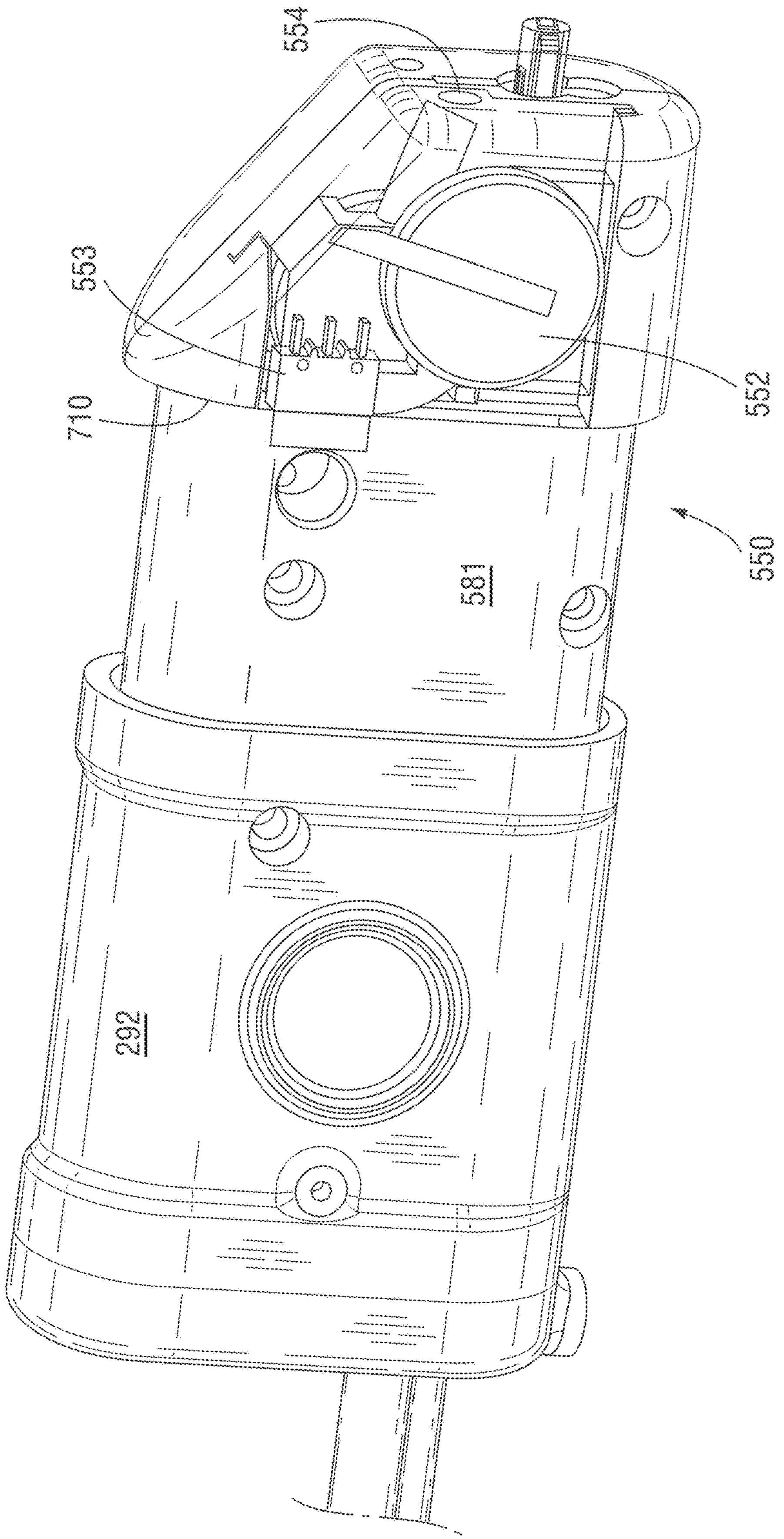
FIG. 71 is a fragmentary, partially transparent, perspective view of the multiple-firing crimp device of FIG. 70.
Figure 72:
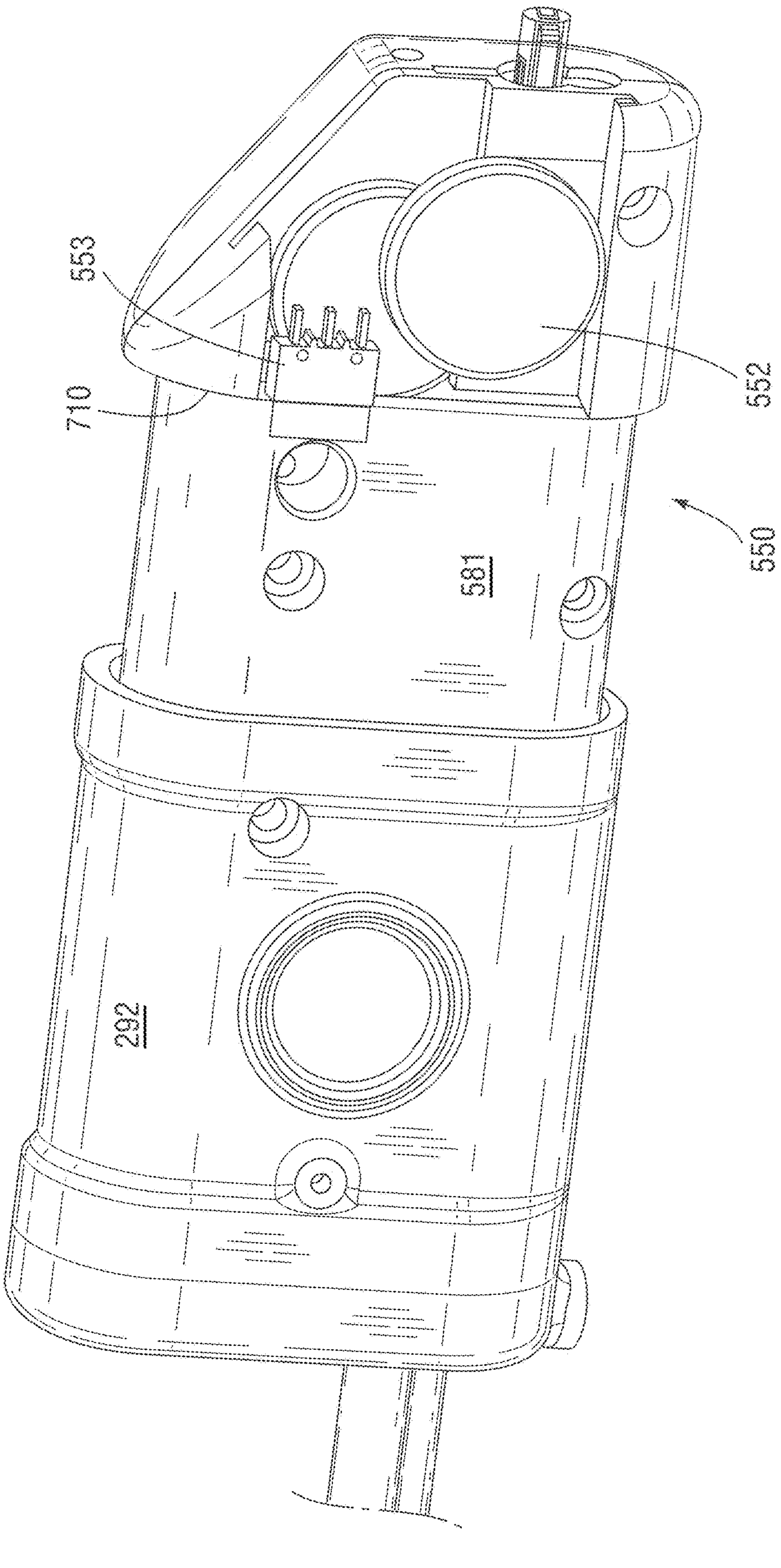
FIG. 72 is a fragmentary, perspective view of the multiple-firing crimp device of FIG. 70 with a headlight cover removed.
Figure 73:
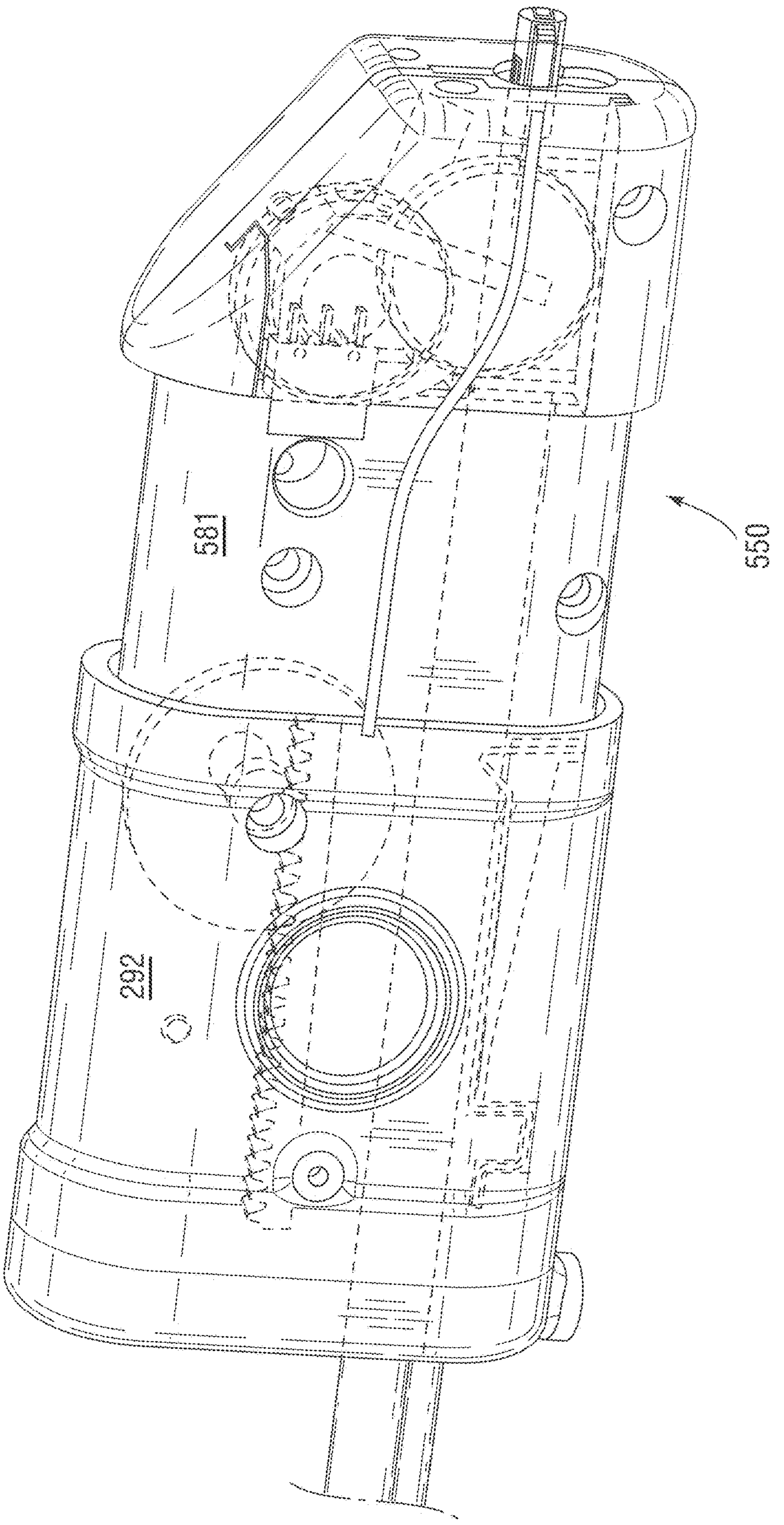
FIG. 73 is a fragmentary, transparent, perspective view of the multiple-firing crimp device of FIG. 70.

FIGS. 58 and 59, respectively, depict the shuttle translating from a retracted position against the handle 100 to an extended position where the snare-extension tube 512 drops into the slot 272 of the outer tube 270. FIGS. 60 to 62 illustrate the shuttle 580 in a state where the snare-extension tube 512 has not reached the slot 272 and, therefore, still remains against the outer surface of the outer tube 270. In comparison, FIGS. 63 to 65 illustrate the shuttle 580 in a state where the snare-extension tube 512 has dropped into the slot 272 and is ready to extend the snare within the outer tube 270 through the crimp 30' (which is not illustrated here). All of the steps for aligning the snare-extension tube 512 are the same as above and, therefore, the details of which are not repeated here.

The body 581 defines an interior snare spool cavity 582 in which a snare spool 583 and a pinion 584 rotatably reside. The snare spool 583 is rotationally fixed to the pinion 584 so that rotation of the pinion 584 results in a corresponding rotation of the snare spool 583. The snare spool 583 is illustrated in cross-section in FIG. 63. The body 581 also defines an interior rack cavity 585 in which a rack 586 resides for longitudinal movement within the rack cavity 585. A distal end of the rack 586 is fixed to the snare-extender slide 292, for example, it is pinned thereto at point 587. The snare 10, which is not illustrated in FIGS. 59 to 68 for purposes of clarity, has a proximal end that is pinned to the snare spool 583. In an exemplary embodiment of the snare spool 583 in FIG. 63, the snare spool 583 has a radial bore extending radially inwards from a spool outer contact surface. The distal end of the snare 10 is positioned inside the bore and is fixed there, for example, with a set screw or pin. The snare 10 is then wound around the snare spool 583 (e.g., counterclockwise with respect to FIG. 63) on the spool contact surface and is threaded into the snare-extension tube 512. The spool sides are raised to have a diameter greater than a diameter of the spool contact surface to keep the snare 10 from sliding off the snare spool 583 laterally.

With such a configuration, as the snare-extender slide 292 is moved distally by the user, the rack 586 moves distally as well, thereby rotating the pinion 584 and the snare spool 583. Because the diameter of the pinion 584 is smaller than the diameter of the snare spool 583, the pinion 584 acts as a speed increasing gear to enable a larger movement of the snare spool 583 and, thereby, a length of the snare 10 that is wound about the snare spool 583. In particular, the overall length of the snare 10 is set to position the tip 14 just outside the distal end of the snare-extension tube 512 when the snare-extender slide 292 and the rack 586 are in their proximal-most, unactuated position (shown in FIG. 63). This tip 14 position is shown, for example, in FIG. 57. As the rack 586 moves distally, the snare spool 583 unwinds the snare 10 (e.g., in a counterclockwise direction with regard to FIG. 63) and extends the snare 10 out from the distal end of the snare-extension tube 512. FIGS. 66 to 69 show the snare-extender slide 292 (and, therefore, the rack 586) extended distally to the fullest extent to, thereby, move the non-illustrated snare 10 out from the distal face of the shuttle 580. With the gearing shown, an approximately one inch (1") movement of the rack 586 causes approximately two and one-half inches (2.5") of snare 10 extension out from the distal end. Thus, the overall length of the shuttle 580 can be reduced significantly.

As indicated above, it is desirable to prevent the shuttle body 581 from movement when the shuttle 580 is in a position where the snare 10 is to be moved. Various retaining features can be provided. One example of this retaining feature is a body interlock 590. In this example, the body interlock 590 is a leaf spring with an extension 593 that rides along the bottom surface of the guide rod 570 as the shuttle 580 moves and, when the shuttle 580 is in a position where snare 10 movement is permitted, a port 592 in the guide rod 590 is located to catch the extension 593 of the body interlock 590 therein and substantially prevent longitudinal movement of the shuttle 580 on the outer tube 270. Once the leaf spring of the body interlock 590 is allowed to move into the port 592, the free end 591 of the body interlock 590 moves out of the way of the extender slide 292, allowing the extender slide 292 to move distally. It is noted that the wrap-around extender slide 292 embodiment of FIGS. 58, 59, 66, and 70 to 74 entirely wraps around the shuttle body 581. In this configuration, the free end 591, is able to positively engage the extender slide 292 and prevent movement. In contrast, the exemplary embodiment of the short extender slide 292 in FIGS. 60 to 65 and 67 to 69 does not wrap around to the bottom surface of the shuttle body 581. Thus, the configuration of the body interlock 590 would not engage the short extender slide 292. For the short extender slide 292 in FIGS. 60 to 65 and 67 to 69, the body interlock 590 would be positioned behind the shaft 270, 570 in the figures and, therefore, would not be visible in these figures. Accordingly, the body interlock 590 is left at the lower surface of the shuttle body 581 for purposes of clarity only.

Once the extender slide 292 has moved any distance distally, it forcibly holds the leaf spring of the body interlock 590 in the port 592 thereby locking the shuttle 580 into the shuttle's distal-most position. When the extender slide 292 is returned to its proximal position (e.g., FIG. 60), the body interlock 590 remains engaged in the port 592. As the body interlock 590 is a leaf spring with ramps on either side of the extension 593, a sufficient force by the user to move the shuttle 580 proximally, overcomes the interlock and slides the extension 593 out from the port 592. In action, the body interlock 590 acts as a removable detent that provides sufficient force to retain the shuttle 580 in position when snare functions occur but that is insufficient to prevent retraction movement of the shuttle 580 by a force imposed by the user.

Figure 74:
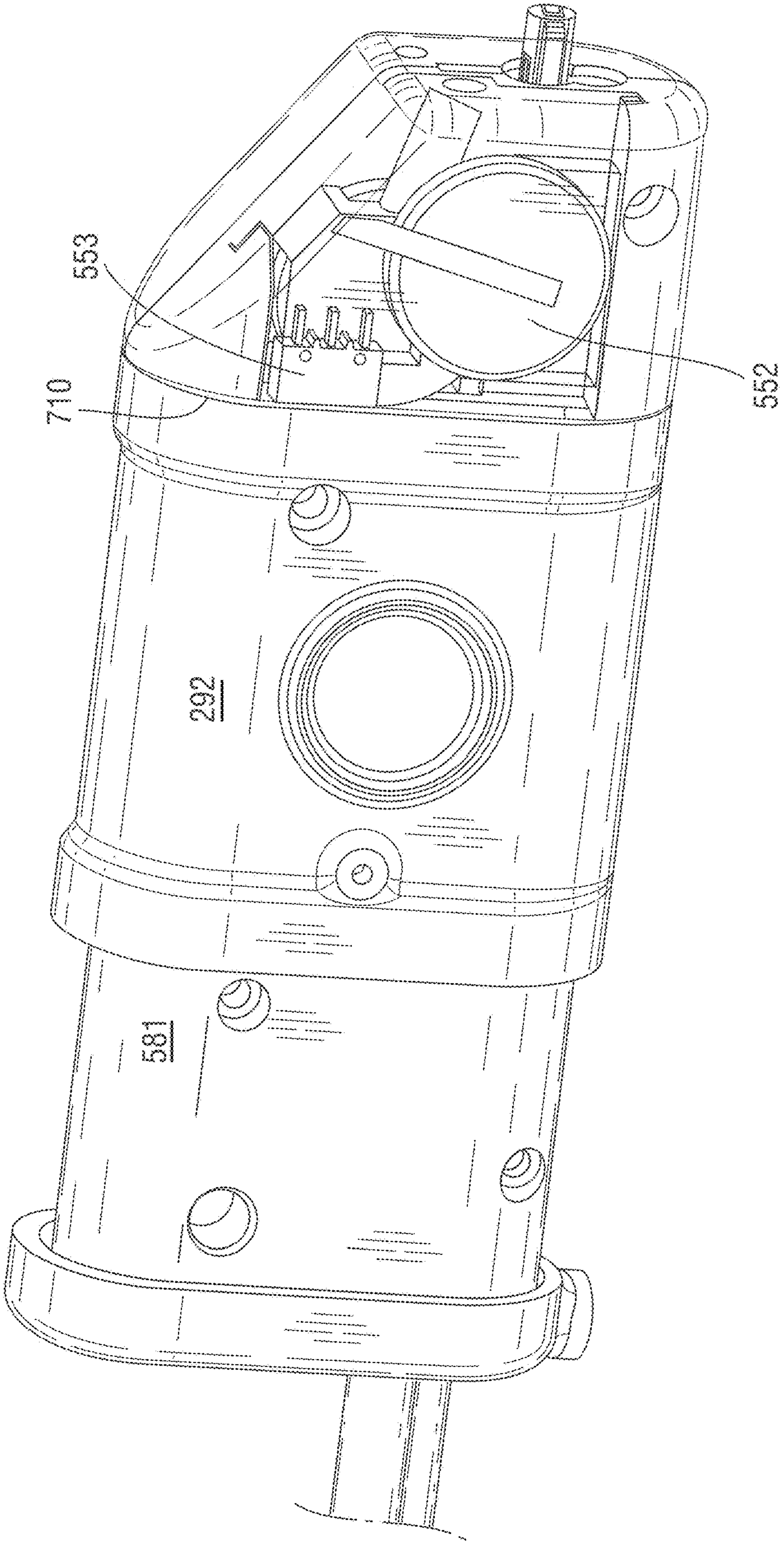
FIG. 74 is a fragmentary, partially transparent, perspective view of the multiple-firing crimp device of FIG. 70 with the shuttle in the snare-extended position.

When the devices described herein are used in surgery, the location where the snare 10 is to capture cords 2 (e.g., sutures), is typically within a surgical site. Even though there is light from the surgical environment, many obstacles present shadows where the snare 10 is located during use. The color and size of the snare 10 also can make it difficult for a surgeon to see the snare 10 within the background of the surgical site. To alleviate this issue, the shuttle body 581 is provided with a distal headlight assembly 550. One or both of the sides of the shuttle body 581 is hollowed out and provided with a cover 551 to contain parts of the headlight assembly 550, as shown in FIGS. 70 to 74. The cover 551 is made transparent in FIG. 71 to show thereunder a power supply 552 (in the form of one or more coin cells) and a headlamp switch 553, which is, in this exemplary embodiment, a micro-switch having the switch on a proximal side thereof with the body of the micro-switch positioned flush with an end-of-travel surface 710 of the shuttle body 581 for the snare-extender slide 292 and with the switch plunger projecting distally from the end-of-travel surface 710. In such a configuration, when the snare-extender slide 292 reaches a point where the snare 10 is extended for snaring one or more cords (as shown in FIG. 74), the switch automatically depresses, thereby turning on the headlamp 554, which can take the form of one or more LEDs, for example. In this configuration, the headlamp 554 remains on until the snare-extender slide 292 is retracted proximally, in which case the snare 10 is within the shuttle 580 and has captured the one or more cords 2.

Figure 76:
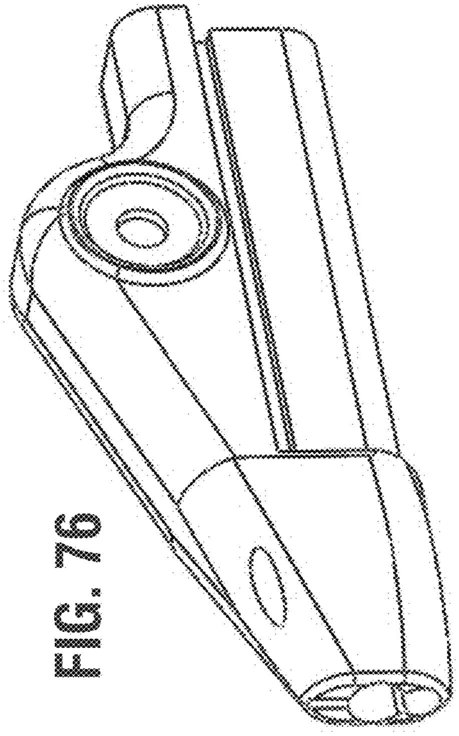
FIG. 76 is a perspective view of a left side of an alternative exemplary embodiment of a shuttle body with snare-extender slide removed.
Figure 77:
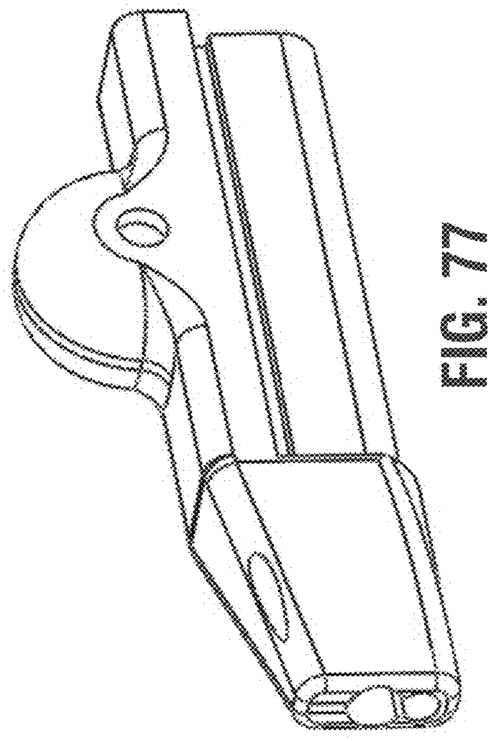
FIG. 77 is a perspective view of a left side of a left half of an alternative exemplary embodiment of a shuttle body with snare-extender slide removed.
Figure 75:
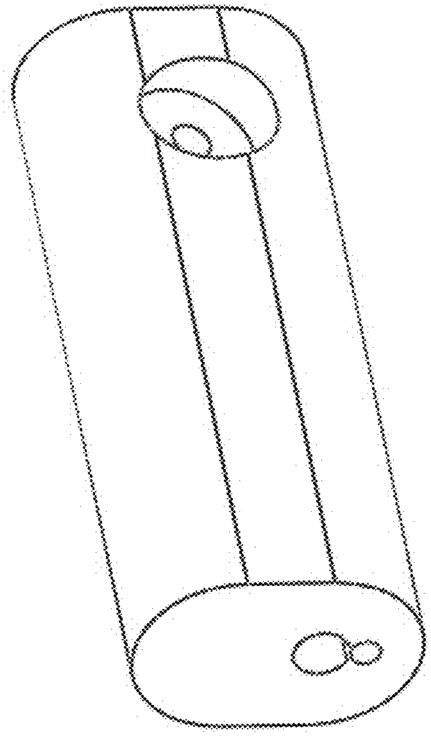
FIG. 75 is a perspective view of a left side of an alternative exemplary embodiment of a shuttle body.
Figure 78:
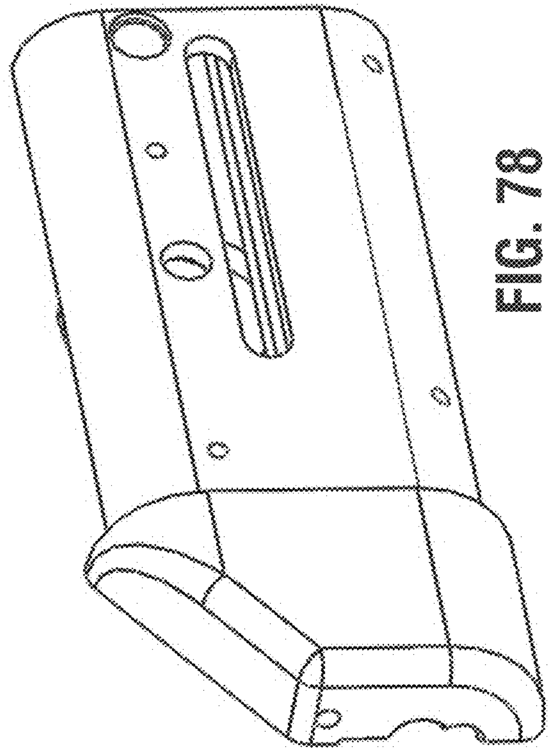
FIG. 78 is a perspective view of a left side of an alternative exemplary embodiment of a shuttle body with snare-extender slide removed.
Figure 76A:
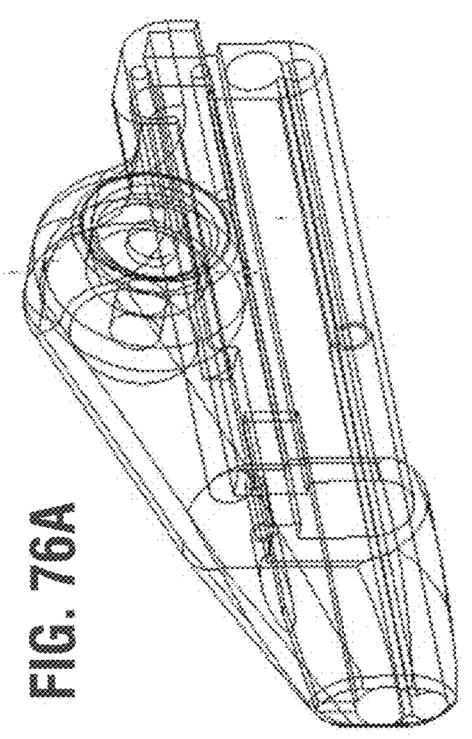
FIG. 76A is a transparent, perspective view of the shuttle body of FIG. 76.
Figure 77A:
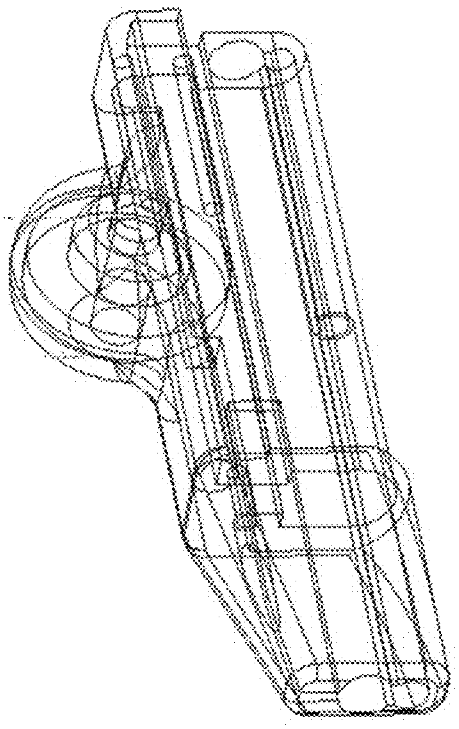
FIG. 77A is a transparent, perspective view of the shuttle body half of FIG. 77.
Figure 75A:
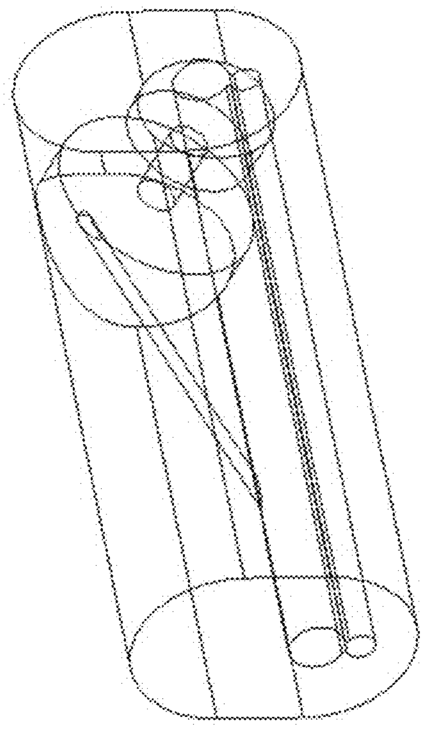
FIG. 75A is a transparent, perspective view of the shuttle body of FIG. 75.
Figure 78A:
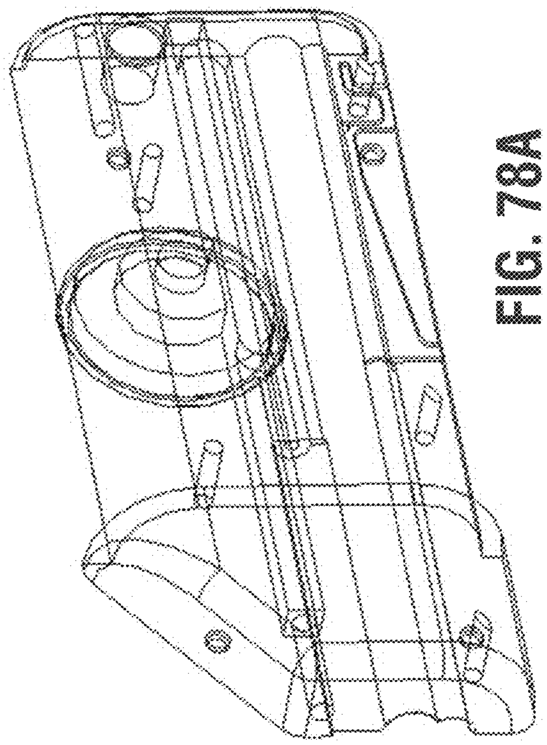
FIG. 78A is a transparent, perspective view of the shuttle body of FIG. 78.
Figure 75B:
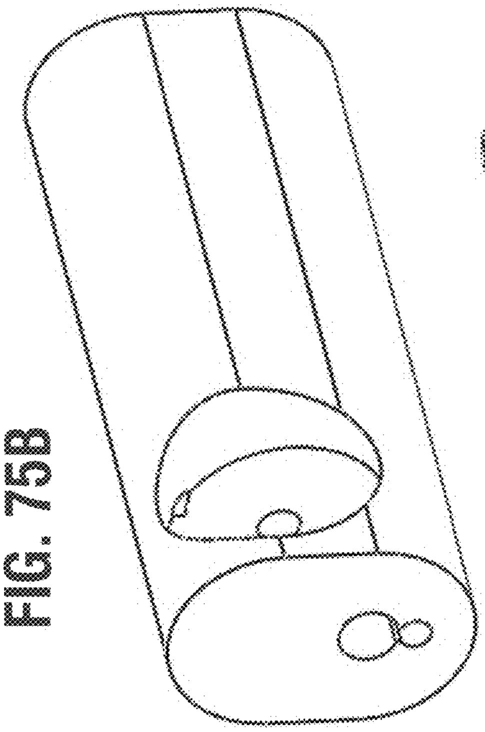
FIG. 75B is a perspective view of a right side of the shuttle body of FIG. 75.
Figure 78B:
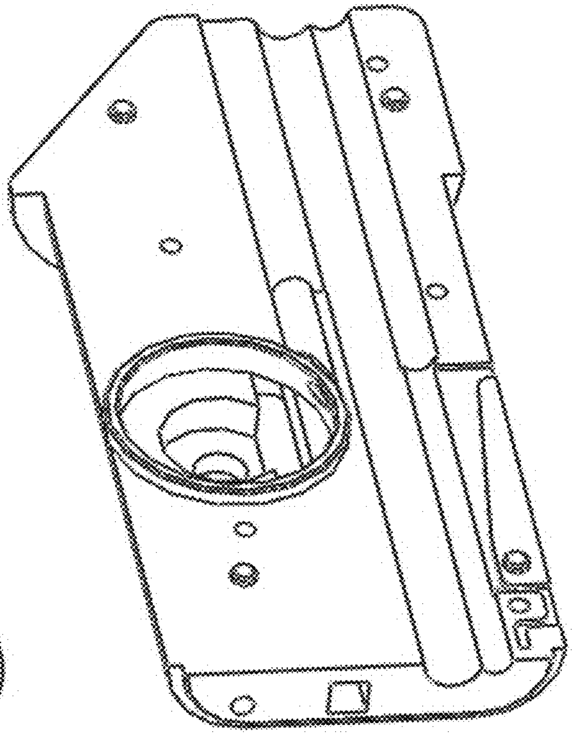
FIG. 78B is a perspective view of a right side of the shuttle body of FIG. 78.
Figure 76B:
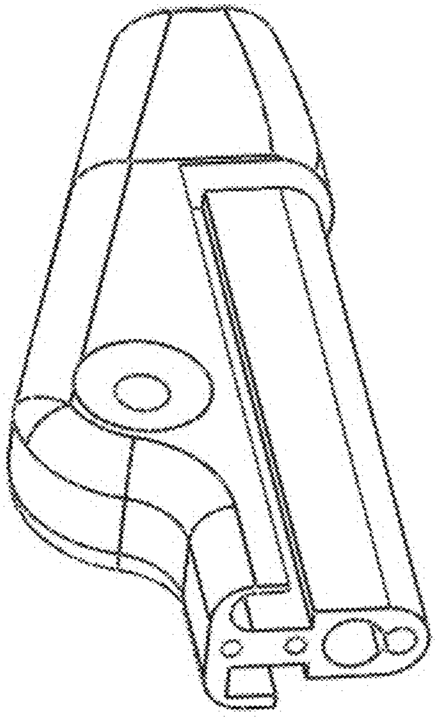
FIG. 76B is a perspective view of a right side of the shuttle body of FIG. 76.
Figure 77B:
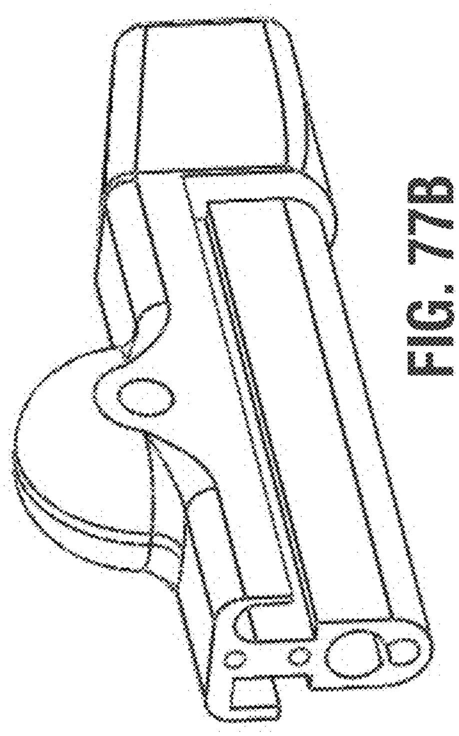
FIG. 77B is a perspective view of a right side of the shuttle body half of FIG. 77.

The shuttle body 581 is not limited to the shapes shown hereinabove. There are other configurations in which various characteristics are maximized or minimized. FIGS. 75, 75A, and 75B illustrate an exemplary embodiment of a shuttle body that allows the snare-extender tube to be relatively straight and positions the snare's exit from the snare spool from above the snare spool instead of below. FIGS. 76, 76A, and 76B illustrate an exemplary embodiment of a shuttle body configuration that removes some of the body material to lighten the shuttle and places the snare-extender slide only on the bottom half of the shuttle. A headlight assembly is also provided. The exemplary configuration in FIGS. 77, 77A, and 77B removes even more material from the shuttle body to further lighten the shuttle. The exemplary configuration of the left half of the shuttle body in FIGS. 78, 78A, and 78B is similar to the shuttle body embodiment of FIGS. 58 to 74 and shows differences in configuration, size, and material from the other shuttle bodies.

Figure 79:
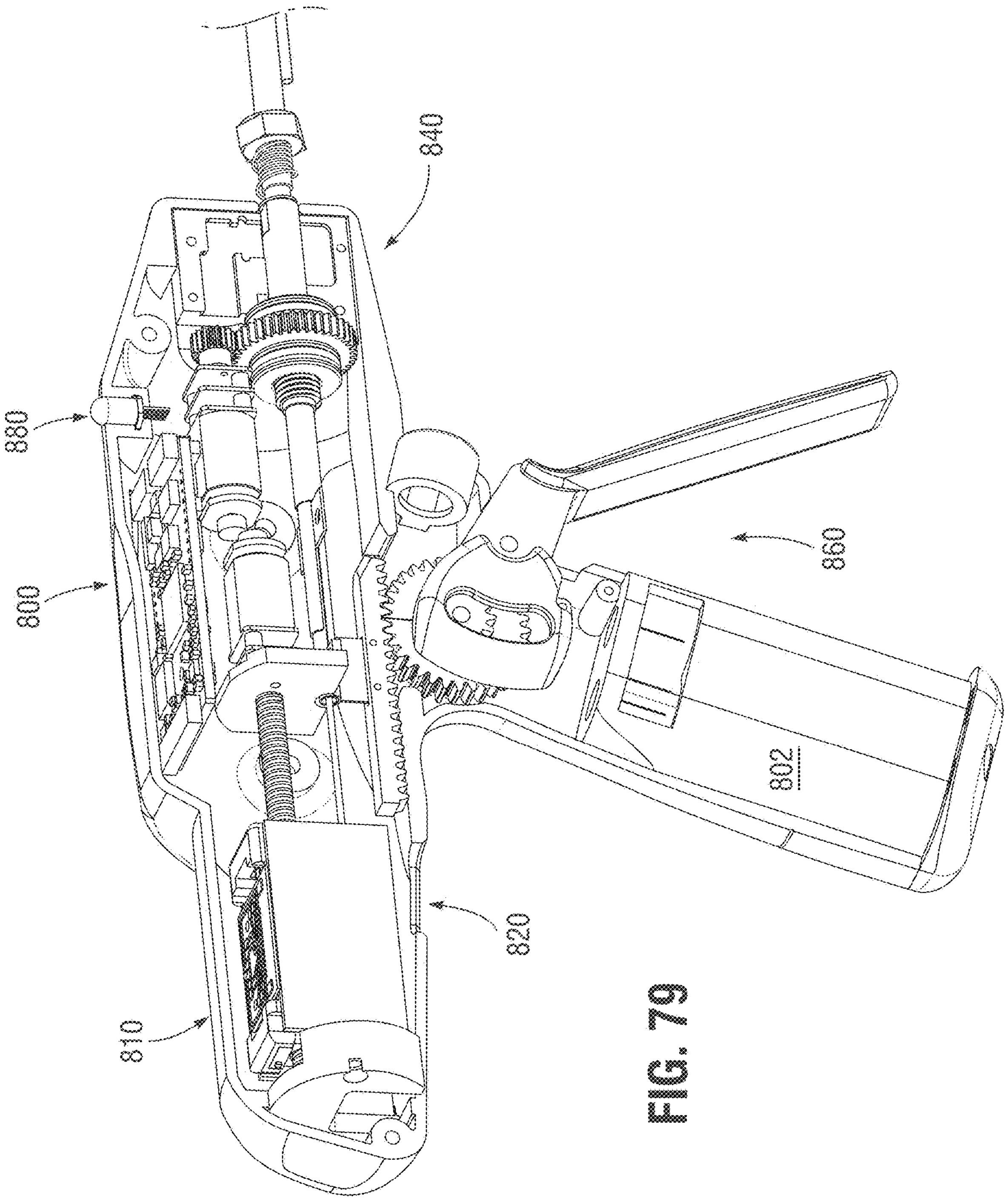
FIG. 79 is a fragmentary, perspective view of a right side of an exemplary embodiment of a handle for a multiple-firing crimp device with the right half of the handle body removed.
Figure 80:
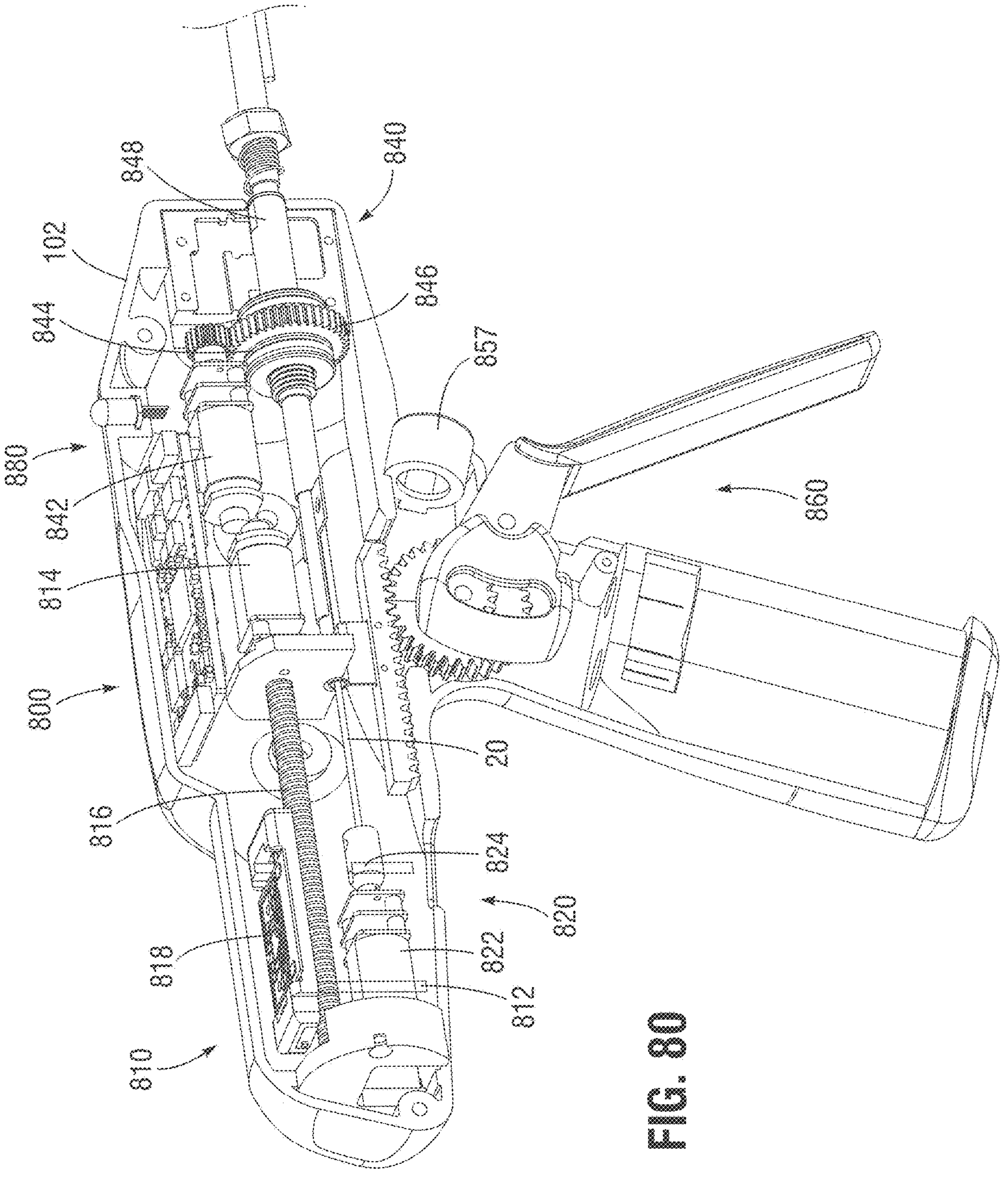
FIG. 80 is a fragmentary, perspective view of the handle of FIG. 79 with a cover of a carriage movement assembly transparent.
Figure 81:
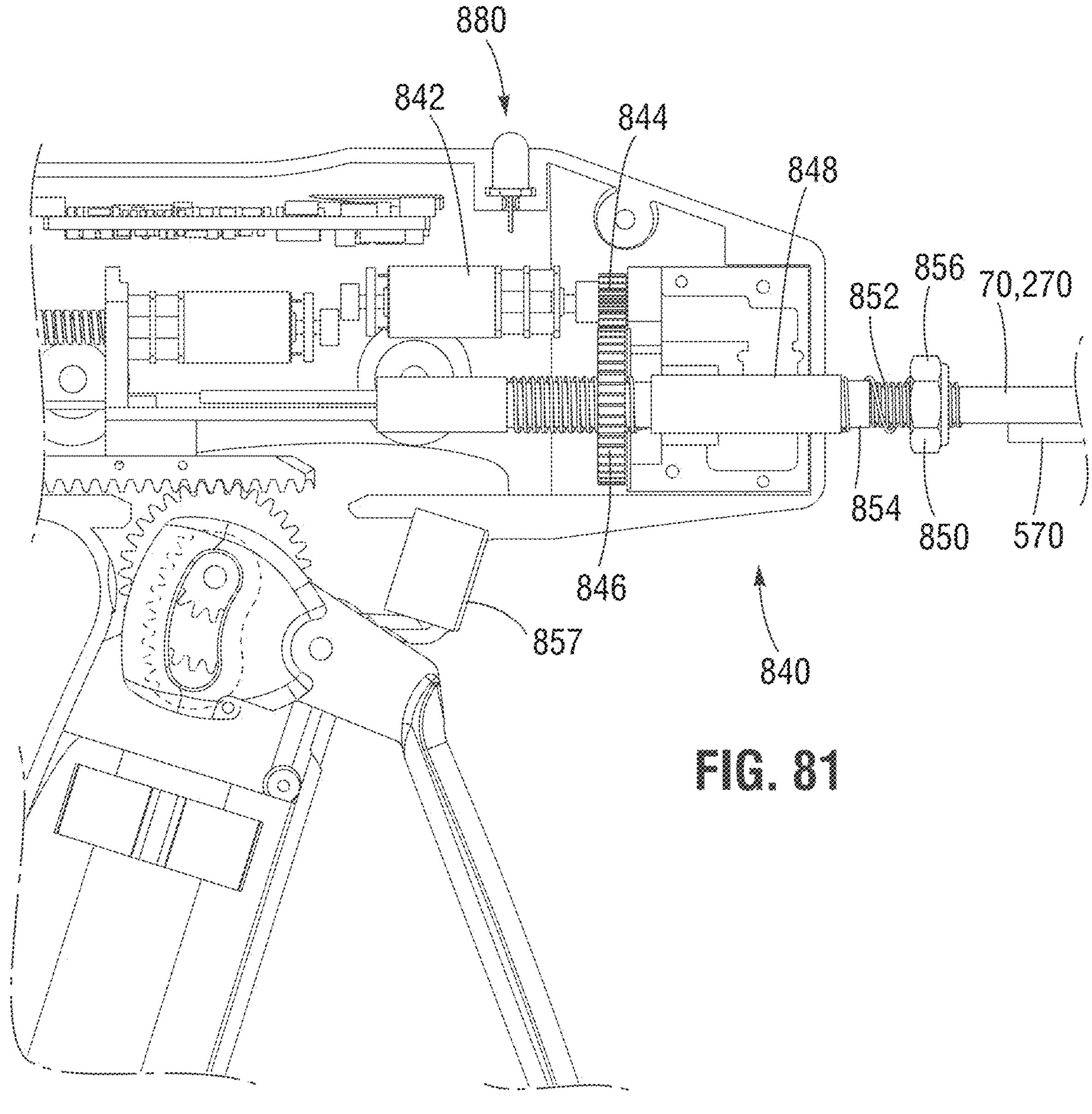
FIG. 81 is a fragmentary, side elevational view of a right side of the handle of FIG. 79 in a crimp-retracted state.

An exemplary embodiment of a handle 100 for the multiple-firing crimp device is illustrated in FIGS. 79 and 80, in FIG. 80, the carriage movement assembly is transparent to illustrate the structures therein. Within the handle 100 are various movement assemblies. Some of the movement assemblies are manual and some are automatic. As set forth herein, any of the automatic movement assemblies shown and described can be manual and any of the manual movement assemblies shown and described can be automatic. In this handle embodiment, the movement assemblies include a system control assembly 800, a carriage movement assembly 810, a carriage rotation assembly 820, a crimping assembly 840, a cutting assembly 860, and a display assembly 880.

The system control assembly 800 includes all circuitry sufficient to power and control all electronics on the multiple-firing crimp device. The system control assembly 800 is electrically connected to a power supply 802, which can be, for example, a pack of batteries, such as one or more CR2 or CR123 batteries. The power supply 802 can be powered by any electricity delivery measures including a supply mains.

The carriage movement assembly 810 includes a carriage conveyor 812 with a transparent cover that is best shown in FIG. 80. Also included in the carriage movement assembly 810 is a carriage motor 814 fixed to the handle 100 and rotating a conveyor spindle 816 that, when rotated, either moves the carriage conveyor 812 proximally or distally with respect to the handle body 102. The carriage conveyor 812 has a rotation sub-assembly 820 that, at its distal end, includes a coupler 824 that is rotationally and longitudinally fixed to the crimp carriage 20. As such, when the carriage conveyor spindle 816 rotates and causes the conveyor 812 to move proximally or distally, the crimp carriage 20 moves correspondingly with the coupler 824. In this regard, the carriage motor 814 is the device that positions the crimp(s) 30 towards and away from the crimp orifice 42 as well as positions the crimp 30' within the crimp orifice 42. Two non-illustrated limit switches are present in the carriage movement assembly 810 to define the extension and retraction limits of carriage conveyor 812 and, thereby, the crimp carriage 20.

The carriage rotation assembly 820 is part of the carriage movement assembly 810 and resides inside the carriage conveyor 812. The carriage rotation assembly 820 comprises a carriage rotation motor 822 and the coupler 824, which is rotationally fixed to the output of the carriage rotation motor 822. As such, when the carriage rotation motor 822 rotates, the crimp carriage 20 rotates to shuttle the crimps 30 and to withdraw from the crimp 30' within the crimp orifice 42. Electrical signals/power are supplied to the carriage rotation assembly 820 through a movable wiring harness 818 that is electrically connected to the main circuit board of the system control assembly 800.

Figure 82:
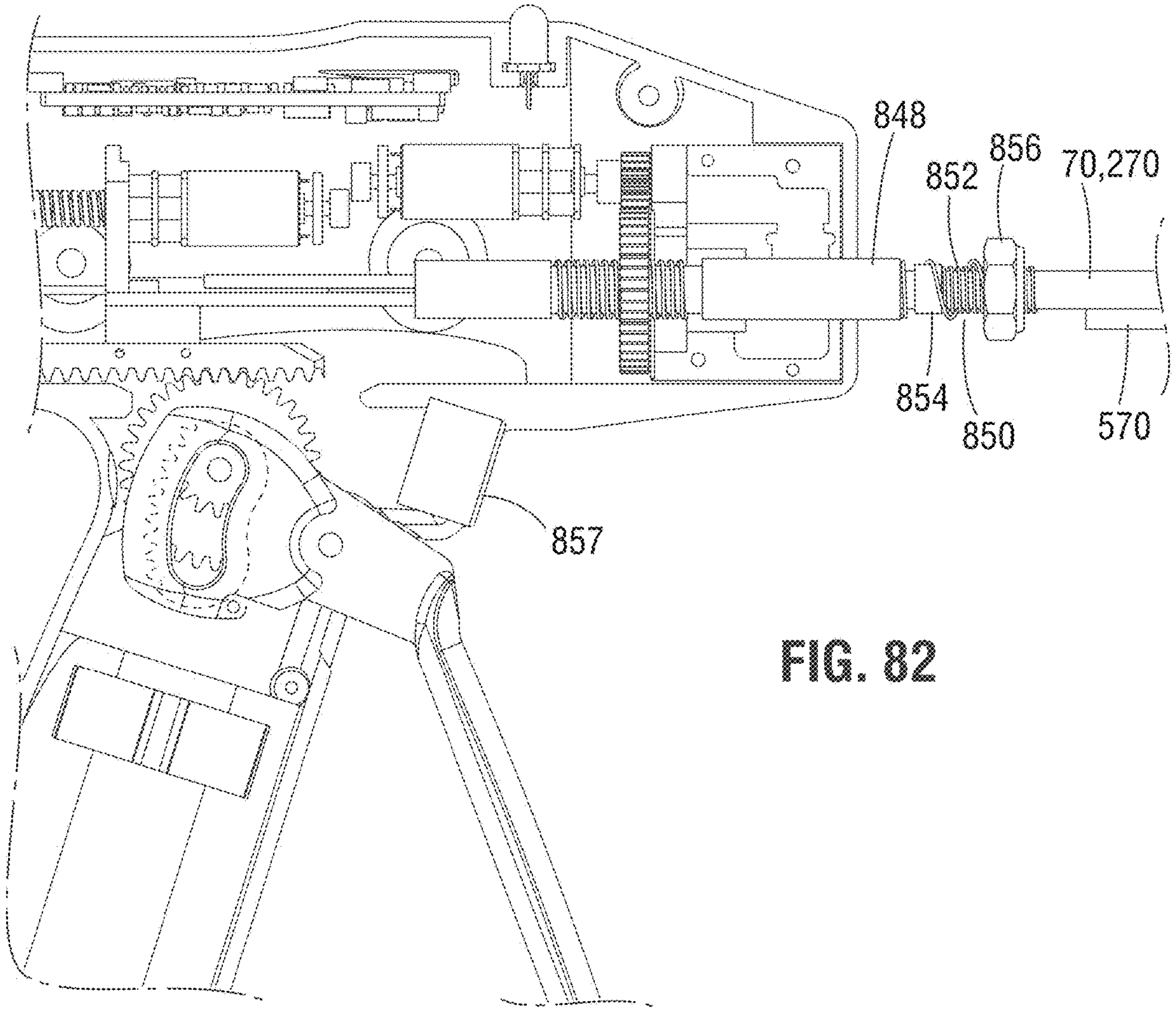
FIG. 82 is a fragmentary, side elevational view of the right side of the handle of FIG. 79 in a crimp-holding state.
Figure 83:
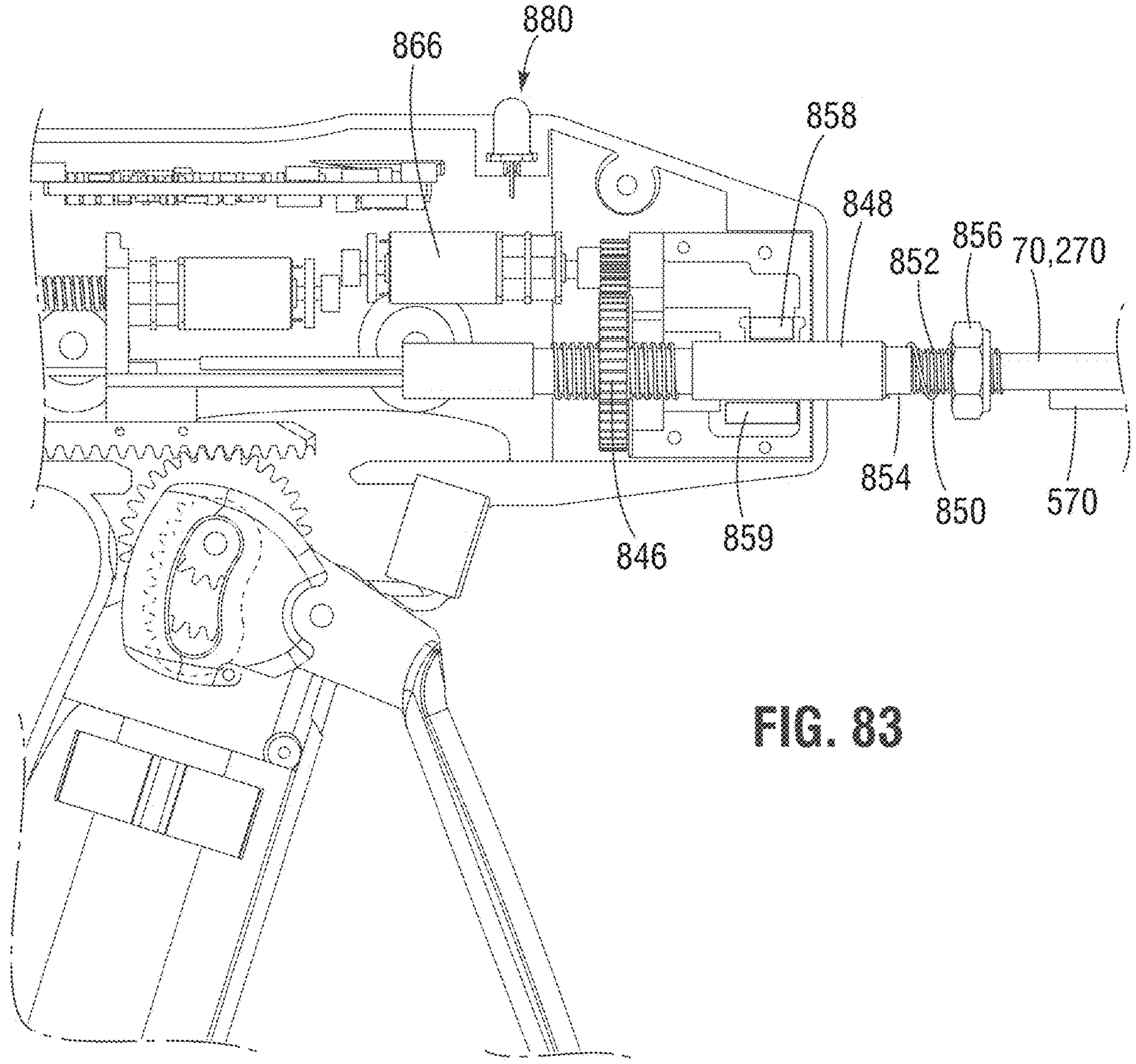
FIG. 83 is a fragmentary, side elevational view of the right side of the handle of FIG. 79 in a clutched state.

The crimping assembly 840 includes a crimping motor 842 fixed to the handle body 102 and rotationally connected a crimping pinion 844. The teeth of the crimping pinion 844 mesh with teeth of a flying gear 846. The flying gear 846 has a central bore with an interior thread corresponding to an exterior thread of a crimping clutch 848. Movement and functionality of the crimping clutch 848 is described with regard to FIGS. 81 to 84. In particular, there are two states in which the outer tube 70, 270, 570 is to be moved. The first is slightly forward so that the hammer 54 is gently pressed against the crimp 30' to hold it within the crimp orifice 42 and to not deform the crimp 30' and the second is forward to have the hammer 54 actively deform and fully crush the crimp 30'. To provide the first function of gently pressing the crimp 30', a clutch bias 850 (in the exemplary form of a spring) is disposed between a distal end of the crimping clutch 848 and a point on the outer tube 70, 270 a distance away from the distal end of the crimping clutch 848. This point is defined by a clutch stop 852 that has a proximal vertical surface 854 intended to contact the distal vertical surface of the crimping clutch 848 and prevent it, after such contact, from moving independent of the outer tube 70, 270. The clutch stop 852 can be simply a radial extension from the outer surface of the outer tube 70, 270, such as an integral collar, which is not adjustable, or it can be an adjustable clutch stop 852, 854, 856 that is formed on or is integral with the outer tube 70, 270 and has, for example, exterior threads 852 and a nut 856 threaded thereon as shown in FIGS. 81 to 84. With the clutch bias 850 disposed between the distal vertical surface of the crimping clutch 848 and the proximal vertical surface of the nut 856, the crimping clutch 848 is able to move asymmetrically with respect to the outer tube 70, 270 as it compresses the clutch bias 850. In this regard, with the clutch stop 852 disposed just distal of the distal end of the crimping clutch 848 to define a clutch distance therebetween and the clutch bias 850 therearound this intermediate portion, as the crimping clutch 848 starts to move distally (as shown in the transition from FIG. 81 to FIG. 82), the clutch bias 850 starts to compress and only moves the outer tube 70, 270 with a force that is proportional to the clutch bias 850. This force is set to be lower than the point at which the hammer 54 actually compresses the crimp 30'. In FIG. 82, for example, the crimping clutch 848 moves distally slightly (as compared to FIG. 81), compresses the clutch bias 850 and, thereby, moves the outer tube 70, 270, 570 distally but only with the force that compressed the spring. In the transition from FIG. 82 to FIG. 83, the crimping clutch 848 closed the distance and contacted the proximal vertical surface of the clutch stop 852. Because the spring of the clutch bias 850 has a coefficient less than a force able to compress the crimp 30', the spring is compressed without further movement of the outer tube 70, 270, 570 in this transition. However, after the crimping clutch 848 contacts the proximal vertical surface of the clutch stop 852, any further movement of the crimping clutch 848 corresponds to a 1:1 movement of the outer tube 70, 270, 570 and, thereby, causes movement of the outer tube 70, 270, 570 and crimping of the crimp 30'

A limit switch 858 is present adjacent the crimping clutch 848 to determine when the crimping clutch 848 has reached it furthest distance from the flying gear 846 and indicates to the system control assembly 800 that the crimping motor 842 should be stopped and prevent further turning of the flying gear 846. Also, to prevent the crimping clutch 848 from rotating with respect to the handle body 102, a keying assembly 859 is provided. This keying assembly can take the form of a pin and slotted block, a tongue-and-groove, or any similar rotation-preventing device.

As is indicated, the crimping assembly 840 is automated with the various motors and gears. The crimping process is started by depressing a non-illustrated trigger button disposed in a button orifice 857 of the handle 100. When this button is pressed, crimping of the crimp 30' occurs. The crimping assembly 840 holds the crimp 30' down and waits to reset the next crimp 30" until there is confirmation that the cords 2 have been cut, at which time a new crimp 30' is transitioned to the crimp orifice 42. Associated with the cutting assembly 860 is a non-illustrated limit switch that indicates a position at which the cutting blade is known to be or past a point where the cords 2 could be or the cutting blade pushrod is known to be or past the cutting tip of a fixed blade. When this limit switch is triggered, the crimping assembly 840 retracts to the crimp-ready position. An exemplary embodiment of an end effector portion of the cutting assembly 860 having a moving pushrod and a fixed blade is explained below with regard to FIGS. 85 to 91.

Figure 84:
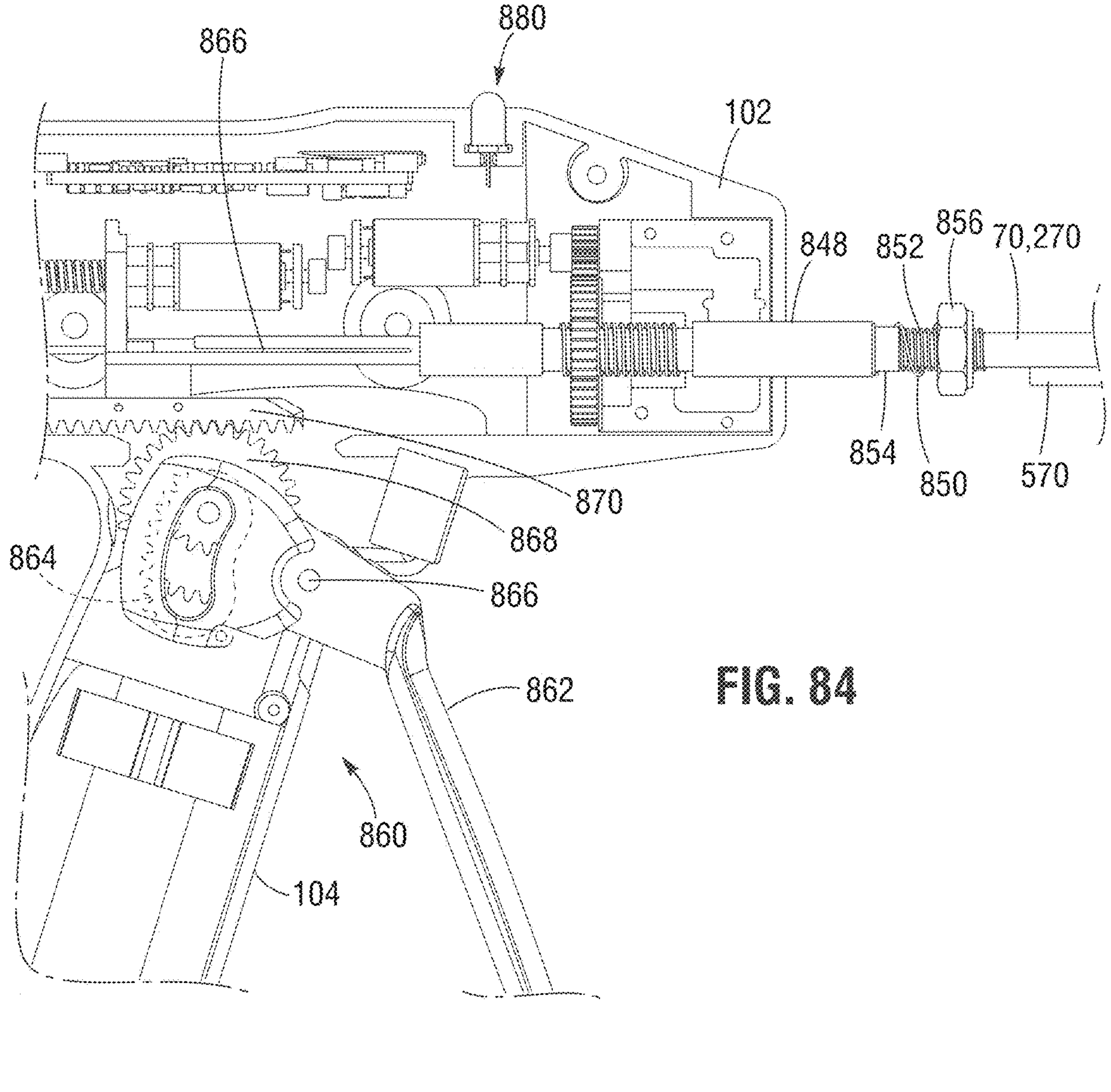
FIG. 84 is a fragmentary, side elevational view of the right side of the handle of FIG. 79 in a crimp-extended state.

Exemplary embodiments of a handle portion of the cutting assembly 860 are shown in FIGS. 81 to 84. With particular reference to FIG. 84, the handle portion of the cutting assembly includes a lever 862 with a kidney-shaped slot having, at a distal surface thereof, teeth 864 that are each disposed on a fixed radius from a pivot point 866 of the lever 862. Centrally fixed but rotatably disposed with respect to handle body 102 is a gear assembly 868 having a smaller gear interfacing with the teeth 864 and a larger gear interfacing with a rack 870. In this configuration with the smaller and larger gears of the gear assembly 868, closing the lever 862 onto the handgrip 104 of the handle 100 causes a distance-multiplied linear translation of the rack 870. The rack 870 is fixedly connected to the cutter push rod 64, thereby effecting a distal displacement of the cutter push rod 64 when the lever 862 is closed.

Figure 85:
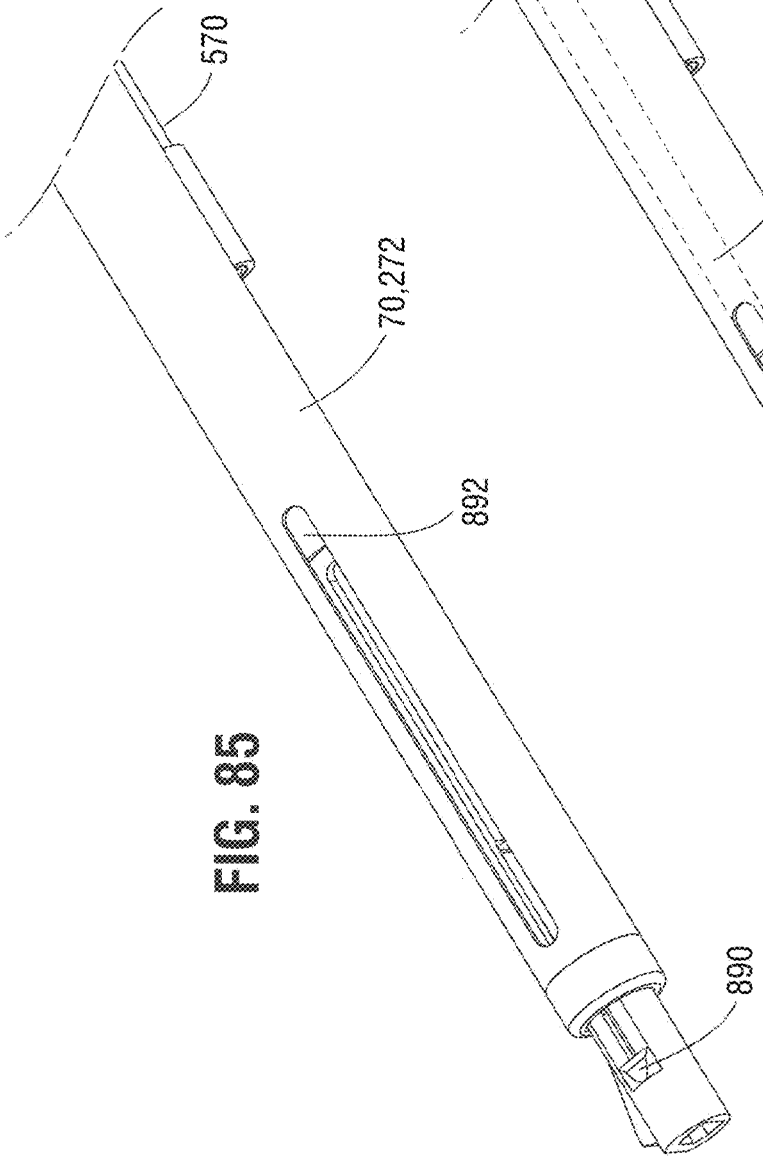
FIG. 85 is a fragmentary, perspective view of an exemplary embodiment of an end effector of a multiple-firing crimp device with a fixed blade and a blade pushrod in a fully retracted position and a crimping assembly in a non-crimping state.
Figure 86:
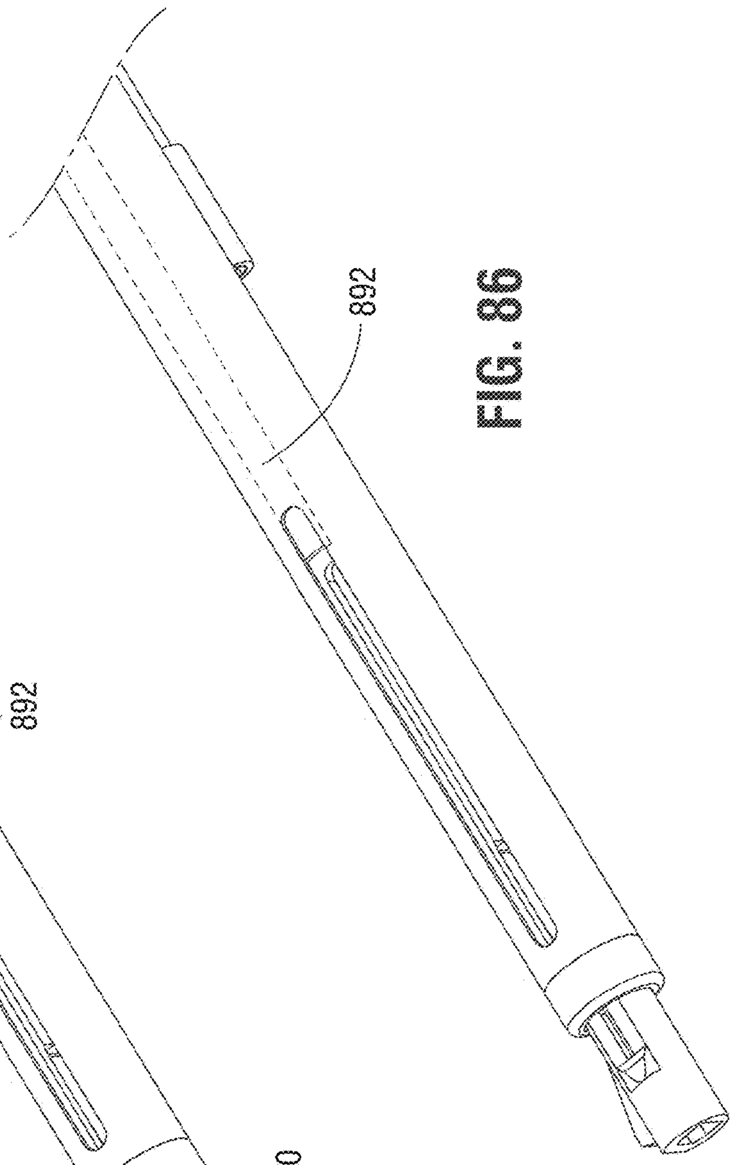
FIG. 86 is a fragmentary, perspective view of the end effector of FIG. 85 with the outer tube transparent.
Figure 88:
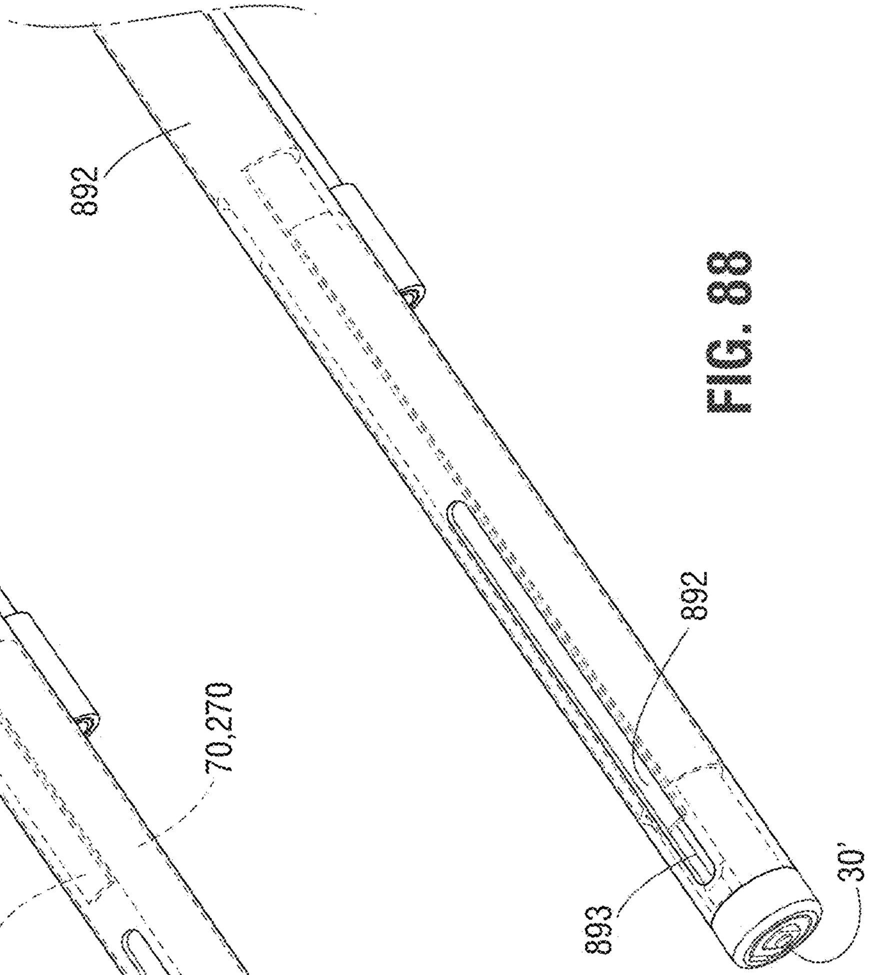
FIG. 88 is a fragmentary, perspective view of the end effector of FIG. 87 with the blade pushrod in a partially actuated state before cutting.
Figure 87:
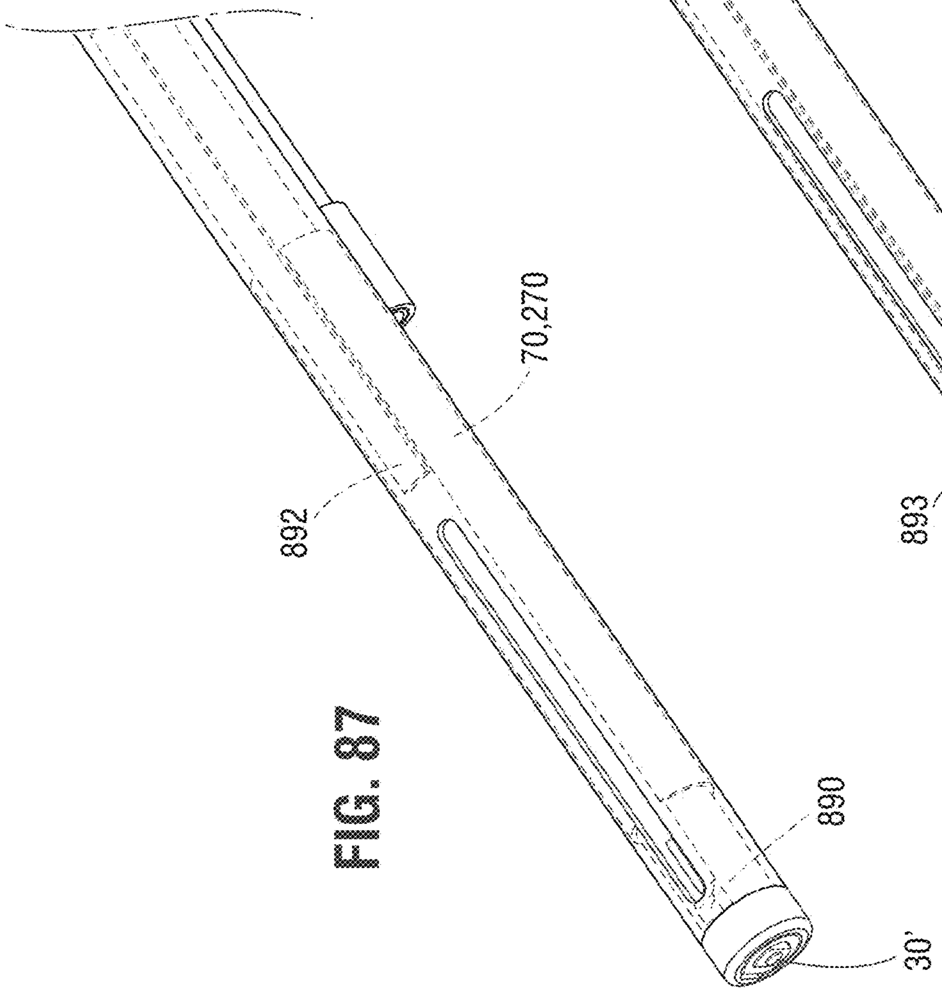
FIG. 87 is a fragmentary, perspective view of the end effector of FIG. 86 with the crimping assembly in a crimped state.
Figure 89:
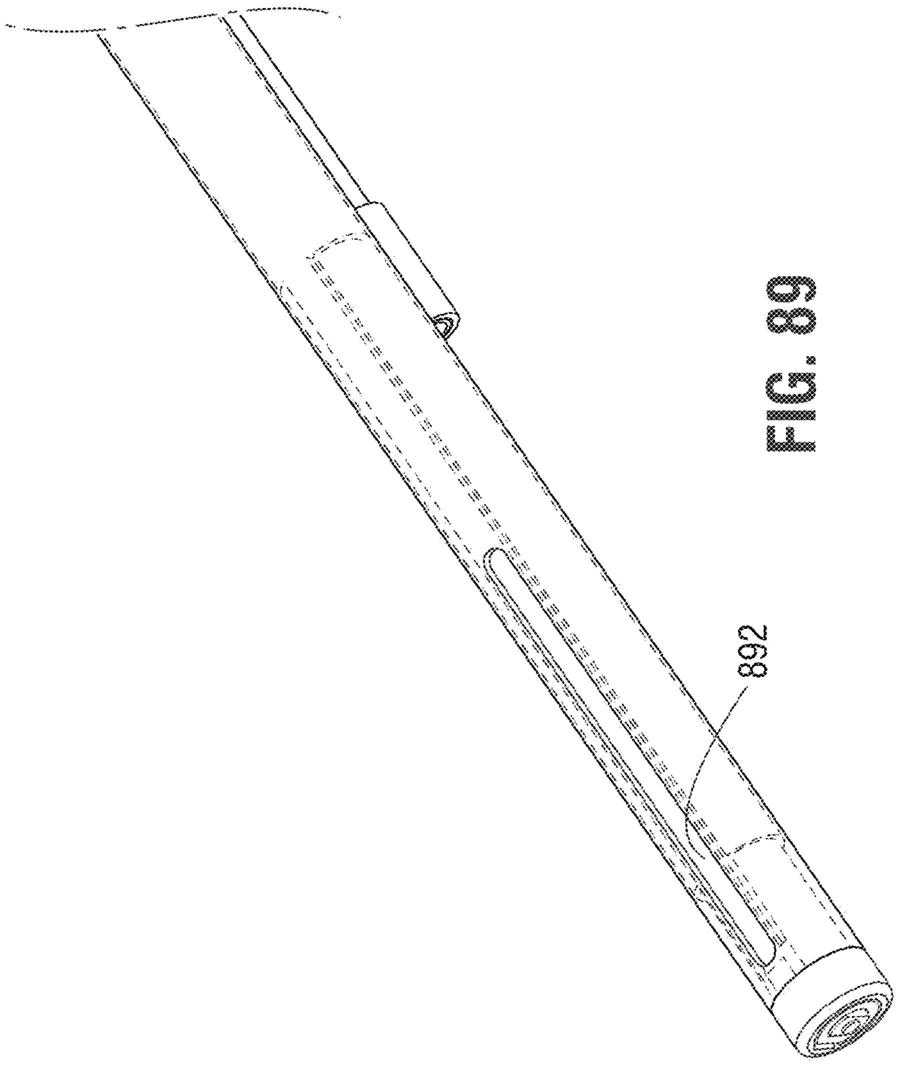
FIG. 89 is a fragmentary, perspective view of the end effector of FIG. 88 with the blade pushrod in a fully actuated state after cutting.
Figure 90:
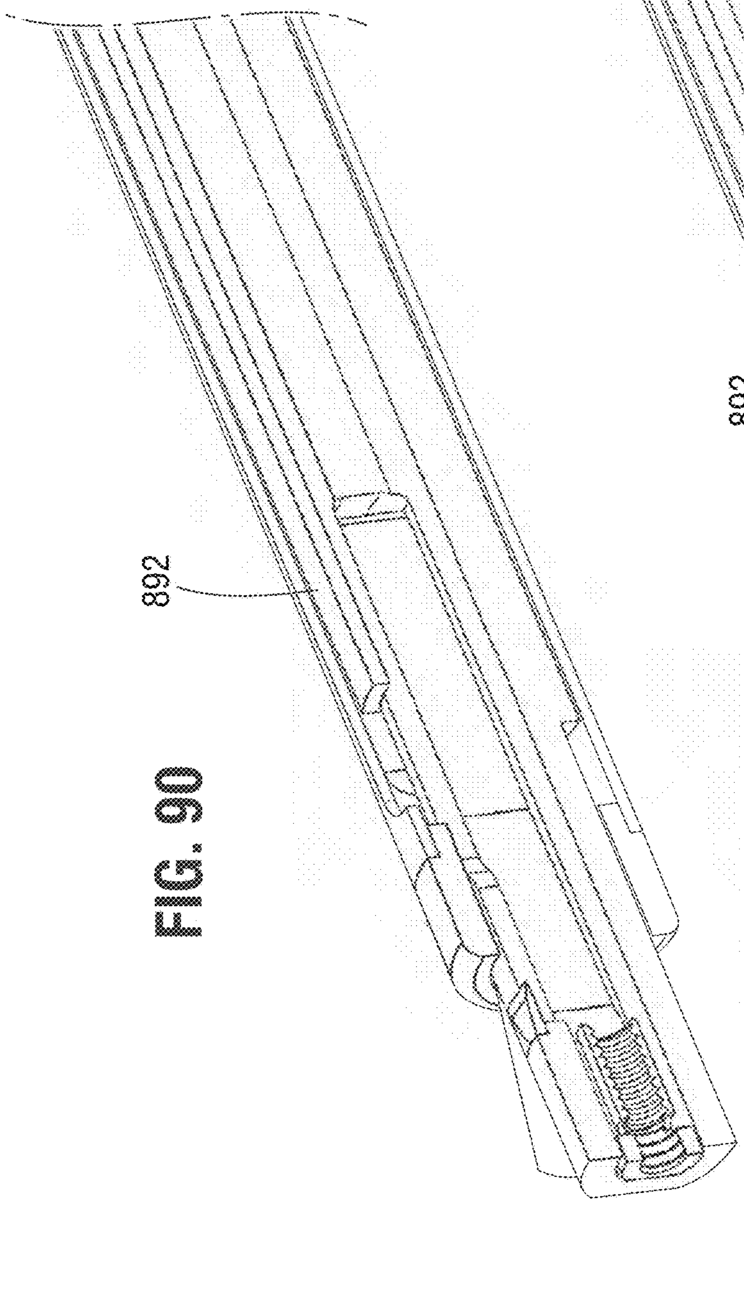
FIG. 90 is a fragmentary, longitudinally cross-sectional, perspective view of a distal end of the end effector of FIG. 85.
Figure 91:
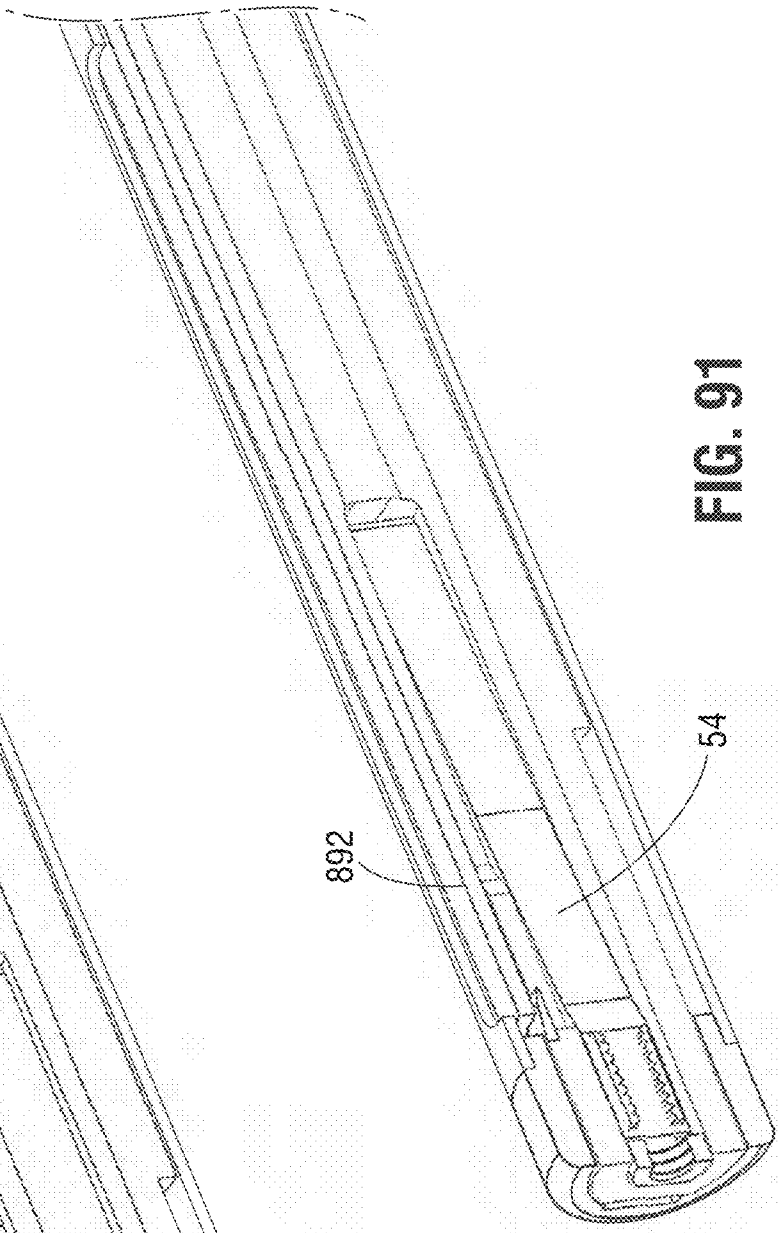
FIG. 91 is a fragmentary, longitudinally cross-sectional, perspective view of a distal end of the end effector of FIG. 89.

An alternative embodiment to the rotating cutter described above is a linear cutter shown in FIGS. 85 to 91. FIGS. 85, 86, and 90 illustrate an end effector of a multiple-firing crimp device with a fixed blade 890 and a blade pushrod 892 in a fully retracted position and with the crimping assembly 840 in a non-crimping state, in other words, the outer tube 70, 270 is retracted. FIG. 87 shows the crimping assembly 840 in a crimped state with the outer tube 70, 270 extended to crimp the crimp 30'. FIG. 88 shows the blade pushrod 892 in a partially actuated state before cutting occurs. It is noted from the right side of FIG. 88 that the blade pushrod 892 is a tube that rides inside the outer tube 70, 270. To insure that the cords 2 are pressed against the fixed blade 890, the slot in which the cords 2 extend out the side of the outer tube 70, 270 narrows at a distal end 893 and terminates at the tip of the blade 890. FIGS. 89 and 91 show the blade pushrod 982 in a fully actuated state after cutting has occurred. (Due to limitations of the graphics software, the inwardly compressed hammer 54 in FIG. 91 is shown within the crimp 30'.)

The display assembly 880 is connected to the system control assembly 800 and, in this exemplary embodiment, is shown as an LED, which can be, for example, an RGB LED that can produce light in various colors, each distinct color (or even a flashing pattern) is able to indicate a particular function or status. The display assembly 880, in an alternative embodiment, can be an LCD or LED or OLED display panel that can produce any colors, text, video, or pictures indicating status or any other characteristic of the multiple-firing crimp device.

Figure 92:
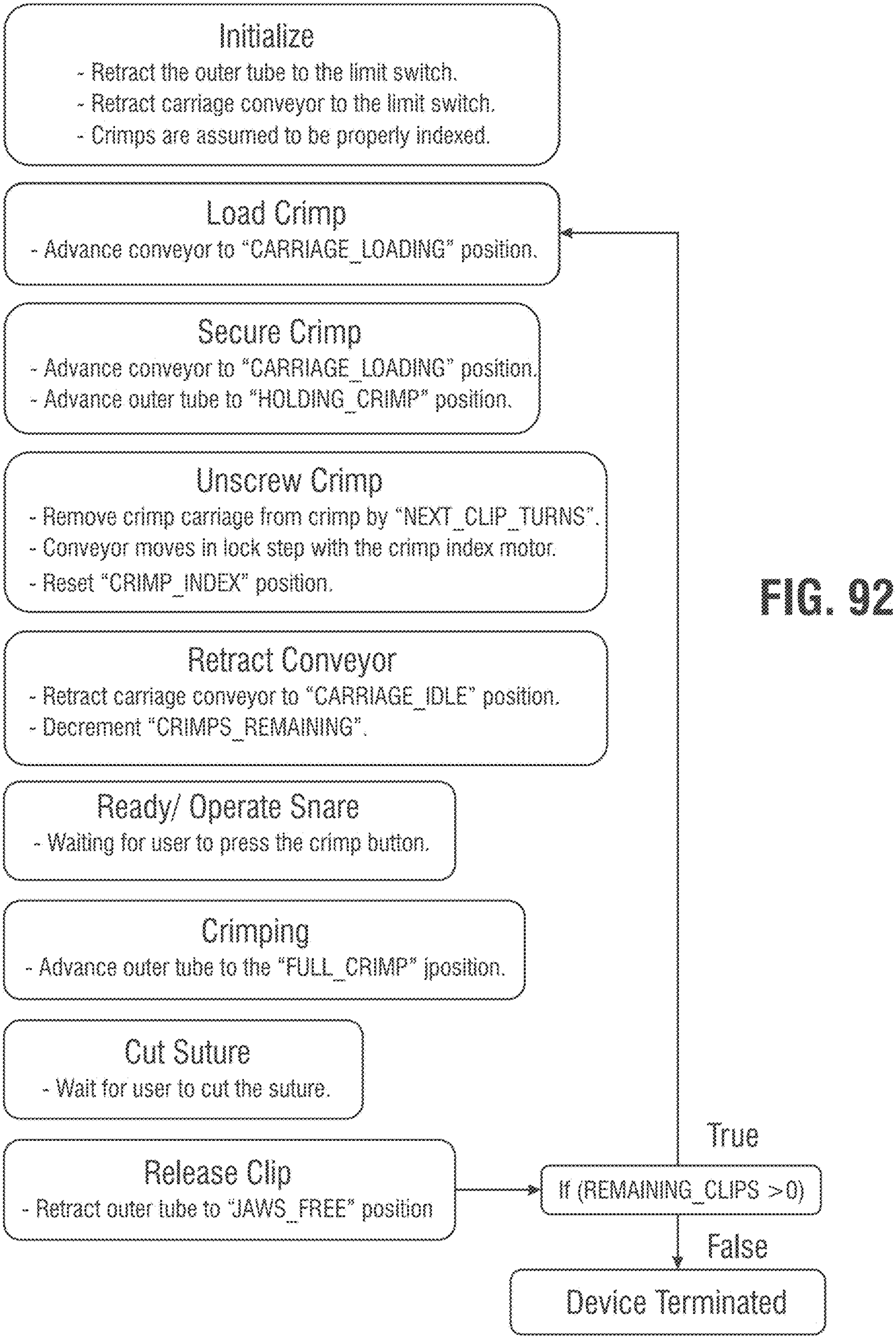
FIG. 92 is a flow chart of a process for completing a crimping procedure with a multiple-firing crimping assembly.
Figure 93:
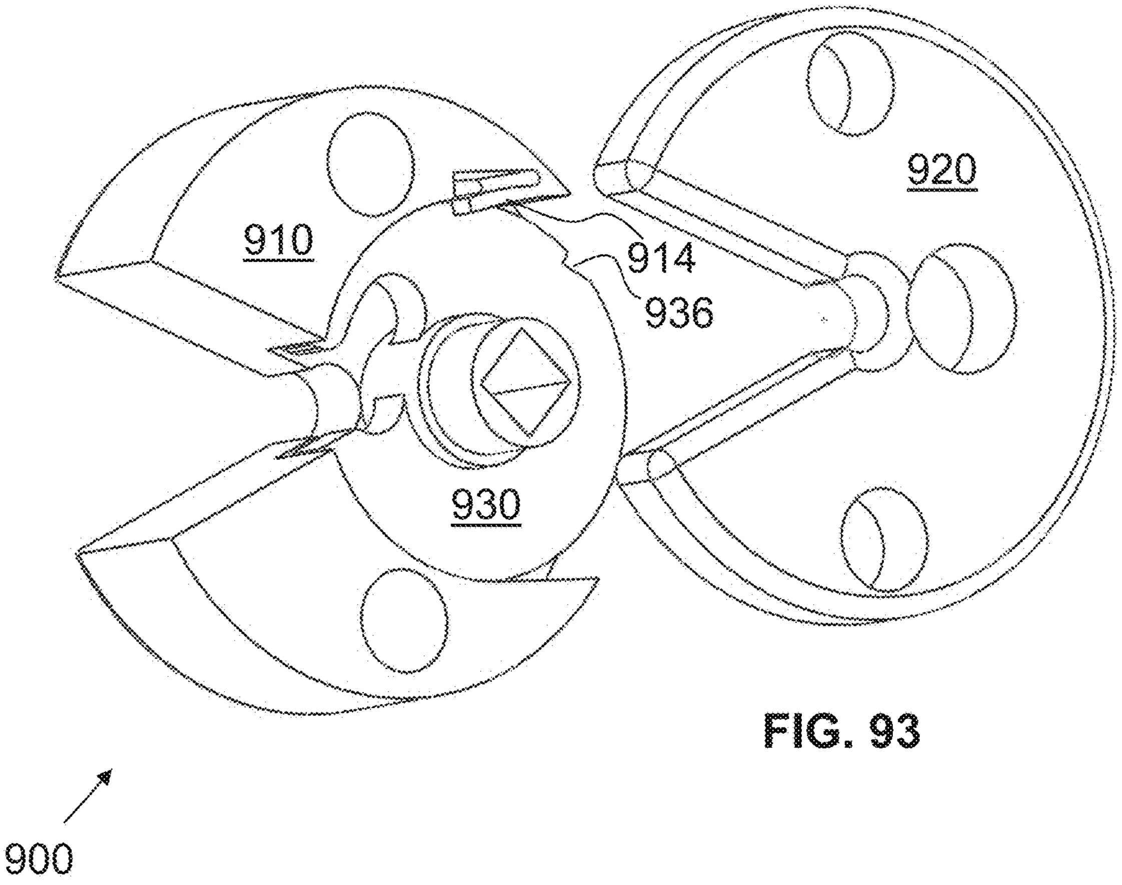
FIGS. 93 to 101 are perspective and exploded views of an exemplary embodiment of a cord, cable, or suture securing clip with a rotatable locking assembly.
Figure 94:
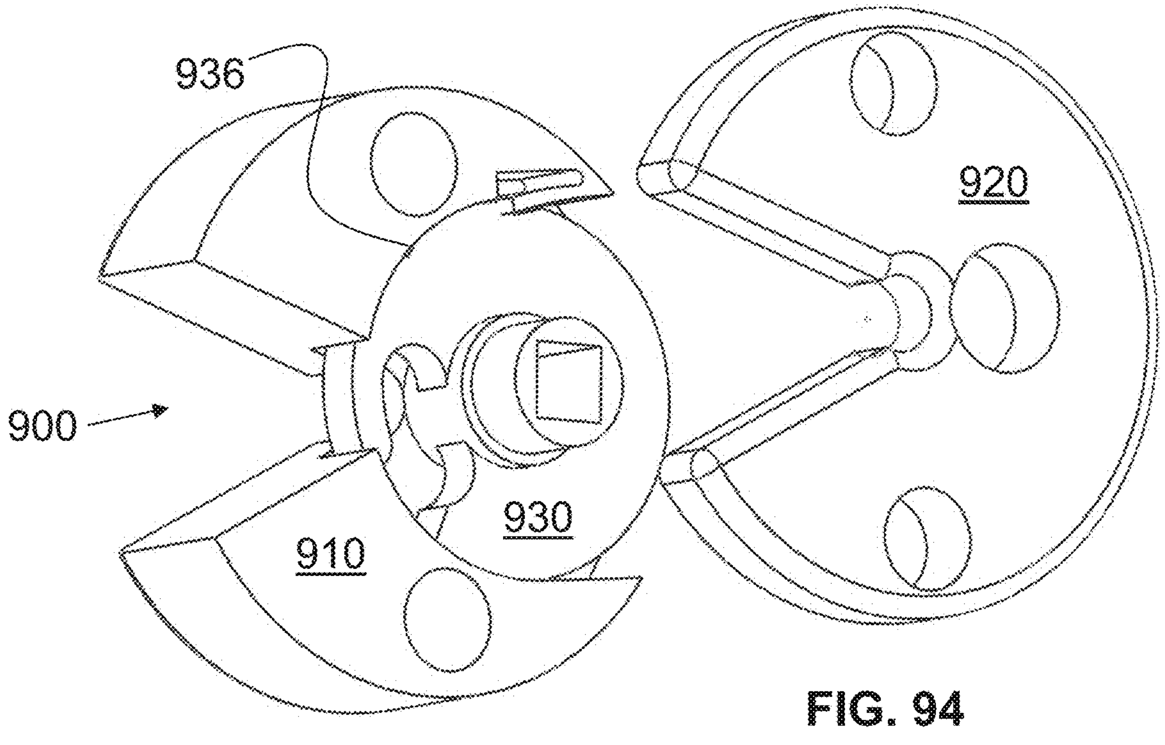

FIG. 92 shows a flow chart of a process for completing a crimping procedure with a multiple-firing crimp device described herein. In order to initialize the device, the outer tube and the crimp carriage are retracted. It is assumed that the crimps come preloaded on the crimp carriage before it is passed to a user. Of course, there can be a pre-initialization requirement that has the user load the crimp carriages with the crimps. Once initialized, the first crimp (the distal-most one) is advanced to the crimp loading orifice. The first crimp is secured at the crimp loading orifice by advancing the outer tube to gently press the hammer against the first crimp and hold it in the orifice. The crimp carriage is then rotated out from the first crimp (e.g., by a predefined number of turns) and further rotated to put the second crimp into a first crimp position at the distal end of the crimp carriage. The crimp carriage is moved proximally away from the end effector sufficiently far to prevent any interference with the crimping procedure into an idle position. The second crimp alignment can occur before, during, or after movement of the crimp carriage. As one crimp is no longer on the crimp carriage, the system can decrement a counter to keep track of the number of remaining crimps. At this point, the device is ready to use.

The user then carries out the manual steps of extending the snare, capturing the cord(s) within the snare, retracting the snare back to hold the cord(s), and then lifting the cord lifter or moving the shuttle proximally to present the end of the cord(s) outside the shaft of the device. The user grasps the exposed free end(s) of the cord(s) and pulls it/them taut. The end effector is then moved distally along the cord(s) to the place where the user desires to set the crimp. For example, where the cord is a surgical suture, the crimp is desired at the surgical site with no length of the suture between the crimp and the tissue. In such a case, the user will move the end effector up against the tissue to make the crimp ready to be fixed.

The automatic crimping can now occur. The user presses the crimp-start button (for example) and the outer tube is advanced to the distal position where the hammer crushes the crimp. The tube is held there in place distally until the cutting assembly is actuated to cut the free ends of the cord/suture at the proximal side of the fixed crimp. When the system indicates that the cutting has completed (e.g., when the cutting stroke is sufficient to insure that cords have been cut), the cutting assembly retracts to its idle position and the outer tube also retracts to its idle position, during which the now-crimped first crimp is released from the end effector. Now, the device is in its state for the next crimping process to begin, which starts with advancing the crimp conveyor to load the next crimp.

Figure 98:
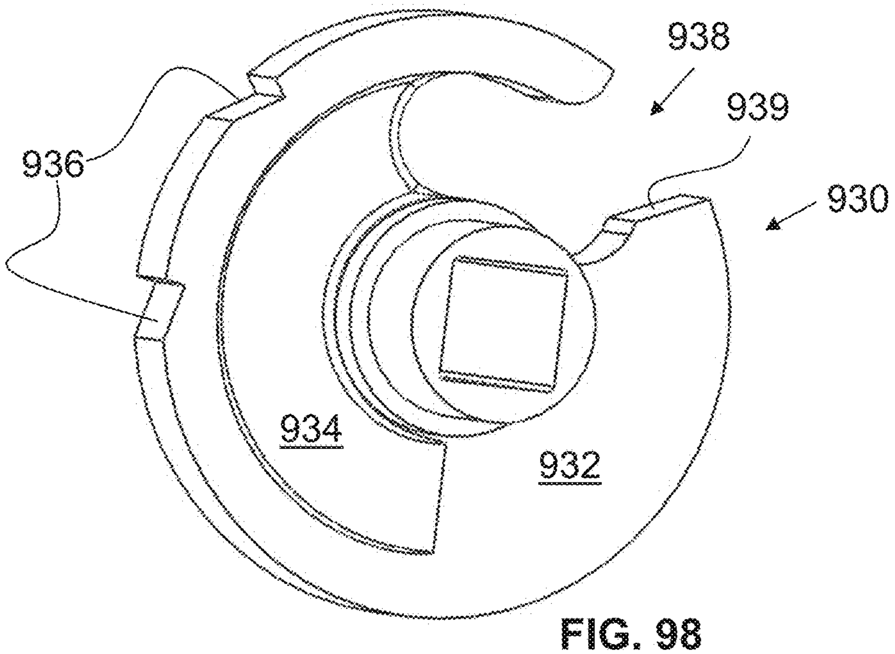
Figure 99:
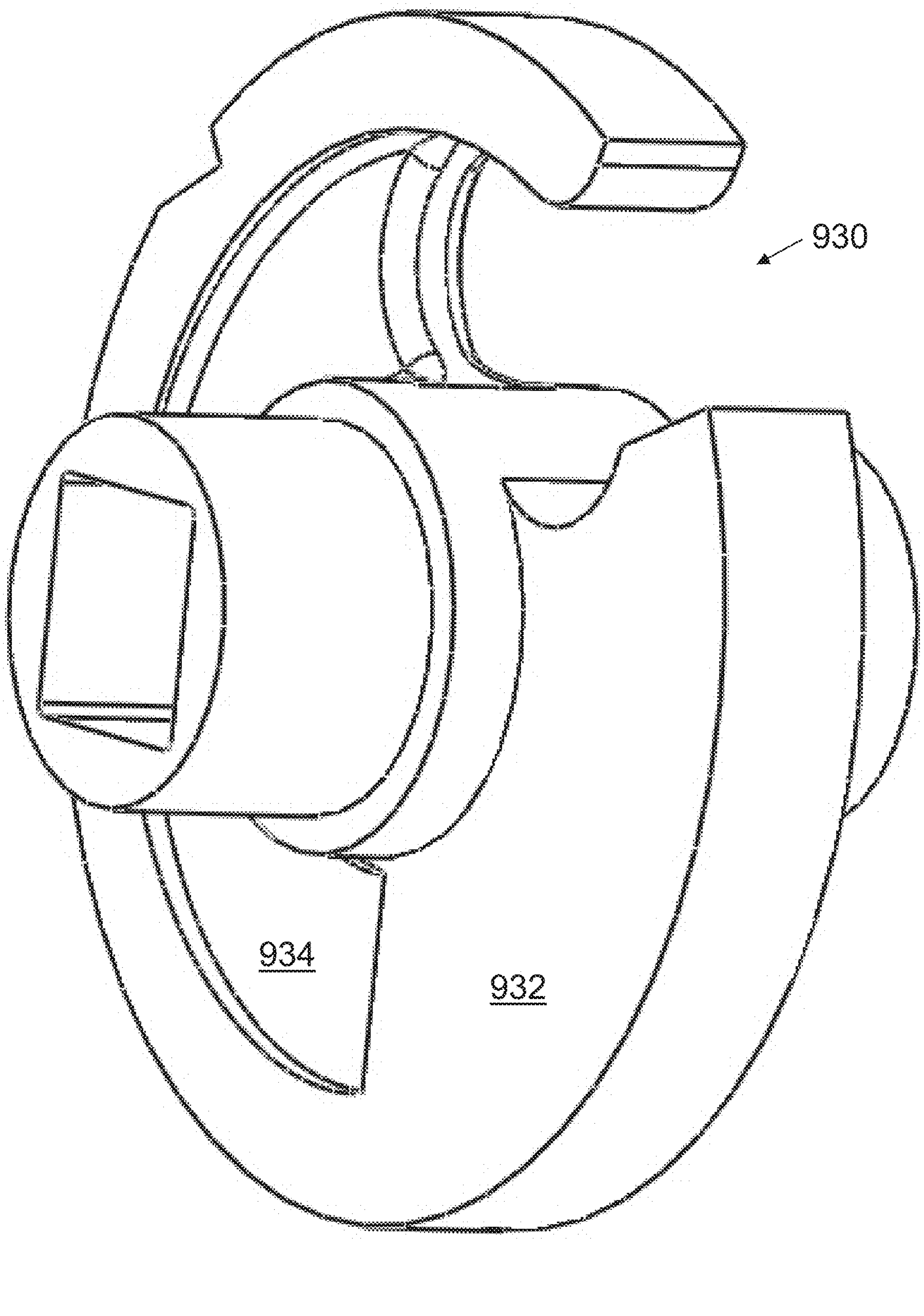
Figure 100:
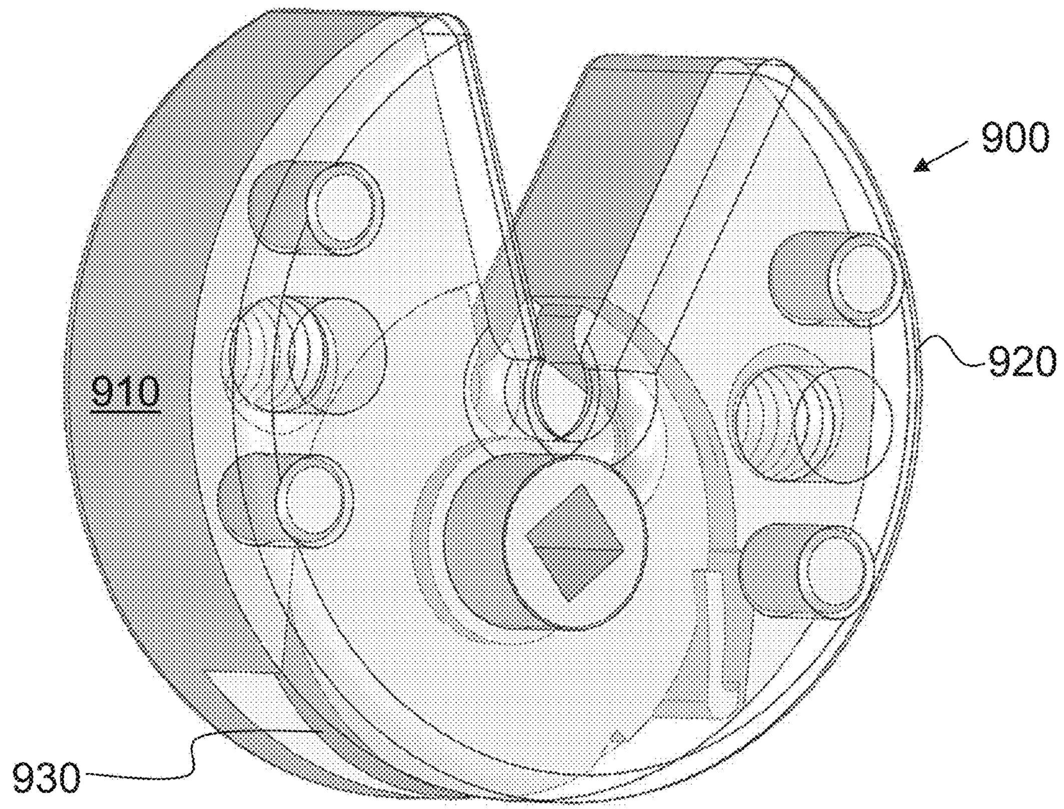
Figure 101:
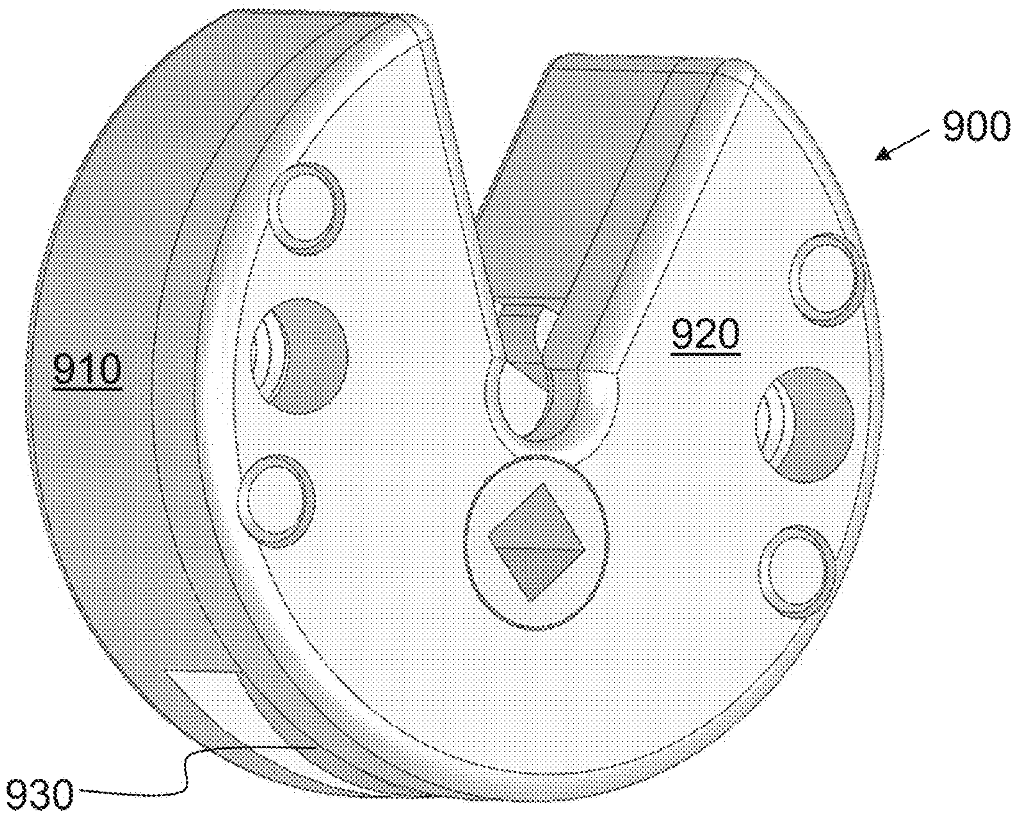

The shape of the crimp shown in FIGS. 32 to 35 is not the only possible shape for a system that can deliver multiple crimps with a single delivery device. Another exemplary configuration provides a mechanical clip 900 that is shown in FIGS. 93 to 101. This clip 900 has a rotator housing 910, a rotator cover 920, and a central rotator 930. The rotator housing 910 and the rotator cover 920 are fixed together with the central rotator 930 rotatably disposed therebetween. The central rotator 930 is able to rotate from an open position shown in FIG. 93, through a cord-captured position shown in FIG. 94, and then to a cord-secured position shown in FIGS. 95 and 96. The difference between the cord-captured and the cord-secured positions is that the cord is captured in the position of FIG. 94. However, the clip 900 could slide along the captured cord. By rotating the central rotator 930 further to the position shown in FIGS. 95 and 96, the cord becomes trapped between the central rotator 930 and the rotator housing 910 within an interface, shown in the exploded view of FIG. 97. This interface is comprised of a housing lateral surface 912 and an opposing lateral surface 932 of the central rotator 930 that is not visible in FIG. 97 but is shown in FIG. 98. The lateral surface 932 contains a groove 934 that, in the exemplary embodiment, starts from a greater depth and ends at a shallow depth. Accordingly, when the central rotator 930 rotates from the cord-captured position to the cord-secured position, the cord is forced between the wall of the groove 934 and the housing lateral surface 912 to lock the clip 900 and the cord(s) trapped therein together. FIGS. 100 and 101 show the clip 900 in its assembled state with the central rotator 930 in the open position.

Figure 95:
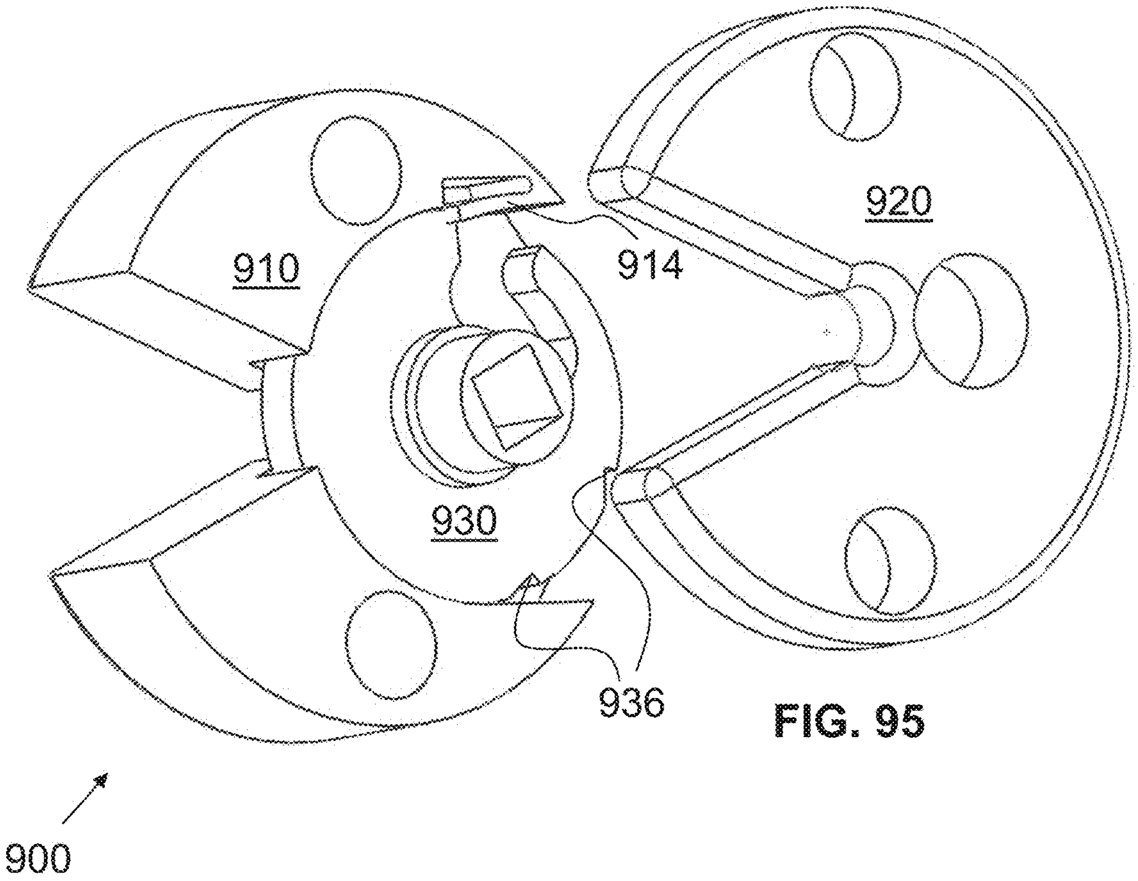
Figure 96:
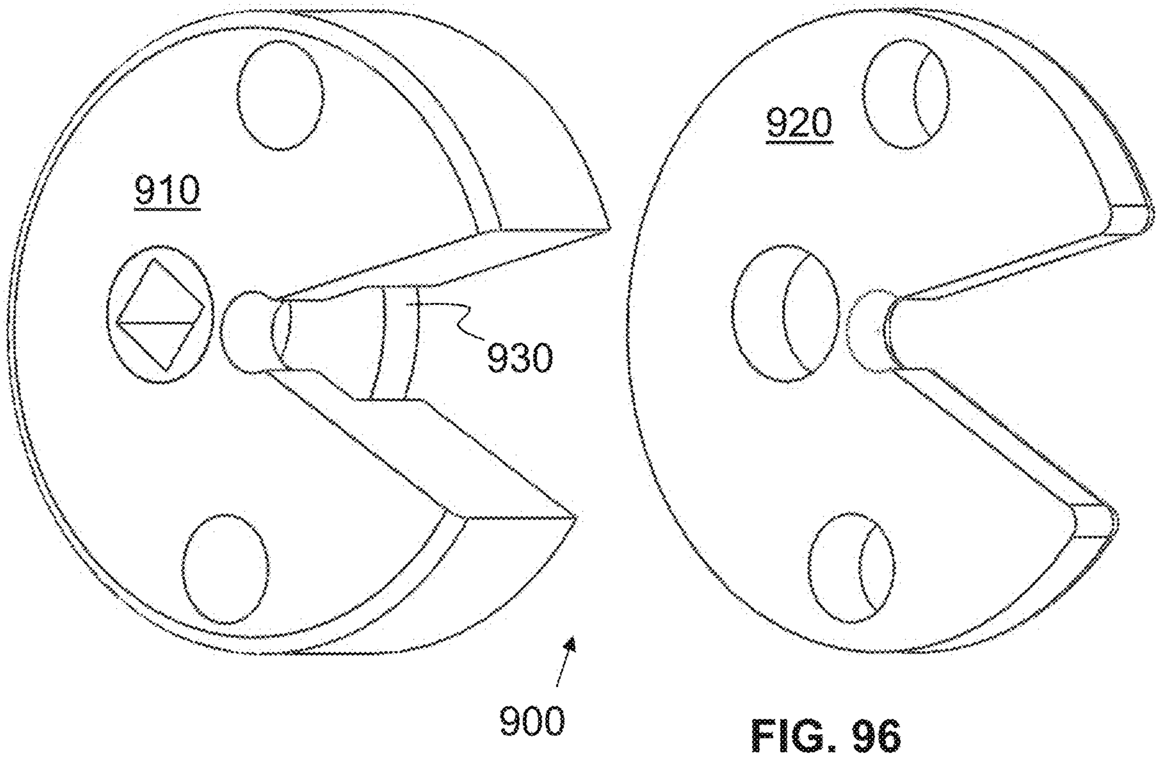
Figure 97:
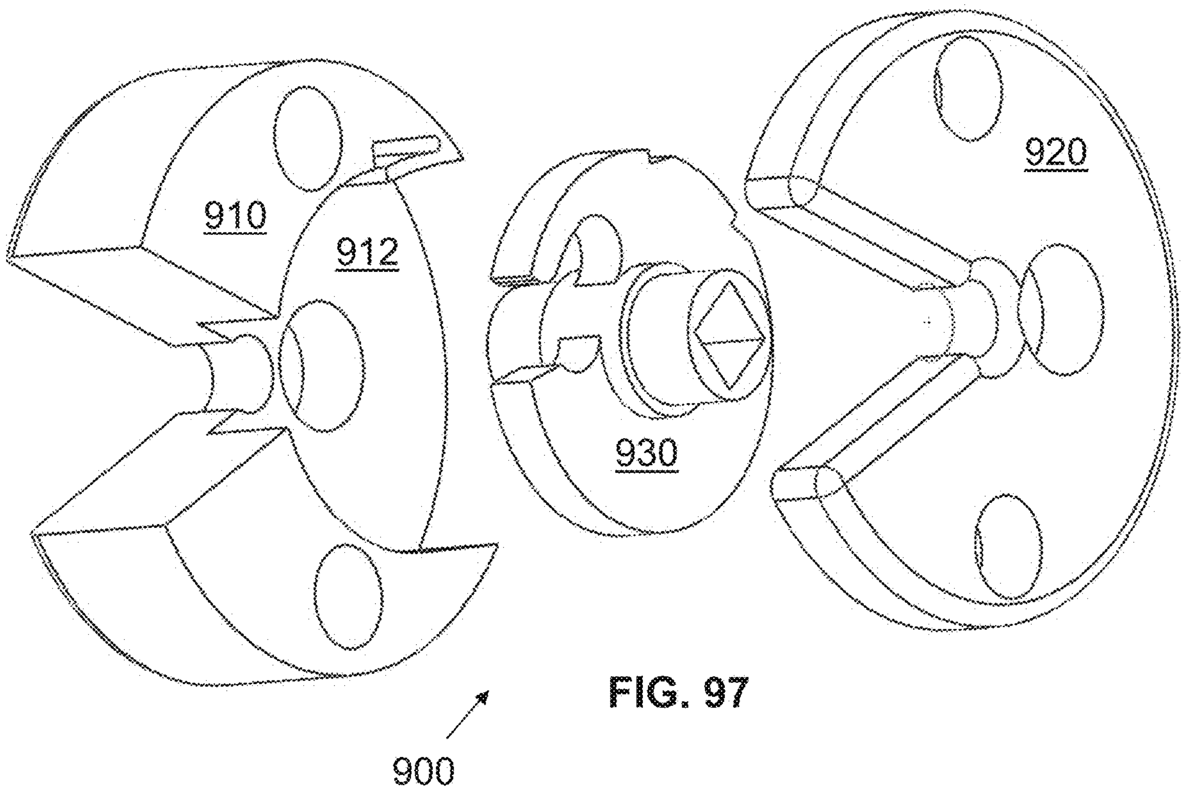

The central rotator 930 also has ratchet grooves 936, two of which are shown in this exemplary embodiment. These ratchet grooves 936 are shaped to mate with a ratchet bar 914 on the rotator housing 910 such that, as the central rotator 930 rotates (counter-clockwise in FIGS. 93 to 94) from the open position to the cord-captured position, the ratchet groove 936 and ratchet bar 914 prevent rotation in the opposite direction, making the clip 900 a one-direction assembly. For a final locking position, the mouth 938 of the central rotator 930 has a final locking surface 939 that connects with the distal end of the ratchet bar 914 as shown in FIG. 95. In this position, the central rotator 930 is locked and is crushing the cord(s) within the groove 934.

Figure 102:
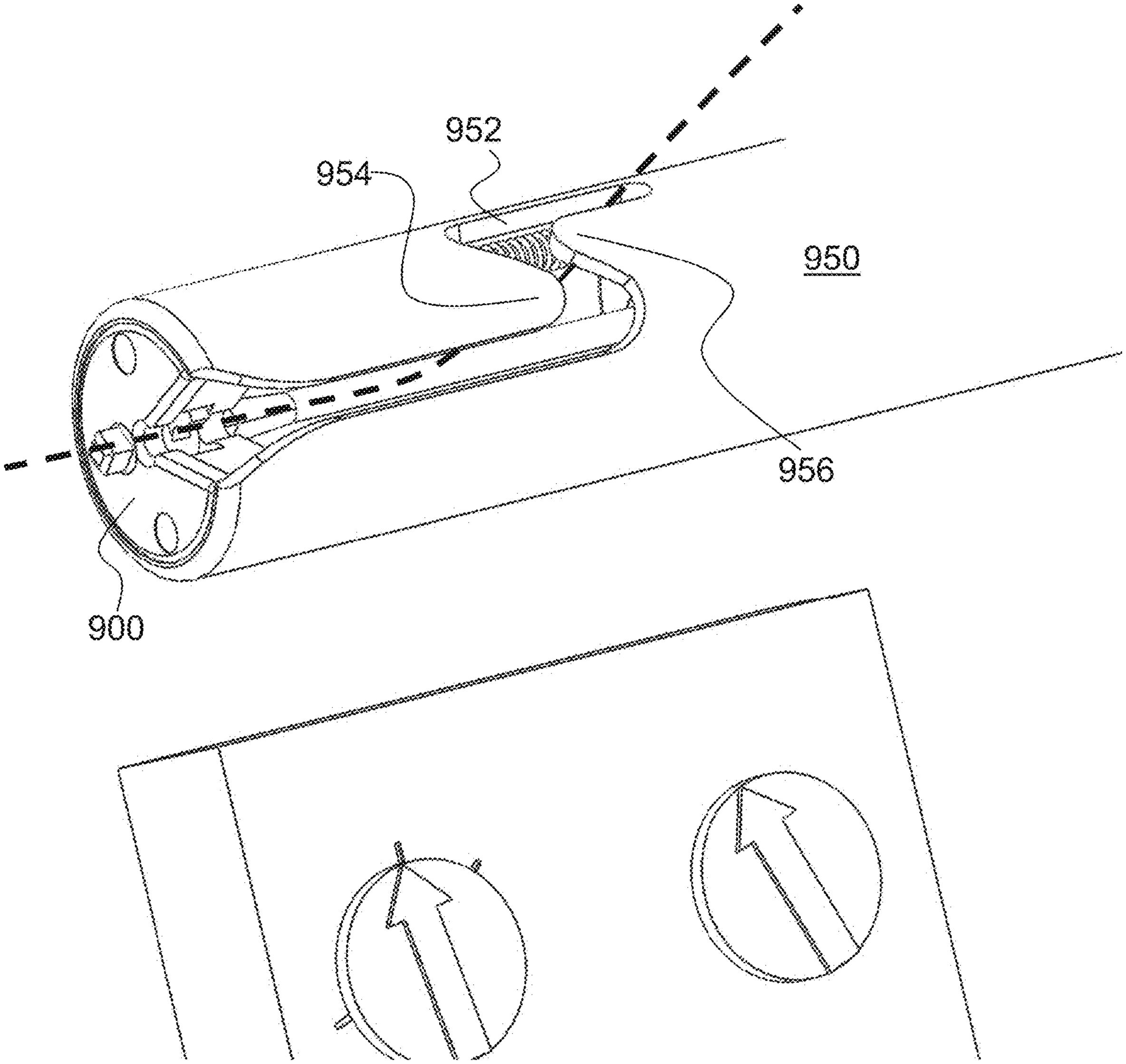
FIG. 102 is a fragmentary perspective view of the securing clip of FIGS. 93 to 101 within a clip-delivery system in a loading orientation.
Figure 103:
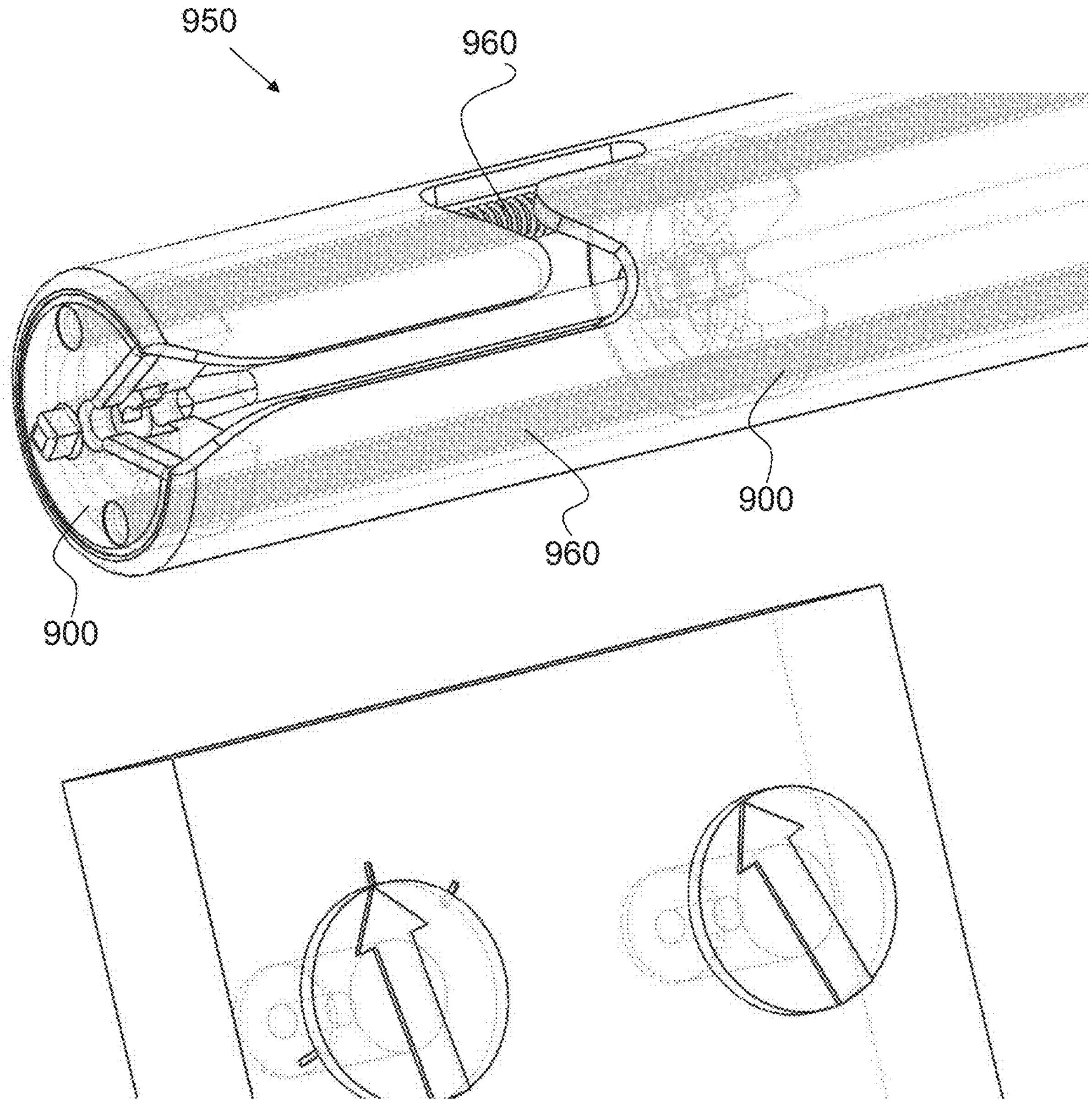
FIG. 103 is a fragmentary perspective and partially transparent view of the securing clip and clip-delivery system of FIG. 102.
Figure 104:
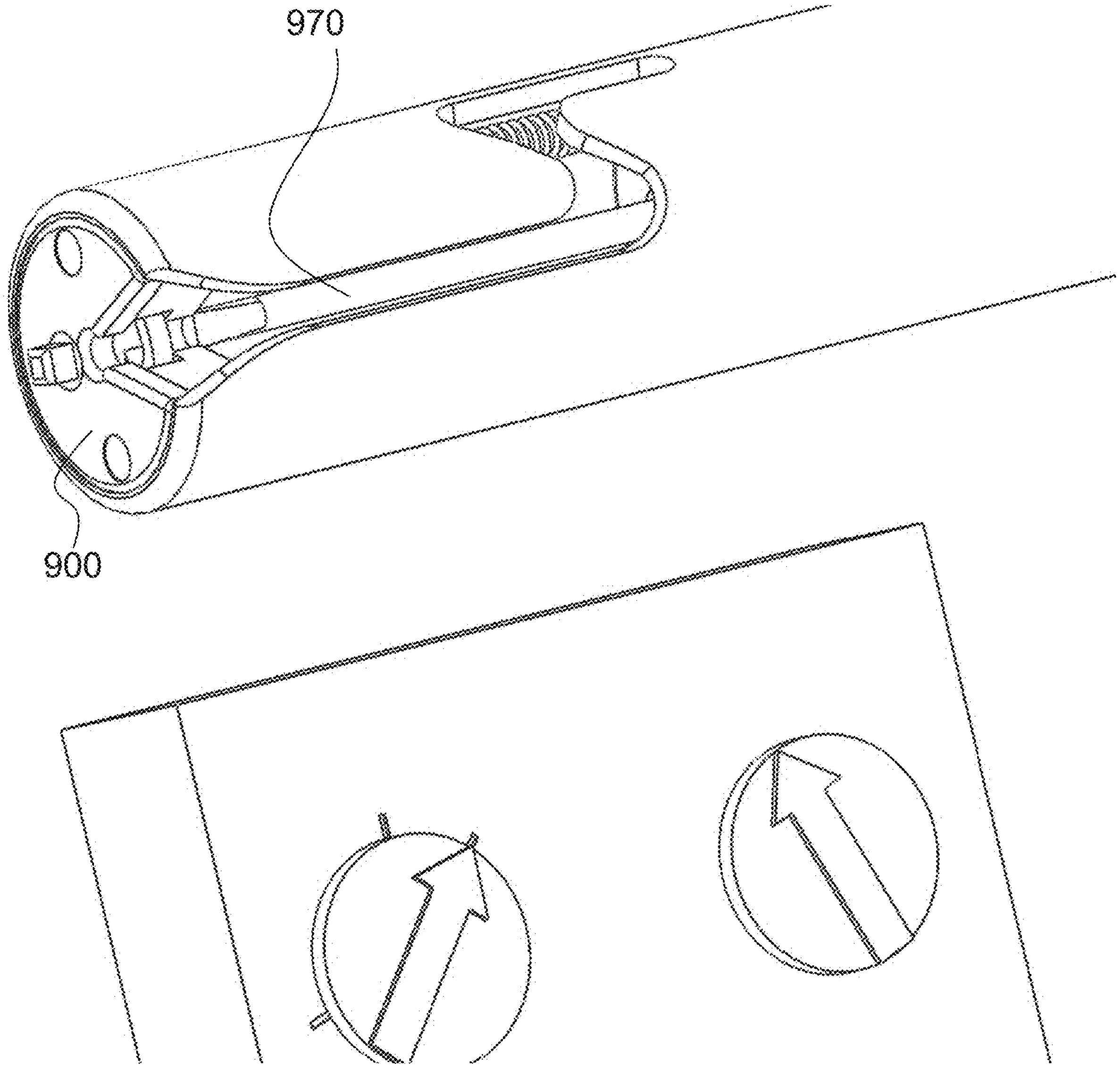
FIG. 104 is a fragmentary perspective view of the securing clip and delivery system of FIG. 102 within the securing clip in a partially locked state.
Figure 105:
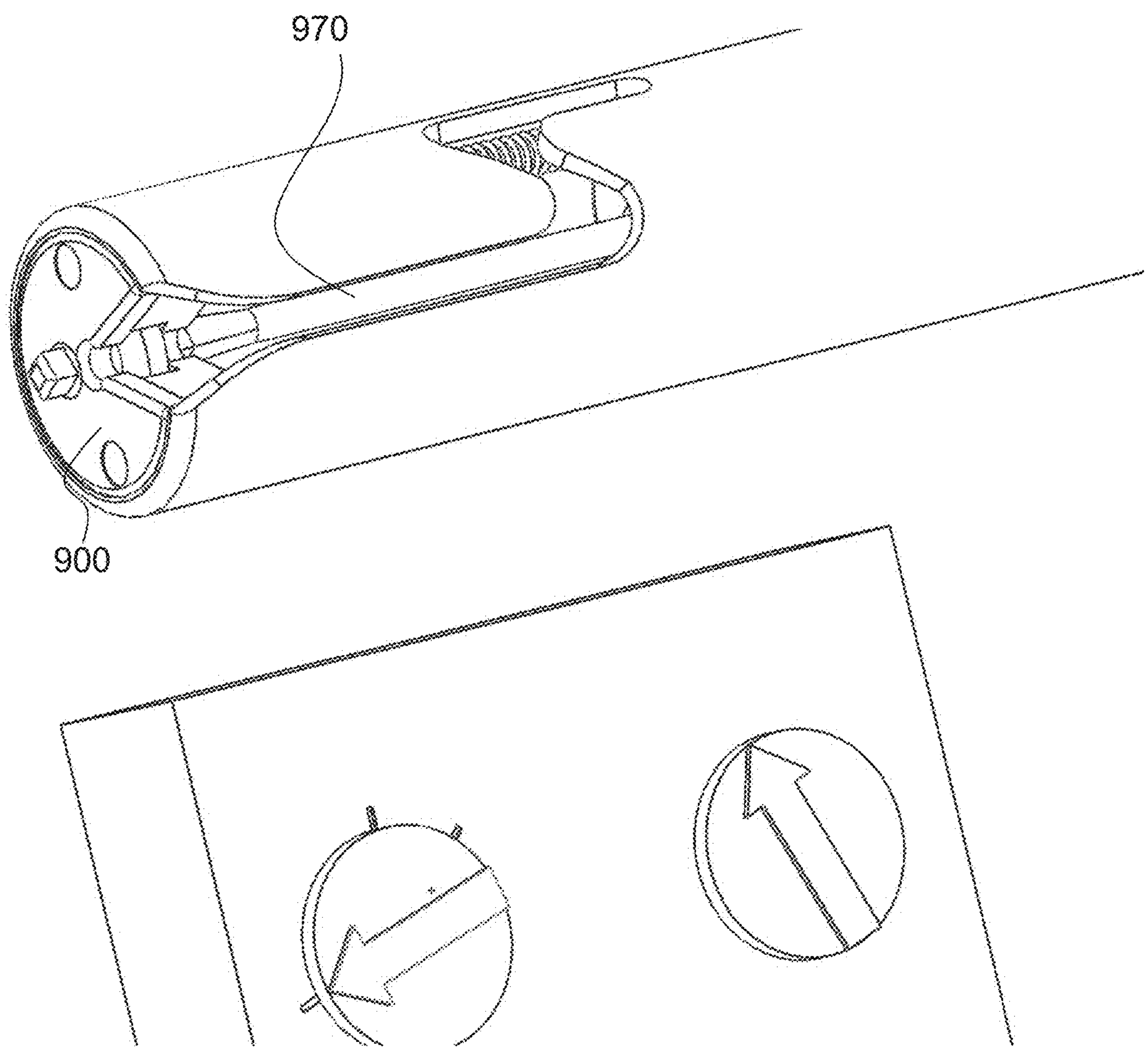
FIG. 105 is a fragmentary perspective view of the securing clip and delivery system of FIG. 102 within the securing clip in a partially locked state.
Figure 106:
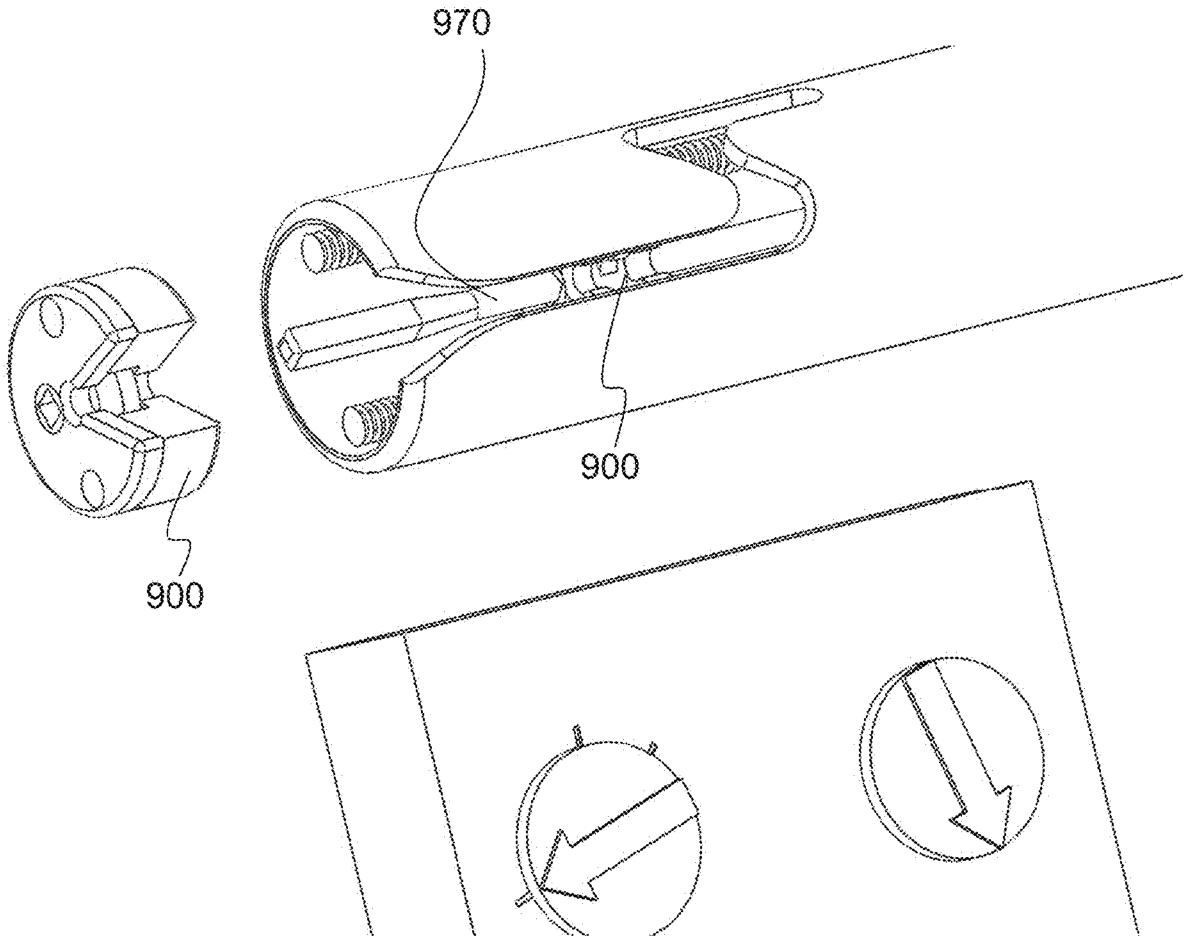
FIG. 106 is a fragmentary perspective view of the securing clip and delivery system of FIG. 102 within the securing clip deployed out from the distal end of the delivery system.
Figure 107:
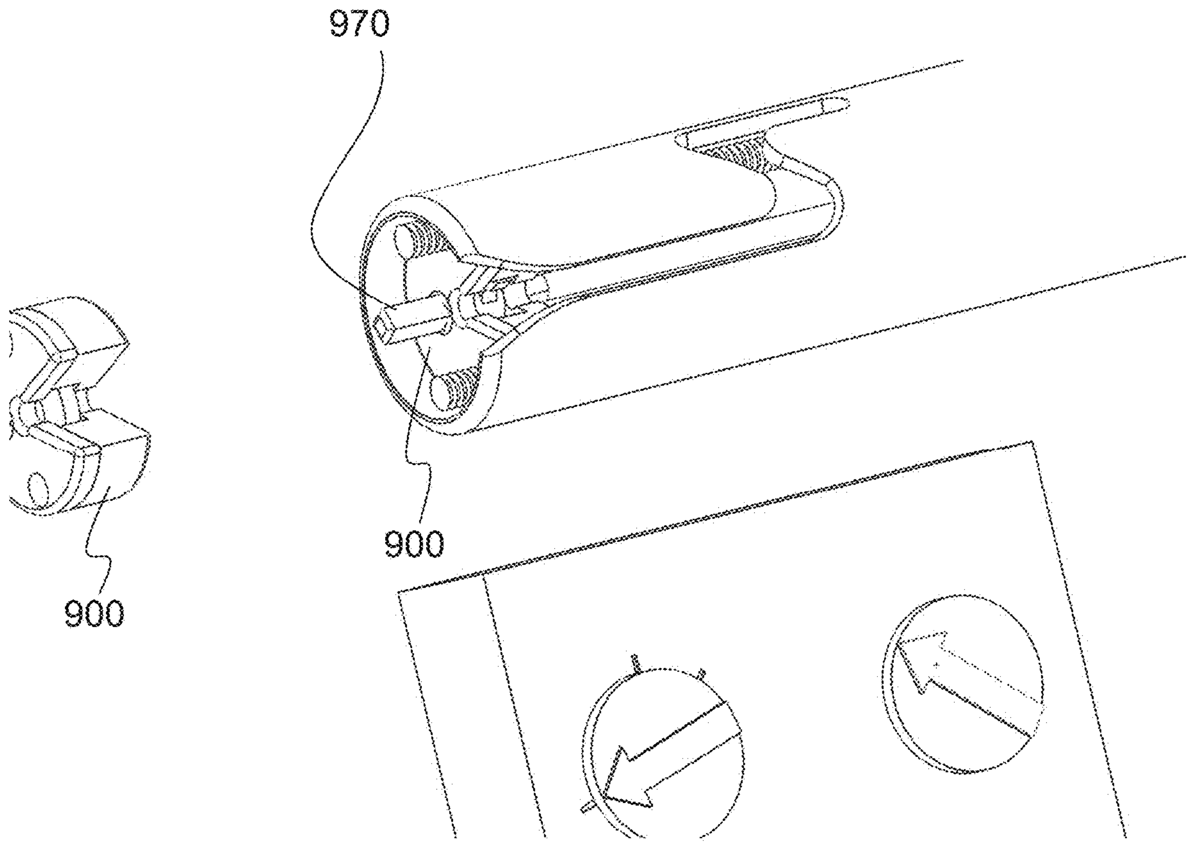
FIG. 107 is a fragmentary perspective view of the securing clip and delivery system of FIG. 102 within a second securing clip advanced toward the distal end of the delivery system.
Figure 108:
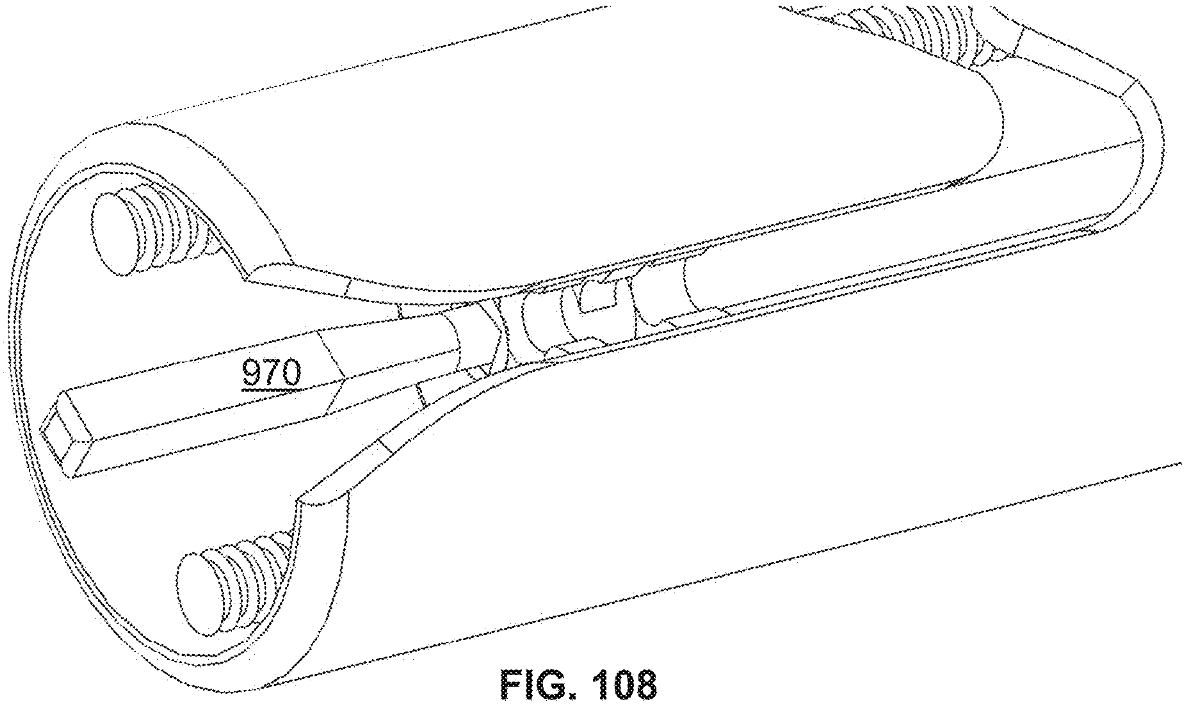
FIG. 108 is a fragmentary perspective view of the second securing clip and delivery system of FIG. 107 enlarged.
Figure 109:
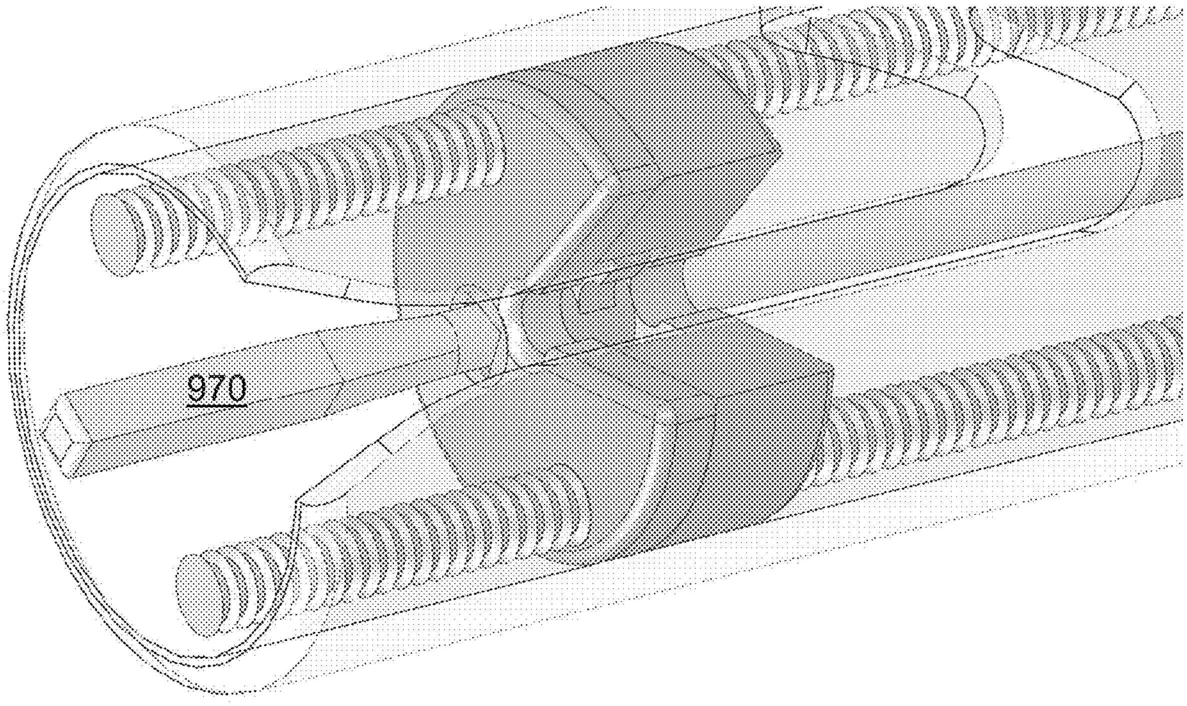
FIG. 109 is a fragmentary, transparent perspective view of the second securing clip and delivery system of FIG. 107 enlarged.

FIGS. 102 to 109 illustrate how one of a set of multiple clips 900 can be installed, one-at-a-time, on various cords over a cord-securing procedure. FIG. 102 shows the clip-delivery system 950 with a clip 900 at a distal clip-installation position aligned with a cord raceway 952. In this state, a cord to be secured is guided through the V-shape of the clip 900 in its open position and around the two turns 954, 956 to a final installed position exiting out from the end of the raceway as indicated by the dashed line. FIG. 103 shows the interior of the clip-delivery system 950 with the exterior shaft transparent. As can be seen here, there are two clips 900 movably installed on clip carrier shafts 960. These carrier shafts 960 allow a set of any number of clips 900 to be used in a given procedure. FIG. 104 shows that the clip 900 has been locked into the cord-captured position by a corresponding rotation of a locking shaft 970. With further rotation of the locking shaft 970, as shown in FIG. 105, the clip 900 is placed in the cord-secured position. Rotation of the carrier shafts 960 forces the clip 900 off the distal end thereof to remain at the location where it is intended to be secured on the cord(s), thus freeing up the distal installation portion of the clip-delivery system 950 for the next clip 900, which is adjacent the installation portion in FIG. 107. FIGS. 108 and 109 show how the locking shaft 970 is formed at the distal end so that only the clip in the installation portion of the clip-delivery system 950 has its central rotator 930 moved when the locking shaft 970 rotates even though many more clips 900 can be located about the locking shaft 970 proximal of the installation portion.

Figure 110:
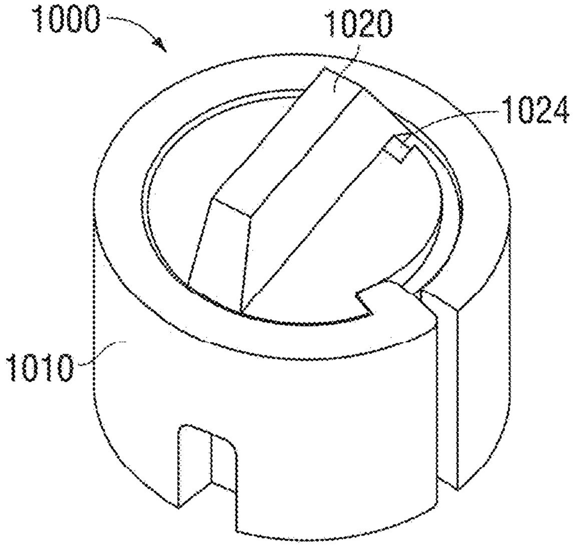
FIG. 110 is a perspective view of an exemplary embodiment of another securing clip not to scale with a rotatable locking assembly in an unlocked state.
Figure 112:
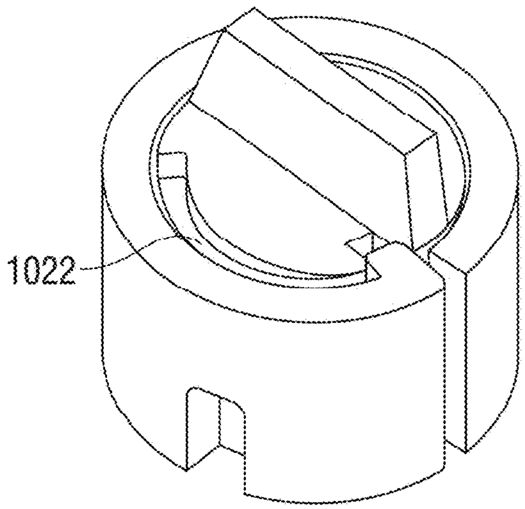
FIG. 112 is a perspective view of the securing clip of FIG. 110 with a rotatable locking assembly in a locked state.
Figure 111:
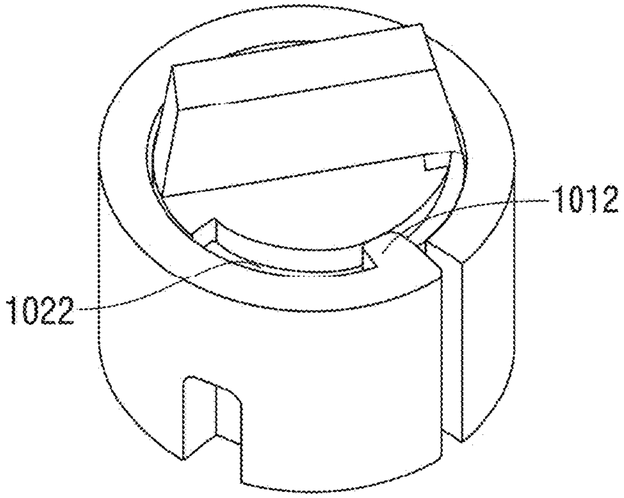
FIG. 111 is a perspective view of the securing clip of FIG. 110 with a rotatable locking assembly in a partially locked state.
Figure 113:
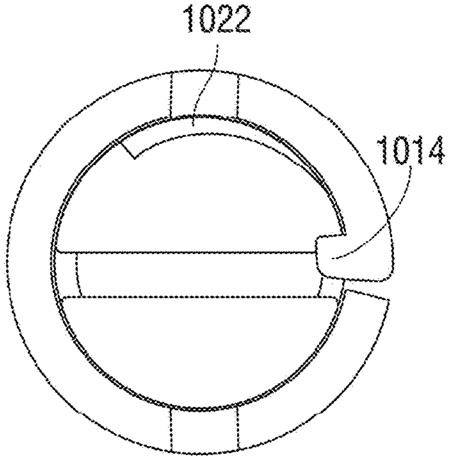
FIG. 113 is a bottom plan view of the securing clip of FIG. 112.

FIGS. 110 to 125 illustrate various configurations of clips 1000, 1100, 1200 that can be loaded with cord(s) from a side thereof instead of through a bore as in the crimp 30. A first exemplary embodiment of a side-loaded clip 1000 illustrated in FIGS. 110 to 116 includes an external shell 1010 and an internal rotator lock 1020. The shell 1010 has an inwardly extending boss 1012 that rides on a groove 1022 of the rotator lock 1020 when the rotator lock 1020 is rotated. FIG. 110 illustrates the rotator lock 1020 in an unlocked position where the boss 1012 is at the deepest portion of the groove 1022. FIG. 111 illustrates the rotator lock 1020 in a intermediate partially locked position where the boss 1012 is at a shallower portion of the groove 1022. FIG. 112 illustrates the rotator lock 1020 in a locked position where the boss 1012 is within a lock cavity 1024 just after the shallowest portion of the groove 1022. As shown in FIG. 113 the lower portion of the shell 1010 has a lower boss 1014 and the lower portion of the rotator lock 1020 has a lower groove 1022.

Figure 114:
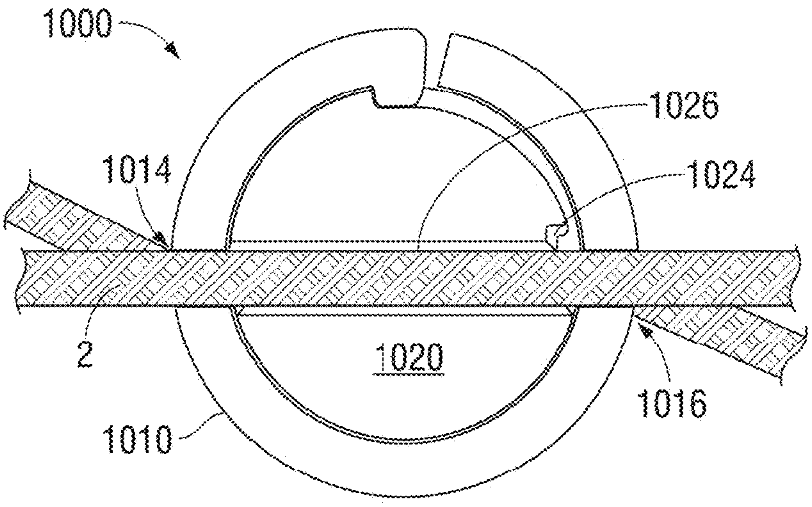
FIG. 114 is a bottom plan view of the securing clip of FIG. 110 with the rotatable locking assembly in an unlocked state with a cord inserted therein.
Figure 115:
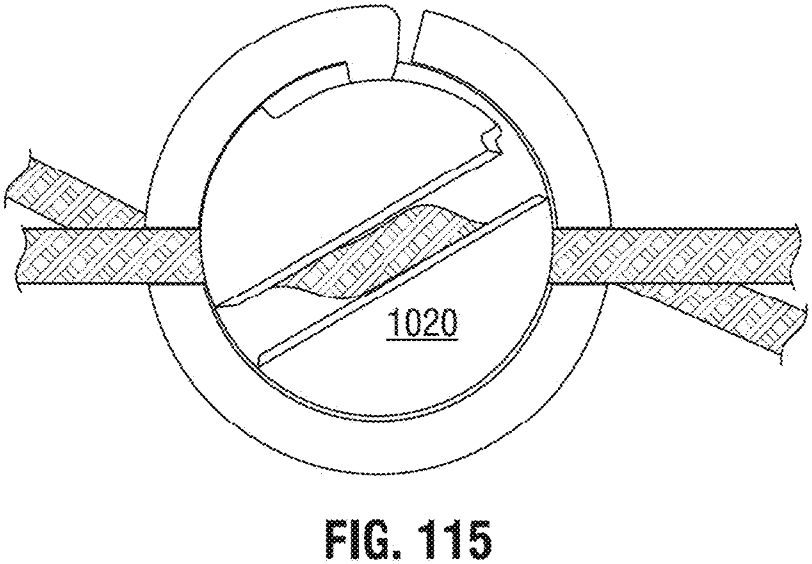
FIG. 115 is a bottom plan view of the securing clip of FIG. 114 with the rotatable locking assembly in a partially locked state.
Figure 116:
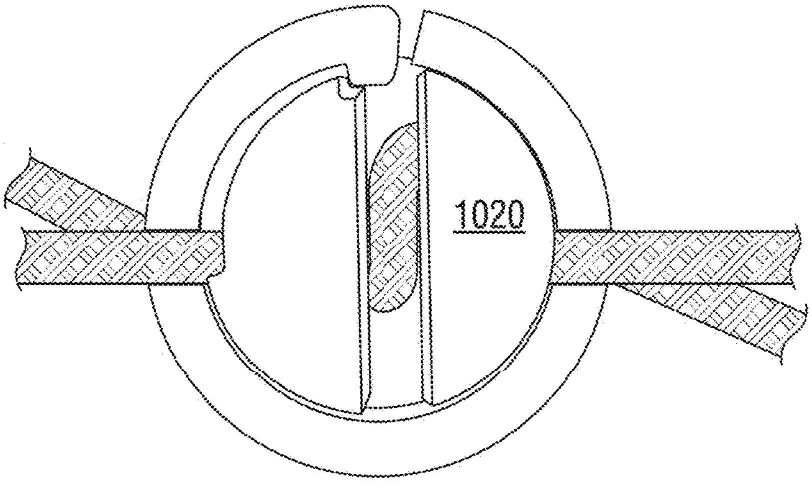
FIG. 116 is a bottom plan view of the securing clip of FIG. 114 with the rotatable locking assembly in a locked state.
Figure 117:
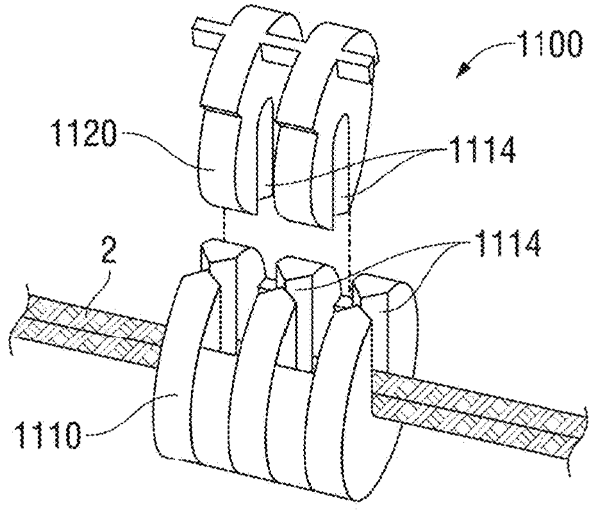
FIG. 117 is a perspective view of an exemplary embodiment of a further securing clip not to scale with a press-fit locking assembly in a separated state.
Figure 118:
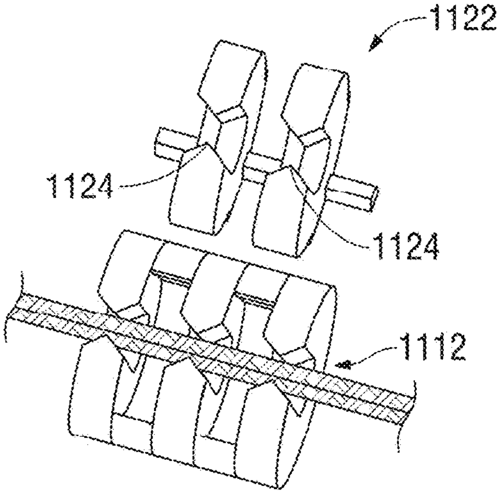

Locking of the clip 1000 to a cord(s) is illustrated with reference to FIGS. 114 to 116. The lower portion of the shell 1010 has cord grooves 1014, 1016. In this embodiment, the cord grooves 1014, 1016 are opposite one another. Similarly, the lower portion of the rotator lock 1020 has a cord cavity 1026 that, when aligned with the cord grooves 1014, 1016, form a channel from one side of the shell 1010 to the other. The cord grooves 1014, 1016 and the cord cavity 1026 are deep enough to allow cords 2 to be inserted therein and, preferably, deep enough to not exit any part of the channel when locked therein. FIG. 114 shows the shell 1010 and the rotator lock 1020 in the open/loading position. In this state, the cords can be stretched and guided into the channel all the way to the bottom of the channel. Locking of the clip 100 to the cords 2 occurs by rotating the rotator lock 1020. FIG. 115 shows the rotator lock 1020 in an intermediate, partially locked state. FIG. 116 shows the rotator lock 1020 in its locked state, which, here, is almost a 180-degree rotation. If desired, the outer cylindrical surface of the rotator lock 1020, which cannot be seen in these figures, can have a circumferential groove to prevent the cords 2 from exiting the pinched state between the interior of the shell 1010 and the exterior of the rotator lock 1020. The surfaces between the shell 1010 and the rotator lock 1020 can be knurled or have other features to increase friction and prevent the cords 2 from exiting the locked clip 1000 without destroying or unlocking the clip 1000.

Figure 119:
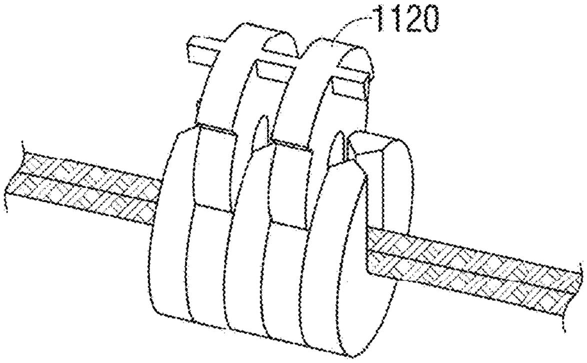
Figure 120:
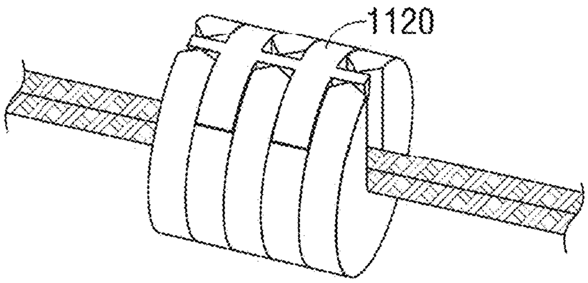
Figure 121:
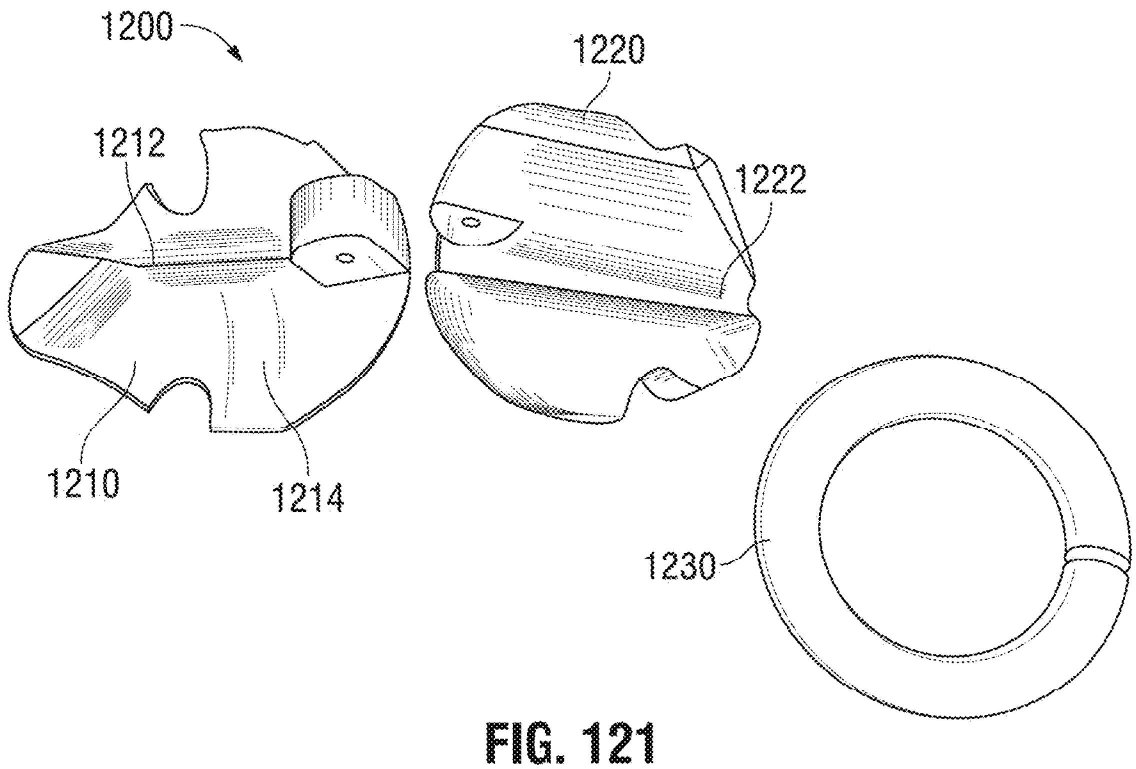

FIGS. 117 to 120 illustrate another exemplary embodiment of a laterally loaded clip 1100 for securing cords 2 therein. The clip 1100 has a main body 1110 and an insert 1120. The main body 1110 has a longitudinal channel 1112 shaped to receive cords 2 therein. At various longitudinal distances along the channel 1112, the body 1110 has sets of opposing protrusions 1114 that provide pinching points to hold the cords 2 therein. The insert 1120 also has a channel 1122 and sets of opposing protrusions 1124. The insert 1120 is shaped, as a puzzle piece, to be inserted into the body 1110 between the protrusion sets and lock the cords 2 therebetween in a press fit, as shown in the views of FIGS. 119 and 120.

Figure 122:
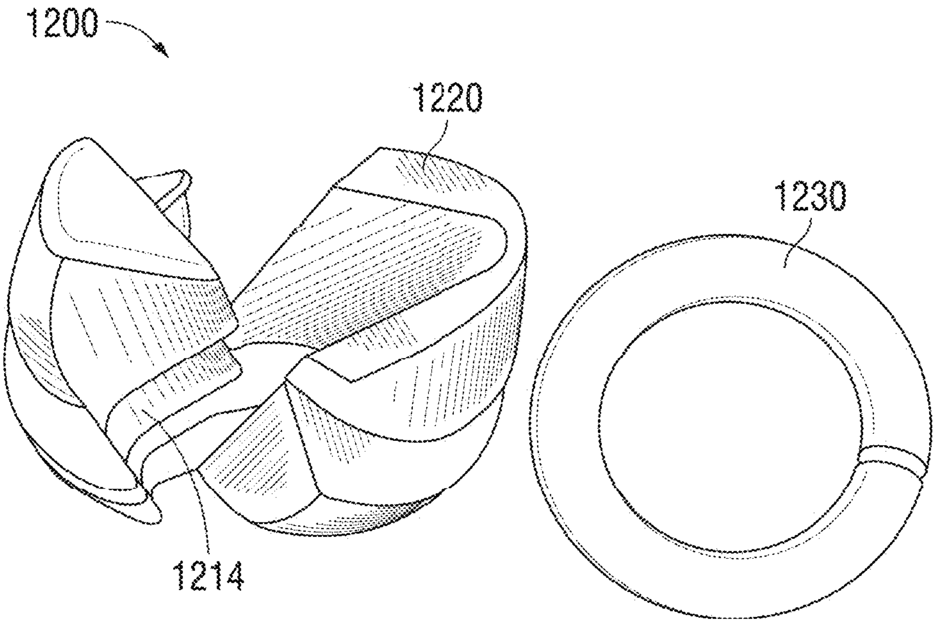
Figure 123:
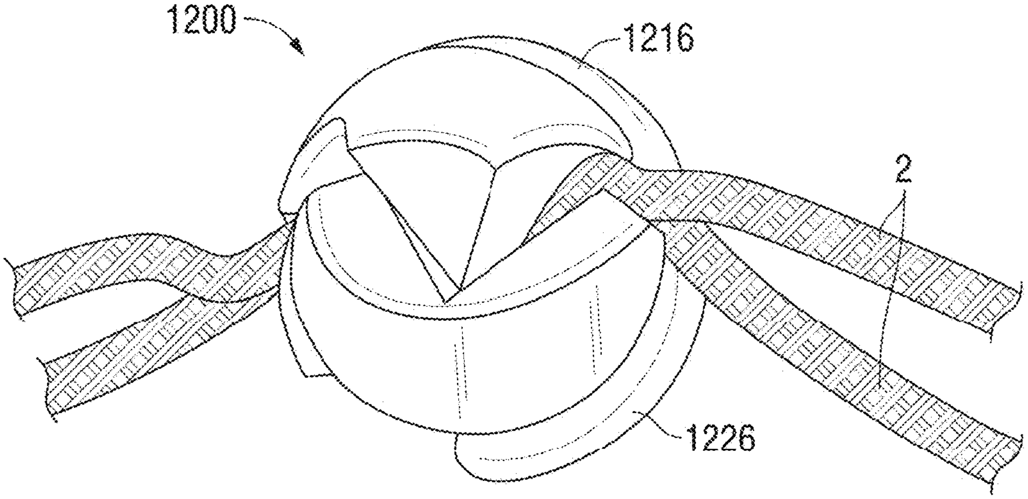
Figure 124:
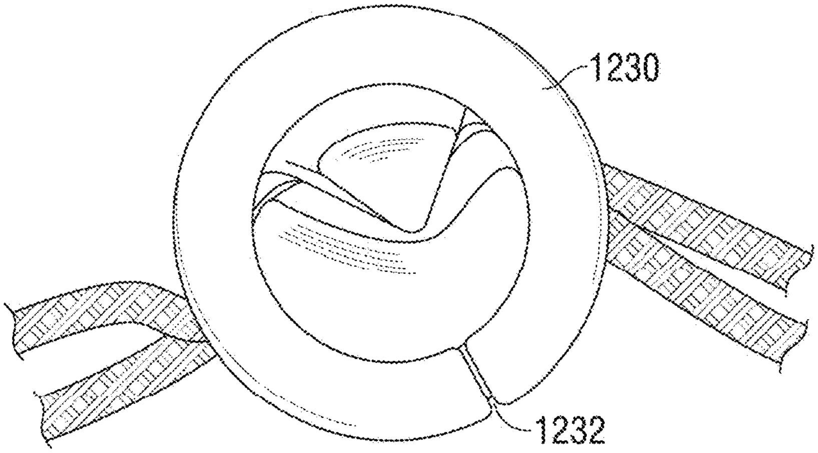
Figure 125:
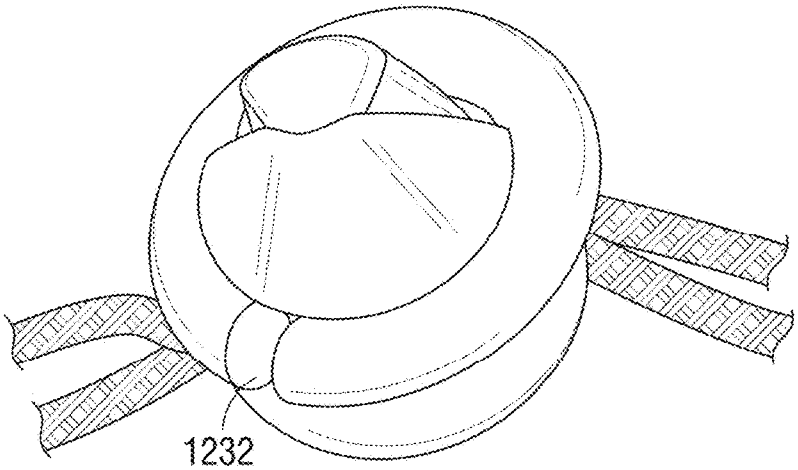

FIGS. 121 to 125 illustrate another exemplary embodiment of a laterally loaded clip 1200 for securing cords 2 therein. The clip 1200 has a two-part body 1210, 1220 and a securing ring 1230. The two parts 1210, 1220 of the body are connected by a hinge 1212, 1222 that allows the two parts to open and close like a shell. One body part 1210 has at least one protrusion 1214 and the other part 1220 has at least one corresponding groove 1224 into which the protrusion 1214 can rest and crimp a cord(s) 2 therebetween when the clam-shell of the two parts 1210, 1220 are hinged closed. Here, one protrusion and one corresponding groove is shown but there can be more than one. The protrusion 1212 provides a pinching point to hold the cords 2 therein. One of the parts, here the first part 1210, has a groove or channel 1214 shaped to conform at least partly to the cords 2 that are to be clamped between the two parts 1210, 1220. FIG. 122 shows the two parts 1210, 1220 in a cord-loading position. The cords 2, as shown in FIG. 123, are loaded in between the parts 1210, 1220 and the parts 1210, 1220 are closed upon the cords 2. As can be seen in FIGS. 122 and 123, the parts 1210, 1220 also provide portions of an exterior circumferential groove 1216, 1226. Together, this circumferential groove 1216, 1226 provides the locking mechanism for the securing ring 1230. The parts 1210, 1220 have ends at which there is a narrowing for receiving the securing ring 1230 thereon. When placed over the narrowing, as shown in FIG. 124, the parts 1210, 1220 no longer can separate from one another. To lock the cords 2 between the two parts 1210, 1220, as shown in the view of FIG. 125, the securing ring 1230 is pressed over the narrowing until the securing ring 1230 rests in the groove 1216, 1226. As can be seen by the separation distance of a split 1232 in the securing ring 1230, the groove 1216, 1226 in the locking state is slightly larger than the interior circumference of the securing ring 1230. As such, the securing ring 1230 provides a strong bias to retain and fix the two parts 1210, 1220 together.

One of the primary features of a laterally loaded clip is that such cord loading eliminates the needs to feed the cord(s) through a structure, such as a tube. In the tubular crimp structures, the cord(s) is fed through the bore. With a laterally loaded clip, the cord(s) needs only to be laid against the side.

When any motors are described herein, they also include, where desirable, any gearing or transmissions that are necessary to reduce the motor turns rate to affect the function of that motor. These transmissions are not described herein in further detail.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The foregoing description and accompanying drawings illustrate the principles, exemplary embodiments, and modes of operation of the devices and methods. However, the devices and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope thereof as defined by the following claims.

What is claimed is:

1. A multiple-firing clip device, comprising:

a plurality of suture fixation clips each having an internal hollow shaped to receive therein at least one suture;

a shaft having a distal fixation location, an exterior surface, and an interior; the plurality of the suture fixation clips positioned in the interior, defining a first clip, and configured to move along a longitudinal axis of the shaft; the shaft defining a lateral opening proximal to the distal fixation location; the lateral opening communicating between the interior and an environment outside the exterior surface; and a shuttle longitudinally movable on the shaft and comprising:

a shuttle body;

a snare coupled to the shuttle body and having a distal snare portion; and a snare-movement assembly comprising:

a snare-extender slide movably disposed with respect to the shuttle body along a given extent, the given extent defining a slide distance and a distal end; and a snare extender coupled to the snare and to the snare-extender slide, the snare extender configured to extend at least the distal snare portion distally to an extent that is at least equal to the slide distance responsive to movement of the snare-extender slide to the distal end of the given extent.

2. The device according to claim 1, wherein:

the shaft comprises a distal shaft end and a distal shaft portion between the lateral opening and the distal shaft end; and the shuttle is configured to pull a portion of the at least one suture temporarily secured in the snare from distal of the distal shaft end proximally through the internal hollow of the first clip, through the distal shaft portion, and out a side of the shaft through the lateral opening.

3. The device according to claim 1, wherein:

the snare-extender slide comprises a rack fixed thereto and moving correspondingly with the snare-extender slide;

the snare has a proximal snare portion and a distal snare end;

the snare extender comprises a pinion having a spool and is operatively connected to the rack to rotate as the rack moves with the snare-extender slide;

the shaft comprises a distal shaft end and a distal shaft portion between the lateral opening and the distal shaft end; and at least the proximal snare portion is attached to the spool such that, as the spool rotates with the pinion, the distal snare end extends away from the spool through the distal shaft portion, through the distal fixation location, and through the internal hollow of the first clip.

4. The device according to claim 3, wherein at least the proximal snare portion is wound on the spool such that, as the spool rotates with the pinion, the distal snare end extends away from the spool through the distal shaft portion, through the distal fixation location, through the internal hollow of the first clip, and distal of the distal shaft end.

5. The device according to claim 3, wherein the rack has teeth and the pinion is a speed-increasing gear sized to rotate at a gear ratio greater than 1:1 with respect to movement of the rack.

6. The device according to claim 1, wherein the snare extender is configured to extend at least the distal snare portion distally to an extent that is longer than the slide distance responsive to movement of the snare-extender slide up to the distal end of the given extent and, with that extension, through the distal fixation location.

7. The device according to claim 1, wherein:

the snare is configured to laterally pass into the interior of the shaft through the lateral opening from the environment, is configured to pass through the internal hollow of the first clip, and is configured to pass out of the interior of the shaft distally past the distal fixation location to temporarily secure a suture portion of the at least one suture within the snare; and the shuttle is configured to pull the suture portion out a side of the shaft through the lateral opening to present at least some of the suture portion out from the lateral opening for access by a user.

8. The device according to claim 7, wherein:

the suture portion temporarily secured in the snare comprises two free ends of a surgical suture;

the suture portion being pulled proximally through the first clip comprises the two free ends such that, at a given time, four lengths of the surgical suture are being pulled through the first clip; and the at least some of the suture portion pulled out through the lateral opening for access by a user is the two free ends of the surgical suture.

9. The device according to claim 1, wherein the internal hollow is one of a lumen and a slot.

10. The device according to claim 1, further comprising a device movement carriage within the interior of the shaft and configured to deliver the first clip to the distal fixation location by moving the first clip longitudinally from a first proximal position to the distal fixation location;

wherein the device movement carriage is configured to deliver the first clip to the distal fixation location by moving the first clip longitudinally from the first proximal position into the distal fixation location and returning without the first clip to a second proximal position one of:

substantially the same as the second proximal position; and different from the first proximal position.

11. The device according to claim 10, wherein, responsive to the device movement carriage returning to the second proximal position, the interior is open to the environment through the lateral opening.

12. The device according to claim 10, wherein, during or after the device movement carriage is in a process of returning to the second proximal position without the first clip, the device movement carriage moves a previously second of the clips into a clip loading position to become a new first clip.

13. The device according to claim 1, wherein:

the first clip has a proximal side;

the snare-movement assembly comprises a hollow snare guide having a distal guide portion movable from external of the shaft into the interior through the lateral opening and up to the proximal side of the first clip;

the distal snare portion is steady with respect to the snare guide when the distal guide portion is external to the shaft; and the distal snare portion is configured to extend from the snare guide responsive to locating the distal guide portion within the interior.

14. The device according to claim 1, wherein the shuttle body defines a lumen surrounding the shaft.

15. The device according to claim 1, wherein the distal snare portion comprises a loop shaped to extend through the interior of the shaft through the lateral opening from the environment, to pass through the internal hollow of the first clip, and to pass out of the interior of the shaft distally past the distal fixation location.

16. The device according to claim 15, wherein the loop is substantially ovular.

17. The device according to claim 1, wherein:

the shuttle body has a distal side;

the snare-extender slide has a proximal-most, unactuated position and a distal-most, actuated position;

the shuttle further comprises a snare-extension tube having a distal tube end adjacent the distal side of the shuttle body; and the snare has a tip and an overall length set to position the tip just outside the distal side of the shuttle body when the snare-extender slide is in the proximal-most, unactuated position.

18. The device according to claim 17, wherein:

the shaft comprises a distal shaft end; and the snare-extension tube is configured to drop at least the distal tube end into the lateral opening of the shaft as the shuttle moves towards the distal shaft end.

19. A multiple-firing clip device, comprising:

a shaft comprising an exterior surface, an interior configured to receive therein a plurality of suture fixation clips, and a distal end opening shaped to eject at least one of the suture fixation clips therefrom; the shaft defining a longitudinal central axis and a longitudinally extending lateral opening communicating between the interior and an environment outside the exterior surface, wherein the lateral opening has proximal and distal ends, and wherein the distal end of the lateral opening is spaced apart from the distal end opening by a distal shaft portion having a closed cross section; and a shuttle longitudinally movable on the shaft and comprising:

a shuttle body positioned on the shaft;

a snare coupled to the shuttle body and having a distal snare portion; and a snare extension slide:

movably disposed with respect to the shuttle body; and operatively connected to the snare to extend the distal snare portion distally, wherein the snare extension slide is operatively connected to the snare to extend the distal snare portion distally from the interior of the shaft, through the lateral opening, and further distally through the closed distal shaft portion toward the distal end opening.

* * * * *